US012691134B2

(12) United States Patent
Rodriguez-Flores et al.

(10) Patent No.: US 12,691,134 B2
(45) Date of Patent: Jul. 28, 2026

(54) TREATMENT OF CEREBROVASCULAR DISEASE WITH NEUROGENIC LOCUS NOTCH HOMOLOG PROTEIN 3 (NOTCH3) AGENTS

(71) Applicants: Regeneron Pharmaceuticals, Inc., Tarrytown, NY (US); Center for Non-Communicable Diseases SMC Private Limited, Karachi (PK)

(72) Inventors: Juan Rodriguez-Flores, Tarrytown, NY (US); Alan Shuldiner, Tarrytown, NY (US); Aris Baras, Tarrytown, NY (US); Danish Saleheen, Scarsdale, NY (US); Shareef Khalid, White Plains, NY (US)

(73) Assignees: Regeneron Pharmaceuticals, Inc., Tarrytown, NY (US); Center for Non-Communicable Diseases SMC Private Limited, Karachi (PK)

( * ) Notice: Subject to any disclaimer, the term of this patent is extended or adjusted under 35 U.S.C. 154(b) by 0 days.

(21) Appl. No.: 17/829,801

(22) Filed: Jun. 1, 2022

(65) Prior Publication Data

US 2023/0000897 A1 Jan. 5, 2023

Related U.S. Application Data

(60) Provisional application No. 63/195,970, filed on Jun. 2, 2021.

(51) Int. Cl.
| | |
|---|---|
| *C12N 15/11* | (2006.01) |
| *A61K 31/7105* | (2006.01) |
| *A61K 38/46* | (2006.01) |
| *C12Q 1/6883* | (2018.01) |
| *C12N 15/113* | (2010.01) |

(52) U.S. Cl.
CPC ........ *A61K 31/7105* (2013.01); *A61K 38/465* (2013.01); *C12Q 1/6883* (2013.01); *C12N 15/1138* (2013.01); *C12Q 2600/156* (2013.01)

(58) Field of Classification Search
CPC .................. C12Q 2600/156; C12Q 2600/178
See application file for complete search history.

(56) References Cited

U.S. PATENT DOCUMENTS

2003/0186290 A1 10/2003 Tournier-Lasserve et al.
2011/0318787 A1* 12/2011 Lesnik Oberstein ..... A61P 9/10
435/375

FOREIGN PATENT DOCUMENTS

| WO | 2010085151 | 7/2010 |
|---|---|---|
| WO | 2018183216 | 10/2018 |
| WO | 2019042983 | 3/2019 |
| WO | 2020198037 | 10/2020 |

OTHER PUBLICATIONS

Zhu et al , Transcription Factor HEY1 Improves Brain Vascular Endothelial Cell Function and Alleviates Ischemic Stroke by Upregulating NOTCH3, Neurochemical Research, 2022, 47: 1442-1458 (Year: 2022).*

GenBank NM_000435.3, 1994, pp. 1-19 (Year: 1994).*

Chabriat et al., CADASIL, Lancet Neurology, 2009 8: 643-653 (Year: 2009).*

Joutel et al., "Notch3 mutations in CADASIL, a hereditary adult-onset condition causing stroke and dementia", Nature, 1996, 383, pp. 707-710.

Singhal et al., "The influence of genetic and cardiovascular risk factors on the CADASIL phenotype", Brain, 2004, 127, pp. 2031-2038.

Ruchoux et al., "Systemic vascular smooth muscle cell impairment in cerebral autosomal dominant arteriopathy with subcortical infarcts and leukoencephalopathy", Acta Neuropathol, 1995, 89, pp. 500-512.

Rutten et al., "Archetypal NOTCH3 mutations frequent in public exome: implications for CADASIL", Ann Clin Transl Neurol, 2016, 3, pp. 844-853.

Masoli et al., "Clinical Outcomes of CADASIL-Associated NOTCH3 Mutations in 451,424 European Ancestry Community Volunteers", Translation Stroke Research, 2018, 10(4), pp. 339-341.

Federico et al., "The spectrum of mutations for CADASIL diagnosis", Neurol Sci, 2005, 26(2), pp. 117-124.

Rinnoci et al., "Cerebral hemorrhages in CADASIL: Report of four cases and a brief review", Journal of Neurological Sciences, 2013, 330(1), pp. 45-51.

Al-Shaar et al.,, "Phenotypic comparison of individuals with homozygous or heterozygous mutation of NOTCH3 in a large CADASIL family", Journal of Neurological Sciences, 2016, 367, pp. 239-243.

Abramycheva et al., "New mutations in the Notch3 gene in patients with cerebral autosomal dominant arteriopathy with subcortical infarcts and leucoencephalopathy (CADASIL)", Journal of Neurological Sciences, 2015, 349(1), pp. 196-201.

* cited by examiner

*Primary Examiner* — Ekaterina Poliakova-Georgantas

(74) *Attorney, Agent, or Firm* — Armstrong Teasdale LLP

(57) ABSTRACT

The present disclosure provides methods of treating subjects having a cerebrovascular disease by administering Neurogenic Locus Notch Homolog Protein 3 (NOTCH3) agents, and methods of identifying subjects having an increased risk of developing a cerebrovascular disease.

2 Claims, 5 Drawing Sheets

Specification includes a Sequence Listing.

| Group | N | Count | | | | | Frequency | | | |
|---|---|---|---|---|---|---|---|---|---|---|
| | | Ref/Ref | Ref/Alt | Alt/Alt | Alt alleles | Total alleles | MAF | Ref/Alt | Alt/alt | Ref/Ref |
| Cases | 1414 | 1370 | 44 | 0 | 44 | 2828 | 0.0156 | 0.0311 | 0.0000 | 0.9689 |
| Controls | 6871 | 6799 | 71 | 1 | 73 | 13742 | 0.0053 | 0.0103 | 0.0001 | 0.9895 |

Figure 2 (cont.)

| Cohort | Phenotype | P-value | Effect Size [LCI\|UCI] | RefRef\|RefAlt\|AltAlt Cases | RefRef\|RefAlt\|AltAlt Controls |
|---|---|---|---|---|---|
| CNCD_Freeze_Two | Subcortical | 2.20E-08 | 2.959[2.024\|4.327] | 1,370\|44\|0 | 6,799\|71\|1 |
| CNCD_Freeze_Two | Hemorrhagic | 5.10E-07 | 2.599[1.791\|3.773] | 1,634\|46\|0 | 6,799\|71\|1 |
| CNCD_Freeze_Two | Stroke | 1.60E-06 | 2.039[1.524\|2.727] | 4,772\|99\|3 | 6,799\|71\|1 |
| CNCD_Freeze_Two | LACI | 1.50E-03 | 2.798[1.483\|5.279] | 379\|9\|1 | 7,086\|71\|1 |
| CNCD_Freeze_Two | SAA | 1.90E-03 | 2.881[1.479\|5.613] | 321\|8\|1 | 6,799\|71\|1 |
| CNCD_Freeze_Two | PACI | 3.20E-03 | 2.070[1.277\|3.356] | 1,260\|25\|1 | 7,086\|71\|1 |
| CNCD_Freeze_Two | Family history of stroke | 4.10E-03 | 1.819[1.209\|2.735] | 1,134\|25\|1 | 13,506\|170\|3 |
| CNCD_Freeze_Two | Small artery probable | 6.00E-03 | 2.610[1.316\|5.176] | 283\|8\|0 | 6,799\|71\|1 |
| CNCD_Freeze_Two | Ischemic | 6.10E-03 | 1.681[1.159\|2.436] | 2,652\|44\|2 | 6,799\|71\|1 |

Figure 4

TREATMENT OF CEREBROVASCULAR DISEASE WITH NEUROGENIC LOCUS NOTCH HOMOLOG PROTEIN 3 (NOTCH3) AGENTS

REFERENCE TO SEQUENCE LISTING

This application includes a Sequence Listing submitted electronically as a text file named 18923806501SEQ, created on May 30, 2022, with a size of 364 kilobytes. The Sequence Listing is incorporated herein by reference.

FIELD

The present disclosure relates generally to methods of treating subjects having a cerebrovascular disease with Neurogenic Locus Notch Homolog Protein 3 (NOTCH3) agents, and methods of identifying subjects having an increased risk of developing a cerebrovascular disease.

BACKGROUND

Cerebrovascular disease includes any abnormality of the brain resulting from a pathologic process of a blood vessel. A pathologic process of a blood vessel includes any one or more of the following: an occlusion of a blood vessel lumen by thrombus or embolus, a rupture of a blood vessel, an altered permeability of a blood-vessel wall, and increased viscosity or other change in the quality of blood. Cerebrovascular disease is typically readily diagnosable because of how it manifests. Cerebrovascular disease typically manifests as a stroke. A stroke can be characterized as a sudden nonconvulsive, focal neurologic deficit. That is, stroke can be characterized as the death of brain tissue that results from lack of blood flow and insufficient oxygen to the brain. After heart disease and cancer, stroke is the leading cause of death in the United States. In the United States, there are approximately 500,000 cases of stroke annually. And these 500,000 cases give rise to about 175,000 fatalities.

Cerebral autosomal dominant arteriopathy with subcortical infarcts and leukoencephalopathy (CADASIL) or CADASIL syndrome, is the most common form of hereditary stroke disorder. The most common clinical manifestations are migraine headaches and transient ischemic attacks or strokes, which usually occur between 40 and 50 years of age, although MRI is able to detect signs of the disease years prior to clinical manifestation of disease. The underlying pathology of CADASIL is progressive hypertrophy of the smooth muscle cells in blood vessels. No specific treatment for CADASIL is available. While most treatments for CADASIL patients' symptoms—including migraine and stroke—are similar to those without CADASIL, these treatments are almost exclusively empiric, as data regarding their benefit to CADASIL patients is limited.

Neurogenic Locus Notch Homolog Protein 3 (NOTCH3) is a receptor for membrane-bound ligands Jagged1, Jagged2, and Delta1 to regulate cell-fate determination. Upon ligand activation through the released notch intracellular domain (NICD), it forms a transcriptional activator complex with RBPJ/RBPSUH and activates genes of the enhancer of split locus. NOTCH3 effects the implementation of differentiation, proliferation and apoptotic programs.

SUMMARY

The present disclosure provides methods of treating a subject having a cerebrovascular disease, the methods comprising administering a Neurogenic Locus Notch Homolog Protein 3 (NOTCH3) agent to the subject.

The present disclosure also provides methods of treating a subject having a subcortical stroke, the methods comprising administering a NOTCH3 agent to the subject.

The present disclosure also provides methods of treating a subject having an ischemic stroke, the methods comprising administering a NOTCH3 agent to the subject.

The present disclosure also provides methods of treating a subject having a hemorrhagic stroke, the methods comprising administering a NOTCH3 agent to the subject.

The present disclosure also provides methods of treating a subject having a parenchymal stroke, the methods comprising administering a NOTCH3 agent to the subject.

The present disclosure also provides methods of treating a subject having cerebral autosomal dominant arteriopathy with subcortical infarcts and leukoencephalopathy (CADASIL), the methods comprising administering a NOTCH3 agent to the subject.

The present disclosure also provides methods of treating a subject with a therapeutic agent that treats or inhibits a cerebrovascular disease, wherein the subject has a cerebrovascular disease, the methods comprising: determining whether the subject has a NOTCH3 missense variant nucleic acid molecule encoding a NOTCH3 predicted gain-of-function polypeptide by: obtaining or having obtained a biological sample from the subject; and performing or having performed a sequence analysis on the biological sample to determine if the subject has a genotype comprising the NOTCH3 missense variant nucleic acid molecule encoding the NOTCH3 predicted gain-of-function polypeptide; and administering or continuing to administer the therapeutic agent that treats or inhibits a cerebrovascular disease in a standard dosage amount to a subject that is NOTCH3 reference, and administering a NOTCH3 agent to the subject; and administering or continuing to administer the therapeutic agent that treats or inhibits a cerebrovascular disease in an amount that is the same as or greater than a standard dosage amount to a subject that is heterozygous or homozygous for the NOTCH3 missense variant nucleic acid molecule, and administering a NOTCH3 agent to the subject; wherein the presence of a genotype having the NOTCH3 missense variant nucleic acid molecule encoding the NOTCH3 predicted gain-of-function polypeptide indicates the subject has an increased risk of developing a cerebrovascular disease.

The present disclosure also provides methods of identifying a subject having an increased risk for developing a cerebrovascular disease, the methods comprising: determining or having determined the presence or absence of a NOTCH3 missense variant nucleic acid molecule encoding a NOTCH3 predicted gain-of-function polypeptide in a biological sample obtained from the subject; wherein: when the subject is NOTCH3 reference, then the subject does not have an increased risk for developing the cerebrovascular disease; and when the subject is heterozygous or homozygous for the NOTCH3 missense variant nucleic acid molecule, then the subject has an increased risk for developing the cerebrovascular disease.

The present disclosure also provides therapeutic agents that treat or inhibit a cerebrovascular disease for use in the treatment of a cerebrovascular disease in a subject identified as having: a genomic nucleic acid molecule having a nucleotide sequence encoding a NOTCH3 polypeptide, wherein the nucleotide sequence comprises a thymine at a position corresponding to position 21,944 according to SEQ ID NO:2, or the complement thereof; an mRNA molecule having a nucleotide sequence encoding a NOTCH3 polypeptide, wherein the nucleotide sequence comprises a uracil at a position corresponding to: position 3,781 according to SEQ ID NO:8, or the complement thereof; position 3,767 according to SEQ ID NO:9, or the complement thereof; position 3,532 according to SEQ ID NO:10, or the complement thereof; position 3,769 according to SEQ ID NO:11, or the complement thereof; or position 3,544 according to SEQ ID NO:12, or the complement thereof; or a cDNA molecule having a nucleotide sequence encoding a NOTCH3 polypeptide, wherein the nucleotide sequence comprises a thymine at a position corresponding to: position 3,781 according to SEQ ID NO:18, or the complement thereof; position 3,767 according to SEQ ID NO:19, or the complement thereof; position 3,532 according to SEQ ID NO:20, or the complement thereof; position 3,769 according to SEQ ID NO:21, or the complement thereof; or position 3,544 according to SEQ ID NO:22, or the complement thereof.

The present disclosure also provides NOTCH3 agents for use in the treatment of a cerebrovascular disease in a subject identified as having: a genomic nucleic acid molecule having a nucleotide sequence encoding a NOTCH3 polypeptide, wherein the nucleotide sequence comprises a thymine at a position corresponding to position 21,944 according to SEQ ID NO:2, or the complement thereof; an mRNA molecule having a nucleotide sequence encoding a NOTCH3 polypeptide, wherein the nucleotide sequence comprises a uracil at a position corresponding to: position 3,781 according to SEQ ID NO:8, or the complement thereof; position 3,767 according to SEQ ID NO:9, or the complement thereof; position 3,532 according to SEQ ID NO:10, or the complement thereof; position 3,769 according to SEQ ID NO:11, or the complement thereof; or position 3,544 according to SEQ ID NO:12, or the complement thereof; or a cDNA molecule having a nucleotide sequence encoding a NOTCH3 polypeptide, wherein the nucleotide sequence comprises a thymine at a position corresponding to: position 3,781 according to SEQ ID NO:18, or the complement thereof; position 3,767 according to SEQ ID NO:19, or the complement thereof; position 3,532 according to SEQ ID NO:20, or the complement thereof; position 3,769 according to SEQ ID NO:21, or the complement thereof; or position 3,544 according to SEQ ID NO:22, or the complement thereof.

BRIEF DESCRIPTION OF THE DRAWINGS

The accompanying figures, which are incorporated in and constitute a part of this specification, illustrate several features of the present disclosure.

FIG. 4 shows a table summarizing the results of PheWAS of NOTCH3 p.Arg1231Cys.

DESCRIPTION

Figure 1:
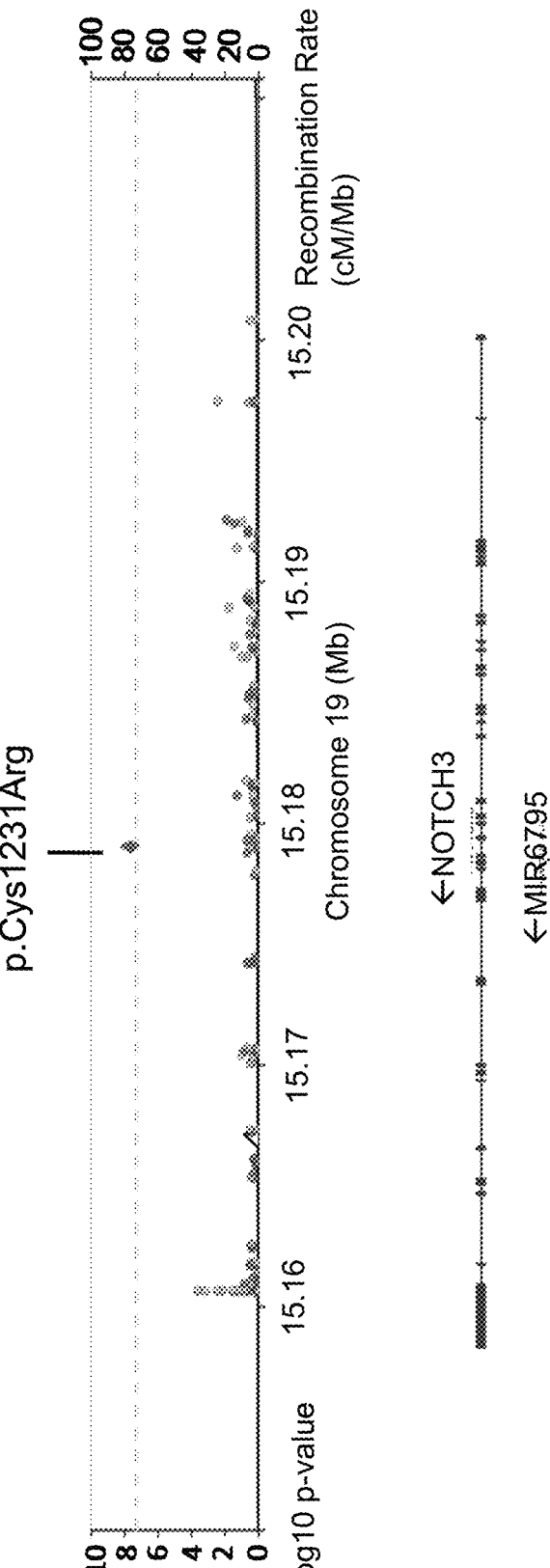
FIG. 1 shows EXWAS results for the NOTCH3 locus.
Figure 2:
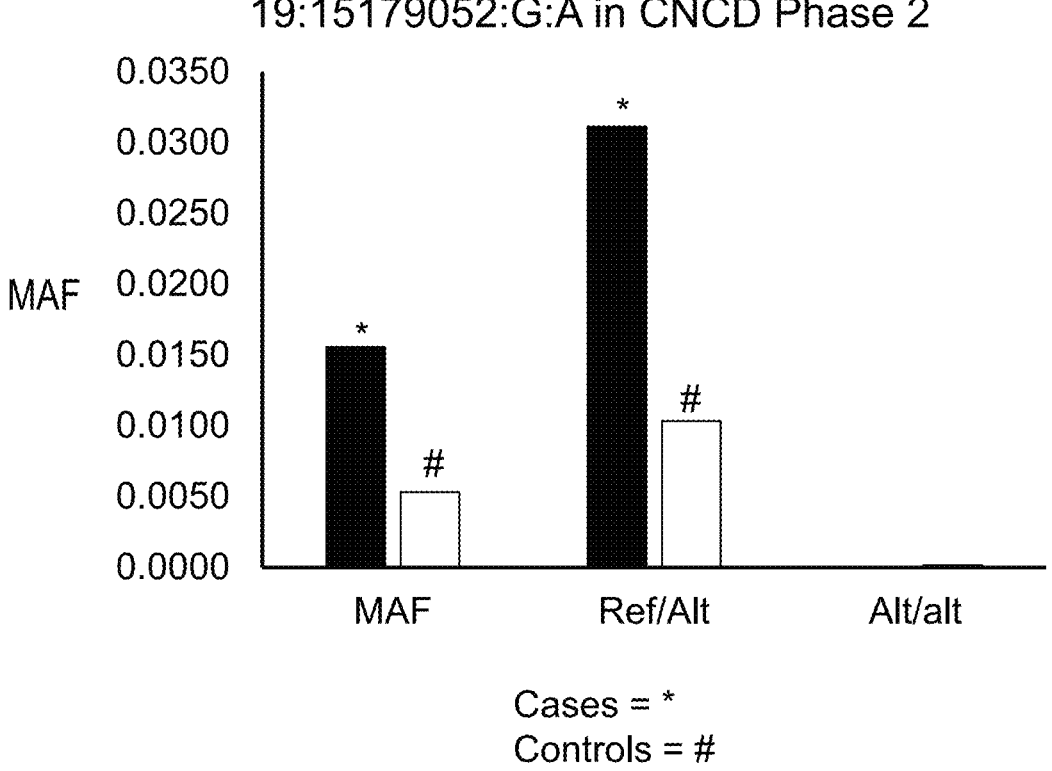
FIG. 2 shows the occurrence of cases and controls in the EXWAS grouped by the presence of rs201680145.

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the term "comprising" may be replaced with "consisting" or "consisting essentially of" in particular embodiments as desired.

As used herein, the term "isolated", in regard to a nucleic acid molecule or a polypeptide, means that the nucleic acid molecule or polypeptide is in a condition other than its native environment, such as apart from blood and/or animal tissue. In some embodiments, an isolated nucleic acid molecule or polypeptide is substantially free of other nucleic acid molecules or other polypeptides, particularly other nucleic acid molecules or polypeptides of animal origin. In some embodiments, the nucleic acid molecule or polypeptide can be in a highly purified form, i.e., greater than 95% pure or greater than 99% pure. When used in this context, the term "isolated" does not exclude the presence of the same nucleic acid molecule or polypeptide in alternative physical forms, such as dimers or alternatively phosphorylated or derivatized forms.

As used herein, the terms "nucleic acid", "nucleic acid molecule", "nucleic acid sequence", "polynucleotide", or "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates (such as, for example, apes and monkeys). In some embodiments, the subject is a human. In some embodiments, the subject is a patient under the care of a physician.

A common variant SNP rs201680145 in the NOTCH3 gene in humans has been identified in accordance with the present disclosure to be associated with an increased risk of developing a cerebrovascular disease, such as CADASIL, subcortical stroke, ischemic stroke, hemorrhagic stroke, or parenchymal stroke. For example, a genetic alteration that changes the cytosine at position 21,944 in the NOTCH3 reference genomic nucleic acid molecule (see, SEQ ID NO:1) to a thymine has been observed to indicate that the subject having such an alteration may have an increased risk of developing a cerebrovascular disease. It is believed that no variants of the NOTCH3 gene or protein have any known significant association, as shown by genome-wide analysis, with a cerebrovascular disease, such as subcortical stroke, ischemic stroke, hemorrhagic stroke, or parenchymal stroke.

In addition, CADASIL was initially reported to be caused by autosomal dominant mutations of the NOTCH3 gene (Joutel et al., Nature, 1996, 383, 707-10), including rs201680145 (Singhal et al., Brain, 2004, 127, 2031-2038). These mutations were believed to lead to an abnormal accumulation of Notch 3 at the cytoplasmic membrane of vascular smooth muscle cells both in cerebral and extracerebral vessels (Joutel et al., J. Clin. Invest., 2000, 105, 597-605) seen as granular osmiophilic deposits on electron microscopy (Ruchoux et al., Acta Neuropathol., 1995, 89, 500-12). In addition, in many cases, leukoencephalopathy follows. All CADASIL pathogenic mutations in NOTCH3 share the common feature of adding or removing a Cys residue from one of 34 EGFR domains in the NOTCH3 extra-cellular domain, where each EGFR normally has 6 Cys residues that are highly conserved in human, mouse and zebrafish NOTCH3. Hundreds of such Cys-add-or-remove variants have been identified. However, the view that the NOTCH3 p.Arg1231Cys mutation is the causative of CADASIL was abandoned as incorrect because of the very high prevalence of this mutation (r5201680145) in South Asians, including, significantly surpassing the frequency that was expected based on CADASIL prevalence (Rutten et al., Ann. Clin. Transl. Neurol., 2016, 3, 844-853). Altogether, the genetic analyses described herein surprisingly indicate that the NOTCH3 gene and, in particular, a gain-of-function variant in the NOTCH3 gene, associates with an increased risk of developing a cerebrovascular disease, such as CADASIL, subcortical stroke, ischemic stroke, hemorrhagic stroke, or parenchymal stroke. Therefore, subjects that have a NOTCH3 missense variant nucleic acid molecule encoding a NOTCH3 predicted gain-of-function polypeptide that have an increased risk of developing a cerebrovascular disease, such as CADASIL, subcortical stroke, ischemic stroke, hemorrhagic stroke, or parenchymal stroke, may be treated such that the cerebrovascular disease is prevented, the symptoms thereof are reduced, and/or development of symptoms is repressed. Accordingly, the present disclosure provides methods of leveraging the identification of such NOTCH3 missense variant nucleic acid molecules in subjects to identify or stratify risk in such subjects of developing a cerebrovascular disease, such as CADASIL, subcortical stroke, ischemic stroke, hemorrhagic stroke, or parenchymal stroke, or to diagnose subjects as having an increased risk of developing a cerebrovascular disease, such as CADASIL, subcortical stroke, ischemic stroke, hemorrhagic stroke, or parenchymal stroke, such that subjects at risk or subjects with active disease may be treated accordingly.

For purposes of the present disclosure, any particular subject can be categorized as having one of three NOTCH3 genotypes: i) NOTCH3 reference; ii) heterozygous for a NOTCH3 missense variant nucleic acid molecule encoding a NOTCH3 predicted gain-of-function polypeptide; or iii) homozygous for a NOTCH3 missense variant nucleic acid molecule encoding a NOTCH3 predicted gain-of-function polypeptide. A subject is NOTCH3 reference when the subject does not have a copy of a NOTCH3 missense variant nucleic acid molecule encoding a NOTCH3 predicted gain-of-function polypeptide. A subject is heterozygous for a NOTCH3 missense variant nucleic acid molecule encoding a NOTCH3 predicted gain-of-function polypeptide when the subject has a single copy of a NOTCH3 missense variant nucleic acid molecule encoding a NOTCH3 predicted gain-of-function polypeptide. As used herein, a NOTCH3 missense variant nucleic acid molecule encoding a NOTCH3 predicted gain-of-function polypeptide is any NOTCH3 nucleic acid molecule (such as, a genomic nucleic acid molecule, an mRNA molecule, or a cDNA molecule) encoding a NOTCH3 polypeptide having a partial gain-of-function, a complete gain-of-function, a predicted partial gain-of-function, or a predicted complete gain-of-function. A subject who has a NOTCH3 polypeptide having a partial gain-of-function (or predicted partial gain-of-function) is hypomorphic for NOTCH3.

In any of the embodiments described herein, the NOTCH3 missense variant nucleic acid molecule encoding a NOTCH3 predicted gain-of-function polypeptide can be any nucleic acid molecule encoding a NOTCH3 Arg1178Cys, Arg1231Cys, or Arg1182Cys. In some embodiments, the NOTCH3 missense variant nucleic acid molecule encodes NOTCH3 Arg1178Cys, Arg1231Cys, or Arg1182Cys. A subject is homozygous for a NOTCH3 missense variant nucleic acid molecule encoding a NOTCH3 predicted gain-of-function polypeptide when the subject has two copies of a NOTCH3 missense variant nucleic acid molecule encoding a NOTCH3 predicted gain-of-function polypeptide.

In any of the embodiments described herein, the NOTCH3 variant nucleic acid molecules can be any Cys-altering variant (they change from or to a cysteine residue). In some embodiments the Cys-altering variant is located within the 34 EGF-like repeats in the NOTCH3 extracellular domain (defined by Uniprot; see world wide web at "uniprot.org/blast/? about=Q9UM47[1335-1373]&key= Domain)). In any of the embodiments described herein, the NOTCH3 variant nucleic acid molecules can be any of the variants listed in Table 1 (ENST00000263388).

TABLE 1

| Cys-Altering Variants | | | |
|---|---|---|---|
| Variant | rsID | HGVS.c | HGVS.p |
| 19:15200890:G:A | rs1189616145 | c.16C > T | p.Arg6Cys |
| 19:15200884:G:A | | c.22C > T | p.Arg8Cys |
| 19:15200881:G:A | | c.25C > T | p.Arg9Cys |
| 19:15200878:G:A | | c.28C > T | p.Arg10Cys |
| 19:15200875:G:A | | c.31C > T | p.Arg11Cys |
| 19:15200872:G:A | | c.34C > T | p.Arg12Cys |
| 19:15200869:G:A | | c.37C > T | p.Arg13Cys |
| 19:15197571:A:AG | rs749829137 | c.125dupC | p.Cys43fs |
| 19:15197552:A:C | | c.145T > G | p.Cys49Gly |
| 19:15197537:G:A | | c.160C > T | p.Arg54Cys |
| 19:15197534:A:C | | c.163T > G | p.Cys55Gly |

TABLE 1-continued

| | Cys-Altering Variants | | |
| --- | --- | --- | --- |
| Variant | rsID | HGVS.c | HGVS.p |
| 19:15197503:C:G | | c.194G > C | p.Cys65Ser |
| 19:15192458:A:T | | c.259T > A | p.Cys87Ser |
| 19:15192452:C:A | | c.265G > T | p.Gly89Cys |
| 19:15192449:G:A | | c.268C > T | p.Arg90Cys |
| 19:15192389:G:A | rs775836288 | c.328C > T | p.Arg110Cys |
| 19:15192256:C:CAA | | c.381_382dupTT | p.Cys128fs |
| 19:15192242:G:A | rs137852642 | c.397C > T | p.Arg133Cys |
| 19:15192218:G:A | | c.421C > T | p.Arg141Cys |
| 19:15192204:G:GGAGCA | | c.430_434dupTGCTC | p.Cys146fs |
| 19:15192182:G:A | rs797045014 | c.457C > T | p.Arg153Cys |
| 19:15192155:A:C | | c.484T > G | p.Cys162Gly |
| 19:15192135:G:T | | c.504C > A | p.Cys168* |
| 19:15192134:G:A | rs28933696 | c.505C > T | p.Arg169Cys |
| 19:15192095:G:A | rs28933697 | c.544C > T | p.Arg182Cys |
| 19:15192085:C:A | | c.554G > T | p.Cys185Phe |
| 19:15192037:C:G | | c.602G > C | p.Cys201Ser |
| 19:15192022:C:T | | c.617G > A | p.Cys206Tyr |
| 19:15192020:G:A | rs775267348 | c.619C > T | p.Arg207Cys |
| 19:15192005:A:T | | c.634T > A | p.Cys212Ser |
| 19:15191980:T:C | | c.659A > G | p.Tyr220Cys |
| 19:15191974:C:T | | c.665G > A | p.Cys222Tyr |
| 19:15191968:C:T | | c.671G > A | p.Cys224Tyr |
| 19:15191850:A:T | | c.697T > A | p.Cys233Ser |
| 19:15191849:C:T | | c.698G > A | p.Cys233Tyr |
| 19:15191848:A:C | | c.699T > G | p.Cys233Trp |
| 19:15191829:A:G | | c.718T > C | p.Cys240Arg |
| 19:15191828:C:G | | c.719G > C | p.Cys240Ser |
| 19:15191827:A:T | | c.720T > A | p.Cys240* |
| 19:15191814:A:G | | c.733T > C | p.Cys245Arg |
| 19:15191796:A:G | | c.751T > C | p.Cys251Arg |
| 19:15191774:T:C | | c.773A > G | p.Tyr258Cys |
| 19:15191588:C:T | | c.872G > A | p.Cys291Tyr |
| 19:15191565:T:A | | c.895A > T | p.Ser299Cys |
| 19:15191529:A:T | | c.931T > A | p.Cys311Ser |
| 19:15191507:C:G | | c.953G > C | p.Cys318Ser |
| 19:15191507:C:A | | c.953G > T | p.Cys318Phe |
| 19:15191466:G:A | rs137852641 | c.994C > T | p.Arg332Cys |
| 19:15191456:G:C | | c.1004C > G | p.Ser335Cys |
| 19:15191450:T:C | | c.1010A > G | p.Tyr337Cys |
| 19:15191446:A:T | | c.1014T > A | p.Cys338* |
| 19:15189386:C:T | | c.1079G > A | p.Cys360Tyr |
| 19:15189321:C:A | | c.1144G > T | p.Gly382Cys |
| 19:15189302:C:T | | c.1163G > A | p.Cys388Tyr |
| 19:15189282:A:G | | c.1183T > C | p.Cys395Arg |
| 19:15189145:A:G | | c.1222T > C | p.Cys408Arg |
| 19:15189112:A:T | | c.1255T > A | p.Cys419Ser |
| 19:15189106:G:A | | c.1261C > T | p.Arg421Cys |
| 19:15189106:G:A | | c.1261C > T | p.Arg421Cys |
| 19:15189083:A:C | | c.1284T > G | p.Cys428Trp |
| 19:15189064:A:G | | c.1303T > C | p.Cys435Arg |
| 19:15189003:C:T | | c.1364G > A | p.Cys455Tyr |
| 19:15188333:T:C | | c.1394A > G | p.Tyr465Cys |
| 19:15188301:T:A | rs886054260 | c.1426A > T | p.Ser476Cys |
| 19:15188286:C:A | rs1263780227 | c.1441G > T | p.Gly481Cys |
| 19:15188276:C:A | | c.1451G > T | p.Cys484Phe |
| 19:15188253:T:A | | c.1474A > T | p.Ser492Cys |
| 19:15188243:C:T | | c.1484G > A | p.Cys495Tyr |
| 19:15187977:A:G | | c.1510T > C | p.Cys504Arg |
| 19:15187956:A:G | | c.1531T > C | p.Cys511Arg |
| 19:15187955:C:A | | c.1532G > T | p.Cys511Phe |
| 19:15187954:G:T | | c.1533C > A | p.Cys511* |
| 19:15187940:C:T | | c.1547G > A | p.Cys516Tyr |
| 19:15187940:C:A | | c.1547G > T | p.Cys516Phe |
| 19:15187922:C:G | | c.1565G > C | p.Cys522Ser |
| 19:15187905:C:A | | c.1582G > T | p.Gly528Cys |
| 19:15187893:G:A | rs1202763005 | c.1594C > T | p.Arg532Cys |
| 19:15187320:C:T | | c.1625G > A | p.Cys542Tyr |
| 19:15187315:G:A | rs201118034 | c.1630C > T | p.Arg544Cys |
| 19:15187315:G:A | rs201118034 | c.1630C > T | p.Arg544Cys |
| 19:15187298:G:C | | c.1647C > G | p.Cys549Trp |
| 19:15187296:G:C | | c.1649C > G | p.Ser550Cys |
| 19:15187284:C:A | | c.1661G > T | p.Cys554Phe |
| 19:15187273:G:A | rs75068032 | c.1672C > T | p.Arg558Cys |
| 19:15187273:G:A | rs75068032 | c.1672C > T | p.Arg558Cys |
| 19:15187243:A:G | | c.1702T > C | p.Cys568Arg |
| 19:15187243:A:C | | c.1702T > G | p.Cys568Gly |

TABLE 1-continued

| Cys-Altering Variants | | | |
| --- | --- | --- | --- |
| Variant | rsID | HGVS.c | HGVS.p |
| 19:15187242:C:T | | c.1703G > A | p.Cys568Tyr |
| 19:15187242:C:CATGAGAA | | c.1696_1702dupTTCTCAT | p.Cys568fs |
| 19:15187219:C:A | | c.1726G > T | p.Gly576Cys |
| 19:15187213:G:A | rs769773673 | c.1732C > T | p.Arg578Cys |
| 19:15187213:G:A | rs769773673 | c.1732C > T | p.Arg578Cys |
| 19:15187209:C:T | | c.1736G > A | p.Cys579Tyr |
| 19:15187186:G:A | rs754554486 | c.1759C > T | p.Arg587Cys |
| 19:15187171:G:A | rs764148985 | c.1774C > T | p.Arg592Cys |
| 19:15187129:A:G | | c.1816T > C | p.Cys606Arg |
| 19:15187128:C:T | | c.1817G > A | p.Cys606Tyr |
| 19:15187128:C:A | | c.1817G > T | p.Cys606Phe |
| 19:15187126:G:A | rs777751303 | c.1819C > T | p.Arg607Cys |
| 19:15187126:G:A | rs777751303 | c.1819C > T | p.Arg607Cys |
| 19:15187121:G:C | | c.1824C > G | p.Cys608Trp |
| 19:15186980:A:G | | c.1849T > C | p.Cys617Arg |
| 19:15186958:C:T | | c.1871G > A | p.Cys624Tyr |
| 19:15186944:A:G | | c.1885T > C | p.Cys629Arg |
| 19:15186926:G:A | rs753801611 | c.1903C > T | p.Arg635Cys |
| 19:15186911:G:A | rs760768552 | c.1918C > T | p.Arg640Cys |
| 19:15186911:G:A | rs760768552 | c.1918C > T | p.Arg640Cys |
| 19:15186902:A:C | | c.1927T > G | p.Cys643Gly |
| 19:15185671:A:C | | c.1960T > G | p.Cys654Gly |
| 19:15185670:C:T | | c.1961G > A | p.Cys654Tyr |
| 19:15185670:C:G | | c.1961G > C | p.Cys654Ser |
| 19:15185669:A:C | | c.1962T > G | p.Cys654Trp |
| 19:15185633:G:T | | c.1998C > A | p.Cys666* |
| 19:15185632:C:A | rs376046941 | c.1999G > T | p.Gly667Cys |
| 19:15185632:C:A | rs376046941 | c.1999G > T | p.Gly667Cys |
| 19:15185619:G:C | | c.2012C > G | p.Ser671Cys |
| 19:15185616:C:T | | c.2015G > A | p.Cys672Tyr |
| 19:15185616:C:A | rs1480573645 | c.2015G > T | p.Cys672Phe |
| 19:15185593:G:A | rs1250956327 | c.2038C > T | p.Arg680Cys |
| 19:15185589:C:T | | c.2042G > A | p.Cys681Tyr |
| 19:15185521:A:C | | c.2110T > G | p.Cys704Gly |
| 19:15185505:C:T | | c.2126G > A | p.Cys709Tyr |
| 19:15185502:T:C | rs1328784046 | c.2129A > G | p.Tyr710Cys |
| 19:15185404:G:A | rs144163298 | c.2149C > T | p.Arg717Cys |
| 19:15185404:G:A | rs144163298 | c.2149C > T | p.Arg717Cys |
| 19:15185395:A:G | | c.2158T > C | p.Cys720Arg |
| 19:15185394:C:T | | c.2159G > A | p.Cys720Tyr |
| 19:15185393:A:T | | c.2160T > A | p.Cys720* |
| 19:15185371:G:A | rs1057519101 | c.2182C > T | p.Arg728Cys |
| 19:15185358:CTCTGGCTG:C | | c.2187_2194delCAGCCAGA | p.Cys729fs |
| 19:15185340:C:T | | c.2213G > A | p.Cys738Tyr |
| 19:15185340:C:A | | c.2213G > T | p.Cys738Phe |
| 19:15185334:G:C | | c.2219C > G | p.Ser740Cys |
| 19:15185325:C:T | | c.2228G > A | p.Cys743Tyr |
| 19:15185306:G:C | | c.2247C > G | p.Cys749Trp |
| 19:15185280:C:T | | c.2273G > A | p.Cys758Tyr |
| 19:15185275:A:G | | c.2278T > C | p.Cys760Arg |
| 19:15185274:C:G | | c.2279G > C | p.Cys760Ser |
| 19:15185017:G:A | rs532100840 | c.2299C > T | p.Arg767Cys |
| 19:15184993:A:G | rs1383763025 | c.2323T > C | p.Cys775Arg |
| 19:15184963:G:A | rs1289281166 | c.2353C > T | p.Arg785Cys |
| 19:15184929:C:T | | c.2387G > A | p.Cys796Tyr |
| 19:15184929:C:G | rs1425871926 | c.2387G > C | p.Cys796Ser |
| 19:15184929:C:A | rs1425871926 | c.2387G > T | p.Cys796Phe |
| 19:15184928:G:C | | c.2388C > G | p.Cys796Trp |
| 19:15184926:G:C | | c.2390C > G | p.Ser797Cys |
| 19:15184924:A:C | | c.2392T > G | p.Cys798Gly |
| 19:15184923:C:T | rs1325571065 | c.2393G > A | p.Cys798Tyr |
| 19:15184922:G:T | | c.2394C > A | p.Cys798* |
| 19:15184910:C:A | | c.2406G > T | p.Trp802Cys |
| 19:15184442:A:T | | c.2419T > A | p.Cys807Ser |
| 19:15184420:C:T | | c.2441G > A | p.Cys814Tyr |
| 19:15184419:A:T | | c.2442T > A | p.Cys814* |
| 19:15184382:TG:T | | c.2478delC | p.Cys826fs |
| 19:15184363:A:C | | c.2498T > G | p.Phe833Cys |
| 19:15184356:GC:G | | c.2504delG | p.Cys835fs |
| 19:15184339:T:C | | c.2522A > G | p.Tyr841Cys |
| 19:15184304:A:G | | c.2557T > C | p.Cys853Arg |
| 19:15184303:C:T | rs1253342689 | c.2558G > A | p.Cys853Tyr |
| 19:15184302:A:C | | c.2559T > G | p.Cys853Trp |
| 19:15181794:G:C | | c.2574C > G | p.Cys858Trp |
| 19:15181787:C:A | rs757098265 | c.2581G > T | p.Gly861Cys |
| 19:15181778:A:T | | c.2590T > A | p.Cys864Ser |

TABLE 1-continued

| Cys-Altering Variants | | | |
| --- | --- | --- | --- |
| Variant | rsID | HGVS.c | HGVS.p |
| 19:15181751:A:G | | c.2617T > C | p.Cys873Arg |
| 19:15181750:C:A | rs867156576 | c.2618G > T | p.Cys873Phe |
| 19:15181744:C:T | | c.2624G > A | p.Cys875Tyr |
| 19:15181712:G:A | rs1325474998 | c.2656C > T | p.Arg886Cys |
| 19:15181682:A:T | | c.2686T > A | p.Cys896Ser |
| 19:15181668:G:GGT | | c.2698_2699dupAC | p.Cys901fs |
| 19:15181667:A:T | | c.2701T > A | p.Cys901Ser |
| 19:15181648:G:C | | c.2720C > G | p.Ser907Cys |
| 19:15181640:A:G | | c.2728T > C | p.Cys910Arg |
| 19:15181639:C:T | rs1399374524 | c.2729G > A | p.Cys910Tyr |
| 19:15181633:C:G | | c.2735G > C | p.Cys912Ser |
| 19:15181621:T:C | | c.2747A > G | p.Tyr916Cys |
| 19:15181607:A:G | | c.2761T > C | p.Cys921Arg |
| 19:15181606:C:A | | c.2762G > T | p.Cys921Phe |
| 19:15181586:AG:A | | c.2781delC | p.Cys928fs |
| 19:15181158:A:C | rs749778923 | c.2797T > G | p.Cys933Gly |
| 19:15181157:C:T | | c.2798G > A | p.Cys933Tyr |
| 19:15181139:C:G | rs1170996533 | c.2816G > C | p.Cys939Ser |
| 19:15181138:A:C | | c.2817T > G | p.Cys939Trp |
| 19:15181131:C:A | rs777577687 | c.2824G > T | p.Gly942Cys |
| 19:15181112:C:A | | c.2843G > T | p.Cys948Phe |
| 19:15181104:G:A | rs775964142 | c.2851C > T | p.Arg951Cys |
| 19:15181094:T:C | | c.2861A > G | p.Tyr954Cys |
| 19:15181080:A:G | | c.2875T > C | p.Cys959Arg |
| 19:15181043:C:T | | c.2912G > A | p.Cys971Tyr |
| 19:15181004:A:C | | c.2951T > G | p.Phe984Cys |
| 19:15181002:G:A | | c.2953C > T | p.Arg985Cys |
| 19:15180999:A:G | rs763321998 | c.2956T > C | p.Cys986Arg |
| 19:15180999:A:C | | c.2956T > G | p.Cys986Gly |
| 19:15180998:C:T | | c.2957G > A | p.Cys986Tyr |
| 19:15180975:C:A | | c.2980G > T | p.Gly994Cys |
| 19:15180964:G:T | | c.2991C > A | p.Cys997* |
| 19:15180812:C:T | | c.3011G > A | p.Cys1004Tyr |
| 19:15180807:G:A | | c.3016C > T | p.Arg1006Cys |
| 19:15180807:G:A | | c.3016C > T | p.Arg1006Cys |
| 19:15180797:C:T | rs1217205469 | c.3026G > A | p.Cys1009Tyr |
| 19:15180780:A:G | | c.3043T > C | p.Cys1015Arg |
| 19:15180778:G:C | | c.3045C > G | p.Cys1015Trp |
| 19:15180761:T:C | rs1167405466 | c.3062A > G | p.Tyr1021Cys |
| 19:15180752:C:T | | c.3071G > A | p.Cys1024Tyr |
| 19:15180738:T:A | | c.3085A > T | p.Ser1029Cys |
| 19:15180732:G:A | | c.3091C > T | p.Arg1031Cys |
| 19:15180703:G:T | | c.3120C > A | p.Cys1040* |
| 19:15180235:C:T | | c.3164G > A | p.Cys1055Tyr |
| 19:15180235:C:G | | c.3164G > C | p.Cys1055Ser |
| 19:15180217:C:T | rs1064794216 | c.3182G > A | p.Cys1061Tyr |
| 19:15180190:C:G | | c.3209G > C | p.Cys1070Ser |
| 19:15180184:C:T | rs1204243987 | c.3215G > A | p.Cys1072Tyr |
| 19:15180184:C:A | | c.3215G > T | p.Cys1072Phe |
| 19:15180173:G:A | rs1438626607 | c.3226C > T | p.Arg1076Cys |
| 19:15180122:A:T | | c.3277T > A | p.Cys1093Ser |
| 19:15180103:C:T | | c.3296G > A | p.Cys1099Tyr |
| 19:15180101:G:A | rs963416165 | c.3298C > T | p.Arg1100Cys |
| 19:15180077:A:G | | c.3322T > C | p.Cys1108Arg |
| 19:15180076:C:T | | c.3323G > A | p.Cys1108Tyr |
| 19:15180075:A:T | | c.3324T > A | p.Cys1108* |
| 19:15179496:A:G | | c.3328T > C | p.Cys1110Arg |
| 19:15179468:C:T | rs1266914122 | c.3356G > A | p.Cys1119Tyr |
| 19:15179468:C:A | | c.3356G > T | p.Cys1119Phe |
| 19:15179432:C:G | | c.3392G > C | p.Cys1131Ser |
| 19:15179421:C:A | rs867379493 | c.3403G > T | p.Gly1135Cys |
| 19:15179415:A:G | | c.3409T > C | p.Cys1137Arg |
| 19:15179414:CA:C | | c.3409delT | p.Cys1137fs |
| 19:15179397:G:A | rs60373464 | c.3427C > T | p.Arg1143Cys |
| 19:15179397:G:A | rs60373464 | c.3427C > T | p.Arg1143Cys |
| 19:15179393:T:C | rs879055341 | c.3431A > G | p.Tyr1144Cys |
| 19:15179381:C:G | | c.3443G > C | p.Cys1148Ser |
| 19:15179381:C:A | | c.3443G > T | p.Cys1148Phe |
| 19:15179274:A:G | | c.3469T > C | p.Cys1157Arg |
| 19:15179272:G:C | | c.3471C > G | p.Cys1157Trp |
| 19:15179253:A:G | | c.3490T > C | p.Cys1164Arg |
| 19:15179250:C:A | | c.3493G > T | p.Gly1165Cys |
| 19:15179244:C:A | | c.3499G > T | p.Gly1167Cys |
| 19:15179216:C:T | | c.3527G > A | p.Cys1176Tyr |
| 19:15179216:C:A | | c.3527G > T | p.Cys1176Phe |
| 19:15179197:G:C | | c.3546C > G | p.Cys1182Trp |

TABLE 1-continued

| Cys-Altering Variants | | | |
| --- | --- | --- | --- |
| Variant | rsID | HGVS.c | HGVS.p |
| 19:15179175:G:A | rs377099118 | c.3568C > T | p.Arg1190Cys |
| 19:15179171:C:G | rs1192888680 | c.3572G > C | p.Cys1191Ser |
| 19:15179166:A:G | | c.3577T > C | p.Cys1193Arg |
| 19:15179165:C:T | | c.3578G > A | p.Cys1193Tyr |
| 19:15179142:G:A | rs772172068 | c.3601C > T | p.Arg1201Cys |
| 19:15179138:C:T | | c.3605G > A | p.Cys1202Tyr |
| 19:15179137:GC:G | | c.3605delG | p.Cys1202fs |
| 19:15179137:G:T | | c.3606C > A | p.Cys1202* |
| 19:15179115:G:A | rs758961316 | c.3628C > T | p.Arg1210Cys |
| 19:15179079:A:G | | c.3664T > C | p.Cys1222Arg |
| 19:15179079:A:C | rs199638166 | c.3664T > G | p.Cys1222Gly |
| 19:15179079:A:C | rs199638166 | c.3664T > G | p.Cys1222Gly |
| 19:15179078:CA:C | | c.3664delT | p.Cys1222fs |
| 19:15179078:C:T | | c.3665G > A | p.Cys1222Tyr |
| 19:15179052:G:A | rs201680145 | c.3691C > T | p.Arg1231Cys |
| 19:15179052:G:A | rs201680145 | c.3691C > T | p.Arg1231Cys |
| 19:15179047:G:C | rs1376921184 | c.3696C > G | p.Cys1232Trp |
| 19:15178936:G:A | rs769660847 | c.3724C > T | p.Arg1242Cys |
| 19:15178912:A:G | | c.3748T > C | p.Cys1250Arg |
| 19:15178896:C:T | | c.3764G > A | p.Cys1255Tyr |
| 19:15178877:G:C | | c.3783C > G | p.Cys1261Trp |
| 19:15178876:G:A | | c.3784C > T | p.Arg1262Cys |
| 19:15178864:C:A | | c.3796G > T | p.Gly1266Cys |
| 19:15178855:C:A | | c.3805G > T | p.Gly1269Cys |
| 19:15178836:C:G | | c.3824G > C | p.Cys1275Ser |
| 19:15178830:C:T | rs1339695535 | c.3830G > A | p.Cys1277Tyr |
| 19:15178824:TGGGCACA:T | | c.3829_3835delTGTGCCC | p.Cys1277fs |
| 19:15178082:C:A | | c.3846G > T | p.Trp1282Cys |
| 19:15178081:C:A | | c.3847G > T | p.Gly1283Cys |
| 19:15178070:G:C | | c.3858C > G | p.Cys1286Trp |
| 19:15178057:G:A | | c.3871C > T | p.Arg1291Cys |
| 19:15178053:G:C | | c.3875C > G | p.Ser1292Cys |
| 19:15178050:C:A | | c.3878G > T | p.Cys1293Phe |
| 19:15178017:CA:C | | c.3910delT | p.Cys1304fs |
| 19:15178003:G:A | | c.3925C > T | p.Arg1309Cys |
| 19:15177990:C:G | | c.3938G > C | p.Cys1313Ser |
| 19:15177989:G:C | | c.3939C > G | p.Cys1313Trp |
| 19:15177984:C:T | rs1432396805 | c.3944G > A | p.Cys1315Tyr |
| 19:15177984:C:A | | c.3944G > T | p.Cys1315Phe |
| 19:15177983:G:C | rs1396345163 | c.3945C > G | p.Cys1315Trp |
| 19:15177958:A:T | rs1486702985 | c.3970T > A | p.Cys1324Ser |
| 19:15177957:C:T | | c.3971G > A | p.Cys1324Tyr |
| 19:15177955:G:A | | c.3973C > T | p.Arg1325Cys |
| 19:15177898:AG:A | | c.4029delC | p.Cys1344fs |
| 19:15177897:CAG:C | | c.4029_4030delCT | p.Cys1344fs |
| 19:15177897:CA:C | | c.4030delT | p.Cys1344fs |
| 19:15177896:A:C | | c.4032T > G | p.Cys1344Trp |
| 19:15177855:A:C | | c.4073T > G | p.Phe1358Cys |
| 19:15177850:G:A | | c.4078C > T | p.Arg1360Cys |
| 19:15177840:C:T | | c.4088G > A | p.Cys1363Tyr |
| 19:15177814:A:G | | c.4114T > C | p.Cys1372Arg |
| 19:15177812:G:C | | c.4116C > G | p.Cys1372Trp |

For subjects that are genotyped or determined to be heterozygous or homozygous for a NOTCH3 missense variant nucleic acid molecule encoding a NOTCH3 predicted gain-of-function polypeptide, such subjects have an increased risk of developing a cerebrovascular disease, such as CADASIL, subcortical stroke, ischemic stroke, hemorrhagic stroke, or parenchymal stroke. For subjects that are genotyped or determined to be heterozygous or homozygous for a NOTCH3 missense variant nucleic acid molecule encoding a NOTCH3 predicted gain-of-function polypeptide, such subjects can be treated with an agent effective to treat a cerebrovascular disease such as CADASIL, subcortical stroke, ischemic stroke, hemorrhagic stroke, or parenchymal stroke. For subjects that are genotyped or determined to be heterozygous or homozygous for a NOTCH3 missense variant nucleic acid molecule encoding a NOTCH3 predicted gain-of-function polypeptide, such subjects can also or independently be treated with a NOTCH3 agent.

In any of the embodiments described herein, the NOTCH3 missense variant nucleic acid molecule encoding a NOTCH3 predicted gain-of-function polypeptide can be any NOTCH3 nucleic acid molecule (such as, for example, genomic nucleic acid molecule, mRNA molecule, or cDNA molecule) encoding a NOTCH3 polypeptide having a partial gain-of-function, a complete gain-of-function, a predicted partial gain-of-function, or a predicted complete gain-of-function. For example, the NOTCH3 missense variant nucleic acid molecule encoding a NOTCH3 predicted gain-of-function polypeptide can be any nucleic acid molecule encoding NOTCH3 Arg1178Cys, Arg1231Cys, or Arg1182Cys. In some embodiments, the NOTCH3 variant nucleic acid molecule encodes NOTCH3 Arg1178Cys. In some embodiments, the NOTCH3 missense variant nucleic acid molecule encodes NOTCH3 Arg1231Cys. In some embodiments, the NOTCH3 missense variant nucleic acid molecule encodes NOTCH3 Arg1182Cys.

In any of the embodiments described herein, the NOTCH3 predicted gain-of-function polypeptide can be any NOTCH3 polypeptide having a partial gain-of-function, a complete gain-of-function, a predicted partial gain-of-function, or a predicted complete gain-of-function. In any of the embodiments described herein, the NOTCH3 predicted gain-of-function polypeptide can be any of the NOTCH3 polypeptides described herein including, for example, NOTCH3 Arg1178Cys, Arg1231Cys, or Arg1182Cys. In some embodiments, the NOTCH3 predicted gain-of-function polypeptide is NOTCH3 Arg1178Cys. In some embodiments, the NOTCH3 predicted gain-of-function polypeptide is NOTCH3 Arg1231Cys. In some embodiments, the NOTCH3 predicted gain-of-function polypeptide is NOTCH3 Arg1182Cys.

In any of the embodiments described herein, the cerebrovascular disease is CADASIL, subcortical stroke, ischemic stroke, hemorrhagic stroke, or parenchymal stroke. In any of the embodiments described herein, the cerebrovascular disease is CADASIL. In any of the embodiments described herein, the cerebrovascular disease is subcortical stroke. In any of the embodiments described herein, the cerebrovascular disease is ischemic stroke. In any of the embodiments described herein, the cerebrovascular disease is hemorrhagic stroke. In any of the embodiments described herein, the cerebrovascular disease is parenchymal stroke.

Symptoms of a cerebrovascular disease include, but are not limited to, dizziness, nausea, or vomiting; unusually severe headache; confusion, disorientation or memory loss; numbness, weakness in an arm, leg or the face, especially on one side; abnormal or slurred speech; difficulty with comprehension; loss of vision or difficulty seeing; or loss of balance, coordination or the ability to walk.

The present disclosure provides methods of treating a subject having a cerebrovascular disease, the methods comprising administering a NOTCH3 agent to the subject.

The present disclosure also provides methods of treating a subject having subcortical stroke, the methods comprising administering a NOTCH3 agent to the subject.

The present disclosure also provides methods of treating a subject having ischemic stroke, the methods comprising administering a NOTCH3 agent to the subject.

The present disclosure also provides methods of treating a subject having hemorrhagic stroke, the methods comprising administering a NOTCH3 agent to the subject.

The present disclosure also provides methods of treating a subject having parenchymal stroke, the methods comprising administering a NOTCH3 agent to the subject.

The present disclosure also provides methods of treating a subject having CADASIL, the methods comprising administering a NOTCH3 agent to the subject.

In some embodiments, the NOTCH3 agent comprises an inhibitory nucleic acid molecule. In some embodiments, the inhibitory nucleic acid molecule comprises an antisense molecule, a small interfering RNA (siRNA) molecule, or a short hairpin RNA (shRNA) molecule. In some embodiments, the inhibitory nucleic acid molecule comprises an antisense molecule. In some embodiments, the inhibitory nucleic acid molecule comprises an siRNA molecule. In some embodiments, the inhibitory nucleic acid molecule comprises an shRNA molecule. Such inhibitory nucleic acid molecules can be designed to target any region of a NOTCH3 nucleic acid molecule, such as an mRNA molecule. In some embodiments, the inhibitory nucleic acid molecule hybridizes to a sequence within a NOTCH3 genomic nucleic acid molecule or mRNA molecule and decreases expression of the NOTCH3 polypeptide in a cell in the subject. In some embodiments, the NOTCH3 agent comprises an antisense RNA that hybridizes to a NOTCH3 genomic nucleic acid molecule or mRNA molecule and decreases expression of the NOTCH3 polypeptide in a cell in the subject. In some embodiments, the NOTCH3 agent comprises an siRNA that hybridizes to a NOTCH3 genomic nucleic acid molecule or mRNA molecule and decreases expression of the NOTCH3 polypeptide in a cell in the subject. In some embodiments, the NOTCH3 agent comprises an shRNA that hybridizes to a NOTCH3 genomic nucleic acid molecule or mRNA molecule and decreases expression of the NOTCH3 polypeptide in a cell in the subject.

In some embodiments, a representative methodology that can be used for designing an inhibitory nucleic acid molecule for NOTCH3 is described in, for example, U.S. Patent Application Publication No. 2021/0115444, which exemplifies allele-specific suppression. Briefly, the technology is based on oligonucleotides having phosphorothioate backbone linkages, wherein the backbone linkages comprise particular stereoisomers at particular positions. Inclusion of particular chiral structures at a particular location within an oligonucleotide can result in improvement in stability, activity, and specificity of cleavage of target nucleotides. The technology is based on chirally controlled (and/or stereochemically pure) oligonucleotide compositions comprising oligonucleotides defined by having: 1) a common base sequence and length; 2) a common pattern of backbone linkages; 3) a common pattern of backbone chiral centers; and 4) a common pattern of backbone P-modifications. Purity of a chirally controlled oligonucleotide composition can be controlled by stereoselectivity of each coupling step in its preparation process. The initial overall structure of stereochemically pure oligonucleotides (e.g., positioning and chirality of internucleotide linkages) is developed through rational design rules developed in structural studies of substrate-ligand complexes of interest, followed by screening of candidate oligonucleotides. The stereochemically pure preparations are generated in a solid support synthesis process, wherein the solid support is treated with various reagents in several synthesis cycles to achieve the stepwise elongation of a growing oligonucleotide chain with individual nucleotide units. The steps of each cycle include treatment with activating reagent, reaction with a chiral agent, stereospecific condensation, capping of unreacted —OH groups with a protection group, a modification step used to install a modified internucleotidic linkage, and deblocking step to deprotect, for instance, a 5'-OH group for subsequent cycle. The oligonucleotides can be antisense nucleic acid molecules, siRNAs, RNaseH guide sequences, etc. useful for a controlled cleavage of a target nucleic acid polymer, such as a transcript from an allele. The increased specificity for a particular sequence (e.g., allele or SNP) is achieved through overall reduction of cleavage sites targeted by chirally controlled oligonucleotides as compared to unmodified oligonucleotides.

In some embodiments, the NOTCH3 agent comprises a nuclease agent that induces one or more nicks or double-strand breaks at a recognition sequence(s) or a DNA-binding protein that binds to a recognition sequence within a NOTCH3 genomic nucleic acid molecule. The recognition sequence can be located within a coding region of the NOTCH3 gene, or within regulatory regions that influence the expression of the gene. A recognition sequence of the DNA-binding protein or nuclease agent can be located in an intron, an exon, a promoter, an enhancer, a regulatory region, or any non-protein coding region. The recognition sequence can include or be proximate to the start codon of the NOTCH3 gene. For example, the recognition sequence can be located about 10, about 20, about 30, about 40, about 50, about 100, about 200, about 300, about 400, about 500, or about 1,000 nucleotides from the start codon. As another example, two or more nuclease agents can be used, each targeting a nuclease recognition sequence including or proximate to the start codon. As another example, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. Any nuclease agent that induces a nick or double-strand break into a desired recognition sequence can be used in the methods and compositions disclosed herein. Any DNA-binding protein that binds to a desired recognition sequence can be used in the methods and compositions disclosed herein.

Suitable nuclease agents and DNA-binding proteins for use herein include, but are not limited to, zinc finger protein or zinc finger nuclease (ZFN) pair, Transcription Activator-Like Effector (TALE) protein or Transcription Activator-Like Effector Nuclease (TALEN), or Clustered Regularly Interspersed Short Palindromic Repeats (CRISPR)/CRISPR-associated (Cas) systems. The length of the recognition sequence can vary, and includes, for example, recognition sequences that are about 30 to about 36 bp for a zinc finger protein or ZFN pair, about 15 to about 18 bp for each ZFN, about 36 bp for a TALE protein or TALEN, and about 20 bp for a CRISPR/Cas guide RNA.

In some embodiments, CRISPR/Cas systems can be used to modify a NOTCH3 genomic nucleic acid molecule within a cell. The methods and compositions disclosed herein can employ CRISPR-Cas systems by utilizing CRISPR complexes (comprising a guide RNA (gRNA) complexed with a Cas protein) for site-directed cleavage of NOTCH3 nucleic acid molecules.

Cas proteins generally comprise at least one RNA recognition or binding domain that can interact with gRNAs. Cas proteins can also comprise nuclease domains (such as, for example, DNase or RNase domains), DNA binding domains, helicase domains, protein-protein interaction domains, dimerization domains, and other domains. Suitable Cas proteins include, for example, a wild type Cas9 protein and a wild type Cpf1 protein (such as, for example, FnCpf1). A Cas protein can have full cleavage activity to create a double-strand break in a NOTCH3 genomic nucleic acid molecule or it can be a nickase that creates a single-strand break in a NOTCH3 genomic nucleic acid molecule. Additional examples of Cas proteins include, but are not limited to, Cas1, Cas1B, Cast, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (Cas6), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof. Cas proteins can also be operably linked to heterologous polypeptides as fusion proteins. For example, a Cas protein can be fused to a cleavage domain, an epigenetic modification domain, a transcriptional activation domain, or a transcriptional repressor domain. Cas proteins can be provided in any form. For example, a Cas protein can be provided in the form of a protein, such as a Cas protein complexed with a gRNA. Alternately, a Cas protein can be provided in the form of a nucleic acid molecule encoding the Cas protein, such as an RNA or DNA.

In some embodiments, targeted genetic modifications of a NOTCH3 genomic nucleic acid molecules can be generated by contacting a cell with a Cas protein and one or more gRNAs that hybridize to one or more gRNA recognition sequences within a target genomic locus in the NOTCH3 genomic nucleic acid molecule. For example, a gRNA recognition sequence can be located within a region of SEQ ID NO:1. The gRNA recognition sequence can also include or be proximate to a position corresponding to position 21,944 according to SEQ ID NO:1. For example, the gRNA recognition sequence can be located about 1000, about 500, about 400, about 300, about 200, about 100, about 50, about 45, about 40, about 35, about 30, about 25, about 20, about 15, about 10, or about 5 nucleotides from a position corresponding to position 21,944 according to SEQ ID NO:1. The gRNA recognition sequence can include or be proximate to the start codon or the stop codon of a NOTCH3 genomic nucleic acid molecule. For example, the gRNA recognition sequence can be located about 10, about 20, about 30, about 40, about 50, about 100, about 200, about 300, about 400, about 500, or about 1,000 nucleotides from the start codon or the stop codon.

The gRNA recognition sequences within a target genomic locus in a NOTCH3 genomic nucleic acid molecule are located near a Protospacer Adjacent Motif (PAM) sequence, which is a 2-6 base pair DNA sequence immediately following the DNA sequence targeted by the Cas9 nuclease. The canonical PAM is the sequence 5'-NGG-3' where "N" is any nucleobase followed by two guanine ("G") nucleobases. gRNAs can transport Cas9 to anywhere in the genome for gene editing, but no editing can occur at any site other than one at which Cas9 recognizes a PAM. In addition, 5'-NGA-3' can be a highly efficient non-canonical PAM for human cells. Generally, the PAM is about 2 to about 6 nucleotides downstream of the DNA sequence targeted by the gRNA. The PAM can flank the gRNA recognition sequence. In some embodiments, the gRNA recognition sequence can be flanked on the 3' end by the PAM. In some embodiments, the gRNA recognition sequence can be flanked on the 5' end by the PAM. For example, the cleavage site of Cas proteins can be about 1 to about 10 base pairs, about 2 to about 5 base pairs, or 3 base pairs upstream or downstream of the PAM sequence. In some embodiments (such as when Cas9 from *S. pyogenes* or a closely related Cas9 is used), the PAM sequence of the non-complementary strand can be 5'-NGG-3', where N is any DNA nucleotide and is immediately 3' of the gRNA recognition sequence of the non-complementary strand of the target DNA. As such, the PAM sequence of the complementary strand would be 5'-CCN-3', where N is any DNA nucleotide and is immediately 5' of the gRNA recognition sequence of the complementary strand of the target DNA.

A gRNA is an RNA molecule that binds to a Cas protein and targets the Cas protein to a specific location within a NOTCH3 genomic nucleic acid molecule. An exemplary gRNA is a gRNA effective to direct a Cas enzyme to bind to or cleave a NOTCH3 genomic nucleic acid molecule, wherein the gRNA comprises a DNA-targeting segment that hybridizes to a gRNA recognition sequence within the NOTCH3 genomic nucleic acid molecule that includes or is proximate to a position corresponding to position 21,944 according to SEQ ID NO:1. For example, a gRNA can be selected such that it hybridizes to a gRNA recognition sequence that is located about 5, about 10, about 15, about 20, about 25, about 30, about 35, about 40, about 45, about 50, about 100, about 200, about 300, about 400, about 500, or about 1,000 nucleotides from a position corresponding to position 21,944 according to SEQ ID NO:1. Other exemplary gRNAs comprise a DNA-targeting segment that hybridizes to a gRNA recognition sequence present within a NOTCH3 genomic nucleic acid molecule that includes or is proximate to the start codon or the stop codon. For example, a gRNA can be selected such that it hybridizes to a gRNA recognition sequence that is located about 5, about 10, about 15, about 20, about 25, about 30, about 35, about 40, about 45, about 50, about 100, about 200, about 300, about 400, about 500, or about 1,000 nucleotides from the start codon or located about 5, about 10, about 15, about 20, about 25, about 30, about 35, about 40, about 45, about 50, about 100, about 200, about 300, about 400, about 500, or about 1,000 nucleotides from the stop codon. Suitable gRNAs can comprise from about 17 to about 25 nucleotides, from about 17 to about 23 nucleotides, from about 18 to about 22 nucleotides, or from about 19 to about 21 nucleotides. In some embodiments, the gRNAs comprise 20 nucleotides.

Examples of suitable gRNA recognition sequences located within the NOTCH3 reference gene are set forth in Table 2 as SEQ ID NOs:29-43.

TABLE 2

| Guide RNA Recognition Sequences Near NOTCH3 Variation(s) | | |
|---|---|---|
| Strand | gRNA Recognition Sequence | SEQ ID NO: |
| + | ATACACTGGTTTGCGCTGCGAGG | 29 |
| + | TCTCAGGTAAGCGTTGGCGAAGG | 30 |
| + | CTACATGCTCCCGCTCGCTCAGG | 31 |
| + | CTCAGGTAAGCGTTGGCGAAGGG | 32 |
| + | TCAGGTAAGCGTTGGCGAAGGGG | 33 |
| + | GACATCAATGAGTGTCGCTCAGG | 34 |
| - | AGTCCCGGGTGTGTGCCGCGTGG | 35 |
| + | CTGGCTTCTCAGGTAAGCGTTGG | 36 |
| - | GCATGTAGATCAGCCACAATGGG | 37 |
| - | GACAGGACAGTCTGACAGCGAGG | 38 |
| - | ATGTAGATCAGCCACAATGGGGG | 39 |
| - | AGCATGTAGATCAGCCACAATGG | 40 |
| - | ACAGCGAGGACCTGAGCGAGCGG | 41 |
| + | GTAAGCGTTGGCGAAGGGGCTGG | 42 |
| - | CATGTAGATCAGCCACAATGGGG | 43 |

The Cas protein and the gRNA form a complex, and the Cas protein cleaves the target NOTCH3 genomic nucleic acid molecule. The Cas protein can cleave the nucleic acid molecule at a site within or outside of the nucleic acid sequence present in the target NOTCH3 genomic nucleic acid molecule to which the DNA-targeting segment of a gRNA will bind. For example, formation of a CRISPR complex (comprising a gRNA hybridized to a gRNA recognition sequence and complexed with a Cas protein) can result in cleavage of one or both strands in or near (such as, for example, within 1, 2, 3, 4, 5, 6, 7, 8, 9, 10, 20, 50, or more base pairs from) the nucleic acid sequence present in the NOTCH3 genomic nucleic acid molecule to which a DNA-targeting segment of a gRNA will bind.

Such methods can result, for example, in a NOTCH3 genomic nucleic acid molecule in which a region of SEQ ID NO:2 is disrupted, the start codon is disrupted, the stop codon is disrupted, or the coding sequence is disrupted or deleted. Optionally, the cell can be further contacted with one or more additional gRNAs that hybridize to additional gRNA recognition sequences within the target genomic locus in the NOTCH3 genomic nucleic acid molecule. By contacting the cell with one or more additional gRNAs (such as, for example, a second gRNA that hybridizes to a second gRNA recognition sequence), cleavage by the Cas protein can create two or more double-strand breaks or two or more single-strand breaks.

In some embodiments, the NOTCH3 agent is an anti-aggregate antibody or agonist antibody that increase processing. Such antibodies include, but are not limited to, 5E1 antibody (or a humanized version thereof) (Ghezali et al., Ann. Neurol. 2018, 84, 246-259) and A13 antibody (Machuca-Parra et al., J. Exp. Med., 2017, 214, 2271-2282).

In some embodiments, the methods of treatment further comprise detecting the presence or absence of a NOTCH3 missense variant nucleic acid molecule encoding a NOTCH3 predicted gain-of-function polypeptide in a biological sample from the subject. As used throughout the present disclosure, "a NOTCH3 missense variant nucleic acid molecule encoding a NOTCH3 predicted gain-of-function polypeptide" is any NOTCH3 nucleic acid molecule (such as, for example, genomic nucleic acid molecule, mRNA molecule, or cDNA molecule) encoding a NOTCH3 polypeptide having a partial gain-of-function, a complete gain-of-function, a predicted partial gain-of-function, or a predicted complete gain-of-function.

The present disclosure also provides methods of treating a subject with a therapeutic agent that treats or inhibits a cerebrovascular disease. In some embodiments, the subject has a cerebrovascular disease. In some embodiments, the methods comprise determining whether the subject has a NOTCH3 missense variant nucleic acid molecule encoding a NOTCH3 predicted gain-of-function polypeptide by obtaining or having obtained a biological sample from the subject, and performing or having performed a sequencing analysis on the biological sample to determine if the subject has a genotype comprising the NOTCH3 missense variant nucleic acid molecule encoding a NOTCH3 predicted gain-of-function polypeptide. The methods further comprise administering or continuing to administer the therapeutic agent that treats or inhibits a cerebrovascular disease in a standard dosage amount to a subject that is NOTCH3 reference, and administering a NOTCH3 agent to the subject. Alternately, the methods further comprise administering or continuing to administer the therapeutic agent that treats or inhibits a cerebrovascular disease in an amount that is the same as or greater than a standard dosage amount to a subject that is heterozygous or homozygous for the NOTCH3 missense variant nucleic acid molecule, and administering a NOTCH3 agent to the subject. The presence of a genotype having the NOTCH3 missense variant nucleic acid molecule encoding the NOTCH3 predicted gain-offunction polypeptide indicates the subject has an increased risk of developing a cerebrovascular disease.

Detecting the presence or absence of a NOTCH3 missense variant nucleic acid molecule encoding the NOTCH3 predicted gain-of-function polypeptide in a biological sample from a subject and/or determining whether a subject has a NOTCH3 missense variant nucleic acid molecule encoding the NOTCH3 predicted gain-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

The present disclosure also provides methods of treating a subject with a therapeutic agent that treats or inhibits a cerebrovascular disease. In some embodiments, the subject has a cerebrovascular disease. In some embodiments, the method comprises determining whether the subject has a NOTCH3 predicted gain-of-function polypeptide by obtaining or having obtained a biological sample from the subject, and performing or having performed an assay on the biological sample to determine if the subject has a NOTCH3 predicted gain-of-function polypeptide. When the subject does not have a NOTCH3 predicted gain-of-function polypeptide, the therapeutic agent that treats or inhibits a cerebrovascular disease is administered or continued to be administered to the subject in a standard dosage amount. When the subject has a NOTCH3 predicted gain-of-function polypeptide, the therapeutic agent that treats or inhibits a cerebrovascular disease is administered or continued to be administered to the subject in an amount that is the same as or greater than a standard dosage amount. The presence of a NOTCH3 predicted gain-of-function polypeptide indicates the subject has an induced risk of developing a cerebrovascular disease. In some embodiments, the subject has a NOTCH3 predicted gain-of-function polypeptide. In some embodiments, the subject does not have a NOTCH3 predicted gain-of-function polypeptide.

Detecting the presence or absence of a NOTCH3 predicted gain-of-function polypeptide in a biological sample from a subject and/or determining whether a subject has a NOTCH3 predicted gain-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the polypeptide can be present within a cell obtained from the subject.

Examples of therapeutic agents that treat or inhibit a cerebrovascular disease include, but are not limited to: tissue plasminogen activator (tPA); anticoagulants such as apixaban, dabigatran, edoxaban, rivaroxaban, and warfarin; blood pressure medications such as diuretics (e.g., bumetanide, ethacrynic acid, furosemide, and torsemide), ACE inhibitors (e.g., benazepril, captopril, enalapril, fosinopril, lisinopril, moexipril, perindopril, quinapril, ramipril, and trandolapril), beta blockers (e.g., acebutolol, atenolol, bisoprolol, metoprolol, nadolol, nebivolol, and propranolol); calcium channel blockers (e.g., amlodipine, felodipine, isradipine, nicardipine, nifedipine, nimodipine, and nitrendipine); and cholesterol-lowering medications such as statins (e.g., atorvastatin, Fluvastatin, lovastatin, pitavastatin, pravastatin, rosuvastatin, and simvastatin), or any combination thereof.

In some embodiments, the dose of the therapeutic agents that treat or inhibit a cerebrovascular disease can be increased by about 10%, by about 20%, by about 30%, by about 40%, by about 50%, by about 60%, by about 70%, by about 80%, or by about 90% for subjects that are heterozygous or homozygous for a NOTCH3 missense variant nucleic acid molecule encoding the NOTCH3 predicted gain-of-function polypeptide (i.e., a greater amount than the standard dosage amount) compared to subjects that are NOTCH3 reference (who may receive a standard dosage amount). In some embodiments, the dose of the therapeutic agents that treat or inhibit a cerebrovascular disease can be increased by about 10%, by about 20%, by about 30%, by about 40%, or by about 50%. In addition, the dose of therapeutic agents that treat or inhibit a cerebrovascular disease in subjects that are heterozygous or homozygous for a NOTCH3 missense variant nucleic acid molecule encoding the NOTCH3 predicted gain-of-function polypeptide can be administered more frequently compared to subjects that are NOTCH3 reference.

In some embodiments, the dose of the therapeutic agents that treat or inhibit a cerebrovascular disease can be increased by about 10%, by about 20%, by about 30%, by about 40%, by about 50%, by about 60%, by about 70%, by about 80%, or by about 90% for subjects that are homozygous for a NOTCH3 missense variant nucleic acid molecule encoding the NOTCH3 predicted gain-of-function polypeptide compared to subjects that are heterozygous for a NOTCH3 missense variant nucleic acid molecule encoding the NOTCH3 predicted gain-of-function polypeptide. In some embodiments, the dose of the therapeutic agents that treat or inhibit a cerebrovascular disease can be increased by about 10%, by about 20%, by about 30%, by about 40%, or by about 50%. In addition, the dose of therapeutic agents that treat or inhibit a cerebrovascular disease in subjects that are homozygous for a NOTCH3 missense variant nucleic acid molecule encoding the NOTCH3 predicted gain-of-function polypeptide can be administered more frequently compared to subjects that heterozygous for a NOTCH3 missense variant nucleic acid molecule encoding the NOTCH3 predicted gain-of-function polypeptide.

Administration of the therapeutic agents that treat or inhibit a cerebrovascular disease and/or NOTCH3 agents can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more.

Administration of the therapeutic agents that treat or inhibit a cerebrovascular disease and/or NOTCH3 agents can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in a cerebrovascular disease, a decrease/reduction in the severity of a cerebrovascular disease (such as, for example, a reduction or inhibition of development of a cerebrovascular disease), a decrease/reduction in symptoms and cerebrovascular disease-related effects, delaying the onset of symptoms and cerebrovascular disease-related effects, reducing the severity of symptoms of cerebrovascular disease-related effects, reducing the severity of an acute episode, reducing the number of symptoms and cerebrovascular disease-related effects, reducing the latency of symptoms and cerebrovascular disease-related effects, an amelioration of symptoms and cerebrovascular disease-related effects, reducing secondary symptoms, reducing secondary infections, preventing relapse to a cerebrovascular disease, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics, and/or an increased survival time of the affected host animal, following administration of the agent or composition comprising the agent. A prophylactic effect may comprise a complete or partial avoidance/inhibition or a delay of a cerebrovascular disease development/progression (such as, for example, a complete or partial avoidance/inhibition or a delay), and an increased survival time of the affected host animal, following administration of a therapeutic protocol. Treatment of a cerebrovascular disease encompasses the treatment of subjects already diagnosed as having any form of a cerebrovascular disease at any clinical stage or manifestation, the delay of the onset or evolution or aggravation or deterioration of the symptoms or signs of a cerebrovascular disease, and/or preventing and/or reducing the severity of a cerebrovascular disease.

The present disclosure also provides methods of identifying a subject having an increased risk for developing a cerebrovascular disease. In some embodiments, the method comprises determining or having determined in a biological sample obtained from the subject the presence or absence of a NOTCH3 missense variant nucleic acid molecule encoding the NOTCH3 predicted gain-of-function polypeptide (such as a genomic nucleic acid molecule, mRNA molecule, and/or cDNA molecule). When the subject lacks a NOTCH3 missense variant nucleic acid molecule encoding the NOTCH3 predicted gain-of-function polypeptide (i.e., the subject is genotypically categorized as a NOTCH3 reference), then the subject does not have an increased risk for developing a cerebrovascular disease. When the subject has a NOTCH3 missense variant nucleic acid molecule encoding the NOTCH3 predicted gain-of-function polypeptide (i.e., the subject is heterozygous or homozygous for a NOTCH3 missense variant nucleic acid molecule encoding the NOTCH3 predicted gain-of-function polypeptide), then the subject has an increased risk for developing a cerebrovascular disease.

Having two copies of a NOTCH3 missense variant nucleic acid molecule encoding the NOTCH3 predicted gain-of-function polypeptide may render the subject to have a greater risk of developing a cerebrovascular disease than having a single copy of a NOTCH3 missense variant nucleic acid molecule encoding the NOTCH3 predicted gain-of-function polypeptide. Without intending to be limited to any particular theory or mechanism of action, it is believed that a single copy of a NOTCH3 missense variant nucleic acid molecule encoding the NOTCH3 predicted gain-of-function polypeptide (i.e., heterozygous for a NOTCH3 missense variant nucleic acid molecule encoding the NOTCH3 predicted gain-of-function polypeptide) renders the subject to have a greater risk of developing a cerebrovascular disease compared to a subject who is NOTCH3 reference, and it is also believed that having two copies of a NOTCH3 missense variant nucleic acid molecule encoding the NOTCH3 predicted gain-of-function polypeptide (i.e., homozygous for a NOTCH3 missense variant nucleic acid molecule encoding the NOTCH3 predicted gain-of-function polypeptide) may render the subject to have an even greater risk of developing a cerebrovascular disease, relative to a subject with a single copy.

Determining whether a subject has a NOTCH3 missense variant nucleic acid molecule encoding the NOTCH3 predicted gain-of-function polypeptide in a biological sample from the subject and/or determining whether a subject has a NOTCH3 missense variant nucleic acid molecule encoding the NOTCH3 predicted gain-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, when a subject is identified as having an increased risk of developing a cerebrovascular disease, the subject is further treated with a therapeutic agent that treats or inhibits a cerebrovascular disease, and/or a NOTCH3 agent, as described herein. For example, when the subject is heterozygous or homozygous for a NOTCH3 missense variant nucleic acid molecule encoding the NOTCH3 predicted gain-of-function polypeptide, and therefore has an increased risk for developing a cerebrovascular disease, the subject is administered a therapeutic agent that treats or inhibits a cerebrovascular disease in a dosage amount that is the same as or greater than a standard dosage amount, and/or a NOTCH3 agent. In some embodiments, when the subject is homozygous for a NOTCH3 missense variant nucleic acid molecule encoding the NOTCH3 predicted gain-of-function polypeptide, the subject is administered a therapeutic agent that treats or inhibits a cerebrovascular disease in a dosage amount that is the same as or greater than the dosage amount that is administered to a subject that is heterozygous for a NOTCH3 missense variant nucleic acid molecule encoding the NOTCH3 predicted gain-of-function polypeptide. In some embodiments, the subject is NOTCH3 reference. In some embodiments, the subject is heterozygous for a NOTCH3 missense variant nucleic acid molecule encoding the NOTCH3 predicted gain-of-function polypeptide. In some embodiments, the subject is homozygous for a NOTCH3 missense variant nucleic acid molecule encoding the NOTCH3 predicted gain-of-function polypeptide.

The present disclosure also provides methods of detecting the presence or absence of a NOTCH3 missense variant genomic nucleic acid molecule encoding a NOTCH3 predicted gain-of-function polypeptide in a biological sample from a subject, and/or a NOTCH3 missense variant mRNA molecule encoding a NOTCH3 predicted gain-of-function polypeptide in a biological sample from a subject, and/or a NOTCH3 missense variant cDNA molecule encoding a NOTCH3 predicted gain-of-function polypeptide produced from an mRNA molecule in a biological sample from a subject. It is understood that gene sequences within a population and mRNA molecules encoded by such genes can vary due to polymorphisms such as single-nucleotide polymorphisms. The sequences provided herein for the NOTCH3 variant genomic nucleic acid molecule, NOTCH3 variant mRNA molecule, and NOTCH3 variant cDNA molecule are only exemplary sequences. Other sequences for the NOTCH3 variant genomic nucleic acid molecule, variant mRNA molecule, and variant cDNA molecule are also possible.

The biological sample can be derived from any cell, tissue, or biological fluid from the subject. The biological sample may comprise any clinically relevant tissue such as, for example, a bone marrow sample, a tumor biopsy, a fine needle aspirate, or a sample of bodily fluid, such as blood, gingival crevicular fluid, plasma, serum, lymph, ascitic fluid, cystic fluid, or urine. In some embodiments, the sample comprises a buccal swab. The biological sample used in the methods disclosed herein can vary based on the assay format, nature of the detection method, and the tissues, cells, or extracts that are used as the sample. A biological sample can be processed differently depending on the assay being employed. For example, when detecting any NOTCH3 variant nucleic acid molecule, preliminary processing designed to isolate or enrich the biological sample for the NOTCH3 variant nucleic acid molecule can be employed. A variety of techniques may be used for this purpose. When detecting the level of any NOTCH3 variant mRNA molecule, different techniques can be used enrich the biological sample with mRNA molecules. Various methods to detect the presence or level of an mRNA molecule or the presence of a particular variant genomic DNA locus can be used.

In some embodiments, detecting a NOTCH3 missense variant nucleic acid molecule encoding a NOTCH3 predicted gain-of-function polypeptide in a subject comprises assaying or analyzing a biological sample obtained from the subject to determine whether a NOTCH3 missense variant genomic nucleic acid molecule encoding a NOTCH3 predicted gain-of-function polypeptide in the biological sample, a NOTCH3 missense variant mRNA molecule encoding a NOTCH3 predicted gain-of-function polypeptide in the biological sample, and/or a NOTCH3 missense variant cDNA molecule encoding a NOTCH3 predicted gain-of-function polypeptide produced from an mRNA molecule in the biological sample, comprises one or more variations that cause a gain-of-function (partial or complete) or are predicted to cause a gain-of-function (partial or complete).

In some embodiments, the methods of detecting the presence or absence of a NOTCH3 missense variant nucleic acid molecule encoding a NOTCH3 predicted gain-of-function polypeptide (such as, for example, a genomic nucleic acid molecule, an mRNA molecule, and/or a cDNA molecule produced from an mRNA molecule) in a subject, comprise performing an assay on a biological sample obtained from the subject. The assay determines whether a nucleic acid molecule in the biological sample comprises a particular nucleotide sequence.

In some embodiments, the nucleotide sequence of the NOTCH3 genomic nucleic acid molecule comprises a thymine at a position corresponding to position 21,944 according to SEQ ID NO:2, or the complement thereof.

In some embodiments, the nucleotide sequence of the NOTCH3 mRNA molecule comprises a uracil at a position corresponding to: position 3,781 according to SEQ ID NO:8, or the complement thereof; position 3,767 according to SEQ ID NO:9, or the complement thereof; position 3,532 according to SEQ ID NO:10, or the complement thereof; position 3,769 according to SEQ ID NO:11, or the complement thereof; or position 3,544 according to SEQ ID NO:12, or the complement thereof. In some embodiments, the nucleotide sequence of the NOTCH3 mRNA molecule comprises a uracil at a position corresponding to position 3,781 according to SEQ ID NO:8, or the complement thereof. In some embodiments, the nucleotide sequence of the NOTCH3 mRNA molecule comprises a uracil at a position corresponding to position 3,767 according to SEQ ID NO:9, or the complement thereof. In some embodiments, the nucleotide sequence of the NOTCH3 mRNA molecule comprises a uracil at a position corresponding to position 3,532 according to SEQ ID NO:10, or the complement thereof. In some embodiments, the nucleotide sequence of the NOTCH3 mRNA molecule comprises a uracil at a position corresponding to position 3,769 according to SEQ ID NO:11, or the complement thereof. In some embodiments, the nucleotide sequence of the NOTCH3 mRNA molecule comprises a uracil at a position corresponding to position 3,544 according to SEQ ID NO:12, or the complement thereof.

In some embodiments, the nucleotide sequence of the NOTCH3 cDNA molecule comprises a thymine at a position corresponding to: position 3,781 according to SEQ ID NO:18, or the complement thereof; position 3,767 according to SEQ ID NO:19, or the complement thereof; position 3,532 according to SEQ ID NO:20, or the complement thereof; position 3,769 according to SEQ ID NO:21, or the complement thereof; or position 3,544 according to SEQ ID NO:22, or the complement thereof. In some embodiments, the nucleotide sequence of the NOTCH3 cDNA molecule comprises a thymine at a position corresponding to position 3,781 according to SEQ ID NO:18, or the complement thereof. In some embodiments, the nucleotide sequence of the NOTCH3 cDNA molecule comprises a thymine at a position corresponding to position 3,767 according to SEQ ID NO:19, or the complement thereof. In some embodiments, the nucleotide sequence of the NOTCH3 cDNA molecule comprises a thymine at a position corresponding to position 3,532 according to SEQ ID NO:20, or the complement thereof. In some embodiments, the nucleotide sequence of the NOTCH3 cDNA molecule comprises a thymine at a position corresponding to position 3,769 according to SEQ ID NO:21, or the complement thereof. In some embodiments, the nucleotide sequence of the NOTCH3 cDNA molecule comprises a thymine at a position corresponding to position 3,544 according to SEQ ID NO:22, or the complement thereof.

In some embodiments, the biological sample comprises a cell or cell lysate. Such methods can further comprise, for example, obtaining a biological sample from the subject comprising a NOTCH3 genomic nucleic acid molecule or mRNA molecule, and if mRNA, optionally reverse transcribing the mRNA into cDNA. Such assays can comprise, for example determining the identity of these positions of the particular NOTCH3 nucleic acid molecule. In some embodiments, the method is an in vitro method.

In some embodiments, the determining step, detecting step, or sequence analysis comprises sequencing at least a portion of the nucleotide sequence of the NOTCH3 genomic nucleic acid molecule, the NOTCH3 mRNA molecule, or the NOTCH3 cDNA molecule produced from the mRNA molecule in the biological sample, wherein the sequenced portion comprises one or more variations that cause a gain-of-function (partial or complete) or are predicted to cause a gain-of-function (partial or complete).

In some embodiments, the determining step, detecting step, or sequence analysis comprises sequencing at least a portion of the nucleotide sequence of the NOTCH3 genomic nucleic acid molecule in the biological sample, wherein the sequenced portion comprises a position corresponding to position 21,944 according to SEQ ID NO:2, or the complement thereof. When the sequenced portion of the NOTCH3 nucleic acid molecule in the biological sample comprises a thymine at a position corresponding to position 21,944 according to SEQ ID NO:2, then the NOTCH3 nucleic acid molecule in the biological sample is a NOTCH3 missense variant nucleic acid molecule encoding a NOTCH3 predicted gain-of-function polypeptide.

In some embodiments, the determining step, detecting step, or sequence analysis comprises sequencing at least a portion of the nucleotide sequence of the NOTCH3 mRNA molecule in the biological sample, or cDNA molecule produced therefrom, wherein the sequenced portion comprises a position corresponding to: position 3,781 according to SEQ ID NO:8, or the complement thereof; and/or position 3,781 according to SEQ ID NO:18, or the complement thereof. When the sequenced portion of the NOTCH3 nucleic acid molecule in the biological sample comprises: a uracil at a position corresponding to position 3,781 according to SEQ ID NO:8, or a thymine at a position corresponding to position 3,781 according to SEQ ID NO:18, then the NOTCH3 nucleic acid molecule in the biological sample is a NOTCH3 missense variant nucleic acid molecule encoding a NOTCH3 predicted gain-of-function polypeptide.

In some embodiments, the determining step, detecting step, or sequence analysis comprises sequencing at least a portion of the nucleotide sequence of the NOTCH3 mRNA molecule in the biological sample, or cDNA molecule produced therefrom, wherein the sequenced portion comprises a position corresponding to: position 3,767 according to SEQ ID NO:9, or the complement thereof; and/or position 3,767 according to SEQ ID NO:19, or the complement thereof. When the sequenced portion of the NOTCH3 nucleic acid molecule in the biological sample comprises: a uracil at a position corresponding to position 3,767 according to SEQ ID NO:9, or a thymine at a position corresponding to position 3,767 according to SEQ ID NO:19, then the NOTCH3 nucleic acid molecule in the biological sample is a NOTCH3 missense variant nucleic acid molecule encoding a NOTCH3 predicted gain-of-function polypeptide.

In some embodiments, the determining step, detecting step, or sequence analysis comprises sequencing at least a portion of the nucleotide sequence of the NOTCH3 mRNA molecule in the biological sample, or cDNA molecule produced therefrom, wherein the sequenced portion comprises a position corresponding to: position 3,532 according to SEQ ID NO:10, or the complement thereof; and/or position 3,532 according to SEQ ID NO:20, or the complement thereof. When the sequenced portion of the NOTCH3 nucleic acid molecule in the biological sample comprises: a uracil at a position corresponding to position 3,532 according to SEQ ID NO:10, or a thymine at a position corresponding to position 3,532 according to SEQ ID NO:20, then the NOTCH3 nucleic acid molecule in the biological sample is a NOTCH3 missense variant nucleic acid molecule encoding a NOTCH3 predicted gain-of-function polypeptide.

In some embodiments, the determining step, detecting step, or sequence analysis comprises sequencing at least a portion of the nucleotide sequence of the NOTCH3 mRNA molecule in the biological sample, or cDNA molecule produced therefrom, wherein the sequenced portion comprises a position corresponding to: position 3,769 according to SEQ ID NO:11, or the complement thereof; and/or position 3,769 according to SEQ ID NO:21, or the complement thereof. When the sequenced portion of the NOTCH3 nucleic acid molecule in the biological sample comprises: a uracil at a position corresponding to position 3,769 according to SEQ ID NO:11, or a thymine at a position corresponding to position 3,769 according to SEQ ID NO:21, then the NOTCH3 nucleic acid molecule in the biological sample is a NOTCH3 missense variant nucleic acid molecule encoding a NOTCH3 predicted gain-of-function polypeptide.

In some embodiments, the determining step, detecting step, or sequence analysis comprises sequencing at least a portion of the nucleotide sequence of the NOTCH3 mRNA molecule in the biological sample, or cDNA molecule produced therefrom, wherein the sequenced portion comprises a position corresponding to: position 3,544 according to SEQ ID NO:12, or the complement thereof; and/or position 3,544 according to SEQ ID NO:22, or the complement thereof. When the sequenced portion of the NOTCH3 nucleic acid molecule in the biological sample comprises: a uracil at a position corresponding to position 3,544 according to SEQ ID NO:12, or a thymine at a position corresponding to position 3,544 according to SEQ ID NO:22, then the NOTCH3 nucleic acid molecule in the biological sample is a NOTCH3 missense variant nucleic acid molecule encoding a NOTCH3 predicted gain-of-function polypeptide.

In some embodiments, the determining step, detecting step, or sequencing analysis comprises sequencing at least a portion of the nucleotide sequence of the NOTCH3 genomic nucleic acid molecule in the biological sample, wherein the sequenced portion comprises a position corresponding to position 21,944 according to SEQ ID NO:2, or the complement thereof. When the sequenced portion of the NOTCH3 nucleic acid molecule in the biological sample comprises a thymine at a position corresponding to position 21,944 according to SEQ ID NO:2, then the NOTCH3 nucleic acid molecule in the biological sample is a NOTCH3 missense variant nucleic acid molecule encoding a NOTCH3 predicted gain-of-function polypeptide.

In some embodiments, the determining step, detecting step, or sequencing analysis comprises sequencing at least a portion of the nucleotide sequence of the NOTCH3 mRNA molecule in the biological sample, wherein the sequenced portion comprises a position corresponding to: position 3,781 according to SEQ ID NO:8, or the complement thereof; position 3,767 according to SEQ ID NO:9, or the complement thereof; position 3,532 according to SEQ ID NO:10, or the complement thereof; position 3,769 according to SEQ ID NO:11, or the complement thereof; or position 3,544 according to SEQ ID NO:12, or the complement thereof. When the sequenced portion of the NOTCH3 nucleic acid molecule in the biological sample comprises a uracil at a position corresponding to: position 3,781 according to SEQ ID NO:8, position 3,767 according to SEQ ID NO:9, position 3,532 according to SEQ ID NO:10, position 3,769 according to SEQ ID NO:11, or position 3,544 according to SEQ ID NO:12, then the NOTCH3 nucleic acid molecule in the biological sample is a NOTCH3 missense variant nucleic acid molecule encoding a NOTCH3 predicted gain-of-function polypeptide.

In some embodiments, the determining step, detecting step, or sequencing analysis comprises sequencing at least a portion of the nucleotide sequence of the NOTCH3 cDNA molecule produced from the mRNA molecule in the biological sample, wherein the sequenced portion comprises a position corresponding to: position 3,781 according to SEQ ID NO:18, or the complement thereof; position 3,767 according to SEQ ID NO:19, or the complement thereof; or position 3,532 according to SEQ ID NO:20, or the complement thereof. When the sequenced portion of the NOTCH3 nucleic acid molecule in the biological sample comprises a thymine at a position corresponding to: position 3,781 according to SEQ ID NO:18, position 3,767 according to SEQ ID NO:19, position 3,532 according to SEQ ID NO:20, position 3,769 according to SEQ ID NO:21, or position 3,544 according to SEQ ID NO:22, then the NOTCH3 nucleic acid molecule in the biological sample is a NOTCH3 missense variant nucleic acid molecule encoding a NOTCH3 predicted gain-of-function polypeptide.

In some embodiments, the determining step, detecting step, or sequencing analysis comprises: a) contacting the biological sample with a primer hybridizing to a portion of the nucleotide sequence of the NOTCH3 genomic nucleic acid molecule that is proximate to a position corresponding to position 21,944 according to SEQ ID NO:2; b) extending the primer at least through the position of the nucleotide sequence of the NOTCH3 genomic nucleic acid molecule corresponding to position 21,944 according to SEQ ID NO:2; and c) determining whether the extension product of the primer comprises a thymine at a position corresponding to position 21,944 according to SEQ ID NO:2.

In some embodiments, the determining step, detecting step, or sequencing analysis comprises: a) contacting the biological sample with a primer hybridizing to a portion of the nucleotide sequence of the NOTCH3 mRNA molecule that is proximate to a position corresponding to position 3,781 according to SEQ ID NO:8; and/or cDNA molecule that is proximate to a position corresponding to position 3,781 according to SEQ ID NO:18; b) extending the primer at least through the position of the nucleotide sequence of the NOTCH3 mRNA molecule corresponding to position 3,781 according to SEQ ID NO:8; and/or cDNA molecule corresponding to position 3,781 according to SEQ ID NO:18; and c) determining whether the extension product of the primer comprises: a uracil at a position corresponding to position 3,781 according to SEQ ID NO:8, and/or a thymine at a position corresponding to position 3,781 according to SEQ ID NO:18.

In some embodiments, the determining step, detecting step, or sequencing analysis comprises: a) contacting the biological sample with a primer hybridizing to a portion of the nucleotide sequence of the NOTCH3 mRNA molecule that is proximate to a position corresponding to position 3,767 according to SEQ ID NO:9; and/or cDNA molecule that is proximate to a position corresponding to position 3,767 according to SEQ ID NO:19; b) extending the primer at least through the position of the nucleotide sequence of the NOTCH3 mRNA molecule corresponding to position 3,767 according to SEQ ID NO:9; and/or cDNA molecule corresponding to position 3,767 according to SEQ ID NO:19; and c) determining whether the extension product of the primer comprises: a uracil at a position corresponding to position 3,767 according to SEQ ID NO:9, and/or a thymine at a position corresponding to position 3,767 according to SEQ ID NO:19.

In some embodiments, the determining step, detecting step, or sequencing analysis comprises: a) contacting the biological sample with a primer hybridizing to a portion of the nucleotide sequence of the NOTCH3 mRNA molecule that is proximate to a position corresponding to position 3,532 according to SEQ ID NO:10; and/or cDNA molecule that is proximate to a position corresponding to position 3,532 according to SEQ ID NO:20; b) extending the primer at least through the position of the nucleotide sequence of the NOTCH3 mRNA molecule corresponding to position 3,532 according to SEQ ID NO:10; and/or cDNA molecule corresponding to position 3,532 according to SEQ ID NO:20; and c) determining whether the extension product of the primer comprises: a uracil at a position corresponding to position 3,532 according to SEQ ID NO:10, and/or a thymine at a position corresponding to position 3,532 according to SEQ ID NO:20.

In some embodiments, the determining step, detecting step, or sequencing analysis comprises: a) contacting the biological sample with a primer hybridizing to a portion of the nucleotide sequence of the NOTCH3 mRNA molecule that is proximate to a position corresponding to position 3,769 according to SEQ ID NO:11; and/or cDNA molecule that is proximate to a position corresponding to position 3,769 according to SEQ ID NO:21; b) extending the primer at least through the position of the nucleotide sequence of the NOTCH3 mRNA molecule corresponding to position 3,769 according to SEQ ID NO:11; and/or cDNA molecule corresponding to position 3,769 according to SEQ ID NO:21; and c) determining whether the extension product of the primer comprises: a uracil at a position corresponding to position 3,769 according to SEQ ID NO:11, and/or a thymine at a position corresponding to position 3,769 according to SEQ ID NO:21.

In some embodiments, the determining step, detecting step, or sequencing analysis comprises: a) contacting the biological sample with a primer hybridizing to a portion of the nucleotide sequence of the NOTCH3 mRNA molecule that is proximate to a position corresponding to position 3,544 according to SEQ ID NO:12; and/or cDNA molecule that is proximate to a position corresponding to position 3,544 according to SEQ ID NO:22; b) extending the primer at least through the position of the nucleotide sequence of the NOTCH3 mRNA molecule corresponding to position 3,544 according to SEQ ID NO:12; and/or cDNA molecule corresponding to position 3,544 according to SEQ ID NO:22; and c) determining whether the extension product of the primer comprises: a uracil at a position corresponding to position 3,544 according to SEQ ID NO:12, and/or a thymine at a position corresponding to position 3,544 according to SEQ ID NO:22.

In some embodiments, the determining step, detecting step, or sequencing analysis comprises: a) contacting the biological sample with a primer hybridizing to a portion of the nucleotide sequence of the NOTCH3 mRNA molecule that is proximate to a position corresponding to: position 3,781 according to SEQ ID NO:8, position 3,767 according to SEQ ID NO:9, position 3,532 according to SEQ ID NO:10; position 3,769 according to SEQ ID NO:11, or position 3,544 according to SEQ ID NO:12; b) extending the primer at least through the position of the nucleotide sequence of the NOTCH3 mRNA molecule corresponding to: position 3,781 according to SEQ ID NO:8, position 3,767 according to SEQ ID NO:9, position 3,532 according to SEQ ID NO:10, position 3,769 according to SEQ ID NO:11, or position 3,544 according to SEQ ID NO:12; and c) determining whether the extension product of the primer comprises a uracil at a position corresponding to: position 3,781 according to SEQ ID NO:8, position 3,767 according to SEQ ID NO:9, position 3,532 according to SEQ ID NO:10, position 3,769 according to SEQ ID NO:11, or position 3,544 according to SEQ ID NO:12.

In some embodiments, the determining step, detecting step, or sequencing analysis comprises: a) contacting the biological sample with a primer hybridizing to a portion of the nucleotide sequence of the NOTCH3 cDNA molecule that is proximate to a position corresponding to: position 3,781 according to SEQ ID NO:18, position 3,767 according to SEQ ID NO:19, position 3,532 according to SEQ ID NO:20, position 3,769 according to SEQ ID NO:21, or position 3,544 according to SEQ ID NO:22; b) extending the primer at least through the position of the nucleotide sequence of the NOTCH3 cDNA molecule corresponding to: position 3,781 according to SEQ ID NO:18, position 3,767 according to SEQ ID NO:19, position 3,532 according to SEQ ID NO:20, position 3,769 according to SEQ ID NO:21, position or 3,544 according to SEQ ID NO:22; and c) determining whether the extension product of the primer comprises a thymine at a position corresponding to: position 3,781 according to SEQ ID NO:18, position 3,767 according to SEQ ID NO:19, position 3,532 according to SEQ ID NO:20, position 3,769 according to SEQ ID NO:21, or position 3,544 according to SEQ ID NO:22.

In some embodiments, the assay comprises sequencing the entire nucleic acid molecule. In some embodiments, only a NOTCH3 genomic nucleic acid molecule is analyzed. In some embodiments, only a NOTCH3 mRNA is analyzed. In some embodiments, only a NOTCH3 cDNA obtained from NOTCH3 mRNA is analyzed.

In some embodiments, the determining step, detecting step, or sequencing analysis comprises: a) amplifying at least a portion of the nucleic acid molecule that encodes the NOTCH3 polypeptide, wherein the amplified portion comprises a thymine at a position corresponding to position 21,944 according to SEQ ID NO:2, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising a thymine at a position corresponding to position 21,944 according to SEQ ID NO:2, or the complement thereof; and d) detecting the detectable label.

In some embodiments, the determining step, detecting step, or sequencing analysis comprises: a) amplifying at least a portion of the nucleic acid molecule that encodes the NOTCH3 polypeptide, wherein the amplified portion comprises: a uracil at a position corresponding to position 3,781 according to SEQ ID NO:8, or the complement thereof; and/or a thymine at a position corresponding to position 3,781 according to SEQ ID NO:18, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: a uracil at a position corresponding to position 3,781 according to SEQ ID NO:8, or the complement thereof; and/or a thymine at a position corresponding to position 3,781 according to SEQ ID NO:18, or the complement thereof; and d) detecting the detectable label.

In some embodiments, the determining step, detecting step, or sequencing analysis comprises: a) amplifying at least a portion of the nucleic acid molecule that encodes the NOTCH3 polypeptide, wherein the amplified portion comprises: a uracil at a position corresponding to position 3,767 according to SEQ ID NO:9, or the complement thereof; and/or a thymine at a position corresponding to position 3,767 according to SEQ ID NO:19, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: a uracil at a position corresponding to position 3,767 according to SEQ ID NO:9, or the complement thereof; and/or a thymine at a position corresponding to position 3,767 according to SEQ ID NO:19, or the complement thereof; and d) detecting the detectable label.

In some embodiments, the determining step, detecting step, or sequencing analysis comprises: a) amplifying at least a portion of the nucleic acid molecule that encodes the NOTCH3 polypeptide, wherein the amplified portion comprises: a uracil at a position corresponding to position 3,532 according to SEQ ID NO:10, or the complement thereof; and/or a thymine at a position corresponding to position 3,532 according to SEQ ID NO:20, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: a uracil at a position corresponding to position 3,532 according to SEQ ID NO:10, or the complement thereof; and/or a thymine at a position corresponding to position 3,532 according to SEQ ID NO:20, or the complement thereof; and d) detecting the detectable label.

In some embodiments, the determining step, detecting step, or sequencing analysis comprises: a) amplifying at least a portion of the nucleic acid molecule that encodes the NOTCH3 polypeptide, wherein the amplified portion comprises: a uracil at a position corresponding to position 3,769 according to SEQ ID NO:11, or the complement thereof; and/or a thymine at a position corresponding to position 3,769 according to SEQ ID NO:21, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: a uracil at a position corresponding to position 3,769 according to SEQ ID NO:11, or the complement thereof; and/or a thymine at a position corresponding to position 3,769 according to SEQ ID NO:21, or the complement thereof; and d) detecting the detectable label.

In some embodiments, the determining step, detecting step, or sequencing analysis comprises: a) amplifying at least a portion of the nucleic acid molecule that encodes the NOTCH3 polypeptide, wherein the amplified portion comprises: a uracil at a position corresponding to position 3,544 according to SEQ ID NO:12, or the complement thereof; and/or a thymine at a position corresponding to position 3,544 according to SEQ ID NO:22, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: a uracil at a position corresponding to position 3,544 according to SEQ ID NO:12, or the complement thereof; and/or a thymine at a position corresponding to position 3,544 according to SEQ ID NO:22, or the complement thereof; and d) detecting the detectable label.

In some embodiments, the determining step, detecting step, or sequencing analysis comprises: a) amplifying at least a portion of the nucleic acid molecule that encodes the NOTCH3 polypeptide, wherein the amplified portion comprises a uracil at a position corresponding to: position 3,781 according to SEQ ID NO:8, or the complement thereof; position 3,767 according to SEQ ID NO:9, or the complement thereof; position 3,532 according to SEQ ID NO:10, or the complement thereof; position 3,769 according to SEQ ID NO:11, or the complement thereof; or position 3,544 according to SEQ ID NO:12, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising a uracil at a position corresponding to: position 3,781 according to SEQ ID NO:8, or the complement thereof; position 3,767 according to SEQ ID NO:9, or the complement thereof; position 3,532 according to SEQ ID NO:10, or the complement thereof; position 3,769 according to SEQ ID NO:11, or the complement thereof; or position 3,544 according to SEQ ID NO:12, or the complement thereof; and d) detecting the detectable label.

In some embodiments, the determining step, detecting step, or sequencing analysis comprises: a) amplifying at least a portion of the nucleic acid molecule that encodes the NOTCH3 polypeptide, wherein the amplified portion comprises a thymine at a position corresponding to: position 3,781 according to SEQ ID NO:18, or the complement thereof; position 3,767 according to SEQ ID NO:19, or the complement thereof; position 3,532 according to SEQ ID NO:20, or the complement thereof; position 3,769 according to SEQ ID NO:21, or the complement thereof; or position 3,544 according to SEQ ID NO:22, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising a thymine at a position corresponding to: position 3,781 according to SEQ ID NO:18, or the complement thereof; position 3,767 according to SEQ ID NO:19, or the complement thereof; position 3,532 according to SEQ ID NO:20, or the complement thereof; position 3,769 according to SEQ ID NO:21, or the complement thereof; or position 3,544 according to SEQ ID NO:22, or the complement thereof; and d) detecting the detectable label.

In some embodiments, the nucleic acid molecule is mRNA and the determining step further comprises reverse-transcribing the mRNA into a cDNA prior to the amplifying step.

In some embodiments, the determining step, detecting step, or sequencing analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising a thymine at a position corresponding to position 21,944 according to SEQ ID NO:2, or the complement thereof; and detecting the detectable label.

In some embodiments, the determining step, detecting step, or sequencing analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising a uracil at a position corresponding to position 3,781 according to SEQ ID NO:8, or the complement thereof; and/or a thymine at a position corresponding to position 3,781 according to SEQ ID NO:18, or the complement thereof; and detecting the detectable label.

In some embodiments, the determining step, detecting step, or sequencing analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: a uracil at a position corresponding to position 3,767 according to SEQ ID NO:9, or the complement thereof; and/or a thymine at a position corresponding to position 3,767 according to SEQ ID NO:19, or the complement thereof; and detecting the detectable label.

In some embodiments, the determining step, detecting step, or sequencing analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: a uracil at a position corresponding to position 3,532 according to SEQ ID NO:10, or the complement thereof; and/or a thymine at a position corresponding to position 3,532 according to SEQ ID NO:20, or the complement thereof; and detecting the detectable label.

In some embodiments, the determining step, detecting step, or sequencing analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: a uracil at a position corresponding to position 3,769 according to SEQ ID NO:11, or the complement thereof; and/or a thymine at a position corresponding to position 3,769 according to SEQ ID NO:21, or the complement thereof; and detecting the detectable label.

In some embodiments, the determining step, detecting step, or sequencing analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: a uracil at a position corresponding to position 3,544 according to SEQ ID NO:12, or the complement thereof; and/or a thymine at a position corresponding to position 3,544 according to SEQ ID NO:22, or the complement thereof; and detecting the detectable label.

In some embodiments, the determining step, detecting step, or sequencing analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising a uracil at a position corresponding to: position 3,781 according to SEQ ID NO:8, or the complement thereof; position 3,767 according to SEQ ID NO:9, or the complement thereof; position 3,532 according to SEQ ID NO:10, or the complement thereof; position 3,769 according to SEQ ID NO:11, or the complement thereof; or position 3,544 according to SEQ ID NO:12, or the complement thereof; and detecting the detectable label.

In some embodiments, the determining step, detecting step, or sequencing analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising a thymine at a position corresponding to: position 3,781 according to SEQ ID NO:18, or the complement thereof; position 3,767 according to SEQ ID NO:19, or the complement thereof; position 3,532 according to SEQ ID NO:20, or the complement thereof; position 3,769 according to SEQ ID NO:21, or the complement thereof; or position 3,544 according to SEQ ID NO:22, or the complement thereof; and detecting the detectable label.

Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the nucleic acid molecule in the sample is mRNA and the mRNA is reverse-transcribed into a cDNA prior to the amplifying step. In some embodiments, the nucleic acid molecule is present within a cell obtained from the subject.

In some embodiments, the assay comprises contacting the biological sample with a primer or probe, such as an alteration-specific primer or alteration-specific probe, that specifically hybridizes to a NOTCH3 variant genomic sequence, variant mRNA sequence, or variant cDNA sequence and not the corresponding NOTCH3 reference sequence under stringent conditions, and determining whether hybridization has occurred.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising a NOTCH3 variant genomic nucleic acid molecule, variant mRNA molecule, or variant cDNA molecule. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

In some embodiments, to determine whether a NOTCH3 nucleic acid molecule (genomic nucleic acid molecule, mRNA molecule, or cDNA molecule), or complement thereof, within a biological sample comprises a nucleotide sequence comprising a thymine at a position corresponding to position 21,944 according to SEQ ID NO:2 (genomic nucleic acid molecule), the biological sample can be subjected to an amplification method using a primer pair that includes a first primer derived from the 5' flanking sequence adjacent to a thymine at a position corresponding to position 21,944 according to SEQ ID NO:2, and a second primer derived from the 3' flanking sequence adjacent to a thymine at a position corresponding to position 21,944 according to SEQ ID NO:2, to produce an amplicon that is indicative of the presence of the SNP at positions encoding a thymine at a position corresponding to position 21,944 according to SEQ ID NO:2. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a thymine at a position corresponding to position 21,944 according to SEQ ID NO:2, and at least 1, 2, 3, 4, 5, 6, 7, 8, 9, 10, or more nucleotides on each side of positions comprising a thymine at a position corresponding to position 21,944 according to SEQ ID NO:2.

In some embodiments, to determine whether a NOTCH3 nucleic acid molecule (genomic nucleic acid molecule, mRNA molecule, or cDNA molecule), or complement thereof, within a biological sample comprises a nucleotide sequence comprising a uracil at a position corresponding to position 3,781 according to SEQ ID NO:8 (mRNA molecule), or a thymine at a position corresponding to position 3,781 according to SEQ ID NO:18 (cDNA molecule), the biological sample can be subjected to an amplification method using a primer pair that includes a first primer derived from the 5' flanking sequence adjacent to a uracil at a position corresponding to position 3,781 according to SEQ ID NO:8, or a thymine at a position corresponding to position 3,781 according to SEQ ID NO:18, and a second primer derived from the 3' flanking sequence adjacent to a uracil at a position corresponding to position 3,781 according to SEQ ID NO:8, or a thymine at a position corresponding to position 3,781 according to SEQ ID NO:18 to produce an amplicon that is indicative of the presence of the SNP at positions encoding a uracil at a position corresponding to position 3,781 according to SEQ ID NO:8, or a thymine at a position corresponding to position 3,781 according to SEQ ID NO:18. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a uracil at a position corresponding to position 3,781 according to SEQ ID NO:8, or a thymine at a position corresponding to position 3,781 according to SEQ ID NO:18, and at least 1, 2, 3, 4, 5, 6, 7, 8, 9, 10, or more nucleotides on each side of positions comprising a uracil at a position corresponding to position 3,781 according to SEQ ID NO:8, or a thymine at a position corresponding to position 3,781 according to SEQ ID NO:18.

In some embodiments, to determine whether a NOTCH3 nucleic acid molecule (mRNA molecule, or cDNA molecule), or complement thereof, within a biological sample comprises a nucleotide sequence comprising a uracil at a position corresponding to position 3,767 according to SEQ ID NO:9 (mRNA molecule), or a thymine at a position corresponding to position 3,767 according to SEQ ID NO:19 (cDNA molecule), the biological sample can be subjected to an amplification method using a primer pair that includes a first primer derived from the 5' flanking sequence adjacent to a uracil at a position corresponding to position 3,767 according to SEQ ID NO:9, or a thymine at a position corresponding to position 3,767 according to SEQ ID NO:19, and a second primer derived from the 3' flanking sequence adjacent to a uracil at a position corresponding to position 3,767 according to SEQ ID NO:9, or a thymine at a position corresponding to position 3,767 according to SEQ ID NO:19 to produce an amplicon that is indicative of the presence of the SNP at positions encoding a uracil at a position corresponding to position 3,767 according to SEQ ID NO:9, or a thymine at a position corresponding to position 3,767 according to SEQ ID NO:19. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a uracil at a position corresponding to position 3,767 according to SEQ ID NO:9, or a thymine at a position corresponding to position 3,767 according to SEQ ID NO:19, and at least 1, 2, 3, 4, 5, 6, 7, 8, 9, 10, or more nucleotides on each side of positions comprising a uracil at a position corresponding to position 3,767 according to SEQ ID NO:9, or a thymine at a position corresponding to position 3,767 according to SEQ ID NO:19.

In some embodiments, to determine whether a NOTCH3 nucleic acid molecule (mRNA molecule, or cDNA molecule), or complement thereof, within a biological sample comprises a nucleotide sequence comprising a uracil at a position corresponding to position 3,532 according to SEQ ID NO:10 (mRNA molecule), or a thymine at a position corresponding to position 3,532 according to SEQ ID NO:20 (cDNA molecule), the biological sample can be subjected to an amplification method using a primer pair that includes a first primer derived from the 5' flanking sequence adjacent to a uracil at a position corresponding to position 3,532 according to SEQ ID NO:10, or a thymine at a position corresponding to position 3,532 according to SEQ ID NO:20, and a second primer derived from the 3' flanking sequence adjacent to a uracil at a position corresponding to position 3,532 according to SEQ ID NO:10, or a thymine at a position corresponding to position 3,532 according to SEQ ID NO:20 to produce an amplicon that is indicative of the presence of the SNP at positions encoding a uracil at a position corresponding to position 3,532 according to SEQ ID NO:10, or a thymine at a position corresponding to position 3,532 according to SEQ ID NO:20. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a uracil at a position corresponding to position 3,532 according to SEQ ID NO:10, or a thymine at a position corresponding to position 3,532 according to SEQ ID NO:20, and at least 1, 2, 3, 4, 5, 6, 7, 8, 9, 10, or more nucleotides on each side of positions comprising a uracil at a position corresponding to position 3,532 according to SEQ ID NO:10, or a thymine at a position corresponding to position 3,532 according to SEQ ID NO:20.

In some embodiments, to determine whether a NOTCH3 nucleic acid molecule (mRNA molecule, or cDNA molecule), or complement thereof, within a biological sample comprises a nucleotide sequence comprising a uracil at a position corresponding to position 3,769 according to SEQ ID NO:11 (mRNA molecule), or a thymine at a position corresponding to position 3,769 according to SEQ ID NO:21 (cDNA molecule), the biological sample can be subjected to an amplification method using a primer pair that includes a first primer derived from the 5' flanking sequence adjacent to a uracil at a position corresponding to position 3,769 according to SEQ ID NO:11, or a thymine at a position corresponding to position 3,769 according to SEQ ID NO:21, and a second primer derived from the 3' flanking sequence adjacent to a uracil at a position corresponding to position 3,769 according to SEQ ID NO:11, or a thymine at a position corresponding to position 3,769 according to SEQ ID NO:21 to produce an amplicon that is indicative of the presence of the SNP at positions encoding a uracil at a position corresponding to position 3,769 according to SEQ ID NO:11, or a thymine at a position corresponding to position 3,769 according to SEQ ID NO:21. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a uracil at a position corresponding to position 3,769 according to SEQ ID NO:11, or a thymine at a position corresponding to position 3,769 according to SEQ ID NO:21, and at least 1, 2, 3, 4, 5, 6, 7, 8, 9, 10, or more nucleotides on each side of positions comprising a uracil at a position corresponding to position 3,769 according to SEQ ID NO:11, or a thymine at a position corresponding to position 3,769 according to SEQ ID NO:21.

In some embodiments, to determine whether a NOTCH3 nucleic acid molecule (mRNA molecule, or cDNA molecule), or complement thereof, within a biological sample comprises a nucleotide sequence comprising a uracil at a position corresponding to position 3,544 according to SEQ ID NO:12 (mRNA molecule), or a thymine at a position corresponding to position 3,544 according to SEQ ID NO:22 (cDNA molecule), the biological sample can be subjected to an amplification method using a primer pair that includes a first primer derived from the 5' flanking sequence adjacent to a uracil at a position corresponding to position 3,544 according to SEQ ID NO:12, or a thymine at a position corresponding to position 3,544 according to SEQ ID NO:22, and a second primer derived from the 3' flanking sequence adjacent to a uracil at a position corresponding to position 3,544 according to SEQ ID NO:12, or a thymine at a position corresponding to position 3,544 according to SEQ ID NO:22 to produce an amplicon that is indicative of the presence of the SNP at positions encoding a uracil at a position corresponding to position 3,544 according to SEQ ID NO:12, or a thymine at a position corresponding to position 3,544 according to SEQ ID NO:22. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising thymine at a position corresponding to position a uracil at a position corresponding to position 3,544 according to SEQ ID NO:12, or a thymine at a position corresponding to position 3,544 according to SEQ ID NO:22, and at least 1, 2, 3, 4, 5, 6, 7, 8, 9, 10, or more nucleotides on each side of positions comprising a uracil at a position corresponding to position 3,544 according to SEQ ID NO:12, or a thymine at a position corresponding to position 3,544 according to SEQ ID NO:22.

Similar amplicons can be generated from the mRNA and/or cDNA sequences. PCR primer pairs can be derived from a known sequence, for example, by using computer programs intended for that purpose, such as the PCR primer analysis tool in Vector NTI version 10 (Informax Inc., Bethesda Md.); PrimerSelect (DNASTAR Inc., Madison, Wis.); and Primer3 (Version 0.4.0.COPYRGT., 1991, Whitehead Institute for Biomedical Research, Cambridge, Mass.). Additionally, the sequence can be visually scanned and primers manually identified using known guidelines.

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. In some embodiments, a polynucleotide primer or probe under stringent conditions will hybridize to its target nucleotide sequence to a detectably greater degree than to other nucleotide sequences by at least 2-fold. In some embodiments, a polynucleotide primer or probe under stringent conditions will hybridize to its target nucleotide sequence to a detectably greater degree than to other nucleotide sequences by at least 3-fold. In some embodiments, a polynucleotide primer or probe under stringent conditions will hybridize to its target nucleotide sequence to a detectably greater degree than to other nucleotide sequences by at least 4-fold. In some embodiments, a polynucleotide primer or probe under stringent conditions will hybridize to its target nucleotide sequence to a detectably greater degree than to other nucleotide sequences by over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in Current Protocols in Molecular Biology, John Wiley & Sons, N.Y. (1989), 6.3.1-6.3.6. Typically, stringent conditions for hybridization and detection will be those in which the salt concentration is less than about 1.5 M Na⁺ ion, typically about 0.01 to 1.0 M Na⁺ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The present disclosure also provides methods of detecting the presence of a NOTCH3 predicted gain-of-function polypeptide comprising performing an assay on a biological sample obtained from the subject to determine whether a NOTCH3 polypeptide in the subject contains one or more variations that causes the polypeptide to have a gain-of-function (partial or complete) or predicted gain-of-function (partial or complete). The NOTCH3 predicted gain-of-function polypeptide can be any of the NOTCH3 variant polypeptides described herein. In some embodiments, the methods detect the presence of NOTCH3 Arg1178Cys, Arg1231Cys, or Arg1182Cys. In some embodiments, the methods detect the presence of NOTCH3 Arg1178Cys. In some embodiments, the methods detect the presence of NOTCH3 Arg1231Cys. In some embodiments, the methods detect the presence of NOTCH3 Arg1182Cys.

In any of the embodiments described herein, the NOTCH3 variant polypeptides can be any Cys-altering variant (they change from or to a cysteine residue). In some embodiments the Cys-altering variant is located within the 34 EGF-like repeats in the NOTCH3 extracellular domain (defined by Uniprot; see world wide web at "uniprot.org/blast/? about=Q9UM47[1335-1373]&key=Domain)). In any of the embodiments described herein, the NOTCH3 variant polypeptide can be any of the variants listed in Table 1 (ENST00000263388).

In some embodiments, the methods comprise performing an assay on a sample obtained from a subject to determine whether a NOTCH3 polypeptide in the sample comprises a cysteine at a position corresponding to position 1,178 according to SEQ ID NO:26. In some embodiments, the methods comprise performing an assay on a sample obtained from a subject to determine whether a NOTCH3 polypeptide in the sample comprises a cysteine at a position corresponding to position 1,231 according to SEQ ID NO:27. In some embodiments, the methods comprise performing an assay on a sample obtained from a subject to determine whether a NOTCH3 polypeptide in the sample comprises a cysteine at a position corresponding to position 1,182 according to SEQ ID NO:28.

In some embodiments, the detecting step comprises sequencing at least a portion of the polypeptide that comprises a position corresponding to position 1,178 according to SEQ ID NO:26 or SEQ ID NO:23. In some embodiments, the detecting step comprises sequencing at least a portion of the polypeptide that comprises a position corresponding to position 1,231 according to SEQ ID NO:27 or SEQ ID NO:24. In some embodiments, the detecting step comprises sequencing at least a portion of the polypeptide that comprises a position corresponding to position 1,182 according to SEQ ID NO:28 or SEQ ID NO:25.

In some embodiments, the detecting step comprises an immunoassay for detecting the presence of a polypeptide that comprises a position corresponding to position 1,178 according to SEQ ID NO:26 or SEQ ID NO:23. In some embodiments, the detecting step comprises an immunoassay for detecting the presence of a polypeptide that comprises a position corresponding to position 1,231 according to SEQ ID NO:27 or SEQ ID NO:24. In some embodiments, the detecting step comprises an immunoassay for detecting the presence of a polypeptide that comprises a position corresponding to position 1,182 according to SEQ ID NO:28 or SEQ ID NO:25.

In some embodiments, when the subject does not have a NOTCH3 predicted gain-of-function polypeptide, the subject does not have an increased risk for developing a cerebrovascular disease or any of CADASIL, subcortical stroke, ischemic stroke, hemorrhagic stroke, or parenchymal stroke. In some embodiments, when the subject has a NOTCH3 predicted gain-of-function polypeptide, the subject has an increased risk for developing a cerebrovascular disease or any of CADASIL, subcortical stroke, ischemic stroke, hemorrhagic stroke, or parenchymal stroke.

The present disclosure also provides isolated nucleic acid molecules that hybridize to NOTCH3 variant genomic nucleic acid molecules, NOTCH3 variant mRNA molecules, and/or NOTCH3 variant cDNA molecules (such as any of the genomic variant nucleic acid molecules, mRNA variant molecules, and cDNA variant molecules disclosed herein). In some embodiments, the isolated nucleic acid molecules hybridize to a portion of the NOTCH3 nucleic acid molecule that includes a position corresponding to position 21,944 according to SEQ ID NO:2. In some embodiments, the isolated nucleic acid molecules hybridize to a portion of the NOTCH3 nucleic acid molecule that includes a position corresponding to: position 3,781 according to SEQ ID NO:8, or position 3,781 according to SEQ ID NO:18. In some embodiments, the isolated nucleic acid molecules hybridize to a portion of the NOTCH3 nucleic acid molecule that includes a position corresponding to: position 3,767 according to SEQ ID NO:9, or position 3,767 according to SEQ ID NO:19. In some embodiments, the isolated nucleic acid molecules hybridize to a portion of the NOTCH3 nucleic acid molecule that includes a position corresponding to: position 3,532 according to SEQ ID NO:10, or position 3,532 according to SEQ ID NO:20. In some embodiments, the isolated nucleic acid molecules hybridize to a portion of the NOTCH3 nucleic acid molecule that includes a position corresponding to: position 3,769 according to SEQ ID NO:11, or position 3,769 according to SEQ ID NO:21. In some embodiments, the isolated nucleic acid molecules hybridize to a portion of the NOTCH3 nucleic acid molecule that includes a position corresponding to: position 3,544 according to SEQ ID NO:12, or position 3,544 according to SEQ ID NO:22.

In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, or at least about 5000 nucleotides. In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides. In some embodiments, the isolated nucleic acid molecules comprise or consist of at least about 18 nucleotides. In some embodiments, the isolated nucleic acid molecules comprise or consists of at least about 15 nucleotides. In some embodiments, the isolated nucleic acid molecules consist of or comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides. In some embodiments, the isolated nucleic acid molecules consist of or comprise from about 18 to about 30 nucleotides. In some embodiments, the isolated nucleic acid molecules comprise or consist of at least about 15 nucleotides to at least about 35 nucleotides.

In some embodiments, such isolated nucleic acid molecules hybridize to NOTCH3 variant nucleic acid molecules (such as genomic nucleic acid molecules, mRNA molecules, and/or cDNA molecules) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to NOTCH3 variant genomic nucleic acid molecules, NOTCH3 variant mRNA molecules, and/or NOTCH3 variant cDNA molecules. In some embodiments, the isolated nucleic acid molecules consist of or comprise from about 15 to about 100 nucleotides, or from about 15 to about 35 nucleotides. In some embodiments, the isolated nucleic acid molecules consist of or comprise from about 15 to about 100 nucleotides. In some embodiments, the isolated nucleic acid molecules consist of or comprise from about 15 to about 35 nucleotides.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a NOTCH3 polypeptide, wherein the portion comprises a position corresponding to position 21,944 according to SEQ ID NO:2, or the complement thereof. In some embodiments, the alteration-specific probe or alteration-specific primer comprises a nucleotide sequence which is complementary to a portion of a nucleotide sequence comprising positions corresponding to positions 21,944-21,946 according to SEQ ID NO:2, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a NOTCH3 polypeptide, wherein the portion comprises a position corresponding to: position 3,781 according to SEQ ID NO:8, or the complement thereof; or position 3,781 according to SEQ ID NO:18, or the complement thereof. In some embodiments, the alteration-specific probe or alteration-specific primer comprises a nucleotide sequence which is complementary to a portion of a nucleotide sequence comprising positions corresponding to: positions 3,781-3,783 according to SEQ ID NO:8, or the complement thereof; and/or positions 3,781-3,783 according to SEQ ID NO:18, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a NOTCH3 polypeptide, wherein the portion comprises a position corresponding to: position 3,767 according to SEQ ID NO:9, or the complement thereof; or position 3,767 according to SEQ ID NO:19, or the complement thereof. In some embodiments, the alteration-specific probe or alteration-specific primer comprises a nucleotide sequence which is complementary to a portion of a nucleotide sequence comprising positions corresponding to: positions 3,767-3,769 according to SEQ ID NO:9, or the complement thereof; and/or positions 3,767-3,769 according to SEQ ID NO:19, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a NOTCH3 polypeptide, wherein the portion comprises a position corresponding to: position 3,532 according to SEQ ID NO:10, or the complement thereof; or position 3,532 according to SEQ ID NO:20, or the complement thereof. In some embodiments, the alteration-specific probe or alteration-specific primer comprises a nucleotide sequence which is complementary to a portion of a nucleotide sequence comprising positions corresponding to: positions 3,532-3,534 according to SEQ ID NO:10, or the complement thereof; and/or positions 3,532-3,534 according to SEQ ID NO:20, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a NOTCH3 polypeptide, wherein the portion comprises a position corresponding to: position 3,769 according to SEQ ID NO:11, or the complement thereof; or position 3,769 according to SEQ ID NO:21, or the complement thereof. In some embodiments, the alteration-specific probe or alteration-specific primer comprises a nucleotide sequence which is complementary to a portion of a nucleotide sequence comprising positions corresponding to: positions 3,769-3,771 according to SEQ ID NO:11, or the complement thereof; and/or positions 3,769-3,771 according to SEQ ID NO:21, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a NOTCH3 polypeptide, wherein the portion comprises a position corresponding to: position 3,544 according to SEQ ID NO:12, or the complement thereof; or position 3,544 according to SEQ ID NO:22, or the complement thereof. In some embodiments, the alteration-specific probe or alteration-specific primer comprises a nucleotide sequence which is complementary to a portion of a nucleotide sequence comprising positions corresponding to: positions 3,544-3,546 according to SEQ ID NO:12, or the complement thereof; and/or positions 3,544-3,546 according to SEQ ID NO:22, or the complement thereof.

In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers specifically hybridize to any of the nucleic acid molecules disclosed herein under stringent conditions.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. Modified primers can be used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. An adaptor can contain a 5'-biotin tag for immobilization of the DNA library onto streptavidin-coated beads.

The probes and primers described herein can be used to detect a nucleotide variation within any of the NOTCH3 variant genomic nucleic acid molecules, NOTCH3 variant mRNA molecules, and/or NOTCH3 variant cDNA molecules disclosed herein. The primers described herein can be used to amplify the NOTCH3 variant genomic nucleic acid molecules, NOTCH3 variant mRNA molecules, or NOTCH3 variant cDNA molecules, or a fragment thereof.

The present disclosure also provides pairs of primers comprising any of the primers described above. For example, if one of the primers' 3'-ends hybridizes to a cytosine at a position corresponding to position 21,944 according to SEQ ID NO:1 (rather than a thymine) in a particular NOTCH3 nucleic acid molecule, then the presence of the amplified fragment would indicate the presence of a NOTCH3 reference genomic nucleic acid molecule. Conversely, if one of the primers' 3'-ends hybridizes to a thymine at a position corresponding to position 21,944 according to SEQ ID NO:2 (rather than a cytosine) in a particular NOTCH3 nucleic acid molecule, then the presence of the amplified fragment would indicate the presence of the NOTCH3 variant genomic nucleic acid molecule. In some embodiments, the nucleotide of the primer complementary to the thymine at a position corresponding to position 21,944 according to SEQ ID NO:2 can be at the 3' end of the primer.

The present disclosure also provides pairs of primers comprising any of the primers described above. For example, if one of the primers' 3'-ends hybridizes to a cytosine at a position corresponding to position 3,781 according to SEQ ID NO:3 (rather than a uracil) in a particular NOTCH3 nucleic acid molecule, then the presence of the amplified fragment would indicate the presence of a NOTCH3 reference mRNA molecule. Conversely, if one of the primers' 3'-ends hybridizes to a uracil at a position corresponding to position 3,781 according to SEQ ID NO:8 (rather than a cytosine) in a particular NOTCH3 mRNA molecule, then the presence of the amplified fragment would indicate the presence of the NOTCH3 variant mRNA molecule. In some embodiments, the nucleotide of the primer complementary to the uracil at a position corresponding to position 3,781 according to SEQ ID NO:8 can be at the 3' end of the primer. In addition, if one of the primers' 3'-ends hybridizes to a cytosine at a position corresponding to position 3,781 according to SEQ ID NO:13 (rather than a thymine) in a particular NOTCH3 nucleic acid molecule, then the presence of the amplified fragment would indicate the presence of a NOTCH3 reference cDNA molecule. Conversely, if one of the primers' 3'-ends hybridizes to a thymine at a position corresponding to position 3,781 according to SEQ ID NO:18 (rather than a cytosine) in a particular NOTCH3 cDNA molecule, then the presence of the amplified fragment would indicate the presence of the NOTCH3 variant cDNA molecule. In some embodiments, the nucleotide of the primer complementary to the uracil at a position corresponding to position 3,781 according to SEQ ID NO:18 can be at the 3' end of the primer.

The present disclosure also provides pairs of primers comprising any of the primers described above. For example, if one of the primers' 3'-ends hybridizes to a cytosine at a position corresponding to position 3,767 according to SEQ ID NO:4 (rather than a uracil) in a particular NOTCH3 nucleic acid molecule, then the presence of the amplified fragment would indicate the presence of a NOTCH3 reference mRNA molecule. Conversely, if one of the primers' 3'-ends hybridizes to a uracil at a position corresponding to position 3,767 according to SEQ ID NO:9 (rather than a cytosine) in a particular NOTCH3 mRNA molecule, then the presence of the amplified fragment would indicate the presence of the NOTCH3 variant mRNA molecule. In some embodiments, the nucleotide of the primer complementary to the uracil at a position corresponding to position 3,767 according to SEQ ID NO:9 can be at the 3' end of the primer. In addition, if one of the primers' 3'-ends hybridizes to a cytosine at a position corresponding to position 3,767 according to SEQ ID NO:14 (rather than a thymine) in a particular NOTCH3 nucleic acid molecule, then the presence of the amplified fragment would indicate the presence of a NOTCH3 reference cDNA molecule. Conversely, if one of the primers' 3'-ends hybridizes to a thymine at a position corresponding to position 3,767 according to SEQ ID NO:19 (rather than a cytosine) in a particular NOTCH3 cDNA molecule, then the presence of the amplified fragment would indicate the presence of the NOTCH3 variant cDNA molecule. In some embodiments, the nucleotide of the primer complementary to the thymine at a position corresponding to position 3,767 according to SEQ ID NO:19 can be at the 3' end of the primer.

The present disclosure also provides pairs of primers comprising any of the primers described above. For example, if one of the primers' 3'-ends hybridizes to a cytosine at a position corresponding to position 3,532 according to SEQ ID NO:5 (rather than a uracil) in a particular NOTCH3 nucleic acid molecule, then the presence of the amplified fragment would indicate the presence of a NOTCH3 reference mRNA molecule. Conversely, if one of the primers' 3'-ends hybridizes to a uracil at a position corresponding to position 3,532 according to SEQ ID NO:10 (rather than a cytosine) in a particular NOTCH3 mRNA molecule, then the presence of the amplified fragment would indicate the presence of the NOTCH3 variant mRNA molecule. In some embodiments, the nucleotide of the primer complementary to the uracil at a position corresponding to position 3,532 according to SEQ ID NO:10 can be at the 3' end of the primer. In addition, if one of the primers' 3'-ends hybridizes to a cytosine at a position corresponding to position 3,532 according to SEQ ID NO:15 (rather than a thymine) in a particular NOTCH3 nucleic acid molecule, then the presence of the amplified fragment would indicate the presence of a NOTCH3 reference cDNA molecule. Conversely, if one of the primers' 3'-ends hybridizes to a thymine at a position corresponding to position 3,532 according to SEQ ID NO:20 (rather than a cytosine) in a particular NOTCH3 cDNA molecule, then the presence of the amplified fragment would indicate the presence of the NOTCH3 variant cDNA molecule. In some embodiments, the nucleotide of the primer complementary to the thymine at a position corresponding to position 3,532 according to SEQ ID NO:20 can be at the 3' end of the primer.

The present disclosure also provides pairs of primers comprising any of the primers described above. For example, if one of the primers' 3'-ends hybridizes to a cytosine at a position corresponding to position 3,769 according to SEQ ID NO:6 (rather than a uracil) in a particular NOTCH3 nucleic acid molecule, then the presence of the amplified fragment would indicate the presence of a NOTCH3 reference mRNA molecule. Conversely, if one of the primers' 3'-ends hybridizes to a uracil at a position corresponding to position 3,769 according to SEQ ID NO:11 (rather than a cytosine) in a particular NOTCH3 mRNA molecule, then the presence of the amplified fragment would indicate the presence of the NOTCH3 variant mRNA molecule. In some embodiments, the nucleotide of the primer complementary to the uracil at a position corresponding to position 3,769 according to SEQ ID NO:11 can be at the 3' end of the primer. In addition, if one of the primers' 3'-ends hybridizes to a cytosine at a position corresponding to position 3,769 according to SEQ ID NO:16 (rather than a thymine) in a particular NOTCH3 nucleic acid molecule, then the presence of the amplified fragment would indicate the presence of a NOTCH3 reference cDNA molecule. Conversely, if one of the primers' 3'-ends hybridizes to a thymine at a position corresponding to position 3,769 according to SEQ ID NO:21 (rather than a cytosine) in a particular NOTCH3 cDNA molecule, then the presence of the amplified fragment would indicate the presence of the NOTCH3 variant cDNA molecule. In some embodiments, the nucleotide of the primer complementary to the thymine at a position corresponding to position 3,769 according to SEQ ID NO:21 can be at the 3' end of the primer.

The present disclosure also provides pairs of primers comprising any of the primers described above. For example, if one of the primers' 3'-ends hybridizes to a cytosine at a position corresponding to position 3,544 according to SEQ ID NO:7 (rather than a uracil) in a particular NOTCH3 nucleic acid molecule, then the presence of the amplified fragment would indicate the presence of a NOTCH3 reference mRNA molecule. Conversely, if one of the primers' 3'-ends hybridizes to a uracil at a position corresponding to position 3,544 according to SEQ ID NO:12 (rather than a cytosine) in a particular NOTCH3 mRNA molecule, then the presence of the amplified fragment would indicate the presence of the NOTCH3 variant mRNA molecule. In some embodiments, the nucleotide of the primer complementary to the uracil at a position corresponding to position 3,544 according to SEQ ID NO:12 can be at the 3' end of the primer. In addition, if one of the primers' 3'-ends hybridizes to a cytosine at a position corresponding to position 3,544 according to SEQ ID NO:17 (rather than a thymine) in a particular NOTCH3 nucleic acid molecule, then the presence of the amplified fragment would indicate the presence of a NOTCH3 reference cDNA molecule. Conversely, if one of the primers' 3'-ends hybridizes to a thymine at a position corresponding to position 3,544 according to SEQ ID NO:22 (rather than a cytosine) in a particular NOTCH3 cDNA molecule, then the presence of the amplified fragment would indicate the presence of the NOTCH3 variant cDNA molecule. In some embodiments, the nucleotide of the primer complementary to the thymine at a position corresponding to position 3,544 according to SEQ ID NO:22 can be at the 3' end of the primer.

In the context of the present disclosure "specifically hybridizes" means that the probe or primer (such as, for example, the alteration-specific probe or alteration-specific primer) does not hybridize to a nucleic acid sequence encoding a NOTCH3 reference genomic nucleic acid molecule, a NOTCH3 reference mRNA molecule, and/or a NOTCH3 reference cDNA molecule.

In some embodiments, the probes (such as, for example, an alteration-specific probe) comprise a label. In some embodiments, the label is a fluorescent label, a radiolabel, or biotin.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well.

The nucleotide sequence of a NOTCH3 reference genomic nucleic acid molecule is set forth in SEQ ID NO:1. Referring to SEQ ID NO:1, position 21,944 is a cytosine.

A variant genomic nucleic acid molecule of NOTCH3 exists, wherein the cytosine at position 21,944 is replaced with a thymine. The nucleotide sequence of this NOTCH3 variant genomic nucleic acid molecule is set forth in SEQ ID NO:2.

The nucleotide sequence of a NOTCH3 reference mRNA molecule is set forth in SEQ ID NO:3. Referring to SEQ ID NO:3, position 3,781 is a cytosine.

The nucleotide sequence of another NOTCH3 reference mRNA molecule is set forth in SEQ ID NO:4. Referring to SEQ ID NO:4, position 3,767 is a cytosine.

The nucleotide sequence of another NOTCH3 reference mRNA molecule is set forth in SEQ ID NO:5. Referring to SEQ ID NO:5, position 3,532 is a cytosine.

The nucleotide sequence of another NOTCH3 reference mRNA molecule is set forth in SEQ ID NO:6. Referring to SEQ ID NO:6, position 3,769 is a cytosine.

The nucleotide sequence of another NOTCH3 reference mRNA molecule is set forth in SEQ ID NO:7. Referring to SEQ ID NO:7, position 3,544 is a cytosine.

A variant mRNA molecule of NOTCH3 exists, wherein the cytosine at position 3,781 is replaced with a uracil. The nucleotide sequence of this NOTCH3 variant mRNA molecule is set forth in SEQ ID NO:8.

Another variant mRNA molecule of NOTCH3 exists, wherein the cytosine at position 3,767 is replaced with a uracil. The nucleotide sequence of this NOTCH3 variant mRNA molecule is set forth in SEQ ID NO:9.

Another variant mRNA molecule of NOTCH3 exists, wherein the cytosine at position 3,532 is replaced with a uracil. The nucleotide sequence of this NOTCH3 variant mRNA molecule is set forth in SEQ ID NO:10.

Another variant mRNA molecule of NOTCH3 exists, wherein the cytosine at position 3,769 is replaced with a uracil. The nucleotide sequence of this NOTCH3 variant mRNA molecule is set forth in SEQ ID NO:11.

Another variant mRNA molecule of NOTCH3 exists, wherein the cytosine at position 3,544 is replaced with a uracil. The nucleotide sequence of this NOTCH3 variant mRNA molecule is set forth in SEQ ID NO:12.

The nucleotide sequence of a NOTCH3 reference cDNA molecule is set forth in SEQ ID NO:13. Referring to SEQ ID NO:13, position 3,781 is a cytosine.

The nucleotide sequence of another NOTCH3 reference cDNA molecule is set forth in SEQ ID NO:14. Referring to SEQ ID NO:14, position 3,767 is a cytosine.

The nucleotide sequence of another NOTCH3 reference cDNA molecule is set forth in SEQ ID NO:15. Referring to SEQ ID NO:15, position 3,532 is a cytosine.

The nucleotide sequence of another NOTCH3 reference cDNA molecule is set forth in SEQ ID NO:16. Referring to SEQ ID NO:16, position 3,769 is a cytosine.

The nucleotide sequence of another NOTCH3 reference cDNA molecule is set forth in SEQ ID NO:17. Referring to SEQ ID NO:17, position 3,544 is a cytosine.

A variant cDNA molecule of NOTCH3 exists, wherein the cytosine at position 3,781 is replaced with a thymine. The nucleotide sequence of this NOTCH3 variant cDNA molecule is set forth in SEQ ID NO:18.

Another variant cDNA molecule of NOTCH3 exists, wherein the cytosine at position 3,767 is replaced with a thymine. The nucleotide sequence of this NOTCH3 variant cDNA molecule is set forth in SEQ ID NO:19.

Another variant cDNA molecule of NOTCH3 exists, wherein the cytosine at position 3,532 is replaced with a thymine. The nucleotide sequence of this NOTCH3 variant cDNA molecule is set forth in SEQ ID NO:20.

Another variant cDNA molecule of NOTCH3 exists, wherein the cytosine at position 3,769 is replaced with a thymine. The nucleotide sequence of this NOTCH3 variant cDNA molecule is set forth in SEQ ID NO:21.

Another variant cDNA molecule of NOTCH3 exists, wherein the cytosine at position 3,544 is replaced with a thymine. The nucleotide sequence of this NOTCH3 variant cDNA molecule is set forth in SEQ ID NO:22.

The genomic nucleic acid molecules, mRNA molecules, and cDNA molecules can be from any organism. For example, the genomic nucleic acid molecules, mRNA molecules, and cDNA molecules can be human or an ortholog from another organism, such as a non-human mammal, a rodent, a mouse, or a rat. It is understood that gene sequences within a population can vary due to polymorphisms such as single-nucleotide polymorphisms. The examples provided herein are only exemplary sequences. Other sequences are also possible.

Also provided herein are functional polynucleotides that can interact with the disclosed nucleic acid molecules. Examples of functional polynucleotides include, but are not limited to, antisense molecules, aptamers, ribozymes, triplex forming molecules, and external guide sequences. The functional polynucleotides can act as effectors, inhibitors, modulators, and stimulators of a specific activity possessed by a target molecule, or the functional polynucleotides can possess a de novo activity independent of any other molecules.

The isolated nucleic acid molecules disclosed herein can comprise RNA, DNA, or both RNA and DNA. The isolated nucleic acid molecules can also be linked or fused to a heterologous nucleic acid sequence, such as in a vector, or a heterologous label. For example, the isolated nucleic acid molecules disclosed herein can be within a vector or as an exogenous donor sequence comprising the isolated nucleic acid molecule and a heterologous nucleic acid sequence. The isolated nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The disclosed nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The nucleic acid molecules disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$ alkyl or $C_{2-10}$ alkenyl, and $C_{2-10}$ alkynyl. Exemplary 2' sugar modifications also include, but are not limited to, $-O[(CH_2)_nO]_mCH_3$, $-O(CH_2)_nOCH_3$, $-O(CH_2)_nNH_2$, $-O(CH_2)_nCH_3$, $-O(CH_2)_n-ONH_2$, and $-O(CH_2)_nON[(CH_2)_nCH_3)]_2$, where n and m, independently, are from 1 to about 10. Other modifications at the 2' position include, but are not limited to, $C_{1-10}$ alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as $CH_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

The present disclosure also provides vectors comprising any one or more of the nucleic acid molecules disclosed herein. In some embodiments, the vectors comprise any one or more of the nucleic acid molecules disclosed herein and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-asso-ciated viruses (AAV), plant viruses such as cauliflower mosaic virus and tobacco mosaic virus, yeast artificial chromosomes (YACs), Epstein-Barr (EBV)-derived epi-somes, and other expression vectors known in the art.

Desired regulatory sequences for mammalian host cell expression can include, for example, viral elements that direct high levels of polypeptide expression in mammalian cells, such as promoters and/or enhancers derived from retroviral LTRs, cytomegalovirus (CMV) (such as, for example, CMV promoter/enhancer), Simian Virus 40 (SV40) (such as, for example, SV40 promoter/enhancer), adenovirus, (such as, for example, the adenovirus major late promoter (AdMLP)), polyoma and strong mammalian pro-moters such as native immunoglobulin and actin promoters. Methods of expressing polypeptides in bacterial cells or fungal cells (such as, for example, yeast cells) are also well known. A promoter can be, for example, a constitutively active promoter, a conditional promoter, an inducible pro-moter, a temporally restricted promoter (such as, for example, a developmentally regulated promoter), or a spa-tially restricted promoter (such as, for example, a cell-specific or tissue-specific promoter).

Percent identity (or percent complementarity) between particular stretches of nucleotide sequences within nucleic acid molecules or amino acid sequences within polypeptides can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

The present disclosure also provides compositions com-prising any one or more of the isolated nucleic acid mol-ecules, genomic nucleic acid molecules, mRNA molecules, and/or cDNA molecules disclosed herein. In some embodi-ments, the composition is a pharmaceutical composition. In some embodiments, the compositions comprise a carrier and/or excipient. Examples of carriers include, but are not limited to, poly(lactic acid) (PLA) microspheres, poly(D,L-lactic-coglycolic-acid) (PLGA) microspheres, liposomes, micelles, inverse micelles, lipid cochleates, and lipid micro-tubules. A carrier may comprise a buffered salt solution such as PBS, HBSS, etc.

As used herein, the phrase "corresponding to" or gram-matical variations thereof when used in the context of the numbering of a particular nucleotide or nucleotide sequence or position refers to the numbering of a specified reference sequence when the particular nucleotide or nucleotide sequence is compared to a reference sequence (such as, for example, SEQ ID NO:1, SEQ ID NO:3, or SEQ ID NO:13). In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide sequence can be aligned to a reference sequence by introducing gaps to optimize residue matches between the two sequences. In these cases, although the gaps are present, the numbering of the residue in the particular nucleotide or nucleotide sequence is made with respect to the reference sequence to which it has been aligned.

For example, a nucleic acid molecule comprising a nucleotide sequence encoding a NOTCH3 polypeptide, wherein the nucleotide sequence comprises a thymine at a position corresponding to position 21,944 according to SEQ ID NO:2 means that if the nucleotide sequence of the NOTCH3 genomic nucleic acid molecule is aligned to the sequence of SEQ ID NO:2, the NOTCH3 sequence has a thymine residue at the position that corresponds to position 21,944 of SEQ ID NO:2. The same applies for mRNA molecules comprising a nucleotide sequence encoding a NOTCH3 polypeptide, wherein the nucleotide sequence comprises a uracil at a position corresponding to position 3,781 according to SEQ ID NO:8, and cDNA molecules comprising a nucleotide sequence encoding a NOTCH3 polypeptide, wherein the nucleotide sequence comprises a thymine at a position corresponding to position 3,781 according to SEQ ID NO:18. In other words, these phrases refer to a nucleic acid molecule encoding a NOTCH3 polypeptide, wherein the genomic nucleic acid molecule has a nucleotide sequence that comprises a thymine residue that is homologous to the thymine residue at position 21,944 of SEQ ID NO:2 (or wherein the mRNA molecule has a nucleotide sequence that comprises a uracil residue that is homologous to the uracil residue at position 3,781 of SEQ ID NO:8, or wherein the cDNA molecule has a nucleotide sequence that comprises a thymine residue that is homolo-gous to the uracil residue at position 3,781 of SEQ ID NO:18).

As described herein, a position within a NOTCH3 genomic nucleic acid molecule that corresponds to position 21,944 according to SEQ ID NO:2, for example, can be identified by performing a sequence alignment between the nucleotide sequence of a particular NOTCH3 nucleic acid molecule and the nucleotide sequence of SEQ ID NO:2. A variety of computational algorithms exist that can be used for performing a sequence alignment to identify a nucleotide position that corresponds to, for example, position 21,944 in SEQ ID NO:2. For example, by using the NCBI BLAST algorithm (Altschul et al., Nucleic Acids Res., 1997, 25, 3389-3402) or CLUSTALW software (Sievers and Higgins, Methods Mol. Biol., 2014, 1079, 105-116) sequence align-ments may be performed. However, sequences can also be aligned manually.

The amino acid sequence of a NOTCH3 reference poly-peptide is set forth in SEQ ID NO:23. Referring to SEQ ID NO:23, the NOTCH3 reference polypeptide is 1,286 amino acids in length. Referring to SEQ ID NO:23, position 1,178 is an arginine.

The amino acid sequence of another NOTCH3 reference polypeptide is set forth in SEQ ID NO:24. Referring to SEQ ID NO:24, the NOTCH3 reference polypeptide is 2,321 amino acids in length. Referring to SEQ ID NO:24, position 1,231 is an arginine.

The amino acid sequence of another NOTCH3 reference polypeptide is set forth in SEQ ID NO:25. Referring to SEQ ID NO:25, the NOTCH3 reference polypeptide is 1,289 amino acids in length. Referring to SEQ ID NO:25, position 1,182 is an arginine.

A variant polypeptide of NOTCH3 exists (Arg1178Cys), the amino acid sequence of which is set forth in SEQ ID NO:26. Referring to SEQ ID NO:26, the NOTCH3 variant polypeptide is 1,286 amino acids in length. Referring to SEQ ID NO:26, position 1,178 is a cysteine.

Another variant polypeptide of NOTCH3 exists (Arg1231Cys), the amino acid sequence of which is set forth in SEQ ID NO:27. Referring to SEQ ID NO:27, the NOTCH3 variant polypeptide is 2,321 amino acids in length. Referring to SEQ ID NO:27, position 1,231 is a cysteine.

Another variant polypeptide of NOTCH3 exists (Arg1182Cys), the amino acid sequence of which is set forth in SEQ ID NO:28. Referring to SEQ ID NO:28, the NOTCH3 variant polypeptide is 1,289 amino acids in length. Referring to SEQ ID NO:28, position 1,182 is a cysteine.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

The present disclosure also provides therapeutic agents that treat or inhibit a cerebrovascular disease for use in the treatment of a cerebrovascular disease (or for use in the preparation of a medicament for treating a cerebrovascular disease) in a subject, wherein the subject has any of the NOTCH3 variant genomic nucleic acid molecules, variant mRNA molecules, and/or variant cDNA molecules encoding a NOTCH3 polypeptide described herein. The therapeutic agents that treat or inhibit a cerebrovascular disease can be any of the therapeutic agents that treat or inhibit a cerebrovascular disease described herein.

In some embodiments, the subject is identified as having a genomic nucleic acid molecule having a nucleotide sequence encoding a NOTCH3 polypeptide, wherein the nucleotide sequence comprises a thymine at a position corresponding to position 21,944 according to SEQ ID NO:2, or the complement thereof.

In some embodiments, the subject is identified as having an mRNA molecule having a nucleotide sequence encoding a NOTCH3 polypeptide, wherein the nucleotide sequence comprises a uracil at a position corresponding to: position 3,781 according to SEQ ID NO:8, or the complement thereof; position 3,767 according to SEQ ID NO:9, or the complement thereof; position 3,532 according to SEQ ID NO:10, or the complement thereof; position 3,769 according to SEQ ID NO:11, or the complement thereof; or position 3,544 according to SEQ ID NO:12, or the complement thereof.

In some embodiments, the subject is identified as having a cDNA molecule having a nucleotide sequence encoding a NOTCH3 polypeptide, wherein the nucleotide sequence comprises a thymine at a position corresponding to: position 3,781 according to SEQ ID NO:18, or the complement thereof; position 3,767 according to SEQ ID NO:19, or the complement thereof; position 3,532 according to SEQ ID NO:20, or the complement thereof; position 3,769 according to SEQ ID NO:21, or the complement thereof; or position 3,544 according to SEQ ID NO:22, or the complement thereof.

The present disclosure also provides NOTCH3 agents for use in the treatment of a cerebrovascular disease (or for use in the preparation of a medicament for treating a cerebrovascular disease) in a subject, wherein the subject has any of the NOTCH3 variant genomic nucleic acid molecules, variant mRNA molecules, and/or variant cDNA molecules encoding a NOTCH3 polypeptide described herein. The NOTCH3 agents can be any of the NOTCH3 agents described herein.

In some embodiments, the subject is identified as having a genomic nucleic acid molecule having a nucleotide sequence encoding a NOTCH3 polypeptide, wherein the nucleotide sequence comprises a thymine at a position corresponding to position 21,944 according to SEQ ID NO:2, or the complement thereof.

In some embodiments, the subject is identified as having an mRNA molecule having a nucleotide sequence encoding a NOTCH3 polypeptide, wherein the nucleotide sequence comprises a uracil at a position corresponding to: position 3,781 according to SEQ ID NO:8, or the complement thereof; position 3,767 according to SEQ ID NO:9, or the complement thereof; position 3,532 according to SEQ ID NO:10, or the complement thereof; position 3,769 according to SEQ ID NO:11, or the complement thereof; or position 3,544 according to SEQ ID NO:12, or the complement thereof.

In some embodiments, the subject is identified as having a cDNA molecule having a nucleotide sequence encoding a NOTCH3 polypeptide, wherein the nucleotide sequence comprises a thymine at a position corresponding to: position 3,781 according to SEQ ID NO:18, or the complement thereof; position 3,767 according to SEQ ID NO:19, or the complement thereof; position 3,532 according to SEQ ID NO:20, or the complement thereof; position 3,769 according to SEQ ID NO:21, or the complement thereof; or position 3,544 according to SEQ ID NO:22, or the complement thereof.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example 1: Association of NOTCH3 with an Increased Risk of Developing a Cerebrovascular Disease Over 19K Pakistanis from 22 clinical sites in 5 cities were recruited for genetic studies, including 4,882 stroke cases and 6,904 controls classified using TOAST and Oxfordshire criteria. The demographics of stroke cases and controls are shown in Table 3 and Table 4.

TABLE 3

Demographics of stroke cases and controls

| Variable | Controls | Cases |
|---|---|---|
| Sex (female) | 43% | 45% |
| Hypertension | 35% | 62% |
| Myocardial infarction | 0% | 4% |
| Angina | 1% | 6% |
| Diabetes mellitus | 18% | 25% |
| Tuberculosis | 1% | 2% |
| Family history diabetes mellitus | 38% | 63% |
| Family history hypertension | 38% | 64% |
| Family history stroke | 0% | 14% |
| Family history sudden death | 30% | 65% |
| Chronic liver disease | 1% | 1% |
| Family history angina | 33% | 64% |
| Valvular disease | 0% | 1% |
| Batch 2 | 51% | 65% |

TABLE 4

Demographics of stroke cases and controls (continued)

| | Controls | | | Cases | | |
|---|---|---|---|---|---|---|
| Variable | Median | SD | Non-missing | Median | SD | Non-missing |
| Age | 55.0 | 10.1 | 100% | 60.0 | 13.0 | 100% |
| Hypertension age | 50.0 | 8.1 | 32% | 50.0 | 10.4 | 53% |
| Cholesterol mg/dl | 183.0 | 49.3 | 67% | 175.0 | 57.6 | 45% |
| TG mg/dl | 171.0 | 132.8 | 67% | 122.1 | 86.1 | 45% |
| Glucose mg/dl | 105.0 | 73.1 | 65% | 123.0 | 66.2 | 44% |
| HDL mg/dl | 36.0 | 11.4 | 67% | 37.3 | 12.5 | 45% |
| LDL mg/dl | 107.4 | 40.0 | 66% | 109.6 | 46.6 | 45% |

TABLE 4-continued

Demographics of stroke cases and controls (continued)

| | Controls | | | Cases | | |
|---|---|---|---|---|---|---|
| Variable | Median | SD | Non-missing | Median | SD | Non-missing |
| Creatinine | 0.8 | 0.9 | 53% | 0.9 | 1.0 | 42% |
| VLDL | 35.0 | 28.3 | 24% | NA | NA | 0% |
| BMI | 26.7 | 4.5 | 27% | 21.2 | 5.0 | 5% |

Exome sequencing and ExWAS was conducted for 12 binary stroke traits, and identified 36 hits (p-value <1e-7), including 29 enriched in Pakistan relative to Europeans, of which 7 were missense or LoF (Table 5).

TABLE 5

Binary stroke traits analyzed in GWAS

| Phenotype | N Cases | Tests | Hits | Drifted Hits | Mis-sense or LoF | Manual QC |
|---|---|---|---|---|---|---|
| Stroke | 4,882 | 1,376,990 | 24 | 21 | 7 | 0 |
| Family history stroke | 691 | 1,530,274 | 0 | 2 | 0 | 0 |
| Cardio-embolism (CE) | 413 | 1,107,635 | 0 | 0 | 0 | 0 |
| CE probable | 387 | 1,105,914 | 0 | 0 | 0 | 0 |
| LAA | 388 | 1,104,571 | 0 | 0 | 0 | 0 |
| LAA probable | 366 | 1,102,944 | 0 | 0 | 0 | 0 |
| SAA | 330 | 1,098,649 | 0 | 0 | 0 | 0 |
| SAA probable | 291 | 1,096,023 | 0 | 0 | 0 | 0 |
| Hemorrhagic | 1,683 | 1,191,892 | 3 | 2 | 0 | 0 |
| Subcortical | 1,416 | 1,174,008 | 1 | 1 | 1 | 1 |
| Parenchymal | 142 | 1,086,417 | 0 | 0 | 0 | 0 |
| Ischemic | 2,668 | 1,249,378 | 8 | 5 | 1 | 0 |
| IS vs HS | 1,683 | 875,142 | 0 | 0 | 0 | 0 |
| LACI | 386 | 1,104,571 | 0 | 0 | 0 | 0 |
| PACI | 1,268 | 1,181,322 | 0 | 0 | 0 | 0 |
| POCI | 481 | 1,129,686 | 0 | 0 | 0 | 0 |
| TACI | 453 | 1,127,104 | 0 | 0 | 0 | 0 |

The read stack QC excluded 7, pairs of adjacent associated variants (PTPRD: 10 bp, ZNF33A: 6 bp, PTPRB: 3 bp, MYCBP2: 5 bp). One variant was excluded due to MAC=5 and irrelevant biology (increased fertility) (GPR149 3:154429224:A:C, p.Phe131Cys, p-value 7.96E-08, effect 28.04, cases 2698|2693|5|0 controls 6871|6871|0|0, MAF 2.6E-04).

A missense SNV in NOTCH3 (p.Arg1231Cys, GRCh38: Chr19:15179052:G:A, rs201680145) was the only significant hit in CNCD F2 subcortical stroke EXWAS (p-value 2.1e-8, effect size 2.97 (2.01, 4.35), MAF 7.1e-3 (Table 6). The variant has elevated MAF in cases, was predicted pathogenic by PolyPhen (score 0.83), and affects an epidermal growth factor (EGF) repeat in a gene highly conserved with mice (93%). The variant adds a Cys in number 31 of 34 EGF repeats in the NOTCH3 extra-cellular domain (ECD), each of which normally has 6 Cys residues. Variants that add or remove a Cys (Cys-altering) from the NOTCH3 ECD are known to be pathogenic in CADASIL.

TABLE 6

Summary of CNCD F2 subcortical stroke EXWAS results

| Gene | NOTCH 3 |
|---|---|
| Genome | GRCh38:19:15179052:G:A |
| DbSNP | rs201680145 |

TABLE 6-continued

| Summary of CNCD F2 subcortical stroke EXWAS results | |
| --- | --- |
| Transcript | C.3691C > T |
| Protein | p.Arg1231Cys |
| Impact | missense |
| P value | 2.18E–08 |
| Effect | 2.97 |
| LCI 95% | 2.03 |
| UCI 95% | 4.35 |
| Cases\|RR\|RA\|AA | 1414\|1370\|44\|0 |
| Controls\|RR\|RA\|AA | 6871\|6799\|71\|1 |
| MAF Pakistan | 7.10E–03 |
| MAF India | 4.20E–03 |
| MAF UK Europeans | 1.90E–04 |

P.Arg1231cys is the only variant associated in the NOTCH3 locus (FIG. 1). The variant has elevated MAF in cases, suggesting a risk-increasing effect. There was 1 homozygote, a control. This individual's age was 45, which is young relative to the average age of stroke onset in Pakistan (50), and younger than the median age of subcortical stroke cases (same as age of recruitment in this cohort, 56). We hypothesize that, while this individual may be asymptomatic for stroke, he may exhibit early symptoms of CADASIL such as migraines, GOM accumulation in the vasculature, and white matter hyperintensity and may be at increased risk for stroke. Prior studies suggest more severe CADASIL phenotypes in homozygotes than heterozygotes for this variant.

TABLE 7

| occurrence of cases and controls in the EXWAS grouped by the presence of rs201680145 | | | | | | |
| --- | --- | --- | --- | --- | --- | --- |
| | | | Count | | | |
| Group | N | Ref/Ref | Ref/Alt | Alt/Alt | Alt alleles | Total alleles |
| Cases | 1414 | 1370 | 44 | 0 | 44 | 2828 |
| Controls | 6871 | 6799 | 71 | 1 | 73 | 13742 |

| | Frequency | | | |
| --- | --- | --- | --- | --- |
| Group | MAF | Ref/Alt | Alt/alt | Ref/Ref |
| Cases | 0.0156 | 0.0311 | 0.0000 | 0.9689 |
| Controls | 0.0053 | 0.0103 | 0.0001 | 0.9895 |

Figure 3:
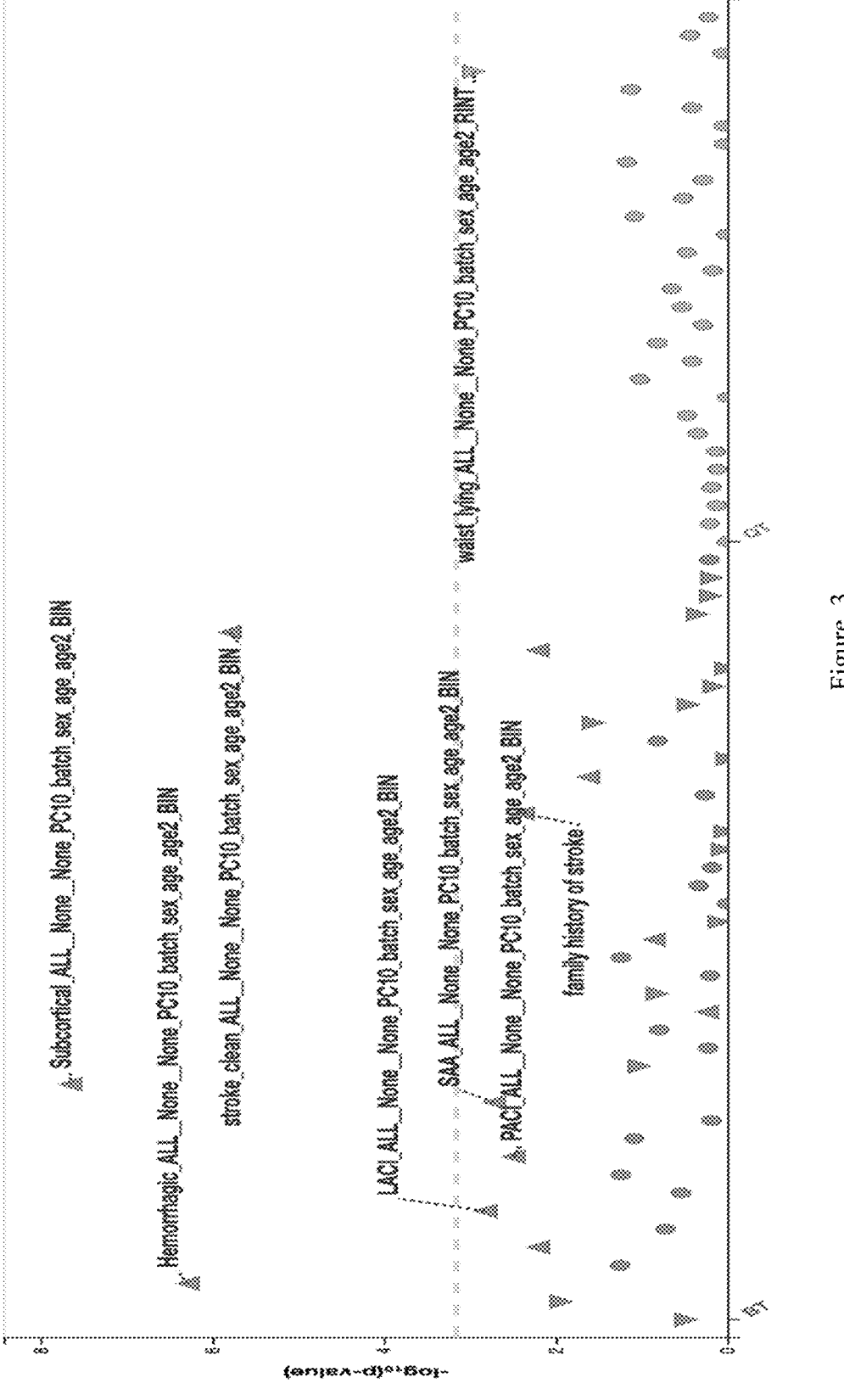
FIG. 3 shows results of PheWAS of NOTCH3 p.Arg1231Cys.

PheWAS of NOTCH3 p.Arg1231Cys revealed nominal p-values for multiple stroke phenotypes, including lacunar artifacts (LACI), small artery atherosclerosis (SAA), partial anterior circulation infarcts (PACI), family history of stroke, and ischemic stroke (FIG. 3 and FIG. 4).

The NOTCH3 Arg1231Cys variant was observed in RGC cohorts of African, European, Admixed American, and South Asian ancestry. The highest prevalence was observed in South Asians (Table 8). One homozygote was observed in the Admixed Americans (Mexico City cohort), male age 55 with blood pressure 80/116, BMI 25, HbA1c 5.2, smoker since age 18, no history of major CNS bleeding or other disease. Similar to the homozygote in CNCD F2, we hypothesize this individual may have other symptoms of CADASIL not collected for this cohort, such as migraines, GOM, vascular pathology, and brain white matter loss.

TABLE 8

| NOTCH3 Arg1231Cys in other RGC datasets | | | | |
| --- | --- | --- | --- | --- |
| Data set | African | Admixed American | European | South Asian |
| Carrier frequency (AA + RA) | 1 in 2,618 | 1 in 1,475 | 1 in 2,066 | 1 in 92 |
| AAF | 0.000191 | 0.000339 | 0.000242 | 0.005426 |
| HET-RA | 24 | 78 | 377 | 420 |
| HOM-AA | 0 | 1 | 0 | 6 |
| N | 62,867 | 117,904 | 777,682 | 39,806 |

The Arginine (R) residue is highly conserved across mammalian species, and the p.Arg1231Cys variant is predicted deleterious (PolyPhen2 score 0.843).

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety and for all purposes.

What is claimed is:

1. A method of treating a subject having a subcortical stroke, an ischemic stroke, a hemorrhagic stroke, or a parenchymal stroke, the method comprising administering a Neurogenic Locus Notch Homolog Protein 3 (NOTCH3) agent to the subject, wherein the NOTCH3 agent comprises an inhibitory nucleic acid molecule, a small interfering RNA (siRNA), or a short hairpin RNA (shRNA) that hybridizes to a NOTCH3 nucleic acid molecule, and wherein the subject is heterozygous or homozygous for a NOTCH3 missense variant nucleic acid molecule encoding NOTCH3 Arg1231Cys, and wherein the subject has no family history of stroke.

2. A method of treating a subject having a subcortical stroke, an ischemic stroke, a hemorrhagic stroke, or a parenchymal stroke, the method comprising:

detecting the presence or absence of a NOTCH3 missense variant nucleic acid molecule encoding a NOTCH3 predicted gain-of-function polypeptide in a biological sample obtained from the subject; and administering a Neurogenic Locus Notch Homolog Protein 3 (NOTCH3) agent to the subject, wherein the NOTCH3 agent comprises an inhibitory nucleic acid molecule, a small interfering RNA (siRNA), or a short hairpin RNA (shRNA) that hybridizes to a NOTCH3 nucleic acid molecule, wherein the subject is heterozygous or homozygous for a NOTCH3 missense variant nucleic acid molecule encoding NOTCH3 Arg1231Cys, and wherein the subject has no family history of stroke.

* * * * *

SEQUENCE LISTING

```
<160> NUMBER OF SEQ ID NOS: 43

<210> SEQ ID NO 1
<211> LENGTH: 41958
<212> TYPE: DNA
<213> ORGANISM: homo sapien
```

-continued

<400> SEQUENCE: 1

```
cttcggcgaa gttggcggcg cggaggctgg cccgggacgc gcccggagcc cagggaagga      60
gggaggaggg gagggtcgcg gccggccgcc atggggccgg gggcccgtgg ccgccgccgc     120
cgccgtcgcc cgatgtcgcc gccaccgcca ccgccacccg tgcgggcgct gcccctgctg     180
ctgctgctag cggggccggg ggctgcaggt gaggggccgg gacctggcgg atgggacgag     240
ggcggcagag ggggagtgca agaaccccca aggccggggc tggcggggggt tcatgggagg     300 caggaaccag ggtcggggaa ggggcgcagg agccccgggc ttcatgccag tcctggagga     360
cccagagatt cagaatgggg aggaccccag aggcccaagg aacagggacc cttgagcgat     420
tagagctgaa gatgaaggga cccaggagtc cgagactggg agctcgaggt gcggggatca     480
gggactcgag gtgggggggt gcgtacagag ttcgggactc gtccccatcc aactcacgcc     540
tggagtcctg ggtaggttat gattgggggc ccaggtactt ctaggccggg gacctctcgc     600
acaaaagccc ccccacccccg ccccccgacac cccgggcggg ctgggccagg cggggggtgg     660 ggaggggggcg cgaagttctg ggagctctga actcggagaa aacttcccag gccggcgcgc     720
agcaagaccc ggagccggat tccgagccgg agcctcggcg gcgcgcgcgc cccctcccccc     780 gcccgcagcc cgcctctctc ctctggccgc ggggacccgg aggccctggg accccgcccc     840
tgcgcgggga ggggaaggggg cgagggccca cgtgctcccc ttcggctcca gcgcccctc     900 cccgcggcca gagcccctcc ccagccggcc aggggccccc gcccctcctc ctctcctccc     960
tcccctcccc cgctcgggac aatggccgcg ccgtctagac acccctccc tccggccggc    1020 ctcgcgcttt ctttgccaga caaagcggga cccgcggctg ggccggggag ggggctgcgg    1080 gggcacccccc ctcaccgcta cgggaggcct ggtgggcggg ggaggggcgc gggccaaggc    1140
ccctggccag gggtcccaga cgccagtgtg gggcttggcg ctgggcgggg tggggggtttc    1200 gggagtgaac ggcctccccca gcccagcccc ggggcccgga cggggcagga ccaggcagga    1260
gccgccgcct ccgccggacc agcggcgcac acacatggcc tgtgacacac tcgctggcac    1320
acatagctct aggtcacgta acagagatgc aaacctgcac acacacagca cactcgcaga    1380
cttgcacacc tggctcagga aagacacacc cagctgcacg cacacagctc acacattgac    1440
atacatacac acacaaatat gatcacacag gtgtggcaca cacgctgcct gcacacactc    1500
agacagcaca tagatgaaga ctcaaggaca tgcttacacc cagctcacac atgcagatgg    1560
acagacacag ccaacccata cacagacaca gcggtgcaca cacaggtcac accaacacac    1620
agctgtacac ccatttacac ggttcacata cacagacgca caacagacac aacctgcata    1680
cagacagcac acacatctgt gcattcccgt atgggtgtgc agctcataca cacacgggca    1740
cacccacgct gacatgcatg tacagataga ctcacatgta gctgcaactg agacacaata    1800
gatgcatgcc caaatccaca tacagacaca caagcccgtg cacgcacaca catgtggctc    1860
acattgccta cagctcaggg tggcccatag cccatgttat gggacccaca gtgtgagttc    1920
acgaacaccc acaggtcctg gtgtgggtga tggtgtccag tcggcttgtc ctgtgaggaa    1980
ggggcatata ctatgtaggc ccatgctcag gttcagctcg acagattctg taactcaccc    2040
tcttgttttc tatttctttc tgtccttctc tctctctttt ttttttttga cacagtctca    2100
ctctgttgcc aggctggcat gcagtggcgc aatctcgggt cactgcaacc tccgcttccc    2160
aggttcaagc gattctcctg cctcagcctc ccgagtagct gggactacag gcgtgcgcca    2220
ccacacccag ctaattttttt tttggagatg gagtttggct cttgttgccc agggtggagt    2280
```

-continued

```
gcaatggcgt gatctcggct cactggaacc tctggctcct gggttcaagc gattctcctg      2340
cctcagcctc ctgagtagct aggattacag gcacctgcta ccatgcccag ctaagtttta      2400 tattttttaga acagactggg tttcactgtg ttggccaggc tggtctcgaa ctcctgacct     2460
caggtgatcc accagcctcg gcctcccaaa gtgttgggat tagaggcgtg agccaccatg      2520
cctggccgct ttctatttct ttctgtcctt ctctgtcttc tcctggtcta tctgcttcta      2580
gttcattctc acgtctttgt gttttttctcg atcttccttc ctctctccat caccctctct     2640
ctgacaagag catgcatgga cacacgcact gtgtccccac acctgatcgc atgcacacag      2700
ttctccacta gctcagaccc agccacaccc tggacccttc tggcaggaca gttagactat      2760
gccacaccct agagggacac agcccttagg gatggcgatg ttggacaggg cagcacatgc      2820
cttgtgccag ttgcccctcc cttcaacaca caccctattc cagcaacgcc cagcgctggc      2880
tgcttctgga gatgctgtgc tcactcgtgg gtacatgcct tggtccctct cccaagagca      2940
ccacgcaggc ctgcctggct ggagtagatg cccatcaggg aaaggaagac ccgtggccct      3000
aggatcccct gcccctccc cttctattac ccctgaacct gggcatgaag ccccagacct       3060
ccctgtaaca ctcagcaccc ttacttcctg tctcagcaca ccccattctg cacatcttag      3120
ctctggcagc ttcccgagcc cccacatctg gcataagaca gccctcctc ctgccttccc       3180 ctgctttgtg gttcccaggg ctcgagctgg cagggacagc tgcagcctca acagctgggg      3240
ctggggcggg ggggggggg gcgtgggaac tgtggatggg gggactccct gcacccgcag       3300 agacgcccc atcccatgc agctgttgcc tggtggaggg agggagggg tttgtcactt         3360 gggcctgggg ttcctgggca cctggctgat cctccacctt ccttcacccc cacacagccc      3420 cccttgcct ggacggaagc ccgtgtgcaa atggaggtcg ttgcacccag ctgccctccc       3480
gggaggctgc ctgcctgtga gtgcctggct cagagccacc agtgggccct gtgtgtgggg      3540
gcggggggga ggggcgattt gtcttctccc tctgcctctg tgttcaccat ggatgtctct      3600
accacttcct acatgtgtgt ggcttgggca acctctcgtg tttccccatt ggaaactgag      3660
caggggctct gcactcttct tggcatgggt tcaagtccca catcatgttg ctgaccggct      3720
aggaattaaa ctctttacat ctcagtgtca tggtctgcaa aatgggccca gtaatcccag      3780
cttcacagtt cttggccacc tgaggtcaca tgtaaagccc cccatgaggt aggtattatt      3840
caatcaacaa actatcaggg accaatcgca gtggctcaca ccctccacac ccctcccatc      3900
tctcaacatt tagtggaggg ggacatagga ggcctataat acagtcccac actgccactt      3960
acttgcagtg tgactttggg ctagtcactt tccctctctg atcatcattg cacctgtgaa      4020
atagggaatg cttcactggc gactgtgaag ggacttaaca atttagttgt tagatatcac      4080
aaggaaaggc aagaggttgc agggagcaga gcagaggctg ggaaggagct gagcagagac      4140
agaaagagct cagcttaaat tctggggtct gggacacctt gagcattcaa gctttttgag      4200
cctcagtttt tgcatctgga aaatggggca ataataactc ctgtatgcac tcaacataca      4260
ttaagtgctc agaatatagt atgtgctcaa cataggcatt attataaata ataatggtag      4320
ggaggcagga aacaggtgct ctaaggagaa gtctctcaag gttatgagga aatgcttggc      4380
tcctttcatg ctatcattaa taacagcagt tcacgcagta gccattgatt gactcattaa      4440
tgtattcatt tattcagcat catgtgtgcc aagtactggg tcaggcccaa gctgggtggg      4500
tctggggtga tttttagacca agaagagccg ctttgaagtt acacctacat ttattttggc     4560
tggatctccc actcgggctc accttgtgg agggctgagc ctgactgaga gggtttcctg       4620
gggctggggg gtctgcgaag gtggggcggg atggggaaaa gtgtgacctt acctggagcc      4680
```

-continued

```
acacacctgg gagggcgagc ggtggggccg ggcgcctgcg cagtggagct ccgcgcctgg    4740
aatactgccg acaggtgaat gagcccgcgg ctgccccgcc cttcgacagg tgaatcaccg    4800
gcgcgcgcgg cgcccggagc ccggatcgcc cggagtggag cgggctcagt cctccgagtt    4860
gggctgtggg aaccactccc tacacgccct ccacccccca cgagtctctt tcacggtctc    4920
aaatactcaa gtcctttcaa ggatgccccc aagctgtcac cccacccatg gatcccccaa    4980
gaccccccca ccggcagcag acgtttccat agacctcgtc cccatctcct agtcctcgcc    5040
tcacccgccg tgccccccct aactaggtct gcgctccccc ctccgtctcc cccaaagctt    5100
aggccgtggg gcggggcgcg ggctggggct ggaaccggcc cgaccggtcg gcgggggcgc    5160
gggacgcaga gcgtgggaac ccgcccgggg cgtcgggagg gggcccgcgc gggtcgcgcc    5220
ctgcctggcg gtgggaccag ctatcctcgg cgcccagcgc agcgcgcccc ctcccgacgc    5280
gcggtcgggg ccgcagtggt cgccctgcgg gccttggagg aggggacggg agctgtgccc    5340
tccctcccca acgccacccg cacccttgct tgctcggccg tgccccgacc tgtttcgctg    5400
ggggccgggg tggggggat cttgcgggtg acgctaagga ctgagtcagc cgcttgttga    5460
gttcagtctc aggcgtctgg gacaagccgg agggaggaca accgcgccag gggcggaggg    5520 tgggggggata gagggggggtg agggttggca gcgtcggggg cggagcttg gactctctgg    5580 cttctctaag cccctccctc tgaccccgct agtgcccctt ggagatttcc agtcttaaga    5640 ccaaccctc ccagttccaa ttcctcacac tccttggtgg gcttggggag ggggctgcag    5700
gttgaaggac cacccccca agatgagggt accaacagtg gtgtcagtac cccaaccctc    5760
caccctccca tccctgcata agaggctata taagtcccag agaagggact tgagggtttg    5820
tgggagccct gctgtctgtc cctgtgagtg agagttgctc atttccgcgt gggatgctgt    5880
gggttggtgt cttgagtgct ggccaggcca tggcgtccaa ttggtgtgtc cctctgtgtg    5940
tgtagctgtg gtttctgggc ctgtctgtgt gtgcctgcgt ggttgtgtcc tggggtctga    6000
gacttctttt tttccttttc cttttttttt ttttttttga gatcgagtat cgctcttgtt    6060
gcccaggctg gagtgcagtg gctcgatctt ggctcactgc agcctctatc tcctgggttc    6120
aagcgatttt cctgcctcag cctccggagt agctgggatt acaggcatgt gccaccacac    6180
ttggctgatt ttttgtgttt ttagtagaga cggagtttct tcatgttggt caggctggtc    6240
tcgaactctt gatgtcaggt gatctacctg cctcggtctc ccaaagtgtt gggattacag    6300
gcgtgagcca ccgcgcttgg acatgggtct gagacttttc atttgctgtt ccctctgcct    6360
ggaatgccgt tccccagaaa gccccatggc ccctcctta ccttcatatg tctgtgaaaa    6420
tagaattcca cctccttgac cccatcattc tatcccctt aaccctgtgg tttagcttcc    6480
tacggctgct ctaacaaatt accataaact gggtagcttg aacaatagta atttattctc    6540
ttgaagttct ggaggttgga agtctgaaat caagatatcg gcaggctga gcctctccat    6600 ggggacccag gggagaactg actcttgcag cttctggtgg ctccagacgt ttctcagcta    6660
gtggctgtct cactccagtc cctgtctctg tcttcttctc ttccttctcc cacccaaatc    6720
tccttttggc tgcctctctc ttttttttgag acagagtctt gctctgtcac ccaggctgga    6780
gtgcagtggt gcaatcttag ttcactgcag ccttcaactc ccaggctgaa gcgatcctcc    6840
cacctcagcc tcccaagaag ctgggactac aggtgtgagc caccacggcc agctaatctt    6900
ttatttttat tttttaggtg gagtctctct ctgtcaccca ggctggagtg cagtggcacg    6960
atctcggctt actgcaacct ccgcctccca ggttcaagca attcttctgt ctcagcctcc    7020
```

-continued

```
tgagtagcgg ggactacacg agtgcaccac cacgcccagc taattttttgt attttttagta    7080 gcgacgaggt ttcaccatat tggccaggct ggtcttgaac tcctgacctc gtgatccgcc    7140
cacctcagtc tcccagagtg ctgggattac aggcatgagc cactgcgcct ggcctgtttg    7200
ttttttttgt tttttgtttt tttttgagat ggagtctccc tctgtcaacc aggctggagt    7260
gcagtggtgc aatttcggct cactgcaacc tccgcctcct gggttcaagc gattctcctg    7320
cctcagcctc cagagtagct gggattacag gctcctgcca ccatgcccgg ttataatttt    7380 taatttttttt ttgtggaaaa aaagtctccc tatgttgctc aagctgatct tgaacttctg    7440
gcttgaagtg attatcctgt cttgacctcc caaagtgttg ggattacagt tgtgagccgt    7500
tctcttgtat gaacacttgt cactgaattt agggcccagg tggataattc agaataatct    7560
catcttgaca tctctcattt aattacatct gcatagccag gcctggtggc gtgtgcctgt    7620
actcccagct acgcaggagg ctgagacaaa gaattgcttg aacccacggga ggtggaggtt    7680 gcagtgagcc aagatcgcgc cactgcactg cagcctgggt gacagagcaa gactccgtct    7740
cttaaaaaaa aaaaattaca tctgcaaaga gccatttaaa aaaaaagtaa ggtcctagtc    7800
acaggttctg ggacatggat gtcatctttt caggggctgt gacccaactg actacatcct    7860
tcatggttct gatggctttc accgcccct gccagcatgt tgtatattaa tttgttattc    7920
gtatatgttc tccttgcctg gacctggctg caaggatcca gagggatagg gacccctttc    7980
attgtgtttg ttgctgtatt tgtattgctc agaacgtagt aggtactcag taaatattcg    8040
ttgcatgaat gaatgtgtgt tttgttttgt tttgtttctt tgagaccgag tcttactctg    8100
tcacccaggc tgcagtgcag tggcgcgatc ttggctcact gcaacctcca cctcccgagt    8160
tcaagcaatt ctcctgcctc agcctcttga gtagctggga ctacaggcac gcaccactat    8220
gcccagcaaa gtttcgtact tttagtagag acggggttac accatgttgg ctaggctggt    8280
cttgaactcc tgaccccaag tgatctgccc gccgcagcct cccaaagttc tgggattaca    8340
ggcgtgagcc actgctccca gcaaatgtgt gtttgctgct ctgtttccct gcgtgtttct    8400
tgcctgtctt gtgtgtatct ttgtgtctgg ggccatcctg ccctgtgctg cccaaccaag    8460
ccatctctgc ccacaggtgc ccgcctggct gggtgggtga gcggtgtcag ctggaggacc    8520
cctgtcactc aggcccctgt gctggccgtg gtgtctgcca gagttcagtg gtggctggca    8580
ccgcccgatt ctcatgccgg tgccccgtg gcttccgagg tgagaggga agagtctgga    8640 ggggaggtag tcgggggtgt ggtcagtcct aaactcaccc tgtcctggtc cctccaggcc    8700
ctgactgctc cctgccagat ccctgcctca gcagcccttg tgcccacggt gcccgctgct    8760
cagtggggcc cgatggacgc ttcctctgct cctgcccacc tggctaccag ggccgcagct    8820
gccgaagcga cgtggatgag tgccgggtgg gtgagccctg ccgccatggt ggcacctgcc    8880
tcaacacacc tggctccttc cgctgccagt gtccagctgg ctacacaggg ccactatgtg    8940 agaacccgc ggtgccctgt gcaccctcac catgccgtaa cggggcacc tgcaggcaga    9000 gtggcgacct cacttacgac tgtgcctgtc ttcctggtga gtgagccta ctcaggagag    9060 tcagaggggt gggcgtgggg acagcaggcc agcccggcgg tgaccatcct tgcccccttc    9120
cctgctaggg tttgagggtc agaattgtga agtgaacgtg gacgactgtc caggacaccg    9180
atgtctcaat gggggggacat gcgtggatgg cgtcaacacc tataactgcc agtgccctcc    9240
tgagtggaca ggtgggcact gcggccagag ggagcgggga ggcaggcctc gggtggacat    9300
gcgccaggtg gctggactgc tgcatctgtg tgccacaggc cagttctgca cggaggacgt    9360
ggatgagtgt cagctgcagc ccaacgcctg ccacaatggg ggtacctgct tcaacacgct    9420
```

-continued

```
gggtggccac agctgcgtgt gtgtcaatgg ctggacaggc gagagctgca gtcagaatat    9480
cgatgactgt gccacagccg tgtgcttcca tggggccacc tgccatgacc gcgtggcttc    9540
tttctactgt gcctgcccca tgggcaagac tggtgagtgg ccgttttctc tgcagggagc    9600
catggatggt ttttagtgag ggcaaataag aagtctgact tgagtgttag aaagattatg    9660
ctaggctggg cacagtggct catgcctgta atcatagcac tttgggaggc ccaggcgggc    9720
ggatcactgg ggtcaggagt ttgagaccag cctggtcaat atggtgaaac cccatctcta    9780
ctaaaaacac aaaaattagc tgcgcgtggt ggtgcacacc tgtaatccaa gtctctcagg    9840
aggctaaggc acgagagtag cttgaaccca ggaggtggag attgcagtga gccaagattg    9900
caccactgca ctctagcctg ggtgacagag tgagactcct tctcaaattt aaaaaataaa    9960
aaaaagatta tgctaggccg ggcacagtgg ctcatgcctg taatcccagc actttgggag   10020
gccaagatgg gaggatcgct tgggcccagg actttgagac cagcctggac aacatagtga   10080
gtttttgtca tctctacaaa aacttggtag gctgggtgtg gtggctcacg cctgtaaccc   10140
caacacattg ggaggcccag gcgggtagat tgcttgagct cagcagtttg agaccagcct   10200
gggcaacatg gcaaaaccct atctctacca aaaatacaaa aaattagctg ggcatggtag   10260
cgcatgcctg tagtcccagc tactctggat gctaaggttg aaggatggct tgagcccaga   10320
aggtggaggt tgcagtgagc tgagactgag ccactgcgtt ccagcctggg agacagtgta   10380
agaccgtgta taacaaaaaa gagagagaaa aaaagatgat gctggaggca gctttagtgg   10440
ggaagtgtaa gcctgggaga ggcttgggag gaggctgaca ttgcactgat gcatggctca   10500
gggcagaagc cattggaatg gggaactcct gggagttacc tttggaagtg gcaaagatca   10560
gagaacatgt ttaggagggg aacgtggata tagaaagagg gcatacatgg cagagggtat   10620
tacagaagca aaggctggag tgtaggaccc ttttgtaatc agaagagtca aaaggtttta   10680
aaacaatatg tggatgtttg caatttattt tattttattt ttgagacaga gtctcacttt   10740
gtcacccagg ctggagtaca gtggcatgat ctcagctcac tgcagcctcg acttcctggg   10800
ctcaagtgat cctcccacct cagtcccca agtagctggg attacaggcg tgcgccacca   10860
tgcccggcta agctttgtat tttttgtaga gacgggtctc actatattgc ccaggctggt   10920
cttgaactct tgaactcaag cgatgcactc accttggcct cccaaagtgc taggattata   10980
gacgtgagcc actgtgcccg gtctgcaatt tattttaaa tggtttagaa aagaagattg   11040
gtagattaag ctaacaatag ttgaatctag gtggtgggta tatgaatggt caacttttct   11100
gtatgtttga tagttctcat aataaatgga ttaaaaaagc agctactaaa tactgtttag   11160
gtttaataaa aacaacaggc cgggcgcggt ggctcacgcc tgtaatccca gcactttggg   11220
aggctgaggc aggcagatca cctgaggtca ggagtttgag accaacctgg ctaacttggt   11280
gaaaccccgt ttctactaaa aatacaaaaa attagccggg cgtggtggca catgcctgta   11340
atcccagcta ctcgggaggc tgagcaggag aatcgcttga acctgggagg tggaggttac   11400
agtgagccaa gatcgcgcta ttgtactcca gcttgggcaa caagagcgaa acttcgtctc   11460
aaaaaacaaa acaaaacaac aacaacgaca aaacaatact caaggggtgt gggcctttg    11520 ggcagagcag gaagatctgc ctatgacttc tgcttaccac ttcccaggcc tcctgtgtca   11580
cctggatgac gcctgtgtca gcaacccctg ccacgaggat gctatctgtg acacaaatcc   11640
ggtgaacggc cggcccattt gcacctgtcc tcccggcttc acgggtgggg catgtgacca   11700
ggatgtggac gagtgctcta tcggtgaggg gagctccatc gtctgtgaat gggctgggaa   11760
```

-continued

```
agagggggaga ggaggggggtc ccggccagcc acgcccacac cgatcgcact ccatccggca   11820
ggcgccaacc cctgcgagca cttgggcagg tgcgtgaaca cgcagggctc cttcctgtgc   11880
cagtgcggtc gtggctacac tggacctcgc tgtgagaccg atgtcaacga gtgtctgtcg   11940
gggccctgcc gaaaccaggc cacgtgcctc gaccgcatag gccagttcac ctgtatctgt   12000
atggcaggtg ggtggtgggc gtggcctggg cgggtcctga ggcaggggc ggggacagag   12060 aagcccgcgg atggggagct gagcagaatg gggtgtaagt gggtttggag tgggacccctt   12120 agagactgaa gcctggaagg aggtggggtc aggaccagaa gggaatactg tgtgattctg   12180 gggggcttggt caaatggagt cagtagaacc tcaggtgggc tgggagtatt cttggcctta   12240
ggacccactc gggaaggggt tggggataga gaggcagagt cggggctgct gtgaggtcaa   12300
ggtgaagcct gcagacaagc ttgcagtaag cctgggcaaa ggctatgggg ggccctgggg   12360
ctgggggctg gggactgggg aaagggctta gtctgaggac tggggagagg aggaggggtt   12420
tgaaggcaag gcctctgcgg acacccatga gccttgggcc agttgggacc acggctgggt   12480
gacagtccag cctgtggctg aaaattaagg ttgggctggg agtgtagagg tggggacgaa   12540
ggctcggggg atttgtcgat gagtaggaag ggaagtacct ccttccttgc accccgttca   12600
caccataggg tagcccccgc tttcctaagc cctattccct gccccaggct tcacaggaac   12660
ctattgcgag gtggacattg acgagtgtca gagtagcccc tgtgtcaacg gtggggtctg   12720
caaggaccga gtcaatggct tcagctgcac ctgcccctcg ggtgaggacc tcaggagagg   12780
gagcccgaaa agacatgtct gggaaggggc aaaaactcca gggtgggaac ctgtaaaacc   12840
acgttagcgg ataacttaca atagaaacca tatgttatga aacattgaag ttaatttaaa   12900
tccaagtaaa tgggtttttc cacccaaaca aggcggggct ggagaggggt gtactgctct   12960 cacccttttct gggcctctgc tcatcccact ccccaccccca ggcttcagcg gctccacgtg   13020
tcagctggac gtggacgaat gcgccagcac gccctgcagg aatggcgcca aatgcgtgga   13080
ccagcccgat ggctacgagt gccgctgtgc cgagggtgag gcgggccaat gacagtccga   13140
caagaatcag gaggcggggc ttgtgggcga cagggccaat aacagacttg gggagagctt   13200
gggggcgggg ttgtagcaag gcaggaccca gtgacagagt tggggggtgg agccaataat   13260
gcatatagac tgacataagg ctacgtgtgg agccaaagtg ttgggctggg cacagggtgc   13320
ctgtaactga atggggaggg cccaatacct tcccctggca cctgccatgt gctcccatct   13380
ccagtggagg gtggggcaga aacagggctg gaggtggggc cacagctggg ggcgggattt   13440 aactgtgggga gagtcttggc tagggacaaa ttctggagct tgtagtgggg tggagtggaa   13500
gtaagtgggg ggtgggggt ggggcctgta ttgagctcgc ctcctgacag cttgatgggc   13560
agggcctcag atagagctga accaggattg gtccgaggcc tcacttgtgg gcaggcccct   13620
ggcaagtggg cggagcctga ccctcttggc cccacaggct ttgagggcac gctgtgtgat   13680
cgcaacgtgg acgactgctc ccctgaccca tgccaccatg gtcgctgcgt ggatggcatc   13740
gccagcttct catgtgcctg tgctcctggc tacacgggca cacgctgcga gagccaggtg   13800
gacgaatgcc gcagccagcc ctgccgccat ggcggcaaat gcctagacct ggtggacaag   13860
tacctctgcc gctgcccttc tgggaccaca ggtgggaccg ggggctgggg cagaaacagc   13920
acacctggag gggcacagag ggtttgggaa tggtgcatct agtggggcac agtggtggcc   13980
actccatgcc atgttcctgg cccctaggtg tgaactgcga agtgaacatt gacgactgtg   14040
ccagcaaccc ctgcaccttt ggagtctgcc gtgatgtgcat caaccgctac gactgtgtct   14100
gccaacctgg cttcacaggt gggcaagtgg ctgccatgag aggggggtcct tagatcgagg   14160
```

```
gtgaagtcac tcgtctctgt gggcctgttt tgcccgtatc tttgcagact cttgtccaac   14220
gaggttgtcc gtgctttgcc ctgagtctgt gctgtctcat tggcataagg ttgtttcgag   14280
attattctgc aggctgggcg cggtggctca cgcctgtaat cccagcgctc tgggaggcca   14340
aggcaagtgg atcacttgag gtcaggagtt cgagaccagc gtggccaacg ttgcgaagcc   14400
ccatctctac taaaaataca aaaattagtc gggtgtggtg gtgggcgcct gtagtcctag   14460
ctactcggga ggctgaggca ggagaattgc ttgacctcag gaggcggagg cggcagtgag   14520
ccaagattgt gccactgtac tccagtctgg gcgacagagt gagacttcat ttcaaacaca   14580
cacacacaca cacacacaca cacacacaca cacacataca aaaacaaaca aaaagattat   14640
tctggaacat agatgaaagt gtccaaactc agtgactagg ttatttctga atgggtctaa   14700
actaatcctt agtggaaatg aatgtgactt tgctaggtgt gttggctcat gtctgtaatc   14760
ccccagcact ttgggaggct gagacatgag gatcacttga gcccaggagt cgagactag   14820 cctgggcaac ataatgaaac cctgtctcta caaaaaataa acacactccc aaagccagat   14880
tagtcaatac gtagataaac acgcacacac atgcacacac aattagccag acgtggtggt   14940
gcgcaactgt agtcccagcc actcgggagg ctgaggtggg agaatcgctt gagcccagga   15000
agtggaggct gtggtgagct atgatcatgc cactgcagtc cagcccgggc gacagagtga   15060
gaccccatct caaaaaataa gaagaagaag aaaagaaaaa gaaagggact tcatggaagt   15120
ttggggacca gaatgatctg gggcaagtca gctcttggtt gaggaggcgg gtgtcctaat   15180
ctgcacaaga gctgatgcgt tatgaaaaag aggtcattgc tcgggggtgt gggtgtgcta   15240
agtggggtca cgtcgtccct ccctggttgt ccctgctgac tttgttctga gatgagattg   15300
cttgtgtact ccccagggcc cctttgtaac gtggagatca atgagtgtgc ttccagccca   15360
tgcggcgagg gaggttcctg tgtggatggg gaaaatggct tccgctgcct ctgcccgcct   15420
ggctccttgc ccccactctg cctcccccg agccatccct gtgccatga gccctgcagt     15480 cacggcatct gctatgatgc acctggcggg tgagggccct tctcagcctc agacactgcc   15540
ccctctccct ggcccacctc cctggcctga ctaccttccc ctgccaggtt ccgctgtgtg   15600
tgtgagcctg gctggagtgg cccccgctgc agccagagcc tggcccgaga cgcctgtgag   15660
tcccagccgt gcagggccgg tgggacatgc agcagcgatg gaatgggttt ccactgcacc   15720
tgcccgcctg gtgtccaggg tgtgtacctc accttccctc tgcagcccca ccaacaccat   15780
gggccttctc atctctcttc tcctctactc tctcctcccg ctatgttagc ttcttttttg   15840
ctttcaatca tttcccctcca ggagcttggg aggtggtat caaggtgggg accctggggt     15900
tgggggaggt ggggggagat gggatcaggg agtccctcaa ggctatctct gcttccctct   15960
cttccacccc caacaggacg tcagtgtgaa ctcctctccc cctgcacccc gaaccccgt     16020 gagcatgggg gccgctgcga gtctgccccct ggccagctgc ctgtctgctc ctgcccccag   16080
ggctggcaag gtatgccacc tgcttctctt ccctcctcct ctccatctcc tctgcccct     16140 accctatcag ggatgatgct ggggatccag agagggaccc atcccagcc ctgcctttga     16200 gaggggcttc cttcttggaa ggacagagct ggacactgat atgcagcctg tgtgggtcag   16260
cccttggaag aggaagagtt atgggctag agatgctggg acttagggcg gggtttaggg     16320
tacagcttcc tggaggagca gacctcatag taggtatttg ccacctactg agacagggag   16380
acggccattc tgaaactgca tatgcaaaat gcccagacac gaatgacagc acggcttatt   16440
ttgccttcac ccatctcggc ctgcaggttc ttcctgagcc ccaggtccct gagaccctgc   16500
```

-continued

```
tctgtaccct gtaaccctag gtgtaacctt gctccctacc cccaggccca cgatgccagc   16560
aggatgtgga cgagtgtgct ggccccgcac cctgtggccc tcatggtatc tgcaccaacc   16620
tggcagggag tttcagctgc acctgccatg gagggtacac tggcccttcc tgcgatcagg   16680
acatcaatga ctgtgacccc agtgagtgca ggggagctct tgggggtgct gctctgggga    16740
acacagtcat taagcttgaa ctgtgtgcct ggcactgtgc tgtcatttca tcttcacagt   16800
tatcttactt ttcccgtttt atttatatgg aaactgaggc ccgaggaggt tgagtgactt   16860
cttgtgcaag cccatggaac gagttaggga atgagctggg cttagaacct tggagtctgt   16920
gtgctgcctc tttttttttt ttttttttt tttttttga  dacagagtct tagctctgtc   16980
gctggagtgc agtgttgcaa tcatcgctca ctgcaacctc tgccttctgg gctcaagcac   17040
ctcagcctcc ccagtggctg cgactatagg cgcacaccac agcgcccagc taatattttg   17100
tgttttttgt agagacggag tttcgccatg ttgcccacgg tggtctccaa ttcctgggct   17160
caagcaatct acctgtctcc acctcccaaa gtgctgggat tacaggcgtg agcaaccaca    17220
cccgacctaa gtgcactgtc tttgagagca atcgagttaa tatcatgtgc aaagtatgag   17280
ataaaaggcc ccccagaggc cgggcgaggt ggctcacacc tgtaatctca gcactttggg   17340
aggccaaggt gggcggatca cctgaggtca ggagtttgag accagcctgg ccaacatgga   17400
gaaaccccat ctctactaaa aatacaaaat tagcagggca tggtggcgca tgcctgtaat   17460
cccagctact tgggaggctg aggcaggaga atcacttgaa ccttggaggt ggagattacg   17520
gtgagctgag attgtgtcat tgtactgcag cctgggcaac aaggcataac tccgtctcaa   17580
aaacgaacaa acaaacaaac aaacaaacaa aaagggggtgc tgccaaacag ataaataaca   17640
caagccacat atgcaatttt aaattttcta gtagccacat taaaaaataa acagaaatgg   17700
gagatattaa atttaatatt ttatatttat ttatttatta tgtattcaga gtgaggctct   17760
gtcgcccagg ctggagtgca gtggtgcgat cttggctcag tgcagtctcg aactcctggg   17820
ctgaggcatt cctcctgtct taacctcctg agtagctagg attacaggca ctcactacat   17880
gcctagctaa tattttatt ttaattctgt agagatgggg tctcactgcg ttgtctaggc   17940
tggtctcaaa ctcctggcct caagccatcc tcctgccttg gactctcaga ctgctgccac   18000
tgtgcctgac caaatttaat atatttaaat ttaatttatt gaatgtatat aatcggctgg   18060
gcgcagtggc tcacaccggt aatcccagca ctttgggagg ctgaggcagg tggatcacct   18120
gaggtcagaa gtttgagacc agcctgacca acatggagaa gccccgtctc tactaaaaac   18180
acaaaattag ctgggcgtgg tggcacatgc ctgtaatctc agctactcag gaggctgagg   18240
taggagaatc acttgaaccc gggaggcgga ggttgtggtg agctgagatc gtgccattgc   18300
actccagcct gggcaacaag agcgaaaccc catctcaaaa aaaataaaaa taaaaataaa   18360
agtaaataaa taaataaata aataaatgta tataatctat ttaacccaat atattaacat   18420
atcatttcaa catgtaacca gtataaaatt gttaatgaga tattttacat tgtttccttt   18480
tttttttttg agacaagttc tcactctgtc gcccagactg gagtgcagtg gtgcgatcat   18540
gactcactgc agccttgacc tcccaggctc aagtgatcct cccgtctcag cctccccact   18600
agctgggact acaggtgtgc accatcatgc ccagctaatt tttgtatttt ttatagaaat   18660
ggggtcttgc catgttgccc aggttggtct cgaactcctg agctcaagtg atctgcccac   18720
ctcggcctcc caaagtgctg ggattacaag tgtgtgccac cacgcccagc ctattttttt   18780
tttcatacca agtcttcaaa atctgaaacc cagtatgtat tttacattta tagcacatct   18840
ccatttagtc acaatttcaa ggactcagta gccacatgtg gctaatggcc actgtccttg   18900
```

```
tcctgttcca agcacaggaa ttagatcagg cacaattagc agcgtttgct tggcagctta    18960
aagggacctt ttggttttcc caacatcctg cccttgccac ataggtgagg tttccagata    19020 aaggaggggga cgaggccaca gaaggggatg gatttagatt cctctgacca aatgcacccc    19080
atcccagttg aacctggttt cctcctgaat tcttctcaat ccaaggcata tcccagtcag    19140
actgggctaa tgggggcaag gtaggtgacc agaccgcctt cctcctgtcc gcagacccat    19200
gcctgaacgg tggctcgtgc caagacggcg tgggctcctt ttcctgctcc tgcctccctg    19260
gtttcgccgg cccacgatgc gcccgcgatg tggatgagtg cctgagcaac ccctgcggcc    19320
cgggcacctg taccgaccac gtggcctcct tcacctgcac ctgcccgcca ggctacggag    19380
gcttccactg cgaacaggac ctgcccgact gcagccccag gtgggcgggg cctctgcttg    19440
gagagcaggg actctggctt gggatggggc ctgggacctg ggacgaagtg gggacagcaa    19500
cgacttgggg gagtcctcag cttggtaccc actgcggact ctgatgactg atggggcagg    19560
gccagggaag gagcagggcg tctgtttgga gctcaccttg gagtctctgg tgcctgagag    19620
ggcatggctt ccaggtggct ctcaccttag ggctgaagtc cctggtgaat tggagctaag    19680
ggacctgatt ggcttctgct ggggctgcag cttcttgccg agataagggt cagggagtgg    19740
gacgtcccca gcgctaacag cgggactcag gaaggagggc agggcctgtg aggggggcgga    19800 gcctgatcct ccctcccact ccttccgctc cagctcctgc ttcaatggcg ggacctgtgt    19860
ggacggcgtg aactcgttca gctgcctgtg ccgtcccggc tacacaggag cccactgcca    19920
acatgaggca gaccctgccc tctcgcggcc ctgcctacac gggggcgtct gcagcgccgc    19980
ccaccctggc ttccgctgca cctgcctcga gagcttcacg ggcccgcagt gccaggtggg    20040
tggagttact ggggacctgg gggaggagcc tgcctgggat cctaggaggg agaagccaag    20100
tcggggcaca gtttctccca gactacccccc caccccacag tactgactct gagtgcttcc    20160
cctccagacg ctggtggatt ggtgcagccg ccagccttgt caaaacgggg gtcgctgcgt    20220
ccagactggg gcctattgcc tttgtccccc tggatggagc ggacgcctct gtgacatccg    20280
aagcttgccc tgcagggagg ccgcagccca gatcggtgag tgggagcatg tgggcgggcg    20340 tgtgggcct tgggaagggg ctcatgcacg tacctcctgc tagtgtgagc cgaatggggg    20400
tgccacagag cctatggggc atgatggggt gtgtggctga gtggtgtggg tgtgtgagca    20460
tgtgacaact ggccgggatg gtgtgtgtct gtcactgtga gacagcaggg atggtgtgtg    20520
tgctacaggg tgtgaccgag ctgctgtgag cgttgaaggc atgtgtgtgt atgtcagtga    20580
tgagaccttg cctgctgggg ggatgtgtga caacctgatg gagtgtgggt gcgatcctgg    20640
ggactcattc caccaaggat gttgaatgat ctgtgtgatg gaggcagaag ggggatgtat    20700
ggggttacct ctgttcctgt gccactctcc tctttgcagg ggtgcggctg gagcagctgt    20760
gtcaggcggg tgggcagtgt gtggatgaag acagctccca ctactgcgtg tgcccagagg    20820
gccgtactgg tagccactgt gagcaggagg tggacccctg cttggcccag ccctgccagc    20880 atgggggggac ctgccgtggc tatatggggg gctacatgtg tgaggtaagg gggcgctccc    20940
caggagaggg aagaggaggt gggcatgctt gggtgcgtct gggcacacat ttctgtgtgg    21000
cttggtatgg gtatgtctct agatatgtct gagtttttgc ttttgtgact cttggtgtat    21060
ctgtgggtgt cactctgggt agatctgggg tgttttttta tttgtttgtt tttttgagac    21120
aggttctcac tctgtcaccc agacgagtgc agtggcgcga tctcagctca ctgcaacctt    21180
tgcctcctgg gttcaggtga ttcttctgct tcagcctctc attatagctg ggagtacagg    21240
```

```
cacccaccac cacgcccagc taatttttgt attttttcata gtgacagggt ttcaccatgt   21300
tggccaggct ggtctcgaac tcctgatctc aggtgatctg cccacctcgg cctcccaaag   21360
tgctgggatt acctactggt agtgcgctga acatctgtgt gtgtcctttt gtgctggggt   21420
tctttgcgtc ttcatgggta tgtccaggtg ggtctgtgtc ccactaagct gagtgggtcc   21480
ctctcttacc ccactgaagt gtcttcctgg ctacaatggt gataactgtg aggacgacgt   21540
ggacgagtgt gcctcccagc cctgccagca cgggggttca tgcattgacc tcgtggcccg   21600
ctatctctgc tcctgtcccc caggaacgct gggtatgcca gggccagggt tggggggaca   21660
ggatgagagg ctgtcttcat tccctcttga ccacccctcg tttcttcccc caggggtgct   21720
ctgcgagatt aatgaggatg actgcggccc aggcccaccg ctggactcag ggccccggtg   21780
cctacacaat ggcacctgcg tggacctggt gggtggtttc cgctgcacct gtccccagg   21840 atacactggt ttgcgctgcg aggcagacat caatgagtgt cgctcaggtg cctgccacgc   21900
ggcacacacc cgggactgcc tgcaggaccc aggcggaggt ttccgttgcc tttgtcatgc   21960
tggcttctca ggtaagcgtt ggcgaagggg ctggcctggg accccgcctg tcattccccc   22020
attgtggctg atctacatgc tcccgctcgc tcaggtcctc gctgtcagac tgtcctgtct   22080
ccctgcgagt cccagccatg ccagcatgga ggccagtgcc gtcctagccc gggtcctggg   22140
ggtgggctga ccttcacctg tcactgtgcc caggtaggtg tgggtggcgg cctttggagg   22200
aggagtaggg gcgtggcctc tggagtagta ggggcgtggc gtctaggagg aggatgtggc   22260
tttaggggag acatcgaagg gaagggagtt tctggaaaat gctgacattt ccgccgggtg   22320
tggtagctca cacctgtaat cccagcacat tgggaggccg aggcgggagg atcacttgag   22380
gccaggagtt agagaccagc ctgggcaaca tggtgaaacc ccgtctctac taaaaatata   22440
aaaattagcc gggcgtagtg gcagctgcct gtaatcccag ctactcggga ggctgaggca   22500
ggagaatcac ttgaacccgg gaggcggagg ttgcagtgag ccatcacgcc attgcactcc   22560
agcctggcga ctgagtgaca ctccgtctca aaaaacaaag aaacaacccc ctgccccgac   22620
atttcctgga ggtttgaagg gaaaagggtg aggatggtga ttggggggcg tggcctcctg   22680
ggatggcagg gcttatctgc caggtggggt ctccagtgtg gaaaggggag cggttgggtg   22740
ggacatgggg aggttgaggg ggtctcaacc ttccttagtc ttgacctctt ctcttccccc   22800
tctctcccct tgactcttct tttccccact cctccatttc ttctcctcct tccctccact   22860
ccccaccctc atttttatcc ctccctcccc aaacccgacc cccagccgtt ctggggtccg   22920
cgttgcgagc gggtggcgcg ctcctgccgg gagctgcagt gcccggtggg cgtcccatgc   22980
cagcagacgc cccgcgggcc gcgctgcgcc tgccccccag ggttgtcggg accctcctgc   23040
cgcagcttcc cggggtcgcc gccggggggcc agcaacgcca gctgcgcggc cgcccccctgt   23100 ctccacgggg gctcctgccg ccccgcgccg ctcgcgccct tcttccgctg cgcttgcgcg   23160
cagggctgga ccgggccgcg ctgcgaggcg cccgccgcgg cacccgaggt ctcggaggag   23220
ccgcggtgcc cgcgcgccgc ctgccaggcc aagcgcgggg accagcgctg cgaccgcgag   23280
tgcaacagcc caggctgcgg ctgggacggc ggcgactgct cgctgagcgt gggcgacccc   23340
tggcggcaat gcgaggcgct gcagtgctgg cgcctcttca acaacagccg ctgcgacccc   23400
gcctgcagct cgcccgcctg cctctacgac aacttcgact gccacgccgg tggccgcgag   23460
cgcacttgca agtgagccca tccacccgat cgatccgtct gtctatgcat ccatcccagt   23520
ctgtttgtcc gtgggccctg cctctctttc cacctgccca tccacttgcc ccgtctgttt   23580
ctctgtgcac tctatctgcc catcggtgtg tcccacgtgt ctgtccgtgt gtctgttcat   23640
```

-continued

```
ccatgtgctc tgtctatctt gttcttgttt ctatctgcct atgcacttct ctgccccgtt    23700
tgtctgccct tttctccatc caataattac tttttttttt ttttcccgag atggagtctt    23760
gctctgtggc ccaggctaga gtgcagtggc gcgatctcgg ctcactgcaa cctctgcctc    23820
ccgggtttaa gcagtactcc tgcctcagcc tctggagtag ctgggattac aggtgtgagc    23880
caccgtgccc agccgaattc cttttttttt tttttttttt ttttaagacg gagtctcgct    23940
ctcttgccca gactggagtg caatggctcc atcttggctc actgcaacct ccgcctcccg    24000
ggttcaagcg attctcctgc ctcagccttc cgagtagctg ggactacagg tacctgccac    24060
cacgcctggc tttttttttg tattttttagt agagacaggg tttcaccata ttggccaggc    24120
tgctcacgaa ctcctgacct tgtgatccgc ccgccttggc ctcccaaagt gctgggatta    24180
caggtgtgag ccaccgcacc tggctccttt tttttttttt tttttttttt tttaagacag    24240
ggtcttgctc tgtggcccag gctggagtgc agtggtgtga tcttggctca gtgcaatctc    24300
tacctcctgg gctcaagtaa ccctcacacc tcagcctccc taggagctgg gaccacaggt    24360
gtgagccacc gcgcccgggt aacttttgtg cttttttctta gagatggggt ttcgccatgt    24420
tgtccaggct agtcttgaac acctgagctc aaagcaatcc acccagctta gcctctcaaa    24480
gtgctgggat tgtgggcctg agccaccaca tctagcctaa aaattccttt tattggccgg    24540
gcacagtgct cacgcctgta atcccagtac tttgggaggc agaggagggc agatcacctg    24600
aggtcaggag tttgagcttg ggcaacatgg tgaaactccg tctctactaa aaatacaaaa    24660
ttagccgggt gtggtggcac atggctgtaa tcccagctac tcaggaggct gaggcaggag    24720
aattgcttga acctgggagg tggaggatga ggtgagctga gatcgtgcca ttgcactcca    24780
gcctgggcag caagagtaaa tctctgtctc accaaaaaaa aaaaaaaaaa aaaaaattgc    24840
ttttgttcct ctgtgtaccc aactgtcttc ctccactcct gtttgtccat ccttgggccg    24900
aatctgtcca tccatgcact cttttttgctc ctctatatgg ctatctgtgg gtgcccctga    24960
ctatctctgc ccctcttctg cccctctctc tgtctgtcct aggcagtcca tctgtccatc    25020
cctacaccct gccccttctg tcctctgcgt acctctctgt ctgcttggaa ccctccaccc    25080
ccttaatctc cacatcctca tcttctctgc tttcccctca ctcactctgt tccagccacc    25140
ctggcctctc tgctgtttcc cagatacccc aggcttgatc ccatatcagg gcctttgcac    25200
aagctgttcc tactgcctgg ctgttccctt cccccacatg gctcctccct cacctccttc    25260
aagtctttgc tgaaatggtg gtaccttctc agtgagcacc tccctggtca cccccagccc    25320
ttcctctgct ttattttttct gcttagcatt taattccatc cagcactatg tgtgtgcgtg    25380
cgtgtgtgtg tgtgtgtgtg tgtgtatata catatatata catatatata tatatatatg    25440
tatttttttt tttttttttt ttagacagga tttctctccc attgcccagg ctggagtgca    25500
gtggtgtgat cttggctcac tgcaacctcc acctcctggg ttcaagctat tctcctgcct    25560
cagcttcccg agtagctggg attacaggcg cccgccacca tgcctgacta attttttgtat    25620 ttttagtaga gacgggggtt tcaccatttt ggccaggctg gcctagaact cctgacctca    25680
ggttatccgt acaccttggc ctcccaaagt gctggaatta gaggcatgag ccaccgcacc    25740
cagcctgtat ttttattttta ttgatgagta atggagatgc tgtatatttg gctcatgtat    25800
ctcccttact atctgtcttc acccagtgga atgccagctg cacgtggacc aggaattgtg    25860
gccgggcctt atccttgtgc ctgcagcagt gcccaacaca tggtagtcag ttagtattta    25920
ctgattaatt aatagttagc cagtgaggcc gggagtgtgg tgtgggtttg tagtcctagc    25980
```

-continued

```
tacttgggag gctgaagagg gaggataatt tgagtccagg agtttgagat tgcagagagc   26040
tatgattgca ccactgcact ccggcgtggg caacagagca agacccatt tcaatcaatc    26100 aatttaaaaa aatattatca agggctgcgt gcggtgactt atgcctgtga tcccagcact   26160
ttgggaggcc gaggcaggtg gatcacctga ggtcaggagt tcaacagcag cctggccaac   26220
atagtaaaac cccgtctctg ctaaaaatac aaaaattaga cgggcgtggt ggtgcatgcc   26280
tgtaatccca gctacttggg aggctgaggc gggagaatcg ctggaaccgg ggaggtggag   26340
gctgcagtga gctgagagat catgctactg cattccggcc tgggcgacag agcaagactc   26400
cgtctcaaaa aaaaaaaaa aaaattatcc agtgaatggc aagatttgca gaaagcctgg    26460
catgggtccg tatattccag tcccctgtgc aagccttgtc tggagtctct gtactctacg   26520
gtgtgaatgc atggaagggg attgtctcct ctgacccctg actccgcccc tctctgcctc   26580
acccttcccc accagcccgg tgtacgagaa gtactgcgcc gaccactttg ccgacggccg   26640
ctgcgaccag ggctgcaaca cggaggagtg cggctgggat gggctggatt gtgccagcga   26700
ggtgccggcc ctgctggccc gcggcgtgct ggtgctcaca gtgctgctgc cgccagagga   26760
gctactgcgt tccagcgccg actttctgca gcggctcagc gccatcctgc gcacctcgct   26820
gcgcttccgc ctggacgcgc acggccaggc catggtcttc ccttaccacc ggcctagtcc   26880
tggctccgaa ccccgggccc gtcgggagct ggcccccgag gtgatcgggt gagtgacccc   26940
acctggaaaa gccgtggtgg ctggggagag gagagatgct gttgatccag gtcttgtgtg    27000
tttcatttca cttaatgcct ttacccacca gatgtcagga gcaccgcctc ctggctgtga   27060
caagcaaaaa atgcctccag atggagctag tgcttctggg gtagaattgc ccaggtctag   27120
tgctggcttg tggggaggca ggttgctaag tggcttggca gagtggttaa atacatgtgt   27180
agggtttttt tcttcttctt cttcttcttc tccttctcct tctccttctc cttctccttc   27240
tccttcttct tttcttttt ttttttttt tgagacggag tctctgtcgc ccaggctgga    27300
gtgcagtggc gtgatctcag ctcactgcaa cctctgcctc ctgggttcaa gcaattctct   27360
gcctcagcct ccagagtagc tgggattaca ggcatccacc accacaccgg gctaattttc    27420
ttcttcttaa agacatagaa gataaagccg ggcacaatat attcttgtag tcccagctac   27480
ttggaggatc acttgagccc aggaattcaa atctagcctg ggcaacatag caagactccc   27540
atctctctct ctcttttttt ttttttttt ttttgagacg gagtctcgct ctgtcgccca   27600
ggctagagtg cagaggcgcg atctcggctt tctgcaagct ccgcctcccg ggttcatgcc   27660
attctcctgc ctcagcctcc cgagtagctg ggactacagg cggccgccac catgcctggc    27720
taattttttg tatttttagt aagagacggg gtttcagtgt gttagccagg atggtctgga   27780
tctcctgact tcgtgatcca cctgcctcgg cctcccaaag tgctgggatt acaggcgtga   27840
gccaccatgc ccggcctccg atctcttaaa aaaaaaaaa aaaaaaaaa agaagaagaa    27900 gaagaagaag aagaagaaga agaagaagaa gaagaagaag agggaggagg gaggggagg    27960 gggaggggga ggaagaggaa gaagaaggaa gagggggagg gggaggagga ggaggaagag    28020
gaagaagaag aaagaaatag gaggggctcg gtggctcacg cctgtaatcc cagcactttg   28080
gaaggcagtt catttgacgt caggagtttg agaccagcct gggcaacatg gcaaaaccct   28140
gtctctacta aaaatacaaa aaattagcca ggcgtggtgg tgtatgcctt tagtcccagc   28200
tactcaggag gctgaggcat gagaatcact tgaactcagg aagtgaaggt tgcagtgagc   28260
caagattgtg ctactgcact ccagccgggg caacagagcc agactctgtc tcaaaaaaaa   28320 aaaaaagaa aaagaaaaaa tatagaagta tcctgctagt ggcctggtag aggtaccaga    28380
```

-continued

```
agggaggtgt agctattgtt gaggagaagg cagagacctg agaggggtgg gtctctgata  28440
cagagaggag ggttgggttt tgcagatatt gggatgtggg tggtggaagg ggaggggtag  28500
agggatgaag gagagtggtt ggtgtaccag cccctggcta agctgagtga tagggccaca  28560
aagtgaaaaa caggtcattt tggagcttgc agagtctgag ggacctggaa gtattgggaa  28620
ggcctccaag gagatacctg ggggctaaag acacaaacaa gaaagatata aaagtgttga  28680
tgatcattga agccatgaga gggactcaaa ggagtgggga gagaaggaac agaagaatta  28740
atctggggac acggagacct aaggattgga tgaatggaat tagctcaaaa aagaggaaga  28800
ggccaggtgt gatggctcac aactgtgatc ccagcacttt gggaggttga ggcgggtgga  28860
tcacctgagg tcgggagttc aagaccagcc tgaccaacat ggagaaaccc tgtgtatact  28920
aaaaatacaa aattactggg gcgtggtggc gcatgcctgt aatcccagct actcaggagg  28980
ctgaggcagg agaattgcct gaaccctgga cgtggaggtt gtggcgagct gagatagcac  29040
cattgcactc cagcctgggc aacaagagtg aaactctgtc tcaaaacaag caaacaaaca  29100
aacaaataca atgtcctggc caacacggtg aaaccccgtc tctactaaaa atacaaaaat  29160
tacctgggcg tggcagcgcg tgcctgtaat cccagctact caggaggctg aggcagagaa  29220
tcacttgaac cagggagtcg gaggttgcag tgagctgaga ttgcaccact gcactccagc  29280
ctgtcgacag agcaagactt catctcaaaa acaaaaaaca aacaatgtcc cttggctggg  29340
cgtagtggcc caggcctgta aacccagcac attgggaggc tgaggtggga ggattgcttg  29400
agccccggag ttcaagacta gcctgggcaa catagtgaca cctaatctct atgcctccac  29460
ccccaacccc ccccaaaaat tagccaggtg tggtggcaca tgtctgtggt cccagatctt  29520
tgggagaatg aggtggaaag attgcttgaa ggcgggaggt caaggctaca gtgagctctg  29580
atttcgccac tgtgctctag cctgggcgac agagtgaaac cgtctcaaaa aacaaaacag  29640
aacaaacaaa caacaaaaaa aacaggccag gcacagtggc ggctcacgcc tgtaatccca  29700
gcactttggg aggccaaggc agggaggatc acttgaggtc aggagttcaa gaccagcctg  29760
gccaacgtgg tgaaaccccg tctctactaa aaatacaaaa aaattagctg ggcatggtgg  29820
cacacgcctg taatcccagc tacttgggag gctgaggcag gagaatcgct tgaacccagg  29880
aggggaagtt gcagtgagcc gagatcgcac cactgcactc cagcctcggt gcaagatcaa  29940
aaaataatat ccattggatt catggctctg gggggactgc tgaccacagc aagacacgtt  30000
ttaggggtgc agtggggttg gatgccaggt ggatgcaggt gggccatgga gacctgtggg  30060
tggagatggc gcttcagagc caggcgctgg ggagggaaag tggggcttgg taccaggggg  30120
tgcatcgggc aattttttgag ccctctggtc cctccctgct gtccctgcag ctcggtagta  30180
atgctggaga ttgacaaccg gctctgcctg cagtcgcctg agaatgatca ctgcttcccc  30240
gatgcccaga gcgccgctga ctacctggga gcgttgtcag cggtggagcg cctggacttc  30300
ccgtacccac tgcgggacgt gcggggtgcg gccctgcctt ggggaggggg tggcgggggc  30360
ggagctgggg gcggccgaag ccccgcctga ggccaaagcc ccgccctcgg ctgaagcccc  30420
gccctctgct tcctgctctt aggggagccg ctggagcctc cagaacccag cgtcccgctg  30480
ctgccactgc tagtggcggg cgctgtcttg ctgctggtca ttctcgtcct gggtgtcatg  30540
gtggcccggc gcaagcgcga gcacagcacc ctctggttcc ctgagggctt ctcactgcac  30600
aaggacgtgg cctctggtca caagggccgg cgggaacccg tgggccagga cgcgctgggc  30660
atgaagtgag aaccctgctc gctccctgtc cctgactacg gggaccttgt gaaccctgga  30720
```

-continued

```
ccccgccttg acctgactca gacctctgac cccaccccaa atcctccttc ccagctggac  30780
acctctagtg tcccctcac atcccctctt cccattgtcc gccaggaaca tggccaaggg  30840
tgagagcctg atgggggagg tggccacaga ctggatggac acagagtgcc cagaggccaa  30900
gcggctaaag gtactgcccc ccctctgacc tttgcccct cctctgaccc ctcccctcag  30960
ggtactgggt ggggtcccca gtggatgatg ggcgtgatca ggggatggca ccgctgtccc  31020
cacctcccta gctccagaga atagtcccag ctttgcaacc ctttcttctc agtgtggttc  31080
tgtgacctca gagggaggaa gatttgccac tggggcccca agggtccctc cgggcaggtg  31140
gaaaatcctc ccctccatcc tgcccctccc cagccaggat cctgcttcct ggccagcctg  31200
cactcttcct ggaggtgtcc ccccagccca gagagcgagt ctgccttatc tctgtcagtt  31260
cctattttgt ccagcatgga cttagcctga aagtgctctg agccggttct gagctcatgg  31320
agtcatgccc ctgggttcag tatgagtcag ctttggctgc cattaaaaaa tcccacagag  31380
gtggatcacc tgaggtcagg agttcgagac cagcctgacc aacatggtga aaccccgtct  31440
gtactaaaaa tacaaaagat tagctgggca tggtggcggg cacctgtaat cccagctact  31500
tgggaggctg aggcaggaga atcccttgaa cctggcactc cagactgggc aacaagagcg  31560
aaactccgtc tcaaaaaaaa aaaaaagtcc cacagcatgg gtgacctaaa caacagaaat  31620
taattttttc acggttctgg aggttggaag tccaagccca aggtgctgtc agggctggtt  31680
cctggtaagg gctctcttcc tggtgtgcag atggccgcct tctcactgta gcctcacatg  31740
gcctttcctc tgtgtacaca gaggggagag agagagagag agagagagag agagagagag  31800
agagagagac agatttgaca tcccatcctc ttcttgtaag gataccaatc ctattggatt  31860
agggtcccac atttataacc tcatataacc ttaattacct ccttaaaggc cctatctcac  31920
caggcttggt agcttgcacc agtaatttca gctacttggg aggctgaggc aggaggatca  31980
cttgagtcca ggagttggag cctgcagtga gctatgactg catcacttca ctccagcctg  32040
ggtaacagag caagaccctg tctaaaaata aagtcctatc ttcaaatgca ggcacatgga  32100
aattttatat attatttagg gtttagtgt atgatttctg tttatttatt tatttatttt  32160
ttgagaccag gtctcactct gttgcccaag ctggagtgca gtggcgtgat cttggctcat  32220
tgcagcctcc acctcccagg ttcaagtgat tcccctgcct cagcctcccg agtagctggg  32280
attataggca tgtgctacca tgcccggcta atttttgtat ttttagtaga gatggggttt  32340
caccatgttg gccaggctgg tctcaagctg cagacctcaa gtgatccacc cgcctcggca  32400
tcccaaagtg ctgggattac agacgtgagc caccgtgccc ggccattgta tgattttag  32460 aggggcaca attgagtcca tacagatcct gctagcatta ctgaggcacc cgctgaatgt  32520
ctctaatgca cataaaacat cttatttcat ctctctgagg acgctgtaaa gtagctattg  32580
acatatactt caatttacaa actcccttcc tctgtccata ttttaatgtt gtgaaatgga  32640
atcatctatt acagtggaca gataaaaaaa cctgctcaac ccagactttt ccttctgcct  32700
tcccatccca aagtaggtat tagaggtatt aaaggggtgg cccaatgtaa ttgtggtggt  32760
atcttagcat ggtggaatgg ctgcgtcatc ctgattttgc caatgagaag ctcagagctt  32820
caaagtgatt tgcccagagc cttccagcta ctaaggggtg gggttggaac ttgaacctgg  32880
atcagatgct atcccaatct gcttatactg tgtgcttata gtcccagcta cttgggccgc  32940
tgaggtggga ggatcatttg agcccaggaa gttgaggctg cagtgaggta tgattgcagc  33000
actgcactcc agcctgagtg acacagtgag actcagtctc taaaaaatat atacataaat  33060
aattaaagcc atttattact caaaaagacc aaaaaaaaaa aaaaaagaa accttgtgtc  33120
```

-continued

```
ttccttttat tacctccttg ggctatggca cacattgatt tcctgttaat ctcagcactt   33180
tgggaggctg agaggggctg atcacctgag gtcaggagtt cgagaccagc ctggccaaca   33240
tggtgaaacc ccttctctac taaaaataca aaaaattagc tggacaccgt ggcatgtgcc   33300
tgtaatccca gctactccag aggctgaggc aggagaatca cttgaacccg ggaggcgggg   33360
gttgcagtga gctgagatca tgccactgca ctccagcctg ggggacagag cgagactctg   33420
tctcaaaaac aaataaaaca ccaaacagat ggtaaatgat ttcccagggc tctgtgtgta   33480
tctcctaaag agaaacctgt aggaatgccc agccccatcc ctggcagtgg ctctccccag   33540
caccaaaggg tgagatctga gatccagggt gcctgcccct ccaggtagag gagccaggca   33600
tgggggctga ggaggctgtg gattgccgtc agtggactca acaccatctg gttgctgctg   33660
acatccgcgt ggcaccagcc atggcactga caccaccaca gggcgacgca gatgctgatg   33720
gcatggatgt caatgtgcgt ggcccaggtt agtgacagtg cccctcccaa agggatgccc   33780
ctcacccatc ctacctgtga gaggttattt ctgactctgt gttttgggga gaactggggg   33840
agtctctaag cttctgtgaa gggtgtgtgt attcagcaac actcttggtt ggaagtgaca   33900
aaggtccaac tcagactagc ttaagtaaaa caagggattt atcaactcat ttaactaaaa   33960
gtggcacatt tggatccagg actcagtttt cccctctcta ccctttgact ccaatcttac   34020
aaaaccttct taatgctcca gaaaagtctc aggatgcatt ctgattggac agactagggt   34080
cacgtgctca tccttgagcc aatcagtatg accagggggc tggaatatgc aaattgacca   34140
agcctgattc acatacctgt ctttgagctg gtgggggtcg ggtctgctgg tggagcgggg   34200
aggtcagtct ctacccaggg cttgagaatg gagaaccgga tgcaagtggc tccctaagaa   34260
aaatgaggac aagtgcttgt gtacagtgtg tgcagtgtag cggactatgt tgtttgatcc   34320
tcttagatcc atctttgtta tgtttcaggg cattcctgcc ttagcttcat tttgcttatg   34380
ctccaaatgg cctgtactta tggctctctt ttgaagtccc tctggctgct ggggcctgaa   34440
gtgcctggga ttttatgtcc ctgggggcag ctcttttttt cccccccccct tttaaaacac   34500 tcaaatgaat tggcagaaag gggcagctcc taaccagtgg gtgcaggagt atgaagggga   34560
tggtttcttt gccttgagtt ggattagaac tctggggtac aacacatgtt ccagagtccc   34620
tttggaggat caaggtggaa taaccctttg ggaatttact ggaggttgca cacttgcttg   34680
actcccagag tcccttgtcc tgtgttccct gtgccctagg agtagttctg tgacaaatca   34740
cgtgcccacg aatcctcatt ctgggtgtgg gtgtgcagac aggaggatct gctaattgtc   34800 attttttccat gtgtcccatt agctcctaat ggggtaccct tgataacatt tcctggaaaa   34860
ggccctgtgt ttaccttcct gctgacacac tcctgtccct gcagatggct tcacccgct   34920 aatgctggct tccttctgtg ggggggctct ggagccaatg ccaactgaag aggatgaggc   34980
agatgacaca tcagctagca tcatctccga cctgatctgc caggggggctc agcttggggc   35040 acggactgac cgtactggcg agactgcttt gcacctggct gcccgttatg cccgtgctga   35100
tgcagccaag cggctgctgg atgctggggc agacaccaat gcccaggacc actcaggccg   35160
cactcccctg cacacagctg tcacagccga tgcccagggt gtcttccagg tgagataggc   35220
acacactttg gacctcagag ctggggcagg cattagactt acctgggttt gagccccagt   35280
tctgcctttc agactcattt tttctcattt ggaaaatggg gatatatggg aatacagtat   35340
ctgtcaagca gctgctccct gaacctcacc aatttcaggg gttggggtat gggggttggg   35400
gacttcatgg gacttagggg tgctcctgat tcctctgttc ctgccatgac ccctcctgct   35460
```

-continued

```
gcatccactc tctgtcctag attctcatcc gaaaccgctc tacagacttg gatgcccgca   35520
tggcagatgg ctcaacggca ctgatcctgg cggcccgcct ggcagtagag ggcatggtgg   35580
aagagctcat cgccagccat gctgatgtca atgctgtgga tgagcttggt aggttggcag   35640
aggaatcaag tctaagctgg gttggtgtca cctgggccct gagggtcatg ttggtgcaaa   35700
ttcataccca tgttgagacc caatcactga agctcacgca cacataacca ggcttcatga   35760
agcctgcagg gtcatgcagg gtcaccacta gtccttaggg tgcctcaggg atttagaaaa   35820
aggtgccttt cccctagata cttcatttcc acctgctttg ttagacggac acactgtact   35880
tccacctgct ggaagttatt ataataaacg tacacatcag gccatgtgtg gtggctcatg   35940
cctgtgatcc caacactttg ggaggctgag gcaggaggat gacttgaggc caggagtttg   36000
agaccagact gggcaacata gtgggttcta caaaagtttt ttgaaagatt agccatgtgc   36060
ggtggtgcat acctgtggcc ctagctactc cagaaactga ggtgggaggg tcgtttgagc   36120
ccaggaggtt gagtctgtga gccgtgattg tgcccctgca ctccagcctg ggggacagac   36180
tccatctcaa aaaaaaaaaa cagtctccag acgttgccaa atgctctggg ggctgggggc   36240
agggagtttc tcctagttga gagccacagt tctagggcag ggctggccaa taggactttc   36300
tgtgatgatg gaattattct ctgcactgtc cagtatagta gccactggcc acatatagtg   36360
acttgaaatg tgactgaggc aaatgaagaa gtaaatgttt tagttcattt aattttttc   36420 tccttatgtt gcccttttt taattttttt ttttgagaca gagtctcact cttgtcaccc   36480
aggctggagt gcaatggtgt gatcttggct cactgcaacc tccactaccc aggttccagt   36540
gattctcctg tctcagcctc ccaagtgtct gggactaaag gtgcccatca ccatgcctgg   36600
ctattttttt gtatttttag tagagacggg gtttcgcaat gttggccagg ctggcctcaa   36660
actcctgacc tcaggtgatc cacctgcctt ggcctcccaa agtgctgggg ttataggcat   36720
gagccactga gtccatcctt ttttttaaaa acaaaaaaca aaaaacaaaa aactgcttta   36780
ttgagatata attaacatgc catacaattc acccatttaa agtgtacaat tcaatggctc   36840
ttagtataat cagagtcata caactattac cacaatcaat tttagaacat ttcatcacct   36900
gaaaaataaa ttctcaccac ttggccatca tctgccaagc ccctcatctg tccagccctg   36960
tgcaaccact gatttgcttt ttgtcttcat ggatttgcct gttctggaca tttcatataa   37020
atgtaatcat atgatacgtg gtcttttttg tctgccttt tttcagttag cattatgttc   37080
tcaaggttca cccatgttgt agcatagttc agctgaataa taatccattg tgtcgatgga   37140 ccacttttt tttctttat ttttagacat agggtatcac tctgtcactc aggctggagt   37200
gcagtggcat gattacggct ctctgcagcc tcaaactccc aggctcaagt gatcctccca   37260
tcccaccctc ctgaatagct ggtattacag gtgtgtgcca gcatacctgg gtaattctta   37320
aattttttgt ggaaatgggg tctcactttg ttgcccaggc tgatctcaaa ctcctggcct   37380
taagcaatac tcccaccttg gcctcccaaa ttgttgagat tataggcgtg agccactgtg   37440
cctggccaaa agtttcaatt ttgatcatgt ccaatttatc tgttttgtag ttgttattgt   37500
tatttgtggt tttggtgtca catctaagaa tcttggccta attcaaggtc atgaagattt   37560
actcttatgt tttcttctag atgtttagtt ctatagttgg agctcatata tttaggtttc   37620
tgatccattt tgagttagtg tttgtataaa gtgtgaggta ggggtccaac ttcattcttt   37680
gaatgtgaat attcagttgt tccagcacca ttagttgaga agaccattct ttccccattg   37740
aatggtcctg gcacctattt tattaaattt aaatctaaag aaccacatgt aggttgggca   37800
cggtggctca tgcctgtaat cccaacactt tgggaggcca aggctggtgg atcacttgag   37860
```

-continued

```
cttaggagtt tgagaccagt ttgggcaaca tagtggaact ctatctctat caaaaataca   37920
aaaaatcagc tgggcatggt ggtacatgcc tgtagtccca gctactaggg aggctgaggc   37980
aggaaaatcg cctgagccca gcaggtagag gttgcagtga actgagattg tgccaatgga   38040
ctccagcctg ggtgacagaa caagacacta cctcaaaaat aaataaatgg ataaataaaa   38100
accacatgtg actgactact gtattggatg tcacaaccct aggttcaact gaaggaggtc   38160
cacacagcac ccctgtgta taaacagtca tgcacatgca cgcacacaca cacacacaca   38220
caaacacaca cacagaca caaagtgctt ccccattgca cagagtcatt ttgcagattt   38280
gcacacacat ggatccagac acaagtactt ggatattcac ggcaggcctg cctcctctac   38340
ccctaggcca cattctagac aatttctgcc tccctgacat gggggcccca ggacaggtgc   38400
ctggtcctga cctctctccc cttcatcctc cagggaaatc agccttacac tgggctgcgg   38460
ctgtgaacaa cgtggaagcc actttggccc tgctcaaaaa tggagccaat aaggacatgc   38520
aggatagcaa ggtgagcccc agccttggt ccactgggtg tcagcagtgg cacagtgcca   38580
ttgcaatcca gcctgggcaa cagagtgaga ctctctcaaa aaacaaaaca aaataaaacc   38640
ccaaacattg gattaaaata taatttactt tggtgactaa agtttttggg ggcccccttaa   38700 attttgtgcc taatggctgg gtgtggtggt tcatgcctat aatcccagca ctttgggagg   38760
tcgagatggg tggattactt gagttcagga gtttgagacc agcctggcca acgtagtaaa   38820
accctgtctc tattaaaaat acaaaaatta gctgggcgta gtggtgcaca cctgtagtcc   38880
cagctgctcg ggaggctgag gcaggagaat cgcttgaacc cggaaggctg aggttgcagt   38940
gaactgaaat ggcgccactg cactccagcc tgggcgacac agtgagactc tgtcaaaaaa   39000 aaaaaaaaa aaagacaaga aaaaaaagt tatgcctaag gtgagtacct cgcttaactc   39060
accctagtcc tggccttgac ctctggcact tagtaggtga tggatgaatg tggtttagag   39120
gaaagaactt gtccaggctc ccccagcaca gccgggattt aacccaggtc tgtcaagctc   39180
cagtgtacaa actcatagct ctcgggctcc cccaagaggc tggaagactt tgctactgtt   39240 agctgggtt tcgctgacct ctgtgggttc tggccccca ggaggagacc cccctattcc   39300
tggccgcccg cgagggcagc tatgaggctg ccaagctgct gttggaccac tttgccaacc   39360
gtgagatcac cgaccacctg gacaggctgc cgcgggacgt agcccaggag agactgcacc   39420
aggacatcgt gcgcttgctg gatcaaccca gtgggccccg cagcccccc ggtccccacg   39480 gcctggggcc tctgctctgt cctccagggg ccttcctccc tggcctcaaa gcggcacagt   39540
cggggtccaa gaagagcagg aggccccccg ggaaggcggg gctggggccg caggggcccc   39600
ggggcggggg caagaagctg acgctggcct gcccgggccc cctggctgac agctcggtca   39660
cgctgtcgcc cgtggactcg ctggactccc cgcggccttt cggtgggccc cctgcttccc   39720
ctggtggctt ccccccttgag gggccctatg cagctgccac tgccactgca gtgtctctgg   39780
cacagcttgg tggcccaggc cgggcgggtc taggcgcca gccccctgga ggatgtgtac   39840
tcagcctggg cctgctgaac cctgtggctg tgcccctcga ttgggcccgg ctgcccccac   39900
ctgcccctcc aggcccctcg ttcctgctgc cactggcgcc gggaccccag ctgctcaacc   39960
cagggacccc cgtctccccg caggagcggc ccccgcctta cctggcagtc ccaggacatg   40020
gcgaggagta cccggcggct ggggcacaca gcagccccc aaaggcccgc ttcctgcggg   40080
ttcccagtga gcaccttac ctgaccccat ccccgaatc ccctgagcac tgggccagcc   40140
cctcacctcc ctccctctca gactggtccg aatccacgcc tagcccagcc actgccactg   40200
```

-continued

```
gggccatggc caccaccact ggggcactgc ctgcccagcc acttcccttg tctgttccca   40260
gctcccttgc tcaggcccag acccagctgg ggccccagcc ggaagttacc cccaagaggc   40320
aagtgttggc ctgagacgct cgtcagttct tagatcttgg gggcctaaag agacccccgt   40380
cctgcctcct ttctttctct gtctcttcct tccttttagt cttttttcatc ctcttctctt   40440 tccaccaacc ctcctgcatc cttgccttgc agcgtgaccg agataggtca tcagcccagg   40500
gcttcagtct tcctttattt ataatgggtg ggggctacca cccaccctct cagtcttgtg   40560
aagagtctgg gacctccttc ttccccactt ctctcttccc tcattccttt ctctctcctt   40620
ctggcctctc atttccttac actctgacat gaatgaatta ttattatttt tattttttctt   40680 ttttttttta cattttgtat agaaacaaat tcatttaaac aaacttatta ttattatttt   40740
ttacaaaata tatatatgga gatgctccct cccctgtga accccccagt gcccccgtgg   40800
ggctgagtct gtgggcccat tcggccaagc tggattctgt gtacctagta cacaggcatg   40860
actgggatcc cgtgtaccga gtacacgacc caggtatgta ccaagtaggc acccttgggc   40920
gcacccactg gggccagggg tcgggggagt gttgggagcc tcctccccac cccacctccc   40980
tcacttcact gcattccaga tgggacatgt tccatagcct tgctgggggaa gggcccactg   41040 ccaactccct ctgcccagc cccacccttg gccatctccc tttgggaact aggggggctgc   41100 tggtgggaaa tgggagccag ggcagatgta tgcattcctt tgtgtccctg taaatgtggg   41160
actacaagaa gaggagctgc ctgagtggta ctttctcttc ctggtaatcc tctgcccag   41220 cctcatggca gaatagaggt attttttaggc tattttttgta atatggcttc tggtcaaaat   41280
ccctgtgtag ctgaattccc aagccctgca ttgtacagcc ccccactccc ctcaccacct   41340
aataaaggaa tagttaacac tcagtgttgt tggtctgtgt ctaggtaagg tggggagtgg   41400
tggcagtggg acttctatct cccccaccca gggctaactt gagctcccat cttggggtaa   41460
atacatttga cttgccagtc tacttatgct tcctcttttg gcagatgact accgattgga   41520
ttagtggttg tcacctgact taagctgagc caatcagatt cttttgctcg agaactttct   41580
ttaatggaga ggctaagaaa gttgtcagtt ggtggagctc ttaaggtcac aatcagattt   41640
agaaatatca gtggccaatt cgaggtggtg ggcaaagaga caagcaaaca gggcagaaga   41700
atgaagctaa tattcaggga gaatcagaaa tgagagctca aatggctcct tgagggctgg   41760
gggggttatc tcggctccca gtgcagttat caattccagt taattgagtg ttcattccat   41820
tgagatcaac aggtatttat taattgcttt ctaagtatct gatcatggtt ctgcatgaat   41880
ttcactttta cttcatgctc ctatgggttt tggagataac cttggaccca tgtaataaat   41940
acttctttac ttgtgcca                                             41958
```

```
<210> SEQ ID NO 2
<211> LENGTH: 41958
<212> TYPE: DNA
<213> ORGANISM: homo sapien

<400> SEQUENCE: 2
```

```
cttcggcgaa gttggcggcg cggaggctgg cccgggacgc gcccggagcc cagggaagga     60
gggaggaggg gagggtcgcg gccggccgcc atggggccgg gggcccgtgg ccgccgccgc    120
cgccgtcgcc cgatgtcgcc gccaccgcca ccgccacccg tgcgggcgct gcccctgctg    180
ctgctgctag cggggccggg ggctgcaggt gaggggccgg gacctggcgg atgggacgag    240
ggcggcagag ggggagtgca agaaccccca aggccggggc tggcggggt tcatgggagg    300 caggaaccag ggtcggggaa ggggcgcagg agccccgggc ttcatgccag tcctggagga    360
```

```
cccagagatt cagaatgggg aggaccccag aggcccaagg aacagggacc cttgagcgat          420
tagagctgaa gatgaaggga cccaggagtc cgagactggg agctcgaggt gcggggatca          480
gggactcgag gtggggggggt gcgtacagag ttcgggactc gtccccatcc aactcacgcc         540
tggagtcctg ggtaggttat gattgggggc ccaggtactt ctaggccggg gacctctcgc          600
acaaaagccc ccccacccccg ccccccgacac cccgggcggg ctgggccagg cgggggggtgg        660 ggaggggggcg cgaagttctg ggagctctga actcggagaa aacttcccag gccggcgcgc         720
agcaagaccc ggagccggat tccgagccgg agcctcggcg gcgcgcgcgc ccctccccc          780 gcccgcagcc cgcctctctc ctctggccgc ggggacccgg aggccctggg accccgcccc          840
tgcgcgggga ggggaagggg cgagggccca cgtgctcccc ttcggctcca gcgccccctc          900
cccgcggcca gagcccctcc ccagccggcc aggggccccc gccctcctc ctctcctccc          960 tcccctcccc cgctcgggac aatggccgcg ccgtctagac accccctccc tccggccggc         1020
ctcgcgcttt ctttgccaga caaagcggga cccgcggctg ggcggggag ggggctgcgg          1080 gggcacccccc ctcaccgcta cgggaggcct ggtgggcggg ggagggggcgc gggccaaggc       1140 ccctggccag gggtcccaga cgccagtgtg gggcttggcg ctgggcgggg tgggggtttc         1200
gggagtgaac ggcctcccca gcccagcccc ggggcccgga cggggcagga ccaggcagga        1260
gccgccgcct ccgccggacc agcggcgcac acacatggcc tgtgacacac tcgctggcac        1320
acatagctct aggtcacgta acagagatgc aaacctgcac acacacagca cactcgcaga        1380
cttgcacacc tggctcagga aagacacacc cagctgcacg cacacagctc acacattgac        1440
atacatacac acacaaatat gatcacacag gtgtggcaca cacgctgcct gcacacactc       1500
agacagcaca tagatgaaga ctcaaggaca tgcttacacc cagctcacac atgcagatgg        1560
acagacacag ccaacccata cacagacaca gcggtgcaca cacaggtcac accaacacac        1620
agctgtacac ccatttacac ggttcacata cacagacgca caacagacac aacctgcata        1680
cagacagcac acacatctgt gcattcccgt atgggtgtgc agctcataca cacacgggca        1740
cacccacgct gacatgcatg tacagataga ctcacatgta gctgcaactg agacacaata        1800
gatgcatgcc caaatccaca tacagacaca caagcccgtg cacgcacaca catgtggctc        1860
acattgccta cagctcaggg tggcccatag cccatgttat gggacccaca gtgtgagttc        1920
acgaacaccc acaggtcctg gtgtgggtga tggtgtccag tcggcttgtc ctgtgaggaa        1980
ggggcatata ctatgtaggc ccatgctcag gttcagctcg acagattctg taactcaccc        2040
tcttgttttc tatttctttc tgtccttctc tctctctttt tttttttttga gacagtctca      2100 ctctgttgcc aggctggcat gcagtggcgc aatctcgggt cactgcaacc tccgcttccc        2160
aggttcaagc gattctcctg cctcagcctc ccgagtagct gggactacag gcgtgcgcca        2220
ccacacccag ctaatttttt tttggagatg gagtttggct cttgttgccc agggtggagt        2280
gcaatggcgt gatctcggct cactggaacc tctggctcct gggttcaagc gattctcctg        2340
cctcagcctc ctgagtagct aggattacag gcacctgcta ccatgcccag ctaagttta         2400 tattttttaga acagactggg tttcactgtg ttggccaggc tggtctcgaa ctcctgacct        2460
caggtgatcc accagcctcg gcctcccaaa gtgttgggat tagaggcgtg agccaccatg        2520
cctggccgct ttctatttct ttctgtcctt ctctgtcttc tcctggtcta tctgcttcta        2580
gttcattctc acgtctttgt gttttttctcg atcttccttc ctctctccat cacccctctct     2640 ctgacaagag catgcatgga cacacgcact gtgtccccac acctgatcgc atgcacacag        2700
```

-continued

```
ttctccacta gctcagaccc agccacaccc tggacccttc tggcaggaca gttagactat    2760
gccacaccct agagggacac agcccttagg gatggcgatg ttggacaggg cagcacatgc    2820
cttgtgccag ttgcccctcc cttcaacaca caccctattc cagcaacgcc cagcgctggc    2880
tgcttctgga gatgctgtgc tcactcgtgg gtacatgcct tggtccctct cccaagagca    2940
ccacgcaggc ctgcctggct ggagtagatg cccatcaggg aaaggaagac ccgtggccct    3000
aggatcccct gccccttccc cttctattac ccctgaacct gggcatgaag ccccagacct    3060
ccctgtaaca ctcagcaccc ttacttcctg tctcagcaca ccccattctg cacatcttag    3120
ctctggcagc ttcccgagcc cccacatctg gcataagaca gcccctcctc ctgccttccc    3180
ctgctttgtg gttcccaggg ctcgagctgg cagggacagc tgcagcctca acagctgggg    3240
ctggggcggg gggggggggg gcgtgggaac tgtggatggg gggactccct gcacccgcag    3300
agacgccccc atccccatgc agctgttgcc tggtggaggg agggaggggg tttgtcactt    3360
gggcctgggg ttcctgggca cctggctgat cctccacctt ccttcacccc cacacagccc    3420
ccccttgcct ggacggaagc ccgtgtgcaa atggaggtcg ttgcacccag ctgccctccc    3480
gggaggctgc ctgcctgtga gtgcctggct cagagccacc agtgggccct gtgtgtgggg    3540
gcggggggga ggggcgattt gtcttctccc tctgcctctg tgttcaccat ggatgtctct    3600
accacttcct acatgtgtgt ggcttgggca acctctcgtg tttccccatt ggaaactgag    3660
caggggctct gcactcttct tggcatgggt tcaagtccca catcatgttg ctgaccggct    3720
aggaattaaa ctctttacat ctcagtgtca tggtctgcaa aatgggccca gtaatcccag    3780
cttcacagtt cttggccacc tgaggtcaca tgtaaagccc cccatgaggt aggtattatt    3840
caatcaacaa actatcaggg accaatcgca gtggctcaca ccctccacac ccctcccatc    3900
tctcaacatt tagtggaggg ggacatagga ggcctataat acagtcccac actgccactt    3960
acttgcagtg tgactttggg ctagtcactt tccctctctg atcatcattg cacctgtgaa    4020
atagggaatg cttcactggc gactgtgaag ggacttaaca atttagttgt tagatatcac    4080
aaggaaaggc aagaggttgc agggagcaga gcagaggctg ggaaggagct gagcagagac    4140
agaaagagct cagcttaaat tctggggtct gggacacctt gagcattcaa gcttttttgag    4200 cctcagtttt tgcatctgga aaatggggca ataataactc ctgtatgcac tcaacataca    4260
ttaagtgctc agaatatagt atgtgctcaa cataggcatt attataaata ataatggtag    4320
ggaggcagga aacaggtgct ctaaggagaa gtctctcaag gttatgagga aatgcttggc    4380
tcctttcatg ctatcattaa taacagcagt tcacgcagta gccattgatt gactcattaa    4440
tgtattcatt tattcagcat catgtgtgcc aagtactggg tcaggcccaa gctgggtggg    4500
tctggggtga ttttagacca agaagagccg ctttgaagtt acacctacat ttattttggc    4560
tggatctccc actcgggctc acctttgtgg agggctgagc ctgactgaga gggtttcctg    4620
gggctggggg gtctgcgaag gtgggcgggg atgggaaaa gtgtgacctt acctggagcc    4680
acacacctgg gagggcgagc ggtgggccg ggcgcctgcg cagtggagct ccgcgcctgg    4740
aatactgccg acaggtgaat gagcccgcgg ctgccccgcc cttcgacagg tgaatcaccg    4800
gcgcgcgcgc cgcccggagc ccggatcgcc cggagtggag cgggctcagt cctccgagtt    4860
gggctgtggg aaccactccc tacacgccct ccacccccca cgagtctctt tcacggtctc    4920
aaatactcaa gtcctttcaa ggatgccccc aagctgtcac cccacccatg gatcccccaa    4980
gaccccccca ccggcagcag acgtttccat agacctcgtc cccatctcct agtcctcgcc    5040
tcacccgccg tgcccccccct aactaggtct gcgctccccc ctccgtctcc cccaaagctt    5100
```

-continued

```
aggccgtggg gcggggcgcg ggctggggct ggaaccggcc cgaccggtcg gcggggcgc      5160 gggacgcaga gcgtgggaac ccgcccgggg cgtcgggagg gggcccgcgc gggtcgcgcc      5220
ctgcctggcg gtgggaccag ctatcctcgg cgcccagcgc agcgcgcccc ctcccgacgc      5280
gcggtcgggg ccgcagtggt cgccctgcgg gccttggagg aggggacggg agctgtgccc      5340 tccctccca acgccacccg caccccttgct tgctcggccg tgccccgacc tgtttcgctg      5400
ggggccgggg tggggggggat cttgcgggtg acgctaagga ctgagtcagc cgcttgttga     5460
gttcagtctc aggcgtctgg dacaagccgg agggaggaca accgcgccag gggcggaggg     5520 tgggggggata gagggggggtg agggttggca gcgtcggggg gcggagcttg gactctctgg     5580
cttctctaag ccctccctc tgaccccgct agtgcccctt ggagatttcc agtcttaaga      5640
ccaacccctc ccagttccaa ttcctcacac tccttggtgg gcttggggag ggggctgcag      5700
gttgaaggac cacccccca agatgagggt accaacagtg gtgtcagtac cccaaccctc       5760
caccctccca tccctgcata agaggctata taagtcccag agaagggact tgagggtttg      5820
tgggagccct gctgtctgtc cctgtgagtg agagttgctc atttccgcgt gggatgctgt      5880
gggttggtgt cttgagtgct ggccaggcca tggcgtccaa ttggtgtgtc cctctgtgtg      5940
tgtagctgtg gtttctgggc ctgtctgtgt gtgcctgcgt ggttgtgtcc tggggtctga      6000 gacttcttttt tttcctttttc cttttttttttt ttttttttga gatcgagtat cgctcttgtt    6060
gcccaggctg gagtgcagtg gctcgatctt ggctcactgc agcctctatc tcctgggttc       6120
aagcgatttt cctgcctcag cctccggagt agctgggatt acaggcatgt gccaccacac      6180
ttggctgatt ttttgtgttt ttagtagaga cggagtttct tcatgttggt caggctggtc      6240
tcgaactctt gatgtcaggt gatctacctg cctcggtctc ccaaagtgtt gggattacag       6300
gcgtgagcca ccgcgcttgg acatgggtct gagactttttc atttgctgtt ccctctgcct       6360
ggaatgccgt tccccagaaa gccccatggc cccctcctta ccttcatatg tctgtgaaaa      6420
tagaattcca cctccttgac cccatcattc tatccccctt aaccctgtgg tttagcttcc        6480
tacggctgct ctaacaaatt accataaact gggtagcttg aacaatagta atttattctc       6540
ttgaagttct ggaggttgga agtctgaaat caagatatcg gcaggctga gcctctccat        6600 ggggacccag gggagaactg actcttgcag cttctggtgg ctccagacgt ttctcagcta       6660
gtggctgtct cactccagtc cctgtctctg tcttcttctc ttccttctcc cacccaaatc      6720
tccttttggc tgcctctctc tttttttgag acagagtctt gctctgtcac ccaggctgga      6780
gtgcagtggt gcaatcttag ttcactgcag ccttcaactc ccaggctgaa gcgatcctcc      6840
cacctcagcc tcccaagaag ctgggactac aggtgtgagc caccacggcc agctaatctt      6900
ttatttttat tttttaggtg gagtctctct ctgtcaccca ggctggagtg cagtggcacg      6960
atctcggctt actgcaacct ccgcctccca ggttcaagca attcttctgt ctcagcctcc      7020
tgagtagcgg ggactacacg agtgcaccac cacgcccagc taattttgt atttttagta       7080 gcgacgaggt ttcaccatat tggccaggct ggtcttgaac tcctgacctc gtgatccgcc      7140
cacctcagtc tcccagagtg ctgggattac aggcatgagc cactgcgcct ggcctgtttg      7200
ttttttttgt ttttttgtttt ttttttgagat ggagtctccc tctgtcaacc aggctggagt     7260
gcagtggtgc aatttcggct cactgcaacc tccgcctcct gggttcaagc gattctcctg       7320
cctcagcctc cagagtagct gggattacag gctcctgcca ccatgcccgg ttataatttt       7380 taatttttttt ttgtggaaaa aaagtctccc tatgttgctc aagctgatct tgaacttctg      7440
```

-continued

```
gcttgaagtg attatcctgt cttgacctcc caaagtgttg ggattacagt tgtgagccgt    7500
tctcttgtat gaacacttgt cactgaattt agggcccagg tggataattc agaataatct    7560
catcttgaca tctctcattt aattacatct gcatagccag gcctggtggc gtgtgcctgt    7620
actcccagct acgcaggagg ctgagacaaa gaattgcttg aaccccggga ggtggaggtt    7680
gcagtgagcc aagatcgcgc cactgcactg cagcctgggt gacagagcaa gactccgtct    7740
cttaaaaaaa aaaaattaca tctgcaaaga gccatttaaa aaaaaagtaa ggtcctagtc    7800
acaggttctg ggacatggat gtcatctttt caggggctgt gacccaactg actacatcct    7860
tcatggttct gatggctttc accgcccct gccagcatgt tgtatattaa tttgttattc     7920
gtatatgttc tccttgcctg gacctggctg caaggatcca gagggatagg gacccctttc    7980
attgtgtttg ttgctgtatt tgtattgctc agaacgtagt aggtactcag taaatattcg    8040
ttgcatgaat gaatgtgtgt tttgtttgt tttgtttctt tgagaccgag tcttactctg     8100
tcacccaggc tgcagtgcag tggcgcgatc ttggctcact gcaacctcca cctcccgagt    8160
tcaagcaatt ctcctgcctc agcctcttga gtagctggga ctacaggcac gcaccactat    8220
gcccagcaaa gtttcgtact tttagtagag acggggttac accatgttgg ctaggctggt    8280
cttgaactcc tgaccccaag tgatctgccc gccgcagcct cccaaagttc tgggattaca    8340
ggcgtgagcc actgctccca gcaaatgtgt gtttgctgct ctgtttccct gcgtgtttct    8400
tgcctgtctt gtgtgtatct ttgtgtctgg ggccatcctg ccctgtgctg cccaaccaag    8460
ccatctctgc ccacaggtgc ccgcctggct gggtgggtga gcggtgtcag ctggaggacc    8520
cctgtcactc aggcccctgt gctggccgtg gtgtctgcca gagttcagtg gtggctggca    8580
ccgcccgatt ctcatgccgg tgccccgtg gcttccgagg tgagagggga agagtctgga     8640
ggggaggtag tcggggtgt ggtcagtcct aaactcaccc tgtcctggtc cctccaggcc     8700
ctgactgctc cctgccagat ccctgcctca gcagcccttg tgcccacggt gcccgctgct    8760
cagtggggcc cgatggacgc ttcctctgct cctgcccacc tggctaccag ggccgcagct    8820
gccgaagcga cgtggatgag tgccgggtgg gtgagccctg ccgccatggt ggcacctgcc    8880
tcaacacacc tggctccttc cgctgccagt gtccagctgg ctacacaggg ccactatgtg    8940 agaacccgc ggtgccctgt gcaccctcac catgccgtaa cggggcacc tgcaggcaga      9000 gtggcgacct cacttacgac tgtgcctgtc ttcctggtga gtgagcccta ctcaggagag    9060
tcagagtggg gggcgtgggg acagcaggcc agcccggcgg tgaccatcct tgccccttc     9120 cctgctaggg tttgagggtc agaattgtga agtgaacgtg gacgactgtc caggacaccg    9180
atgtctcaat gggggacat gcgtggatgg cgtcaacacc tataactgcc agtgccctcc     9240
tgagtggaca ggtgggcact gcggccagag ggagcgggga ggcaggcctc gggtggacat    9300
gcgccaggtg gctggactgc tgcatctgtg tgccacaggc cagttctgca cggaggacgt    9360
ggatgagtgt cagctgcagc ccaacgcctg ccacaatggg ggtacctgct tcaacacgct    9420
gggtggccac agctgcgtgt gtgtcaatgg ctggacaggc gagagctgca gtcagaatat    9480
cgatgactgt gccacagccg tgtgcttcca tggggccacc tgccatgacc gcgtggcttc    9540
tttctactgt gcctgcccca tgggcaagac tggtgagtgg ccgttttctc tgcagggagc    9600
catggatggt ttttagtgag ggcaaataag aagtctgact tgagtgttag aaagattatg    9660
ctaggctggg cacagtggct catgcctgta atcatagcac tttgggaggc caggcgggc      9720 ggatcactgg ggtcaggagt ttgagaccag cctggtcaat atggtgaaac cccatctcta    9780
ctaaaaacac aaaaattagc tgcgcgtggt ggtgcacacc tgtaatccaa gtctctcagg    9840
```

```
aggctaaggc acgagagtag cttgaaccca ggaggtggag attgcagtga gccaagattg   9900
caccactgca ctctagcctg ggtgacagag tgagactcct tctcaaattt aaaaaataaa   9960
aaaaagatta tgctaggccg ggcacagtgg ctcatgcctg taatcccagc actttgggag   10020
gccaagatgg gaggatcgct tgggcccagg actttgagac cagcctggac aacatagtga   10080 gttttttgtca tctctacaaa aacttggtag gctgggtgtg gtggctcacg cctgtaaccc   10140
caacacattg ggaggcccag gcgggtagat tgcttgagct cagcagtttg agaccagcct   10200
gggcaacatg gcaaaaccct atctctacca aaaatacaaa aaattagctg ggcatggtag   10260
cgcatgcctg tagtcccagc tactctggat gctaaggttg aaggatggct tgagcccaga   10320
aggtggaggt tgcagtgagc tgagactgag ccactgcgtt ccagcctggg agacagtgta   10380
agaccgtgta taacaaaaaa gagagagaaa aaaagatgat gctggaggca gctttagtgg   10440
ggaagtgtaa gcctgggaga ggcttgggag gaggctgaca ttgcactgat gcatggctca   10500
gggcagaagc cattggaatg gggaactcct gggagttacc ttttggaagtg gcaaagatca   10560 gagaacatgt ttaggagggg aacgtggata tagaaagagg gcatacatgg cagagggtat   10620
tacagaagca aaggctggag tgtaggaccc ttttgtaatc agaagagtca aaaggtttta   10680
aaacaatatg tggatgtttg caatttattt tattttattt ttgagacaga gtctcacttt   10740
gtcacccagg ctggagtaca gtggcatgat ctcagctcac tgcagcctcg acttcctggg   10800
ctcaagtgat cctcccacct cagtccccca agtagctggg attacaggcg tgcgccacca   10860
tgcccggcta agctttgtat tttttgtaga gacgggtctc actatattgc ccaggctggt   10920
cttgaactct tgaactcaag cgatgcactc accttggcct cccaaagtgc taggattata   10980
gacgtgagcc actgtgcccg gtctgcaatt tattttttaaa tggtttagaa aagaagattg   11040
gtagattaag ctaacaatag ttgaatctag gtggtgggta tatgaatggt caacttttct   11100
gtatgtttga tagttctcat aataaatgga ttaaaaaagc agctactaaa tactgtttag   11160
gtttaataaa aacaacaggc cgggcgcggt ggctcacgcc tgtaatccca gcactttggg   11220
aggctgaggc aggcagatca cctgaggtca ggagtttgag accaacctgg ctaacttggt   11280
gaaaccccgt ttctactaaa aatacaaaaa attagccggg cgtggtggca catgcctgta   11340
atcccagcta ctcgggaggc tgagcaggag aatcgcttga acctgggagg tggaggttac   11400
agtgagccaa gatcgcgcta ttgtactcca gcttgggcaa caagagcgaa acttcgtctc   11460
aaaaaacaaa acaaaacaac aacaacgaca aaacaatact caagggggtgt gggccttttg   11520 ggcagagcag gaagatctgc ctatgacttc tgcttaccac ttcccaggcc tcctgtgtca   11580
cctggatgac gcctgtgtca gcaacccctg ccacgaggat gctatctgtg acacaaatcc   11640
ggtgaacggc cgggccattt gcacctgtcc tcccggcttc acgggtgggg catgtgacca   11700
ggatgtggac gagtgctcta tcggtgaggg gagctccatc gtctgtgaat gggctgggaa   11760
agaggggaga ggagggggtc ccggccagcc acgcccacac cgatcgcact ccatccggca   11820
ggcgccaacc cctgcgagca cttgggcagg tgcgtgaaca cgcagggctc cttcctgtgc   11880
cagtgcggtc gtggctacac tggacctcgc tgtgagaccg atgtcaacga gtgtctgtcg   11940
gggccctgcc gaaaccaggc cacgtgcctc gaccgcatag gccagttcac ctgtatctgt   12000
atggcaggtg ggtggtgggc gtggcctggg cgggtcctga ggcagggggc ggggacagag   12060
aagcccgcgg atggggagct gagcagaatg gggtgtaagt gggtttggag tgggacccctt   12120 agagactgaa gcctggaagg aggtgggggtc aggaccagaa gggaatactg tgtgattctg   12180
```

-continued

```
ggggcttggt caaatggagt cagtagaacc tcaggtgggc tgggagtatt cttggcctta   12240
ggacccactc gggaaggggt tggggataga gaggcagagt cggggctgct gtgaggtcaa   12300
ggtgaagcct gcagacaagc ttgcagtaag cctgggcaaa ggctatgggg ggccctgggg   12360
ctgggggctg gggactgggg aaagggctta gtctgaggac tggggagagg aggaggggtt   12420
tgaaggcaag gcctctgcgg acacccatga gccttgggcc agttgggacc acggctgggt   12480
gacagtccag cctgtggctg aaaattaagg ttgggctggg agtgtagagg tggggacgaa   12540
ggctcggggg atttgtcgat gagtaggaag ggaagtacct ccttccttgc accccgttca   12600
caccataggg tagcccccgc tttcctaagc cctattccct gccccaggct tcacaggaac   12660
ctattgcgag gtggacattg acgagtgtca gagtagcccc tgtgtcaacg gtggggtctg   12720
caaggaccga gtcaatggct tcagctgcac ctgcccctcg ggtgaggacc tcaggagagg   12780
gagcccgaaa agacatgtct gggaaggggc aaaaactcca gggtgggaac ctgtaaaacc   12840
acgttagcgg ataacttaca atagaaacca tatgttatga aacattgaag ttaatttaaa   12900
tccaagtaaa tgggtttttc cacccaaaca aggcgggggct ggagaggggt gtactgctct   12960
caccctttct gggcctctgc tcatcccact ccccacccca ggcttcagcg gctccacgtg   13020
tcagctggac gtggacgaat gcgccagcac gccctgcagg aatggcgcca aatgcgtgga   13080
ccagcccgat ggctacgagt gccgctgtgc cgagggtgag gcgggccaat gacagtccga   13140
caagaatcag gaggcggggc ttgtgggcga cagggccaat aacagacttg gggagagctt   13200
gggggcgggg ttgtagcaag gcaggaccca gtgacagagt tggggggtgg agccaataat   13260
gcatatagac tgacataagg ctacgtgtgg agccaaagtg ttgggctggg cacagggtgc   13320
ctgtaactga atggggaggg cccaatacct tccctggca cctgccatgt gctcccatct   13380
ccagtggagg gtggggcaga aacagggctg gaggtggggc cacagctggg ggcgggattt   13440
aactgtggga gagtcttggc tagggacaaa ttctggagct tgtagtgggg tggagtggaa   13500
gtaagtgggg ggtggggggt ggggcctgta ttgagctcgc ctcctgacag cttgatgggc   13560
agggcctcag atagagctga accaggattg gtccgaggcc tcacttgtgg gcaggcccct   13620
ggcaagtggg cggagcctga ccctcttggc cccacaggct ttgagggcac gctgtgtgat   13680
cgcaacgtgg acgactgctc ccctgaccca tgccaccatg gtcgctgcgt ggatggcatc   13740
gccagcttct catgtgcctg tgctcctggc tacacgggca cacgctgcga gagccaggtg   13800
gacgaatgcc gcagccagcc ctgccgccat ggcggcaaat gcctagacct ggtggacaag   13860
tacctctgcc gctgcccttc tgggaccaca ggtgggaccg ggggctgggg cagaaacagc   13920
acacctggag gggcacagag ggtttgggaa tggtgcatct agtggggcac agtggtggcc   13980
actccatgcc atgttcctgg cccctaggtg tgaactgcga agtgaacatt gacgactgtg   14040
ccagcaaccc ctgcaccttt ggagtctgcc gtgatggcat caaccgctac gactgtgtct   14100
gccaacctgg cttcacaggt gggcaagtgg ctgccatgag aggggtcct tagatcgagg   14160 gtgaagtcac tcgtctctgt gggcctgttt tgcccgtatc tttgcagact cttgtccaac   14220
gaggttgtcc gtgctttgcc ctgagtctgt gctgtctcat tggcataagg ttgtttcgag   14280
attattctgc aggctgggcg cggtggctca cgcctgtaat cccagcgctc tgggaggcca   14340
aggcaagtgg atcacttgag gtcaggagtt cgagaccagc gtggccaacg ttgcgaagcc   14400
ccatctctac taaaaataca aaaattagtc gggtgtggtg gtgggcgcct gtagtcctag   14460
ctactcggga ggctgaggca ggagaattgc ttgacctcag gaggcggagg cggcagtgag   14520
ccaagattgt gccactgtac tccagtctgg gcgacagagt gagacttcat ttcaaacaca   14580
```

-continued

```
cacacacaca cacacacaca cacacacaca cacacataca aaaacaaaca aaaagattat   14640
tctggaacat agatgaaagt gtccaaactc agtgactagg ttatttctga atgggtctaa   14700
actaatcctt agtggaaatg aatgtgactt tgctaggtgt gttggctcat gtctgtaatc   14760
ccccagcact ttgggaggct gagacatgag gatcacttga gcccaggagt tcgagactag   14820
cctgggcaac ataatgaaac cctgtctcta caaaaaataa acacactccc aaagccagat   14880
tagtcaatac gtagataaac acgcacacac atgcacacac aattagccag acgtggtggt   14940
gcgcaactgt agtcccagcc actcgggagg ctgaggtggg agaatcgctt gagcccagga   15000
agtggaggct gtggtgagct atgatcatgc cactgcagtc cagcccgggc gacagagtga   15060
gaccccatct caaaaaataa gaagaagaag aaaagaaaaa gaaagggact tcatggaagt   15120
ttggggacca gaatgatctg gggcaagtca gctcttggtt gaggaggcgg gtgtcctaat   15180
ctgcacaaga gctgatgcgt tatgaaaaag aggtcattgc tcgggggtgt gggtgtgcta   15240
agtggggtca cgtcgtccct ccctggttgt ccctgctgac tttgttctga gatgagattg   15300
cttgtgtact ccccagggcc cctttgtaac gtggagatca atgagtgtgc ttccagccca   15360
tgcggcgagg gaggttcctg tgtggatggg gaaaatggct tccgctgcct ctgcccgcct   15420
ggctccttgc ccccactctg cctccccccg agccatccct gtgcccatga gccctgcagt   15480
cacggcatct gctatgatgc acctggcggg tgagggccct tctcagcctc agacactgcc   15540
ccctctccct ggcccacctc cctggcctga ctaccttccc ctgccaggtt ccgctgtgtg   15600
tgtgagcctg gctggagtgg cccccgctgc agccagagcc tggcccgaga cgcctgtgag   15660
tcccagccgt gcagggccgg tgggacatgc agcagcgatg gaatgggttt ccactgcacc   15720
tgcccgcctg gtgtccaggg tgtgtacctc accttccctc tgcagcccca ccaacaccat   15780
gggccttctc atctctcttc tcctctactc tctcctcccg ctatgttagc ttctttttg   15840 ctttcaatca tttccctcca ggagcttggg aggtgggtat caaggtgggg accctggggt   15900
tgggggaggt ggggggagat gggatcaggg agtccctcaa ggctatctct gcttccctct   15960
cttccacccc caacaggacg tcagtgtgaa ctcctctccc cctgcacccc gaacccctgt   16020
gagcatgggg gccgctgcga gtctgccct ggccagctgc ctgtctgctc ctgccccag   16080 ggctggcaag gtatgccacc tgcttctctt ccctcctcct ctccatctcc tctgccccct   16140
accctatcag ggatgatgct ggggatccag agagggaccc atccccagcc ctgcctttga   16200
gaggggcttc cttcttggaa ggacagagct ggacactgat atgcagcctg tgtgggtcag   16260
cccttggaag aggaagagtt atggggctag agatgctggg acttagggcg gggtttaggg   16320
tacagcttcc tggaggagca gacctcatag taggtatttg ccacctactg agacagggag   16380
acggccattc tgaaactgca tatgcaaaat gcccagacac gaatgacagc acggcttatt   16440
ttgccttcac ccatctcggc ctgcaggttc ttcctgagcc ccaggtccct gagaccctgc   16500
tctgtaccct gtaaccctag gtgtaacctt gctccctacc cccaggccca cgatgccagc   16560
aggatgtgga cgagtgtgct ggccccgcac cctgtggccc tcatggtatc tgcaccaacc   16620
tggcagggag tttcagctgc acctgccatg gagggtacac tggcccttcc tgcgatcagg   16680
acatcaatga ctgtgacccc agtgagtgca ggggagctct tgggggtgct gctctgggga   16740
acacagtcat taagcttgaa ctgtgtgcct ggcactgtgc tgtcatttca tcttcacagt   16800
tatcttactt ttcccgtttt atttatatgg aaactgaggc ccgaggaggt tgagtgactt   16860
cttgtgcaag cccatggaac gagttaggga atgagctggg cttagaacct tggagtctgt   16920
```

-continued

```
gtgctgcctc tttttttttt tttttttttt tttttttga gacagagtct tagctctgtc   16980
gctggagtgc agtgttgcaa tcatcgctca ctgcaacctc tgccttctgg gctcaagcac   17040
ctcagcctcc ccagtggctg cgactatagg cgcacaccac agcgcccagc taatattttg   17100
tgttttttgt agagacggag tttcgccatg ttgcccacgg tggtctccaa ttcctgggct   17160
caagcaatct acctgtctcc acctcccaaa gtgctgggat tacaggcgtg agcaaccaca   17220
cccgacctaa gtgcactgtc tttgagagca atcgagttaa tatcatgtgc aaagtatgag   17280
ataaaaggcc ccccagaggc cgggcgaggt ggctcacacc tgtaatctca gcactttggg   17340
aggccaaggt gggcggatca cctgaggtca ggagtttgag accagcctgg ccaacatgga   17400
gaaacCCCat ctctactaaa aatacaaaat tagcagggca tggtggcgca tgcctgtaat   17460
cccagctact tgggaggctg aggcaggaga atcacttgaa ccttggaggt ggagattacg   17520
gtgagctgag attgtgtcat tgtactgcag cctgggcaac aaggcataac tccgtctcaa   17580
aaacgaacaa acaaacaaac aaacaaacaa aaggggtgc tgccaaacag ataaataaca   17640
caagccacat atgcaatttt aaattttcta gtagccacat taaaaaataa acagaaatgg   17700
gagatattaa atttaatatt ttatatttat ttatttatta tgtattcaga gtgaggctct   17760
gtcgcccagg ctggagtgca gtggtgcgat cttggctcag tgcagtctcg aactcctggg   17820
ctgaggcatt cctcctgtct taacctcctg agtagctagg attacaggca ctcactacat   17880
gcctagctaa tattttatt ttaattctgt agagatgggg tctcactgcg ttgtctaggc   17940
tggtctcaaa ctcctggcct caagccatcc tcctgccttg gactctcaga ctgctgccac   18000
tgtgcctgac caaatttaat atatttaaat ttaatttatt gaatgtatat aatcggctgg   18060
gcgcagtggc tcacaccggt aatcccagca ctttgggagg ctgaggcagg tggatcacct   18120
gaggtcagaa gtttgagacc agcctgacca acatggagaa gccccgtctc tactaaaaac   18180
acaaaattag ctgggcgtgg tggcacatgc ctgtaatctc agctactcag gaggctgagg   18240
taggagaatc acttgaaccc gggaggcgga ggttgtggtg agctgagatc gtgccattgc   18300
actccagcct gggcaacaag agcgaaaccc catctcaaaa aaaataaaaa taaaaataaa   18360
agtaaataaa taaataaata aataaatgta tataatctat ttaacccaat atattaacat   18420
atcatttcaa catgtaacca gtataaaatt gttaatgaga tattttacat tgtttccttt   18480 ttttttttg agacaagttc tcactctgtc gcccagactg gagtgcagtg gtgcgatcat   18540
gactcactgc agccttgacc tcccaggctc aagtgatcct cccgtctcag cctccccact   18600
agctgggact acaggtgtgc accatcatgc ccagctaatt tttgtatttt ttatagaaat   18660
ggggtcttgc catgttgccc aggttggtct cgaactcctg agctcaagtg atctgcccac   18720
ctcggcctcc caaagtgctg ggattacaag tgtgtgccac cacgcccagc ctattttttt   18780
tttcatacca agtcttcaaa atctgaaacc cagtatgtat tttacattta tagcacatct   18840
ccatttagtc acaatttcaa ggactcagta gccacatgtg gctaatggcc actgtccttg   18900
tcctgttcca agcacaggaa ttagatcagg cacaattagc agcgtttgct tggcagctta   18960
aagggacctt ttggttttcc caacatcctg cccttgccac ataggtgagg tttccagata   19020
aaggagggga cgaggccaca gaaggggatg gatttagatt cctctgacca aatgcacccc   19080
atcccagttg aacctggttt cctcctgaat tcttctcaat ccaaggcata tcccagtcag   19140
actgggctaa tggggggcaag gtaggtgacc agaccgcctt cctcctgtcc gcagacccat   19200
gcctgaacgt ggctcgtgc caagacggcg tgggctcctt ttcctgctcc tgcctccctg   19260
gtttcgccgg cccacgatgc gcccgcgatg tggatgagtg cctgagcaac ccctgcggcc   19320
```

-continued

```
cgggcacctg taccgaccac gtggcctcct tcacctgcac ctgcccgcca ggctacggag   19380
gcttccactg cgaacaggac ctgcccgact gcagccccag gtgggcgggg cctctgcttg   19440
gagagcaggg actctggctt gggatggggc ctgggacctg ggacgaagtg gggacagcaa   19500
cgacttgggg gagtcctcag cttggtaccc actgcggact ctgatgactg atggggcagg   19560
gccagggaag gagcagggcg tctgtttgga gctcaccttg gagtctctgg tgcctgagag   19620
ggcatggctt ccaggtggct ctcaccttag ggctgaagtc cctggtgaat tggagctaag   19680
ggacctgatt ggcttctgct ggggctgcag cttcttgccg agataagggt cagggagtgg   19740
gacgtcccca gcgctaacag cgggactcag gaaggagggc agggcctgtg aggggcgga   19800 gcctgatcct ccctcccact ccttccgctc cagctcctgc ttcaatggcg ggacctgtgt   19860
ggacggcgtg aactcgttca gctgcctgtg ccgtcccggc tacacaggag cccactgcca   19920
acatgaggca gacccctgcc tctcgcggcc ctgcctacac gggggcgtct gcagcgccgc   19980
ccaccctggc ttccgctgca cctgcctcga gagcttcacg ggcccgcagt gccaggtggg   20040
tggagttact ggggacctgg gggaggagcc tgcctgggat cctaggaggg agaagccaag   20100
tcggggcaca gtttctccca gactaccccc caccccacag tactgactct gagtgcttcc   20160
cctccagacg ctggtggatt ggtgcagccg ccagccttgt caaaacgggg gtcgctgcgt   20220
ccagactggg gcctattgcc tttgtccccc tggatggagc ggacgcctct gtgacatccg   20280
aagcttgccc tgcagggagg ccgcagccca gatcggtgag tgggagcatg tgggcgggcg   20340 tgtgggcct tgggaagggg ctcatgcacg tacctcctgc tagtgtgagc cgaatggggg   20400
tgccacagag cctatggggc atgatggggt gtgtggctga gtggtgtggg tgtgtgagca   20460
tgtgacaact ggccgggatg gtgtgtgtct gtcactgtga gacagcaggg atggtgtgtg   20520
tgctacaggg tgtgaccgag ctgctgtgag cgttgaaggc atgtgtgtgt atgtcagtga   20580
tgagaccttg cctgctgggg ggatgtgtga caacctgatg gagtgtgggt gcgatcctgg   20640
ggactcattc caccaaggat gttgaatgat ctgtgtgatg gaggcagaag ggggatgtat   20700
ggggttacct ctgttcctgt gccactctcc tctttgcagg ggtgcggctg gagcagctgt   20760
gtcaggcggg tgggcagtgt gtggatgaag acagctccca ctactgcgtg tgcccagagg   20820
gccgtactgg tagccactgt gagcaggagg tggacccctg cttggcccag ccctgccagc   20880
atggggggac ctgccgtggc tatatggggg gctacatgtg tgaggtaagg gggcgctccc   20940
caggagaggg aagaggaggt gggcatgctt gggtgcgtct gggcacacat ttctgtgtgg   21000
cttggtatgg gtatgtctct agatatgtct gagttttgc ttttgtgact cttggtgtat   21060
ctgtgggtgt cactctgggt agatctgggg tgtttttta tttgtttgtt tttttgagac   21120
aggttctcac tctgtcaccc agacgagtgc agtggcgcga tctcagctca ctgcaacctt   21180
tgcctcctgg gttcaggtga ttcttctgct tcagcctctc attatagctg ggagtacagg   21240
cacccaccac cacgcccagc taattttgt attttcata gtgacagggt ttcaccatgt   21300
tggccaggct ggtctcgaac tcctgatctc aggtgatctg cccacctcgg cctcccaaag   21360
tgctgggatt acctactggt agtgcgctga acatctgtgt gtgtcctttt gtgctggggt   21420
tctttgcgtc ttcatgggta tgtccaggtg ggtctgtgtc ccactaagct gagtgggtcc   21480
ctctcttacc ccactgaagt gtcttcctgg ctacaatggt gataactgtg aggacgacgt   21540
ggacgagtgt gcctcccagc cctgccagca cgggggttca tgcattgacc tcgtggcccg   21600
ctatctctgc tcctgtcccc caggaacgct gggtatgcca gggccaggt tgggggggaca   21660
```

-continued

```
ggatgagagg ctgtcttcat tccctcttga ccacccctcg tttcttcccc caggggtgct   21720
ctgcgagatt aatgaggatg actgcggccc aggcccaccg ctggactcag ggccccggtg   21780
cctacacaat ggcacctgcg tggacctggt gggtggtttc cgctgcacct gtcccccagg   21840
atacactggt ttgcgctgcg aggcagacat caatgagtgt cgctcaggtg cctgccacgc   21900
ggcacacacc cgggactgcc tgcaggaccc aggcggaggt ttctgttgcc tttgtcatgc   21960
tggcttctca ggtaagcgtt ggcgaagggg ctggcctggg accccgcctg tcattccccc   22020
attgtggctg atctacatgc tcccgctcgc tcaggtcctc gctgtcagac tgtcctgtct   22080
ccctgcgagt cccagccatg ccagcatgga ggccagtgcc gtcctagccc gggtcctggg   22140
ggtgggctga ccttcacctg tcactgtgcc caggtaggtg tgggtggcgg cctttggagg   22200
aggagtaggg gcgtggcctc tggagtagta ggggcgtggc gtctaggagg aggatgtggc   22260
tttaggggag acatcgaagg gaagggagtt tctggaaaat gctgacattt ccgccgggtg   22320
tggtagctca cacctgtaat cccagcacat tgggaggccg aggcgggagg atcacttgag   22380
gccaggagtt agagaccagc ctgggcaaca tggtgaaacc ccgtctctac taaaaatata   22440
aaaattagcc gggcgtagtg gcagctgcct gtaatcccag ctactcggga ggctgaggca   22500
ggagaatcac ttgaacccgg gaggcggagg ttgcagtgag ccatcacgcc attgcactcc   22560
agcctggcga ctgagtgaca ctccgtctca aaaacaaag aaacaacccc ctgccccgac   22620
atttcctgga ggtttgaagg gaaaaggggt aggatggtga ttgggggggcg tggcctcctg   22680 ggatggcagg gcttatctgc caggtggggt ctccagtgtg gaaaggggag cggttgggtg   22740
ggacatgggg aggttgaggg ggtctcaacc ttccttagtc ttgacctctt ctcttccccc   22800
tctctcccct tgactcttct tttccccact cctccatttc ttctcctcct tccctccact   22860 ccccacccctc attttttatcc ctccctcccc aaacccgacc cccagccgtt ctggggtccg   22920
cgttgcgagc gggtggcgcg ctcctgccgg gagctgcagt gcccggtggg cgtcccatgc   22980
cagcagacgc cccgcgggcc gcgctgcgcc tgccccccag ggttgtcggg accctcctgc   23040
cgcagcttcc cggggtcgcc gccgggggcc agcaacgcca gctgcgcggc cgcccctgt   23100 ctccacggggg gctcctgccg ccccgcgcg ctcgcgccct tcttccgctg cgcttgcgcg   23160
cagggctgga ccgggccgcg ctgcgaggcg cccgccgcgg cacccgaggt ctcggaggag   23220
ccgcggtgcc cgcgcgccgc ctgccaggcc aagcgcgggg accagcgctg cgaccgcgag   23280
tgcaacagcc caggctgcgg ctgggacggc ggcgactgct cgctgagcgt gggcgacccc   23340
tggcggcaat gcgaggcgct gcagtgctgg cgcctcttca acaacagccg ctgcgacccc   23400
gcctgcagct cgcccgcctg cctctacgac aacttcgact gccacgccgg tggccgcgag   23460
cgcacttgca agtgagccca tccacccgat cgatccgtct gtctatgcat ccatcccagt   23520
ctgtttgtcc gtgggccctg cctctctttc cacctgccca tccacttgcc ccgtctgttt   23580
ctctgtgcac tctatctgcc catcggtgtg tcccacgtgt ctgtccgtgt gtctgttcat   23640
ccatgtgctc tgtctatctt gttcttgttt ctatctgcct atgcacttct ctgccccgtt   23700
tgtctgccct tttctccatc caataattac ttttttttttt ttttcccgag atggagtctt   23760
gctctgtggc ccaggctaga gtgcagtggc gcgatctcgg ctcactgcaa cctctgcctc   23820
ccgggtttaa gcagtactcc tgcctcagcc tctggagtag ctgggattac aggtgtgagc   23880
caccgtgccc agccgaattc cttttttttt tttttttttt ttttaagacg gagtctcgct   23940
ctcttgccca gactggagtg caatggctcc atcttggctc actgcaacct ccgcctcccg   24000
ggttcaagcg attctcctgc ctcagccttc cgagtagctg ggactacagg tacctgccac   24060
```

```
cacgcctggc tttttttttg tattttttagt agagacaggg tttcaccata ttggccaggc   24120
tgctcacgaa ctcctgacct tgtgatccgc ccgccttggc ctcccaaagt gctgggatta   24180
caggtgtgag ccaccgcacc tggctccttt tttttttttt tttttttttt tttaagacag   24240
ggtcttgctc tgtggcccag gctggagtgc agtggtgtga tcttggctca gtgcaatctc   24300
tacctcctgg gctcaagtaa ccctcacacc tcagcctccc taggagctgg gaccacaggt   24360
gtgagccacc gcgcccgggt aactttttgtg ctttttctta gagatggggt ttcgccatgt   24420
tgtccaggct agtcttgaac acctgagctc aaagcaatcc acccagctta gcctctcaaa   24480
gtgctgggat tgtgggcctg agccaccaca tctagcctaa aaattccttt tattggccgg   24540
gcacagtgct cacgcctgta atcccagtac tttgggaggc agaggagggc agatcacctg   24600
aggtcaggag tttgagcttg ggcaacatgg tgaaactccg tctctactaa aaatacaaaa   24660
ttagccgggt gtggtggcac atggctgtaa tcccagctac tcaggaggct gaggcaggag   24720
aattgcttga acctgggagg tggaggatga ggtgagctga gatcgtgcca ttgcactcca   24780
gcctgggcag caagagtaaa tctctgtctc accaaaaaaa aaaaaaaaa aaaaaattgc   24840 ttttgttcct ctgtgtaccc aactgtcttc ctccactcct gtttgtccat ccttgggccg   24900
aatctgtcca tccatgcact cttttttgctc ctctatatgg ctatctgtgg gtgcccctga   24960
ctatctctgc ccctcttctg cccctctctc tgtctgtcct aggcagtcca tctgtccatc   25020
cctacaccct gccccttctg tcctctgcgt acctctctgt ctgcttggaa ccctccaccc   25080
ccttaatctc cacatcctca tcttctctgc tttcccctca ctcactctgt tccagccacc   25140
ctggcctctc tgctgtttcc cagataccc aggcttgatc ccatatcagg gcctttgcac   25200
aagctgttcc tactgcctgg ctgttccctt cccccacatg gctcctccct cacctccttc   25260
aagtctttgc tgaaatggtg gtaccttctc agtgagcacc tccctggtca cccccagccc   25320
ttcctctgct ttattttttct gcttagcatt taattccatc cagcactatg tgtgtgcgtg   25380
cgtgtgtgtg tgtgtgtgtg tgtgtatata catatatata catatatata tatatatatg   25440 tattttttt ttttttttttt ttagacagga tttctctccc attgcccagg ctggagtgca   25500
gtggtgtgat cttggctcac tgcaacctcc acctcctggg ttcaagctat tctcctgcct   25560
cagcttcccg agtagctggg attacaggcg cccgccacca tgcctgacta attttttgtat   25620 ttttagtaga cggggggtt tcaccatttt ggccaggctg gcctagaact cctgacctca   25680
ggttatccgt acaccttggc ctcccaaagt gctggaatta gaggcatgag ccaccgcacc   25740
cagcctgtat ttttatttta ttgatgagta atggagatgc tgtatatttg gctcatgtat   25800
ctcccttact atctgtcttc acccagtgga atgccagctg cacgtggacc aggaattgtg   25860
gccgggcctt atccttgtgc ctgcagcagt gcccaacaca tggtagtcag ttagtattta   25920
ctgattaatt aatagttagc cagtgaggcc gggagtgtgg tgtgggtttg tagtcctagc   25980
tacttgggag gctgaagagg gaggataatt tgagtccagg agtttgagat tgcagagagc   26040
tatgattgca ccactgcact ccggcgtggg caacagagca agaccccatt tcaatcaatc   26100
aatttaaaaa aatattatca agggctgcgt gcggtgactt atgcctgtga tcccagcact   26160
ttgggaggcc gaggcaggtg gatcacctga ggtcaggagt tcaacagcag cctggccaac   26220
atagtaaaac cccgtctctg ctaaaaatac aaaaattaga cgggcgtggt ggtgcatgcc   26280
tgtaatccca gctacttggg aggctgaggc gggagaatcg ctggaaccgg ggaggtggag   26340
gctgcagtga gctgagagat catgctactg cattccggcc tgggcgacag agcaagactc   26400
```

```
cgtctcaaaa aaaaaaaaaa aaaattatcc agtgaatggc aagatttgca gaaagcctgg   26460
catgggtccg tatattccag tcccctgtgc aagccttgtc tggagtctct gtactctacg   26520
gtgtgaatgc atggaagggg attgtctcct ctgacccctg actccgcccc tctctgcctc   26580
acccttcccc accagcccgg tgtacgagaa gtactgcgcc gaccactttg ccgacggccg   26640
ctgcgaccag ggctgcaaca cggaggagtg cggctgggat gggctggatt gtgccagcga   26700
ggtgccggcc ctgctggccc gcggcgtgct ggtgctcaca gtgctgctgc cgccagagga   26760
gctactgcgt tccagcgccg actttctgca gcggctcagc gccatcctgc gcacctcgct   26820
gcgcttccgc ctggacgcgc acggccaggc catggtcttc ccttaccacc ggcctagtcc   26880
tggctccgaa ccccgggccc gtcgggagct ggcccccgag gtgatcgggt gagtgacccc   26940
acctggaaaa gccgtggtgg ctggggagag gagagatgct gttgatccag gtcttgtgtg   27000
tttcatttca cttaatgcct ttacccacca gatgtcagga gcaccgcctc ctggctgtga   27060
caagcaaaaa atgcctccag atggagctag tgcttctggg gtagaattgc ccaggtctag   27120
tgctggcttg tggggaggca ggttgctaag tggcttggca gagtggttaa atacatgtgt   27180
agggtttttt tcttcttctt cttcttcttc tccttctcct tctccttctc cttctccttc   27240
tccttcttct tttctttttt tttttttttt tgagacggag tctctgtcgc ccaggctgga   27300
gtgcagtggc gtgatctcag ctcactgcaa cctctgcctc ctgggttcaa gcaattctct   27360
gcctcagcct ccagagtagc tgggattaca ggcatccacc accaccggg gctaattttc   27420 ttcttcttaa agacatagaa gataaagccg ggcacaatat attcttgtag tcccagctac   27480
ttggaggatc acttgagccc aggaattcaa atctagcctg ggcaacatag caagactccc   27540
atctctctct ctctttttt ttttttttt ttttgagacg gagtctcgct ctgtcgccca   27600
ggctagagtg cagaggcgcg atctcggctt tctgcaagct ccgcctcccg ggttcatgcc   27660
attctcctgc ctcagcctcc cgagtagctg ggactacagg cggccgccac catgcctggc   27720 taatttttg tattttttagt aagagacggg gtttcagtgt gttagccagg atggtctgga   27780
tctcctgact tcgtgatcca cctgcctcgg cctcccaaag tgctgggatt acaggcgtga   27840
gccaccatgc ccggcctccg atctcttaaa aaaaaaaaa aaaaaaaaaa agaagaagaa   27900
gaagaagaag aagaagaaga agaagaagaa gaagaagaag agggaggagg gagggggagg   27960
gggaggggga ggaagaggaa gaagaaggaa gagggggagg gggaggagga ggaggaagag   28020
gaagaagaag aaagaaatag gaggggctcg gtggctcacg cctgtaatcc cagcactttg   28080
gaaggcagtt catttgacgt caggagtttg agaccagcct gggcaacatg gcaaaaccct   28140
gtctctacta aaaatacaaa aaattagcca ggcgtggtgg tgtatgcctt tagtcccagc   28200
tactcaggag gctgaggcat gagaatcact tgaactcagg aagtgaaggt tgcagtgagc   28260
caagattgtg ctactgcact ccagccgggg caacagagcc agactctgtc tcaaaaaaaa   28320
aaaaaaagaa aaagaaaaaa tatagaagta tcctgctagt ggcctggtag aggtaccaga   28380
agggaggtgt agctattgtt gaggagaagg cagagacctg agaggggtgg gtctctgata   28440
cagagaggag ggttgggttt tgcagatatt gggatgtggg tggtggaagg ggaggggtag   28500
agggatgaag gagagtggtt ggtgtaccag cccctggcta agctgagtga tagggccaca   28560
aagtgaaaaa caggtcattt tggagcttgc agagtctgag ggacctggaa gtattgggaa   28620
ggcctccaag gagatacctg ggggctaaag acacaaacaa gaaagatata aaagtgttga   28680
tgatcattga agccatgaga gggactcaaa ggagtgggga gagaaggaac agaagaatta   28740
atctggggac acggagacct aaggattgga tgaatggaat tagctcaaaa aagaggaaga   28800
```

```
ggccaggtgt gatggctcac aactgtgatc ccagcacttt gggaggttga ggcgggtgga   28860
tcacctgagg tcgggagttc aagaccagcc tgaccaacat ggagaaaccc tgtgtatact   28920
aaaaatacaa aattactggg gcgtggtggc gcatgcctgt aatcccagct actcaggagg   28980
ctgaggcagg agaattgcct gaaccctgga cgtggaggtt gtggcgagct gagatagcac   29040
cattgcactc cagcctgggc aacaagagtg aaactctgtc tcaaaacaag caaacaaaca   29100
aacaaataca atgtcctggc caacacggtg aaaccccgtc tctactaaaa atacaaaaat   29160
tacctgggcg tggcagcgcg tgcctgtaat cccagctact caggaggctg aggcagagaa   29220
tcacttgaac cagggagtcg gaggttgcag tgagctgaga ttgcaccact gcactccagc   29280
ctgtcgacag agcaagactt catctcaaaa acaaaaaaca aacaatgtcc cttggctggg   29340
cgtagtggcc caggcctgta aacccagcac attgggaggc tgaggtggga ggattgcttg   29400
agccccggag ttcaagacta gcctgggcaa catagtgaca cctaatctct atgcctccac   29460
ccccaacccc ccccaaaaat tagccaggtg tggtggcaca tgtctgtggt cccagatctt   29520
tgggagaatg aggtggaaag attgcttgaa ggcgggaggt caaggctaca gtgagctctg   29580
atttcgccac tgtgctctag cctgggcgac agagtgaaac cgtctcaaaa aacaaaacag   29640
aacaaacaaa caacaaaaaa aacaggccag gcacagtggc ggctcacgcc tgtaatccca   29700
gcactttggg aggccaaggc agggaggatc acttgaggtc aggagttcaa gaccagcctg   29760
gccaacgtgg tgaaaccccg tctctactaa aaatacaaaa aaattagctg ggcatggtgg   29820
cacacgcctg taatcccagc tacttgggag gctgaggcag gagaatcgct tgaacccagg   29880
aggggaagtt gcagtgagcc gagatcgcac cactgcactc cagcctcggt gcaagatcaa   29940
aaaataatat ccattggatt catggctctg gggggactgc tgaccacagc aagacacgtt   30000
ttaggggtgc agtgggggttg gatgccaggt ggatgcaggt gggccatgga gacctgtggg   30060
tggagatggc gcttcagagc caggcgctgg ggagggaaag tggggcttgg taccaggggg   30120
tgcatcgggc aattttttgag ccctctggtc cctccctgct gtccctgcag ctcggtagta   30180
atgctggaga ttgacaaccg gctctgcctg cagtcgcctg agaatgatca ctgcttcccc   30240
gatgcccaga gcgccgctga ctacctggga gcgttgtcag cggtggagcg cctggacttc   30300
ccgtacccac tgcgggacgt gcgggggtgcg gccctgcctt ggggagggggg tggcgggggc   30360 ggagctgggg gcggccgaag ccccgcctga ggccaaagcc ccgccctcgg ctgaagcccc   30420
gccctctgct tcctgctctt aggggagccg ctggagcctc cagaacccag cgtcccgctg   30480
ctgccactgc tagtggcggg cgctgtcttg ctgctggtca ttctcgtcct gggtgtcatg   30540
gtggcccggc gcaagcgcga gcacagcacc ctctggttcc ctgagggctt ctcactgcac   30600
aaggacgtgg cctctggtca caaggccggg cgggaacccg tgggccagga cgcgctgggc   30660
atgaagtgag aaccctgctc gctccctgtc cctgactacg gggaccttgt gaaccctgga   30720
ccccgccttg acctgactca gacctctgac cccaccccaa atcctccttc ccagctggac   30780
acctctagtg tcccctcac atccctctt cccattgtcc gccaggaaca tggccaaggg   30840
tgagagcctg atgggggagg tggccacaga ctggatggac acagagtgcc cagaggccaa   30900
gcggctaaag gtactgcccc ccctctgacc tttgcccccc cctctgaccc ctccctcag   30960 ggtactgggt ggggtcccca gtggatgatg ggcgtgatca ggggatggca ccgctgtccc   31020
cacctcccta gctccagaga atagtcccag ctttgcaacc ctttcttctc agtgtggttc   31080
tgtgacctca gagggaggaa gatttgccac tggggcccca agggtccctc cgggcaggtg   31140
```

-continued

```
gaaaatcctc ccctccatcc tgcccctccc cagccaggat cctgcttcct ggccagcctg    31200
cactcttcct ggaggtgtcc ccccagccca gagagcgagt ctgccttatc tctgtcagtt    31260
cctattttgt ccagcatgga cttagcctga aagtgctctg agccggttct gagctcatgg    31320
agtcatgccc ctgggttcag tatgagtcag ctttggctgc cattaaaaaa tcccacagag    31380
gtggatcacc tgaggtcagg agttcgagac cagcctgacc aacatggtga aaccccgtct    31440
gtactaaaaa tacaaaagat tagctgggca tggtggcggg cacctgtaat cccagctact    31500
tgggaggctg aggcaggaga atcccttgaa cctggcactc cagactgggc aacaagagcg    31560
aaactccgtc tcaaaaaaaa aaaaaagtcc cacagcatgg gtgacctaaa caacagaaat    31620 taatttttc acggttctgg aggttggaag tccaagccca aggtgctgtc agggctggtt    31680
cctggtaagg gctctcttcc tggtgtgcag atggccgcct tctcactgta gcctcacatg    31740
gcctttcctc tgtgtacaca gaggggagag agagagagag agagagagag agagagagag    31800
agagagagac agatttgaca tcccatcctc ttcttgtaag gataccaatc ctattggatt    31860
agggtcccac atttataacc tcatataacc ttaattacct ccttaaaggc cctatctcac    31920
caggcttggt agcttgcacc agtaatttca gctacttggg aggctgaggc aggaggatca    31980
cttgagtcca ggagttggag cctgcagtga gctatgactg catcacttca ctccagcctg    32040
ggtaacagag caagaccctg tctaaaaata aagtcctatc ttcaaatgca ggcacatgga    32100
aattttatat attatttagg gttttagtgt atgatttctg tttatttatt tatttatttt    32160
ttgagaccag gtctcactct gttgcccaag ctggagtgca gtggcgtgat cttggctcat    32220
tgcagcctcc acctcccagg ttcaagtgat tcccctgcct cagcctcccg agtagctggg    32280
attataggca tgtgctacca tgcccggcta atttttgtat ttttagtaga gatggggttt    32340
caccatgttg gccaggctgg tctcaagctg cagacctcaa gtgatccacc cgcctcggca    32400
tcccaaagtg ctgggattac agacgtgagc caccgtgccc ggccattgta tgattttag    32460 aggggggcaca attgagtcca tacagatcct gctagcatta ctgaggcacc cgctgaatgt    32520
ctctaatgca cataaaacat cttatttcat ctctctgagg acgctgtaaa gtagctattg    32580
acatatactt caatttacaa actcccttcc tctgtccata tttaatgtt gtgaaatgga    32640 atcatctatt acagtggaca gataaaaaaa cctgctcaac ccagactttt ccttctgcct    32700
tcccatccca aagtaggtat tagaggtatt aaaggggtgg cccaatgtaa ttgtggtggt    32760
atcttagcat ggtggaatgg ctgcgtcatc ctgattttgc caatgagaag ctcagagctt    32820
caaagtgatt tgcccagagc cttccagcta ctaaggggtg gggttggaac ttgaacctgg    32880
atcagatgct atcccaatct gcttatactg tgtgcttata gtcccagcta cttgggccgc    32940
tgaggtggga ggatcatttg agcccaggaa gttgaggctg cagtgaggta tgattgcagc    33000
actgcactcc agcctgagtg acacagtgag actcagtctc taaaaaatat atacataaat    33060
aattaaagcc atttattact caaaaagacc aaaaaaaaaa aaaaaagaa accttgtgtc    33120 ttcctttat tacctccttg ggctatggca cacattgatt tcctgttaat ctcagcactt    33180
tgggaggctg agaggggctg atcacctgag gtcaggagtt cgagaccagc ctggccaaca    33240
tggtgaaacc ccttctctac taaaaataca aaaaattagc tggacaccgt ggcatgtgcc    33300
tgtaatccca gctactccag aggctgaggc aggagaatca cttgaacccg ggaggcgggg    33360
gttgcagtga gctgagatca tgccactgca ctccagcctg ggggacagag cgagactctg    33420
tctcaaaaac aaataaaaca ccaaacagat ggtaaatgat ttcccagggc tctgtgtgta    33480
tctcctaaag agaaacctgt aggaatgccc agccccatcc ctggcagtgg ctctccccag    33540
```

-continued

```
caccaaaggg tgagatctga gatccagggt gcctgccccat ccaggtagag gagccaggca   33600
tgggggctga ggaggctgtg gattgccgtc agtggactca acaccatctg gttgctgctg   33660
acatccgcgt ggcaccagcc atggcactga caccaccaca gggcgacgca gatgctgatg   33720
gcatggatgt caatgtgcgt ggcccaggtt agtgacagtg cccctcccaa agggatgccc   33780
ctcacccatc ctacctgtga gaggttattt ctgactctgt gttttgggga gaactggggg   33840
agtctctaag cttctgtgaa gggtgtgtgt attcagcaac actcttggtt ggaagtgaca   33900
aaggtccaac tcagactagc ttaagtaaaa caagggattt atcaactcat ttaactaaaa   33960
gtggcacatt tggatccagg actcagtttt cccctctcta ccctttgact ccaatcttac   34020
aaaaccttct taatgctcca gaaaagtctc aggatgcatt ctgattggac agactagggt   34080
cacgtgctca tccttgagcc aatcagtatg accaggggggc tggaatatgc aaattgacca   34140
agcctgattc acatacctgt ctttgagctg gtgggggtcg ggtctgctgg tggagcgggg   34200
aggtcagtct ctacccaggg cttgagaatg gagaaccgga tgcaagtggc tccctaagaa   34260
aaatgaggac aagtgcttgt gtacagtgtg tgcagtgtag cggactatgt tgtttgatcc   34320
tcttagatcc atctttgtta tgtttcaggg cattcctgcc ttagcttcat tttgcttatg   34380
ctccaaatgg cctgtactta tggctctctt ttgaagtccc tctggctgct ggggcctgaa   34440
gtgcctggga ttttatgtcc ctgggggcag ctcttttttt cccccccct tttaaaacac   34500 tcaaatgaat tggcagaaag gggcagctcc taaccagtgg gtgcaggagt atgaagggga   34560
tggtttcttt gccttgagtt ggattagaac tctggggtac aacacatgtt ccagagtccc   34620
tttggaggat caaggtggaa taacccttttg ggaatttact ggaggttgca cacttgcttg   34680
actcccagag tcccttgtcc tgtgttccct gtgccctagg agtagttctg tgacaaatca   34740
cgtgcccacg aatcctcatt ctgggtgtgg gtgtgcagac aggaggatct gctaattgtc   34800 attttttccat gtgtcccatt agctcctaat ggggtaccct tgataacatt tcctggaaaa   34860
ggccctgtgt ttaccttcct gctgacacac tcctgtccct gcagatggct tcaccccgct   34920
aatgctggct tccttctgtg ggggggctct ggagccaatg ccaactgaag aggatgaggc   34980
agatgacaca tcagctagca tcatctccga cctgatctgc caggggggctc agcttggggc   35040 acggactgac cgtactggcg agactgcttt gcacctggct gccgttatg cccgtgctga   35100 tgcagccaag cggctgctgg atgctggggc agacaccaat gcccaggacc actcaggccg   35160
cactcccctg cacacagctg tcacagccga tgcccagggt gtcttccagg tgagataggc   35220
acacactttg gacctcagag ctggggcagg cattagactt acctgggttt gagcccagt   35280 tctgcctttc agactcattt tttctcattt ggaaaatggg gatatatggg aatacagtat   35340
ctgtcaagca gctgctccct gaacctcacc aatttcaggg gttgggggtat gggggttggg   35400 gacttcatgg gacttagggg tgctcctgat tcctctgttc ctgccatgac ccctcctgct   35460
gcatccactc tctgtcctag attctcatcc gaaaccgctc tacagacttg gatgcccgca   35520
tggcagatgg ctcaacggca ctgatcctgg cggcccgcct ggcagtagag ggcatggtgg   35580
aagagctcat cgccagccat gctgatgtca atgctgtgga tgagcttggt aggttggcag   35640
aggaatcaag tctaagctgg gttggtgtca cctgggccct gagggtcatg ttggtgcaaa   35700
ttcataccca tgttgagacc caatcactga agctcacgca cacataacca ggcttcatga   35760
agcctgcagg gtcatgcagg gtcaccacta gtccttaggg tgcctcaggg atttagaaaa   35820
aggtgccttt cccctagata cttcatttcc acctgctttg ttagacggac acactgtact   35880
```

```
tccacctgct ggaagttatt ataataaacg tacacatcag gccatgtgtg gtggctcatg   35940
cctgtgatcc caacactttg ggaggctgag gcaggaggat gacttgaggc caggagtttg   36000
agaccagact gggcaacata gtgggttcta caaaagtttt ttgaaagatt agccatgtgc   36060
ggtggtgcat acctgtggcc ctagctactc cagaaactga ggtgggaggg tcgtttgagc   36120
ccaggaggtt gagtctgtga gccgtgattg tgcccctgca ctccagcctg ggggacagac   36180
tccatctcaa aaaaaaaaaa cagtctccag acgttgccaa atgctctggg ggctgggggc   36240
agggagtttc tcctagttga gagccacagt tctagggcag ggctggccaa taggactttc   36300
tgtgatgatg gaattattct ctgcactgtc cagtatagta gccactggcc acatatagtg   36360
acttgaaatg tgactgaggc aaatgaagaa gtaaatgttt tagttcattt aatttttttc   36420
tccttatgtt gccctttttt taattttttt ttttgagaca gagtctcact cttgtcaccc   36480
aggctggagt gcaatggtgt gatcttggct cactgcaacc tccactaccc aggttccagt   36540
gattctcctg tctcagcctc ccaagtgtct gggactaaag gtgcccatca ccatgcctgg   36600
ctattttttt gtattttag tagagacggg gtttcgcaat gttggccagg ctggcctcaa   36660
actcctgacc tcaggtgatc cacctgcctt ggcctcccaa agtgctgggg ttataggcat   36720
gagccactga gtccatcctt ttttttaaaa acaaaaaaca aaaacaaaa aactgcttta   36780 ttgagatata attaacatgc catacaattc acccatttaa agtgtacaat tcaatggctc   36840
ttagtataat cagagtcata caactattac cacaatcaat tttagaacat ttcatcacct   36900
gaaaaataaa ttctcaccac ttggccatca tctgccaagc ccctcatctg tccagccctg   36960
tgcaaccact gatttgcttt ttgtcttcat ggatttgcct gttctggaca tttcatataa   37020
atgtaatcat atgatacgtg gtctttttg tctgcctttt tttcagttag cattatgttc   37080
tcaaggttca cccatgttgt agcatagttc agctgaataa taatccattg tgtcgatgga   37140
ccactttttt tttctttat ttttagacat agggtatcac tctgtcactc aggctggagt   37200
gcagtggcat gattacggct ctctgcagcc tcaaactccc aggctcaagt gatcctccca   37260
tcccaccctc ctgaatagct ggtattacag gtgtgtgcca gcatacctgg gtaattctta   37320
aattttttgt ggaaatgggg tctcactttg ttgcccaggc tgatctcaaa ctcctggcct   37380
taagcaatac tcccaccttg gcctcccaaa ttgttgagat tataggcgtg agccactgtg   37440
cctggccaaa agtttcaatt ttgatcatgt ccaatttatc tgttttgtag ttgttattgt   37500
tatttgtggt tttggtgtca catctaagaa tcttggccta attcaaggtc atgaagatt   37560 actcttatgt tttcttctag atgtttagtt ctatagttgg agctcatata tttaggtttc   37620
tgatccattt tgagttagtg tttgtataaa gtgtgaggta ggggtccaac ttcattcttt   37680
gaatgtgaat attcagttgt tccagcacca ttagttgaga agaccattct ttccccattg   37740
aatggtcctg gcacctattt tattaaattt aaatctaaag aaccacatgt aggttgggca   37800
cggtggctca tgcctgtaat cccaacactt tgggaggcca aggctggtgg atcacttgag   37860
cttaggagtt tgagaccagt ttgggcaaca tagtggaact ctatctctat caaaaataca   37920
aaaaatcagc tgggcatggt ggtacatgcc tgtagtccca gctactgggg aggctgaggc   37980
aggaaaatcg cctgagccca gcaggtagag gttgcagtga actgagattg tgccaatgga   38040
ctccagcctg ggtgacagaa caagacacta cctcaaaaat aaataaatgg ataaataaaa   38100
accacatgtg actgactact gtattggatg tcacaaccct aggttcaact gaaggaggtc   38160
cacacagcac cccctgtgta taaacagtca tgcacatgcg cgcacacaca cacacacaca   38220
caaacacaca cacacagaca caaagtgctt ccccattgca cagagtcatt ttgcagattt   38280
```

-continued

```
gcacacacat ggatccagac acaagtactt ggatattcac ggcaggcctg cctcctctac   38340
ccctaggcca cattctagac aatttctgcc tccctgacat gggggcccca ggacaggtgc   38400
ctggtcctga cctctctccc cttcatcctc cagggaaatc agccttacac tgggctgcgg   38460
ctgtgaacaa cgtggaagcc actttggccc tgctcaaaaa tggagccaat aaggacatgc   38520
aggatagcaa ggtgagcccc agcccttggt ccactgggtg tcagcagtgg cacagtgcca   38580
ttgcaatcca gcctgggcaa cagagtgaga ctctctcaaa aaacaaaaca aaataaaacc   38640
ccaaacattg gattaaaata taatttactt tggtgactaa agttttttggg ggccccttaa   38700 attttgtgcc taatggctgg gtgtggtggt tcatgcctat aatcccagca ctttgggagg   38760
tcgagatggg tggattactt gagttcagga gtttgagacc agcctggcca acgtagtaaa   38820
accctgtctc tattaaaaat acaaaaatta gctgggcgta gtggtgcaca cctgtagtcc   38880
cagctgctcg ggaggctgag gcaggagaat cgcttgaacc cggaaggctg aggttgcagt   38940
gaactgaaat ggcgccactg cactccagcc tgggcgacac agtgagactc tgtcaaaaaa   39000
aaaaaaaaaa aaagacaaga aaaaaaagt tatgcctaag gtgagtacct cgcttaactc   39060
accctagtcc tggccttgac ctctggcact tagtaggtga tggatgaatg tggtttagag   39120
gaaagaactt gtccaggctc ccccagcaca gccgggattt aacccaggtc tgtcaagctc   39180
cagtgtacaa actcatagct ctcgggctcc cccaagaggc tggaagactt tgctactgtt   39240 agctgggggtt tcgctgacct ctgtgggttc tggccccccca ggaggagacc ccctattcc   39300 tggccgcccg cgagggcagc tatgaggctg ccaagctgct gttggaccac tttgccaacc   39360
gtgagatcac cgaccacctg gacaggctgc cgcgggacgt agcccaggag agactgcacc   39420
aggacatcgt gcgcttgctg gatcaaccca gtgggccccg cagccccccc ggtccccacg   39480
gcctggggcc tctgctctgt cctccagggg ccttcctccc tggcctcaaa gcggcacagt   39540
cggggtccaa gaagagcagg aggccccccg ggaaggcggg gctggggccg cagggccccc   39600
gggggcgggg caagaagctg acgctggcct gcccgggccc cctggctgac agctcggtca   39660
cgctgtcgcc cgtggactcg ctggactccc cgcggccttt cggtgggccc cctgcttccc   39720
ctggtggctt cccccttgag gggccctatg cagctgccac tgccactgca gtgtctctgg   39780
cacagcttgg tggcccaggc cgggcgggtc tagggcgcca gcccctgga ggatgtgtac   39840 tcagcctggg cctgctgaac cctgtggctg tgccctcga ttgggcccgg ctgccccac   39900 ctgcccctcc aggcccctcg ttcctgctgc cactggcgcc gggaccccag ctgctcaacc   39960
cagggacccc cgtctccccg caggagcggc ccccgcctta cctggcagtc ccaggacatg   40020
gcgaggagta cccggcggct ggggcacaca gcagcccccc aaaggcccgc ttcctgcggg   40080
ttcccagtga gcaccttac ctgaccccat ccccgaatc ccctgagcac tgggccagcc   40140
cctcacctcc ctccctctca gactggtccg aatccacgcc tagcccagcc actgccactg   40200
gggccatggc caccaccact ggggcactgc ctgcccagcc acttcccttg tctgttccca   40260
gctcccttgc tcaggcccag acccagctgg gccccagcc ggaagttacc cccaagaggc   40320
aagtgttggc ctgagacgct cgtcagttct tagatcttgg gggcctaaag agacccccgt   40380
cctgcctcct ttctttctct gtctcttcct tcctttttagt cttttttcatc ctcttctctt   40440 tccaccaacc ctcctgcatc cttgccttgc agcgtgaccg agataggtca tcagcccagg   40500
gcttcagtct tcctttattt ataatgggtg ggggctacca cccaccctct cagtcttgtg   40560
aagagtctgg gacctccttc ttccccactt ctctcttccc tcattccttt ctctctcctt   40620
```

```
ctggcctctc atttccttac actctgacat gaatgaatta ttattatttt tattttttct    40680
ttttttttta cattttgtat agaaacaaat tcatttaaac aaacttatta ttattatttt    40740
ttacaaaata tatatatgga gatgctccct cccctgtga accccccagt gccccgtgg     40800 ggctgagtct gtgggcccat tcggccaagc tggattctgt gtacctagta cacaggcatg    40860
actgggatcc cgtgtaccga gtacacgacc caggtatgta ccaagtaggc acccttgggc    40920
gcacccactg gggccagggg tcgggggagt gttgggagcc tcctccccac cccacctccc    40980
tcacttcact gcattccaga tgggacatgt tccatagcct tgctggggaa gggcccactg    41040
ccaactccct ctgccccagc cccacccttg gccatctccc tttgggaact aggggggctgc   41100 tggtgggaaa tgggagccag ggcagatgta tgcattcctt tgtgtccctg taaatgtggg    41160
actacaagaa gaggagctgc ctgagtggta ctttctcttc ctggtaatcc tctggcccag    41220
cctcatggca gaatagaggt attttttaggc tattttttgta atatggcttc tggtcaaaat    41280
ccctgtgtag ctgaattccc aagccctgca ttgtacagcc ccccactccc ctcaccacct    41340
aataaaggaa tagttaacac tcagtgttgt tggtctgtgt ctaggtaagg tggggagtgg    41400
tggcagtggg acttctatct cccccacccca gggctaactt gagctcccat cttggggtaa    41460
atacatttga cttgccagtc tacttatgct tcctcttttg gcagatgact accgattgga    41520
ttagtggttg tcacctgact taagctgagc caatcagatt cttttgctcg agaactttct    41580
ttaatggaga ggctaagaaa gttgtcagtt ggtggagctc ttaaggtcac aatcagattt    41640
agaaatatca gtggccaatt cgaggtggtg ggcaaagaga caagcaaaca gggcagaaga    41700
atgaagctaa tattcaggga gaatcagaaa tgagagctca aatggctcct tgagggctgg    41760
gggggttatc tcggctccca gtgcagttat caattccagt taattgagtg ttcattccat    41820
tgagatcaac aggtatttat taattgcttt ctaagtatct gatcatggtt ctgcatgaat    41880 ttcacttttta cttcatgctc ctatgggttt tggagataac cttggaccca tgtaataaat    41940
acttctttac ttgtgcca                                                  41958
```

```
<210> SEQ ID NO 3
<211> LENGTH: 8680
<212> TYPE: RNA
<213> ORGANISM: homo sapien

<400> SEQUENCE: 3
cuucggcgaa guuggcggcg cggaggcugg cccgggacgc gcccggagcc cagggaagga      60
gggaggaggg gagggucgcg gccggccgcc auggggccgg gggcccgugg ccgccgccgc     120
cgccgucgcc cgaugucgcc gccaccgcca ccgccacccg ugcgggcgcu gccccugcug     180
cugcugcuag cggggccggg ggcugcagcc ccccuugcc uggacggaag cccgugugca      240
aauggagguc guugcaccca gcugcccucc cgggaggcug ccugccugug cccgccuggc     300 uggguggggug agcggugtuca gcuggaggac cccugucacu caggcccug ugcuggccgu      360 ggugucugcc agaguucagu gguggcuggc accgcccgau ucucaugccg gugccccgu      420 ggcuuccgag gcccugacug cucccugcca gaucccugcc ucagcagccc uugugcccac     480
ggugcccgcu gcucaguggg gcccgaugga cgcuuccucu gccccugccc accugctuac     540
cagggccgca gcugccgaag cgacguggau gagugccggg ugggugagcc cugccgccau      600
gguggcaccu gccucaacac accuggcucc uuccgcugcc agugccagc uggcuacaca      660 gggccacuau gugagaaccc cgcggugccc ugugcaccu caccaugccg uaacgggggc      720
accugcaggc agaguggcga ccucacuuac gacugugccu gucuuccugg guuugagggu      780
```

-continued

```
cagaauugug aagugaacgu ggacgacugu ccaggacacc gaugucucaa uggggggaca      840
ugcguggaug cgucaacac cuauaacugc cagugcccuc cugaguggac aggccaguuc       900
ugcacggagg acguggauga gugucagcug cagcccaacg ccugccacaa uggggguacc      960
ugcuucaaca cgcugggugg ccacagcugc guguguguca auggcuggac aggcgagagc     1020
ugcagucaga auaucgauga cugugccaca gccgugugcu uccauggggc caccugccau     1080
gaccgcgugg cuucuuucua cugugccugc cccaugggga agacuggccu ccugugucac     1140
cuggaugacg ccugugucag caaccccugc cacgaggaug cuaucuguga cacaaauccg     1200
gugaacggcc gggccauuug caccuguccu cccggcuuca cggguggggc augugaccag     1260
gauguggacg agugcucuau cggcgccaac cccugcgagc acuugggcag gugcgugaac     1320
acgcagggcu ccuuccugug ccagugcggu cguggcuaca cuggaccucg cuguugagacc    1380 gaugucaacg agugucuguc ggggcccugc cgaaaccagg ccacgugccu cgaccgcaua     1440
ggccaguuca ccuguaucug uauggcaggc uucacaggaa ccuauugcga gguggacauu     1500
gacgagaguc agaguagccc cugugucaac gguggggucu gcaaggaccg agucaauggc     1560
uucagcugca ccugcccuc gggcuucagc ggcuccacgu gucagcugga cguggacgaa      1620
ugcgccagca cgcccugcag gaauggcgcc aaaugcgugg accagcccga uggcuacgag     1680
ugccgcugug ccgagggcuu ugagggcacg cugugugauc gcaacgugga cgacugcucc     1740
ccugacccau gccaccaugg ucgcugcgug gauggcaucg ccagcuucuc augugccugu     1800
gcuccuggcu acacgggcac acgcugcgag agccaggugg acgaaugccg cagccagccc     1860
ugccgccaug gcggcaaaug ccuagaccug guggacaagu accucugccg cugcccuucu     1920
gggaccacag gugugaacug cgaagugaac auugacgacu gugccagcaa ccccugcacc     1980
uuuggagucu gccgugaugg caucaaccgc uacgacgug ucugccaacc uggcuucaca      2040 gggcccuuu guaacgugga gaucaaugag ugugcuucca gcccaugcgg cgagggaggu     2100
uccugugugg auggggaaaa uggcuuccgc ugccucugcc cgccuggcuc cuugcccca      2160 cucugccucc ccccgagcca ucccugugcc caugagcccu gcagcacgg caucugcuau      2220 gaugcaccug gcgggguuccg cugugugugu gagccuggcu ggagugggcc ccgcugcagc    2280
cagagccugg cccgagacgc cugugagucc cagccgugca gggccggugg gacaugcagc     2340
agcgauggaa ugggguuucca cugcaccugc ccgccuggug uccagggacg ucagugugaa    2400
cuccucuccc ccugcacccc gaaccccugu gagcauggg ccgcugcga gucugcccu       2460 ggccagcugc cugucugcuc cugccccag ggcuggcaag cccacgaug ccagcaggau      2520 guggacgagu gugcuggccc cgcacccugu ggcccucaug guaucugcac caaccuggca    2580
gggaguuuca gcugcaccug ccauggaggg uacacuggcc cuuccugcga ucaggacauc    2640
aaugacugug accccaaccc augccugaac gguggcucgu gccaagacgg cguggggcucc   2700 uuuuccugcu ccugccuccc ugguuucgcc ggccacgau gcgcccgcga ugaggaugag      2760
ugccugagca ccccugcgg cccgggcacc uguaccgacc acguggccuc cuucaccugc     2820
accugcccgc caggcuacgg aggcuuccac ugcgaacagg accugcccga cugcagcccc    2880
agcuccugcu ucaauggcgg gaccugugug gacggcgauga acucguucag cugccuugugc   2940 cgucccggcu acacaggagc ccacugccaa caugaggcag accccugccu cucgcggccc     3000
ugccuacacg gggcgucug cagcgccgcc caccuggcu uccgcucac cugccucgag       3060 agcuucacgg gcccgcagug ccagacgcug guggauuggu gcagccgcca gccuugucaa     3120
```

-continued

```
aacggggguc gcugcgucca gacuggggcc uauugccuuu guccccuugg auggagcgga    3180
cgccucugug acauccgaag cuugcccugc agggaggccg cagcccagau cggggugcgg    3240
cuggagcagc ugugucaggc gggugggcag ugugguggau aagacagcuc ccacuacugc    3300
gugugcccag agggccguac ugguagccac ugugagcagg agguggaccc cugcuuggcc    3360
cagcccugcc agcauggggg gaccugccgu ggcuauaugg ggggcuacau guguagagu    3420 cuuccuggcu acaaugguga uaacugugag gacgacgugg acgagugugc cucccagccc    3480
ugccagcacg ggggguucaug cauugaccuc guggcccgcu aucucugcuc cuguccccca    3540
ggaacgcugg gggugcucug cgagauuaau gaggaugacu gcggcccagg cccaccgcug    3600
gacucagggc cccggugccu acacaauggc accugcgugg accggugggg ugguuuccgc    3660
ugcaccuguc ccccaggaua cacugguuug cgcugcgagg cagacaucaa ugagugucgc    3720
ucaggugccu gccacgcggc acacacccgg gacugccugc aggacccagg cggagguuuc    3780
cguugccuuu gucaugcugg cuucucaggu ccucgcuguc agacuguccu gucucccugc    3840
gagucccagc caugccagca uggaggccag ugccguccua gcccgggucc uggggguggg    3900
cugaccuuca ccugucacug ugcccagccg uucgggggguc cgcguugcga gcgggguggcg    3960 cgcuccugcc gggagcugca gugccccggug ggcgucccau gccagcagac gccccgcggg    4020
ccgcgcugcg ccugcccccc aggguugucg ggacccuccu gccgcagcuu cccggggucg    4080
ccgccggggg ccagcaacgc cagcugcgcg gccgccccu gucuccacgg gggcuccugc    4140
cgccccgcgc cgcucgcgcc cuucuuccgc ugcgcuugcg cgcagggcug gaccgggccg    4200
cgcugcgagg cgcccgccgc ggcacccgag gucucggagg agccgcggug cccgcgcgcc    4260
gccugccagg ccaagcgcgg ggaccagcgc ugcgaccgcg agugcaacag cccaggcugc    4320
ggcugggacg gcggcgacug cucgcugagc gugggcgacc ccuggcggca augcgaggcg    4380
cugcagugcu ggcgccucuu caacaacagc cgcugcgacc ccgccugcag cucgcccgcc    4440
ugccucuacg acaacuucga cugccacgcc gguggccgcg agcgcacuug caacccggug    4500
uacgagaagu acugcgccga ccacuuugcc gacggccgcu gcgaccaggg cugcaacacg    4560
gaggagugcg gcugggaugg gcuggauugu gccagcgagg ugccggcccu gcuggcccgc    4620
ggcgugcugg ugcucacagu gcugcugccg ccagaggagc uacugcguuc cagcgccgac    4680
uuucugcagc ggcucagcgc cauccugcgc accucgcugc gcuuccgccu ggacgcgcac    4740
ggccaggcca uggucuuccc uuaccaccgg ccuaguccug gcuccgaacc ccgggcccgu    4800
cgggagcugg cccccgaggu gaucggcucg guaguaaugc uggagauuga caaccggcuc    4860
ugccugcagu cgccugagaa ugaucacugc uuccccgaug cccagagcgc cgcugacuac    4920 cuggagcgu ugucagcggu ggagcgccug gacuucccgu acccacugcg ggacgugcgg    4980
ggggagccgc uggagccucc agaacccagc guccgcugc ugccacugcu aguggcgggc    5040
gcugucuugc ugcuggucau ucucguccug gugucaugg uggcccggcg caagcgcgag    5100
cacagcaccc ucugguuccc ugagggcuuc ucacugcaca aggacguggc cucuggucac    5160
aagggccggc gggaacccgu gggccaggac gcgcugggca ugaagaacau ggccaagggu    5220
gagagccuga uggggggagu ggccacagac uggaugggaca cagagugccc agaggccaag    5280
cggcuaaagg uagaggagcc aggcauggg gcugaggagg cuguggauug ccgucagugg    5340
acucaacacc aucuguugc ugcugacauc cgcguggcac cagccauggc acugacacca    5400 ccacagggc acgcagaugc ugauggcaug gaugucaaug ugcguggccc agauggcuuc    5460
accccgcuaa ugcuggcuuc cuucuguggg ggggcucugg agccaaugcc aacugaagag    5520
```

```
gaugaggcag augacacauc agcuagcauc aucuccgacc ugaucugcca gggggcucag   5580 cuugggcac ggacugaccg uacuggcgag acugcuuugc accuggcugc ccguuaugcc    5640
cgugcugaug cagccaagcg gcugcuggau gcuggggcag acaccaaugc ccaggaccac    5700
ucaggccgca cuccccugca cacagcuguc acagccgaug cccagggugu cuuccagauu    5760
cucauccgaa accgcucuac agacuuggau gcccgcaugg cagauggcuc aacggcacug    5820
auccuggcgg cccgccuggc aguagagggc augguggaag agcucaucgc cagccaugcu    5880
gaugucaaug cuguggauga gcuugggaaa ucagccuuac acugggcugc ggcugugaac    5940
aacguggaag ccacuuuggc ccugcucaaa aauggagcca auaaggacau gcaggauagc    6000
aaggaggaga cccccuauu ccuggccgcc cgcgagggca gcuaugaggc ugccaagcug     6060
cuguuggacc acuuugccaa ccgugagauc accgaccacc uggacaggcu gccgcgggac    6120
guagcccagg agagacugca ccaggacauc gugcgcuugc uggaucaacc cagugggccc    6180
cgcagccccc ccggucccca cggccugggg ccucugcucu guccuccagg ggccuuccuc    6240
ccuggccuca aagcggcaca gucggggucc aagaagagca ggaggccccc cgggaaggcg    6300
gggcuggggc cgcagggggcc ccggggggcgg ggcaagaagc ugacgcuggc cugcccgggc   6360
ccccuggcug acagcucggu cacgcugucg cccguggacu cgcuggacuc cccgcggccu    6420
uucggugggc cccugcuuc cccugguggc uuccccuug aggggcccua ugcagcugcc      6480
acugccacug cagugucucu ggcacagcuu gguggcccag gccgggcggg ucuagggcgc     6540 cagccccug gaggaugugu acucagccug ggccugcuga acccgugggc ugugcccuc       6600 gauugggccc ggcugccccc accugccccu ccaggccccu cguuccugcu gccacuggcg     6660 ccggacccc agcugcucaa cccagggacc cccgucuccc cgcaggagcg gccccgccu      6720 uaccuggcag ucccaggaca uggcgaggag uacccggcgg cuggggcaca cagcagcccc    6780
ccaaaggccc gcuuccugcg gguucccagu gagcacccuu accugacccc auccccgaa     6840 uccccugagc acugggccag ccccucaccu cccuccgcucu cagacugguc cgaauccacg   6900
ccuagcccag ccacugccac uggggccaug gccaccacca cuggggcacu gccugcccag     6960
ccacuccccu ugucuguucc cagcucccuu gcucaggccc agaccagcu ggggccccag      7020 ccggaaguua cccccaagag gcaaguguug gccugagacg cucgucaguu cuuagaucuu    7080 gggggcuaa agagacccccc guccugccuc cuuucuuucu cugucucuuc cuuccuuuua    7140
gucuuuuuca uccucuucuc uuuccaccaa cccuccugca uccuugccuu gcagcgugac    7200
cgagauaggu caucagccca gggcuucagu cuuccuuuau uuauaaugggg uggggggcuac   7260 cacccacccu cucagucuug ugaagagucu gggaccuccu ucuuccccac uucucucuuc   7320
ccucauuccu uucucucucc uucuggccuc ucauuuccuu acacucugac augaaugaau     7380
uauuauuauu uuuauuuuuc uuuuuuuuuu uacauuuugu auagaaacaa auucauuuaa    7440
acaaacuuau uauuauuauu uuuuacaaaa uauuauauaug gagaugcucc cucccccugu    7500 gaaccccccca gugcccccgu ggggcugagu cuguggggccc auucggccaa gcuggauucu    7560
guguaccuag uacacaggca ugacugggau cccguguacc gaguacacga cccaggauaug   7620 uaccaaguag gcacccuugg gcgcacccac uggggccagg ggcucgggggga guguuggggag   7680 ccuccucccc accccaccuc ccucacuuca cugcauucca gauggggacau guuccauagc    7740 cuugcugggg aagggcccac ugccaacucc cucugcccca gccccacccu uggccaucuc    7800
ccuuugggaa cuagggggggcu gcuggugggga aaugggagcc agggcagaug uaugcauucc   7860
```

```
uuuguguccc uguaaaugug ggacuacaag aagaggagcu gccugagugg uacuuucucu    7920
uccugguaau ccucuggccc agccucaugg cagaauagag guauuuuuag gcuauuuuug    7980
uaauauggcu ucuggucaaa aucccugugu agcugaauuc ccaagcccug cauuguacag    8040 cccccacuc  cccucaccac cuaauaaagg aauaguuaac acucaguguu guuggucugu    8100
gucuagguaa ggugggggagu ggggcagug  ggacuucuau cuccccccacc cagggcuaac    8160 uugagcuccc aucuuggggu aaauacauuu gacuugccag ucuacuuaug cuuccucuuu    8220
uggcagauga cuaccgauug gauuaguggu ugucaccuga cuuaagcuga gccaaucaga    8280
uucuuuugcu cgagaacuuu cuuuaaugga gaggcuaaga aaguugucag uuggguggagc    8340 ucuuaagguc acaaucagau uuagaaauau caguggccaa uucgaggugg ugggcaaaga    8400
gacaagcaaa cagggcagaa gaaugaagcu aauauucagg gagaaucaga aaugagagcu    8460
caaauggcuc cuugagggcu ggggggguua ucucggcucc cagugcaguu aucaauucca    8520
guuaauugag uguucauucc auugagauca acaggauuu  auuaauugcu uucuaaguau    8580
cugaucaugg uucugcauga auuucacuuu uacuucaugc uccuaugggu uuuggagaua    8640
accuuggacc cauguaauaa auacuucuuu acuugugcca                          8680
```

```
<210> SEQ ID NO 4
<211> LENGTH: 8666
<212> TYPE: RNA
<213> ORGANISM: homo sapien

<400> SEQUENCE: 4
gcggcgcgga ggcuggcccg ggacgcgccc ggagcccagg gaaggaggga ggaggggagg      60
gucgcggccg gccgccaugg ggccggggggc ccguggccgc cgccgccgcc gucgcccgau     120
gucgccgcca ccgccaccgc cacccgugcg ggcgcugccc cugcugcugc ugcuagcggg     180
gccgggggcu gcagccccccc cuugccugga cggaagcccg ugugcaaaug gaggucguug     240
cacccagcug cccucccggg aggcugccug ccugugcccg ccuggcuggg ugggugagcg     300
gugucagcug gaggacccccu gucacucagg ccccugugcu ggccguggug ucugccagag     360
uucaguggug gcuggcaccg cccgauucuc augccggugc ccccguggcu uccgaggccc     420
ugacugcucc cugccagauc ccugccucag cagcccuugu gcccacgguug cccgcugcuc     480 aguggggccc gauggacgcu uccucugcuc cugcccaccu ggcuaccagg gccgcagcug     540
ccgaagcgac guggaugagu gccgggguggg ugagcccugc cgccaugguug gcaccugccu     600 caacacaccu ggcuccuucc gcugccagug uccagcuggc uacacagggc cacuauguga     660 gaacccccgcg gugcccugug caccccucacc augccguaac gggggcaccu gcaggcagag     720
uggcgaccuc acuuacgacu gugccugucu uccugggguu gagggucaga auugugaagu     780
gaacguggac gacuguccag gacaccgaug ucucaauggg gggacaugcg uggauggcgu     840
caacaccuau aacugccagu gccuccccuga guggacaggc caguucugca cggaggacgu     900
ggaugagugu cagcugcagc ccaacgccug ccacaauggg gguaccugcu ucaacacgcu     960 gggugggccac agcugcgugu gugucaaugg cuggacaggc gagagcugca gucagaauau    1020
cgaugacugu gccacagccg ugugcuucca uggggccacc ugccaugacc gcguggcuuc    1080
uuucuacugu gccugcccca uggggcaagac uggccuccug uguaccuggg augacgccug    1140
ugucagcaac cccugccacg aggaugcuau cugugacaca aauccgguga acggccgggc    1200
cauuugcacc uguccucccg gcuucacggg uggggcaugu gaccaggaug uggacgagug    1260
cucuaucggc gccaacccccu gcgagcacuu gggcagguggc gugaacacgc agggcuccuu    1320
```

-continued

```
ccugugccag ugcggucgug gcuacacugg accucgcugu gagaccgaug ucaacgagug   1380
ucugucgggg cccugccgaa accaggccac gugccucgac cgcauaggcc aguucaccug   1440
uaucuguaug gcaggcuuca caggaaccua uugcgaggug gacauugacg agugucagag   1500
uagccccugu gucaacggug gggucugcaa ggaccgaguc aauggcuuca gcugcaccug   1560
ccccucgggc uucagcggcu ccacguguca gcuggacgug gacgaaugcg ccagcacgcc   1620
cugcaggaau ggcgccaaau gcguggacca gcccgauggc uacgagugcc gcugugccga   1680
gggcuuugag ggcacgcugu gugaucgcaa cguggacgac ugcuccccug acccaugcca   1740
ccauggucgc ugcguggaug gcaucgccag cuucucaugu gccugugcuc cuggcuacac   1800
gggcacacgc ugcgagagcc agguggacga augccgcagc cagcccugcc gccauggcgg   1860
caaaugccua gaccuggugg acaaguaccu cugccgcugc ccuucgggga ccacaggugu   1920
gaacugcgaa gugaacauug acgacugugc cagcaacccc ugcaccuuug gagucugccg   1980
ugauggcauc aaccgcuacg acugugucug ccaaccuggc uucacaggge cccuuuguaa   2040 cguggagauc aaugagugug cuuccagccc augcggcgag ggagguuccu guguggaugg   2100
ggaaaauggc uuccgcugcc ucugcccgcc uggcuccuug ccccacucu gccucccccc   2160 gagccauccc ugugcccaug agcccugcag ucacggcauc ugcuaugaug caccuggcgg   2220
guuccgcugu gugugugagc cuggcuggag uggccccgc ugcagccaga gccuggcccg   2280
agacgccugu gagucccagc cgugcagggc cgguuggaca ugcagcagcg auggaauggg   2340
uuuccacugc accugcccgc cuggugucca gggacgucag ugugaacucc ucuccccug   2400 cacccccgaac cccugugagc auggggggccg cugcgagucu gccccuggcc agcugccugu   2460
cugcuccugc ccccagggcu ggcaaggccc acgaugccag caggaugugg acgagugugc   2520
uggccccgca cccuguggcc cucaugguau cugcaccaac cuggcaggga guuucagcug   2580
caccugccau ggaggguaca cuggcccuuc cugcgaucag gacaucaaug acugugaccc   2640
caacccaugc cugaacggug gcucgugcca agacggcgug ggcucccuuu ccugcuccug   2700 ccuccccuggu uucgccggcc cacgaugcgc ccgcgaugug gaugagugcc ugagcaaccc   2760
cugcggcccg ggcaccugua ccgaccacgu ggccuccuuc accugcaccu gcccgccagg   2820
cuacggaggc uuccacugcg aacaggaccu gcccgacugc agcccccagcu ccugcuucaa   2880 uggcgggacc ugugugacg gcgugaacuc guucagcugc cugugccguc ccggcucacac   2940 aggagcccac ugccaacaug aggcagaccc cugccucucg cggcccugcc uacacggggg   3000
cgucugcagc gccgcccacc cuggcuuccg cugcaccugc cucgagagcu ucacgggccc   3060
gcagugccag acgcugguigg auuggugcag ccgccagccu ugucaaaacg ggggucgcug   3120
cguccagacu ggggccuauu gccuuugucc cccuggaugg agcggacgcc ucugugacau   3180
ccgaagcuug cccugcaggg aggccgcagc ccagaucggg gugcggcugg agcagcugug   3240
ucaggcgggu gggcagugug uggaugaaga cagcucccac uacugcgugu gcccagaggg   3300
ccguacuggu agccacugug agcaggaggu ggaccccugc uuggcccagc ccugccagca   3360 ugggggggacc ugccguggcu auauggggggg cuacaugugu gagugucuuc cuggcuacaa   3420
uggugauaac ugugaggacg acggggacga gugugccucc cagcccugcc agcacggggg   3480
uucaugcauu gaccucgugg cccgcuaucu cugcuccugu ccccccaggaa cgcuggggu   3540 gcucugcgag auuaaugagg augacugcgg cccaggccca ccgcuggacu cagggccccg   3600
gugccuacac aauggcaccu gcguggaccu ggugggguggu uuccgcugca ccugucccccc   3660
```

-continued

```
aggauacacu gguuugcgcu gcgaggcaga caucaaugag ugucgcucag gugccugcca    3720
cgcggcacac acccgggacu gccugcagga cccaggcgga gguuuccguu gccuuuguca    3780
ugcuggcuuc ucagguccuc gcugucagac uguccugucu cccugcgagu cccagccaug    3840
ccagcaugga ggccagugcc guccuagccc ggguccuggg ggugggcuga ccuucaccug    3900
ucacugugcc cagccguucu ggggguccgcg uugcgagcgg guggcgcgcu ccugccggga    3960
gcugcagugc ccggugggcg ucccaugcca gcagacgccc cgcgggccgc gcugcgccug    4020
ccccccaggg uugucgggac ccuccugccg cagcuucccg gggucgccgc cggggggccag    4080 caacgccagc ugcgcggccg ccccccugucu ccacggggggc uccugccgcc ccgcgccgcu    4140
cgcgcccuuc uuccgcugcg cuugcgcgca gggcuggacc gggccgcgcu gcgaggcgcc    4200
cgccgcggca cccgaggucu cggaggagcc gcggugcccg cgcgccgccu gccaggccaa    4260
gcgcggggac cagcgcugcg accgcgagug caacagccca ggcugcggcu gggacggcgg    4320
cgacugcucg cugagcgugg gcgacccccug gcggcaaugc gaggcgcugc agugcuggcg    4380
ccucuucaac aacagccgcu gcgaccccgc cugcagcucg cccgccugcc ucuacgacaa    4440
cuucgacugc cacgccggug gccgcgagcg cacuugcaac ccgguguacg agaaguacug    4500
cgccgaccac uuugccgacg gccgcugcga ccagggcugc aacacggagg agugcggcug    4560
ggaugggcug gauugugcca gcgaggugcc ggcccugcug gcccgcggcg ugcuggugcu    4620 cacagucug cugccgccag aggagcuacu gcguuccagc gccgacuuuc ugcagcggcu    4680
cagcgccauc cugcgcaccu cgcugcgcuu ccgccuggac gcgcacggcc aggccauggu    4740
cuucccuuac caccggccua guccuggcuc cgaaccccgg gcccgucggg agcuggcccc    4800
cgaggugauc ggcucgguag uaaugcugga gauugacaac cggcucugcc ugcagucgcc    4860
ugagaaugau cacugcuucc ccgaugccca gagcgccgcu gacuaccugg gagcguuguc    4920
agcgguggag cgccuggacu ucccguaccc acugcgggac gugcgggggg agccgcugga    4980
gccuccagaa cccagcgucc cgcugcugcc acugcuagug gcgggcgcug ucuugcgcu    5040 ggucauucuc guccuggggug ucaugguggc ccggcgcaag cgcgagcaca gcacccucug    5100
guucccugag ggcuucucac ugcacaagga cguggccucu ggucaaagg gccggcggga    5160 acccgugggc caggacgcgc ugggcaugaa gaacauggcc aagggugaga gccugauggg    5220
ggaggguggc acagacugga uggacacaga gugcccagag gccaagcggc uaaaggagaga    5280 ggagccaggc auggggggcug aggaggcugu ggauugccgu caguggacuc aacaccaucu    5340
gguugcugcu gacauccgcg uggcaccagc cauggcacug acaccaccac agggcgacgc    5400
agaugcugau ggcauggaug ucaaugugcg uggcccagau ggcuucaccc cgcuaaugcu    5460
ggcuuccuuc ugugggggggg cucuggagcc aaugccaacu gaagaggaug aggcagauga    5520
cacaucagcu agcaucaucu ccgaccugau cugccagggg gcucagcuug gggcacggac    5580
ugaccguacu ggcgagacug cuuugcaccu ggcugcccgu uaugcccgug cugaugcagc    5640
caagcggcug cuggaugcug gggcagacac caaugcccag gaccacucag gccgcacucc    5700
ccugcacaca gcugucacag ccgaugccca gggugucuuc cagauucuca uccgaaaccg    5760
cucuacagac uuggaugccc gcauggcaga uggcucaacg gcacugaucc uggcggcccg    5820 ccuggcaguua gagggcaugg uggaagagcu caucgccagc caugcugaug ucaaugcgu    5880 ggaugagcuu gggaaaucag ccuuacacug ggcugcgggcu gugaacaacg uggaagccac    5940
uuuggcccug cucaaaaaug gagccaauaa ggacaugcag gauagcaagg aggagacccc    6000
ccuauuccug gccgcccgcg agggcagcua ugaggcugcc aagcugcgu uggaccacuu    6060
```

-continued

```
ugccaaccgu gagaucaccg accaccugga caggcugccg cgggacguag cccaggagag    6120
acugcaccag gacaucgugc gcuugcugga ucaacccagu gggccccgca gccccccgg     6180 uccccacggc cugggggccuc ugcucugucc uccaggggcc uuccuccccug gccucaaagc  6240 ggcacagucg ggguccaaga agagcaggag gcccccgggg aaggcggggc uggggccgca    6300 ggggcccgg gggcggggca agaagcugac gcuggccugc ccgggccccc uggcugacag     6360
cucggucacg cugucgcccg uggacucgcu ggacucccg cggccuuucg gugggccccc     6420
ugcuuccccu gguggcuucc cccuugaggg gcccuaugca gcugccacug ccacugcagu    6480
gucucuggca cagcuuggug gcccaggccg ggcgggucua gggcgccagc ccccuggagg    6540
auguguacuc agccugggcc ugcugaaccc uguggcugug ccccucgauu gggcccggcu     6600
gcccccaccu gccccuccag gccccucguu ccugcugcca cuggcgccgg gaccccagcu    6660 gcucaacccca gggacccccg ucuccccgca ggagcggccc ccgccuuacc uggcagucccc   6720 aggacauggc gaggaguacc cggcggcugg ggcacacagc agcccccaaa aggcccgcuu   6780
ccugcggguu cccagugagc acccuuaccu gaccccaucc cccgaauccc cugagcacug    6840
ggccagcccc ucaccucccu cccucucaga cugguccgaa uccacgccua gcccagccac    6900
ugccacuggg gccauggcca ccaccacugg ggcacugccu gcccagccac uucccuuguc    6960
uguucccagc ucccuugcuc aggcccagac ccagcugggg cccagccgg aaguuacccc     7020 caagaggcaa guguuggccu gagacgcucg ucaguucuua gaucuugggg gccuaaagag    7080 accccgucc ugccuccuuu cuuucucugu cucuuccuuc cuuuuagucu uuuucauccu     7140
cuucucuuuc caccaacccu ccugcauccu ugccuugcag cgugaccgag auaggucauc     7200
agcccagggc uucagucuuc cuuuauuuau aaugggugg ggcuaccacc caccucuca      7260 gucuguguaa gagucuggga ccuccuucu ccccacuucu cucuucccuc auuccuuucu     7320
cucuccuucu ggccucucau uuccuuacac ucugacauga augaauuauu auuauuuuua    7380
uuuuucuuuu uuuuuuuaca uuuuguauag aaacaaauuc auuuaaacaa acuuauuauu    7440
auuauuuuuu acaaaauaua uauauggaga ugcucccucc cccugugaac cccccagugc    7500
ccccgugggg cugagucugu gggcccauuc ggccaagcug gauucugugu accuaguaca    7560
caggcaugac ugggaucccg uguaccgagu acacgacccca gguauguacc aaguaggcac   7620
ccuugggcgc acccacuggg gccaggggguc ggggggagugu ugggagccuc cucccccaccc  7680 caccuccccuc acuucacugc auuccagaug ggacauguuc cauagccuug cugggggaagg  7740 gcccacugcc aacuccccucu gccccagccc caccccuuggc caucuccccuu ugggaacuag  7800 ggggcugcug gugggaaaug ggagccaggg cagauguaug cauuccuuug ugucccugua    7860
aaugugggac uacaagaaga ggagcugccu gagugguacu uucucuuccu gguaauccuc     7920
uggcccagcc ucauggcaga auagagguau uuuuaggcua uuuuuguaau auggcuucug    7980
gucaaaaucc cuguguagcu gaauucccaa gcccugcauu uacacagcccc ccaccuccccu   8040 caccaccuaa uaaaggaaua guuaacacuc agucuuuguug gucugugucu agguaagggug   8100 gggagugggug gcagugggac uucuaucucc cccacccagg gcuaacuuga gcucccaucu    8160 uggggguaaau acauuugacu ugccagucua cuuaugcuuc cucuuuuggc agaugacuac    8220
cgauuggauu agugguuguc accugacuua agcugagcca aucagauucu uuugcucgag    8280
aacuuucuuu aauggagagg cuaagaaagu ugucaguugg uggagcucuu aaggucacaa    8340
ucagauuuag aaauaucagu ggccaauucg agguggugg caaagagaca agcaaacagg     8400
```

```
gcagaagaau gaagcuaaua uucagggaga aucagaaaug agagcucaaa uggcuccuug      8460
agggcugggg ggguuaucuc ggcucccagu gcaguuauca auuccaguua auugagugu       8520 cauuccauug agaucaacag guauuuauua auugcuuucu aaguaucuga ucaugguucu      8580
gcaugaauuu cacuuuuacu ucaugcuccu auggguuuug gagauaaccu uggacccaug      8640
uaauaaauac uucuuuacuu gugcca                                          8666

<210> SEQ ID NO 5
<211> LENGTH: 3858
<212> TYPE: RNA
<213> ORGANISM: homo sapien

<400> SEQUENCE: 5
gggccggggg cccguggccg ccgccgccgc cgucgcccga ugucgccgcc accgccaccg        60
ccacccgugc gggcgcugcc ccugcugcug cugcuagcgg ggccgggggc ugcagccccc       120
ccuugccugg acggaagccc gugugcaaau ggaggucguu gcacccagcu gcccucccgg       180
gaggcugccu ccugugccc  gccuggcugg gugggugagc ggugucagcu ggaggacccc       240
ugucacucag gccccugugc uggccgguggu gucugccaga guucaguggu ggcuggcacc      300
gcccgauucu caugccggug cccccguggc uuccgaggcc cugacugcuc ccugccagau       360
cccugccuca gcagcccuug ugcccacggu gcccgcugcu caguggggcc cgauggacgc       420
uuccucugcu ccugcccacc uggcuaccag ggccgcagcu gccgaagcga cguggaugag       480
ugccgggugg gugagcccug ccgccauggu ggcaccugcc ucaacacacc uggcuccuuc       540
cgcugccagu guccagcugg cuacacaggg ccacuaugug agaaccccgc ggugcccugu       600
gcacccucac caugccguaa cggggggcacc ugcaggcaga guggcgaccu cacuuacgac      660
ugugccuguc uuccuggguu ugagggucag aauugugaag ugaacgugga cgacugucca       720
ggacaccgau gucucaaugg ggggacaugc guggauggcg ucaacaccua uaacugccag       780
ugcccuccug aguggacagg ccaguucugc acggaggacg uggaugagug ucagcugcag       840
cccaacgccu gccacaaugg ggguaccugc uucaacacgc ugggugggcca cagcugcgug       900 ugugucaaug gcuggacagg cgagagcugc agucagaaua ucgaugacug ugccacagcc       960
gugugcuucc augggggccac cugccaugac cgcguggcuu cuuucuacug ugccugcccc      1020
augggcaaga cuggccuccu ugucaccgug gaugacgccu gugucagcaa ccccugccac      1080
gaggaugcua ucugugacac aaauccgggug aacggccggg ccauuugcac cuguccuccc     1140
ggcuucacgg gugggcaug  ugaccaggau guggacgagu gcucuaucgg cgccaacccc      1200
ugcgagcacu ugggcaggug cgugaacacg cagggcuccu uccugugcca gugcgguucgu     1260 ggcuacacug gaccucgcug ugagaccgau gucaacgagu gucugucggg gcccugccga      1320
aaccaggcca cgugccucga ccgcauaggc caguucaccu guaucuguau ggcaggcuuc      1380
acaggaaccu auugcgaggu ggacauugac gagugucaga guagcccug  ugucaacggu       1440 ggggucugca aggaccgagu caauggcuuc agcugcaccu gccccucggg cuucagcggc      1500
uccacguguc agcuggacgu ggacgaaugc gccagcacgc ccugcaggaa uggcgccaaa      1560
ugcguggacc agcccgaugg cuacgagugc cgcugugccg agggcuuuga gggcacgcgu      1620
ugugaucgca acguggacga cugcucccu  gacccaugcc accauggucg cugcguggau      1680
ggcaucgcca gcuucucaug ugccugugcu ccuggcuaca cgggcacacg cugcgagagc      1740 caggugggacg aauuccgcag ccagcccugc cgccauggcg gcaaaugccu agaccugguug     1800 gacaaguacc ucugccgcug cccuucuggg accacagguug ugaacugcga agugaacauu      1860
```

-continued

```
gacgacugug ccagcaaccc cugcaccuuu ggagucugcc gugauggcau caaccgcuac      1920
gacugugucu gccaaccugg cuucacaggg ccccuuugua acguggagau caaugagugu      1980
gcuuccagcc caugcggcga gggagguucc uguguggaug gggaaaaugg cuuccgcugc      2040
cucugcccgc cuggcuccuu gcccccacuc ugccuccccc cgagccaucc cugugcccau      2100
gagcccugca gucacggcau cugcuaugau gcaccuggcg gguuccgcug ugugugugag      2160
ccuggcugga guggcccccg cugcagccag agccuggccc gagacgccug ugagucccag      2220
ccgugcaggg ccggugggac augcagcagc gauggaaugg guuuccacug caccugcccg      2280
ccuggugucc agggacguca gugugaacuc cucucccccu gcaccccgaa ccccugugag      2340
caugggggcc gcugcgaguc ugccccuggc cagcugccug ucugcuccug cccccagggc      2400
uggcaagacc caugccugaa cgguggcucg ugccaagacg gcgugggcuc cuuuuccugc      2460
uccugccucc cugguuucgc cggcccacga ugcgcccgcg auguggauga gugccugagc      2520
aaccccugcg gcccgggcac cuguaccgac cacguggccu ccuucaccug caccugcccg      2580
ccaggcuacg gaggcuucca cugcgaacag gaccugcccg acugcagccc cagcuccugc      2640
uucaauggcg ggaccugugu ggacggcgug aacucguuca gcugccugug ccgucccggc      2700
uacacaggag cccacugcca acaugaggca gaccccugcc ucucgcggcc cugccuacac      2760
gggggcgucu gcagcgccgc ccacccuggc uuccgcugca ccugccucga gagcuucacg      2820
ggcccgcagu gccagacgcu gguggauugg ugcagccgcc agccuuguca aaacggggu     2880 cgcugcgucc agacuggggc cuauugccuu uguccccug gauggagcgg acgccucugu       2940
gacauccgaa gcuugcccug caggggaggcc gcagcccaga ucggggugcg gcuggagcag     3000
cugugucagg cggguggca gugugugga aagacagcu cccacuacug cgugugccca      3060
gagggccgua cugguagcca cugugagcag gaggugacc ccugcuuggc ccagcccugc      3120
cagcaugggg ggaccugccg uggcuauaug gggggcuaca ugugugagug ucuuccuggc     3180 uacaaugug auaacuguga ggacgacgug gacgagugug ccucccagcc cugccagcac      3240 gggggguucau gcauugaccu cguggcccgc uaucucugcu ccuguccccc aggaacgcug      3300
ggggugcucu gcgagauuaa ugaggaugac ugcggcccag gcccaccgcu ggacucaggg      3360
ccccggugcc uacacaaugg caccugcgug gaccuggugg ugguuuccg cugcaccugu      3420 ccccaggau acacugguuu gcgcugcgag gcagacauca augaguugcg cucaggugcc      3480
ugccacgcgg cacacacccg ggacugccug caggacccag gcggagguuu ccguugccuu      3540
ugucaugcug gcuucucagg uccucgcugu cagacugucc ugucucccug cgagucccag      3600
ccaugccagc auggaggcca gugccgucc agcccggguc cuggggugg gcugaccuuc     3660 accgucacu gucccagcc guucgggguu ccgcguugcg agcgggugc gcgcuccugc       3720 cgggagcugc agugccccggu gggcguccca ugccagcaga cgccccgcgg ccgcgcugc       3780 gccugccccc caggguuguc gggacccucc ugccgcagcu ucccggggguc gccgccgggg     3840 gccagcaacg ccagcugc                                                     3858
```

<210> SEQ ID NO 6
<211> LENGTH: 8091
<212> TYPE: RNA
<213> ORGANISM: homo sapien

<400> SEQUENCE: 6

```
acgcggcgcg gaggcuggcc cgggacgcgc ccggagccca gggaaggagg gaggagggga        60
```

-continued

```
gggucgcggc cggccgccau gggggccgggg gcccguggcc gccgccgccg ccgucgcccg    120
augucgccgc caccgccacc gccacccgug cgggcgcugc cccugcugcu gcugcuagcg    180
gggccggggg cugcagcccc cccuugccug gacggaagcc cgugugcaaa uggaggucgu    240
ugcacccagc ugcccucccg ggaggcugcc ugccugugcc cgccuggcug ggugggugag    300
cggugucagc uggaggaccc cugucacuca ggccccugug cuggccgugg ugucugccag    360
aguucagugg uggcuggcac cgcccgauuc ucaugccggu gccccguggg cuuccgaggc    420
ccugacugcu cccugccaga ucccugccuc agcagcccuu gugcccacgg ugcccgcugc    480 ucagugggc ccgauggacg cuuccucugc uccugcccac cuggcuacca gggccgcagc    540
ugccgaagcg acguggauga gugccgggug ggugagcccu gccgccaugg uggcaccugc    600
cucaacacac cuggcuccuu ccgcugccag uguccagcug gcuacacagg gccacuaugu    660
gagaaccccg cggugcccug ugcgcccuca ccaugccgua acgggggcac cugcaggcag    720
aguggcgacc ucacuuacga cugugccgu cuuccugggu uugaggguca gaauugugaa    780
gugaacgugg acgacugucc aggacaccga ugucucaaug gggggacaug cguggauggc    840
gucaacaccu auaacugcca gugcccuccu gaguggacag gccaguucug cacggaggac    900
guggaugagu gucagcugca gcccaacgcc ugccacaaug ggguaccug cuucaacacg    960 cuggguggcc acagcugcgu gugugucaau ggcuggacag gugagagcug cagucagaau    1020
aucgaugacu gugccacagc cgugugcuuc caugggggcca ccugccauga ccgcguggcu    1080
ucuuucuacu gugccugccc caugggcaag acuggccucc ugugucaccu ggaugacgcc    1140
ugugucagca cccccugcca cgaggaugcu aucugugaca caaauccggu gaacggccgg    1200
gccauuugca ccugucuccc cggcuucacg ggugggggcau gugaccagga uguggacgag    1260
ugcucuaucg cgccaacccc cugcgagcac uugggcaggu gcgugaacac gcagggcucc    1320
uuccugugcc agugcggucg uggcuacacu ggaccucgcu gugagaccga ugucaacgag    1380
ugucugucgg ggcccugccg aaaccaggcc acgugccucg accgcauagg ccaguucacc    1440
uguaucugua uggcaggcuu cacaggaacc uauugcgagg uggacauuga cgagugucag    1500
aguagccccu gugucaacgg uggggucugc aaggaccgag ucaauggcuu cagcugcacc    1560
ugccccucgg gcuucagcgg cuccacgugu cagcuggacg uggacgaaug cgccagcacg    1620
cccugcagga auggcgccaa augcguggac cagcccgaug cuacgagug ccgcugugcc    1680 gagggcuuug agggcacgcu gugugaucgc aacguggacg acugcucccc ugacccaugc    1740
caccaugguc gcugcgugga uggcaucgcc agcuucucau gugccugugc uccuggcuac    1800
acgggcacac gcugcgagag ccagguggac gaaugccgca gccagcccug ccgccauggc    1860
ggcaaaugcc uagaccuggu ggacaaguac cucugccgcu gcccuucugg gaccacaggu    1920
gugaacugcg aagugaacau ugacgacugu gccagcaacc cugcaccuu uggagucugc    1980 cgugauggca ucaaccgcua cgacugugc ugccaaccug cuucacagg gcccuuugu    2040 aacguggaga ucaaugagug ugcuuccagc ccaugcggcg agggagguuc cuguguggau    2100
ggggaaaaug gcuuccgcug ccucugcccg ccuggcuccu ugcccccacu cugccucccc    2160
ccgagccauc ccugugccca ugagcccgc agucacggca ucugcuauga ugcaccggc    2220 ggguuccgcu gugugugga gccuggcugg agggccccc gcugcagcca gagccuggcc    2280
cgagacgccu gugagucccca gccgucagg gccgguggga caugcagcag cgauggaaug    2340 gguuccacu gcaccugccc gccuggguc cagggacguc agugugaacu ccucccccc    2400 ugcaccccga accccuguga gcaugggggc cgcugcgagu cugcccugg ccagcugccu    2460
```

-continued

```
gucugcuccu gcccccaggg cuggcaaggc ccacgaugcc agcaggaugu ggacgagugu   2520
gcuggccccg cacccugugg cccucauggu aucugcacca accuggcagg gaguuucagc   2580
ugcaccugcc auggaggggua cacuggcccu uccugugauc aggacaucaa ugacugugac   2640
cccaacccau gccugaacgg uggcucgugc caagacggcg ugggcuccuu uuccugcucc   2700
ugccucccug guuucgccgg cccacgaugc gcccgcgaug uggaugagug ccugagcaac   2760
cccugcggcc cgggcaccug uaccgaccac guggccuccu ucaccugcac cugcccgccg   2820
ggcuacggag gcuuccacug cgaacaggac cugcccgacu gcagccccag cuccugcuuc   2880
aauggcggga ccugugugga cggcgugaac ucguucagcu gccugugccg ucccggcuac   2940
acaggagccc acugccaaca ugaggcagac cccugccucu cgcggcccug ccuacacggg   3000
ggcgucugca gcgccgccca cccuggcuuc cgcugcaccu gccucgagag cuucacgggc   3060
ccgcagugcc agacgcuggu ggauuggugc agccgccagc cuugucaaaa cgggggucgc   3120
ugcguccaga cugggggccua uugccuuugu ccccccuggau ggagcggacg ccucugugac   3180
auccgaagcu ugcccugcag ggaggccgca gcccagaucg gggugcggcu ggagcagcug   3240
ugucaggcgg gugggcagug uguggaugaa gacagcuccc acuacugcgu gugcccagag   3300
ggccguacug guagccacug ugagcaggag guggacccccu gcuuggccca gcccugccag   3360
caugggggga ccugccgugg cuauaugggg ggcuacaugu gugagugucu uccuggcuac   3420
aauggugaua acugugagga cgacguggac gagugugccu cccagcccug ccagcacggg   3480
gguucaugca uugaccucgu ggcccgcuau cucugcuccu guccccccagg aacgcuqggg   3540 gugcucugcg agauuaauga ggaugacugc ggcccaggcc caccgcugga cucagggccc   3600
cggugccuac acaauggcac cugccguggac cugguggguq guuuccgcug caccugucccc   3660 ccaggauaca cugguuugcg cugcgaggca gacaucaaug agugucgcuc aggugccugc   3720
cacgcggcac acacccggga cugccugcag gacccaggcg gagguuuccg uugccuuugu   3780
caugcuggcu ucucaggucc ucgcugucag acuguccugu cucccugcga guccagcca   3840 ugccagcaug gaggccagug ccguccuagc ccggguccug gggguggggcu gaccuucacc   3900 ugucacugug cccagccguu cuggggguccg cguugcgagc gggguggcgcg cuccugccgg   3960 gagcugcagu gccggguggg cgucccaugc cagcagacgc cccgcggggcc gcgcugcgcc   4020 ugcccccag gguugucggg acccuccugc cgcagcuucc cgggggucgcc gccggggggc   4080 agcaacgcca gcugcgcggc cgcccccugu uccacggggg gcuccugccg ccccgcgccg   4140
cucgcgcccu ucuuccgcug cgcuugcgcg caggcuqgga ccgggccgcg cugcgaggcg   4200
cccgccgcgg cacccgaggu cucggaggag ccgcggugcc cgcgcgccgc cugccaggcc   4260
aagcgcgggg accagcgcug cgaccgcgag ugcaacagcc caggcugcgg cugggacggc   4320
ggcgacugcu cgcugagcgu gggcgacccc uggcggcaau gcgaggcgcu gcagugcugg   4380
cgccucuuca acaacagccg cugcgacccc gccugcagcu cgcccgccug ccucuacgac   4440
aacuucgacu gccacgccgg uggccgcgag cgcacuugca acccgggugua cgagaaguac   4500 ugcgccgacc acuuugccga cggccgcugc gaccagggcu gcaacacgga ggagugcggc   4560
ugggaugggc uggauugugc cagcgaggug ccggcccugc ugggcccgcgg cgugcuggug   4620 cucacagugc ugcugccgcc ggaggagcua cugcguucca gcgccgacuu ucugcagcgg   4680
cucagcgcca uccugcgcac cucgcugcgc uuccgccugg acgcgcacgg ccaggccaug   4740
gucuucccuu accaccggcc uaguccuggc uccgaacccc gggcccgucg ggagcuggcc   4800
```

-continued

```
cccgagguga ucggcucggu aguaaugcug gagauugaca accggcucug ccugcagucg     4860
ccugagaaug aucacugcuu ccccgaugcc cagagcgccg cugacuaccu gggagcguug     4920
ucagcggugg agcgccugga cuucccguac ccacugcggg acgugcgggg ggagccgcug     4980
gagcccccag aacccagcgu cccgcugcug ccacugcuag uggcgggcgc ugucuugcug     5040
cuggucauuc ucguccuggg ugucauggug gcccggcgca agcgcgagca cagcaccuc     5100 ugguucccug agggcuucuc acugcacaag gacguggccu cuggucacaa gggcgggcgg     5160
gaacccgugg gccaggacgc gcugggcaug aagaacaugg ccaaggguga gagccugaug     5220
ggggaggugg ccacagacug gauggacaca gagugcccag aggccaagcg gcuaaaggua     5280
gaggagccag gcauggggc ugaggaggcu guggauugcc gucaguggac ucaacaccau     5340
cugguugcug cugacauccg cguggcacca gccauggcac ugacaccacc acagggcgac     5400
gcagaugcug auggcaugga ugucaaugug cguggcccag auggcuucac cccgcuaaug     5460
cuggcuuccu ucuguggggg ggcucuggag ccaaugccaa cugaagagga ugaggcagau     5520
gacacaucag cuagcaucau cuccgaccug aucugccagg gggcucagcu uggggcacgg     5580
acugaccgua cuggcgagac ugcuuugcac cuggcugccc guuaugcccg ugcugaugca     5640
gccaagcggc ugcuggaugc uggggcagac accaaugccc aggaccacuc aggccgcacu     5700
ccccugcaca cagcugucac agccgaugcc caggggugucu uccagauucu cauccgaaac     5760
cgcucuacag acuuggaugc ccgcauggca gauggcucaa cggcacugau ccuggcggcc     5820
cgccuggcag uagagggcau gguggaagag cucaucgcca gccaugcuga ugucaaugcu     5880
guggaugagc uugggaaauc agccuuacac uggcugcgg cugugaacaa cguggaagcc     5940
acuuuggccc ugcucaaaaa uggagccaau aaggacaugc aggauagcaa ggaggagacc     6000
ccccuauucc uggccgcccg cgagggcagc uaugaggcug ccaagcugcu guuggaccac     6060
uuugccaacc gugagaucac cgaccaccug gacaggcugc cgcgggacgu agcccaggag     6120
agacugcacc aggacaucgu gcgcuugcug gaucaaccca gugggccccg cagccccccc     6180 ggucccacg gccugggggcc ucugcucugu ccuccagggg ccuuccuccc uggccucaaa     6240
gcggcacagu cgggguccaa gaagagcagg aggccccccg ggaaggcggg gcuggggccg     6300
caggggcccc gggggcgggg caagaagcug acgcuggccu gcccgggccc ccuggcugac     6360
agcucgguca cgcugucgcc cguggacucg cuggacuccc cgcggccuuu cgguggggccc     6420 ccugcuuccc cugguggcuu ccccccuugag gggcccuaug cagcugccac ugccacugca     6480
gugucucugg cacagcuugg uggcccaggc cgggcagguc uagggcgcca gccccccgga     6540 ggaugugcuac ucagccuggg ccugcugaac ccuguggcug ugccccucga uugggcccgg     6600
cugcccccac cugcccccucc aggccccucg uuccugcugc cacugcgcc gggacccccag     6660 cugcucaacc cagggacccc cgucucccccg caggagcggc ccccgccuua ccuggcaguc     6720
ccaggacaug gcgaggagua cccggugggcu ggggcacaca gcagcccccc aaaggcccgc     6780
uuccugcggg uucccaguga gcacccuuac cugacccccau ccccccgaauc cccugagcac     6840 ugggccagcc ccucaccucc cucccucuca gacugguccg aauccacgcc uagcccagcc     6900
acugccacug gggccauggc caccaccacu ggggcacugc cugcccagcc acuucccuug     6960
ucuguuccca gcucccuugc ucaggcccag acccagcugg ggcccagcc ggaaguuacc     7020 cccaagaggc aagguguggc cugagacgcu cgucaguucu uagaucuugg gggccuaaag     7080 agaccccgu ccugccuccu uucuuucucu gucucuccu uccuuuuagu cuuuuucauc     7140
cucuucucuu uccaccaacc cuccugcauc cuugccuugc agcgugaccg agauagguca     7200
```

-continued

```
ucagcccagg gcuucagucu uccuuuauuu auaaugggug gggcuacca cccacccucu    7260 cagucuugug aagagucugg gaccuccuuc uuccccacuu cucucuuccc ucauuccuuu    7320
cucucuccuu cuggccucuc auuuccuuac acucugacau gaaugaauua uuauuauuuu    7380
ucuuuuucuu uuuuuuuua cauuuugau agaaacaaau ucauuuaaac aaacuuauua    7440
uuauuauuuu uuacaaaaua uauauaugga gaugcuccu cccccuguga accccccagu    7500
gcccccgugg ggcugagucu gugggcccau ucggccaagc uggauucugu guaccuagua    7560
cacaggcaug acugggaucc cguguaccga guacacgacc cagguaugua ccaaguaggc    7620
acccuugggc gcacccacug gggccagggg ucggggagu guugggagcc uccuccccac    7680
cccaccuccc ucacuucacu gcauuccaga uuggacaugu uccauagccu ugcuggggaa    7740
gggcccacug ccaacucccu cugccccagc cccacccuug gccaucuccc uuugggaacu    7800
agggggcugc uggugggaaa ugggagccag ggcagaugua ugcauuccuu uaugucccug    7860
uaaauguggg acuacaagaa gaggagcugc cugaguggua cuuucucuuc cugguaaucc    7920
ucuggcccag ccuuauggca gaauagaggu auuuuuaggc uauuuuugua auauggcuuc    7980
uggucaaaau cccuguguag cugaauuccc aagcccugca uuguacagcc ccccacuccc    8040
cucaccaccu aauaaaggaa uaguuaacac ucaaaaaaaa aaaaaaaaa a           8091
```

<210> SEQ ID NO 7
<211> LENGTH: 3870
<212> TYPE: RNA
<213> ORGANISM: homo sapien

<400> SEQUENCE: 7

```
ggcgcggagg cuggcccggg ggcccgguggc cgccgccgcc gccgucgccc gaugucgccg      60
ccaccgccac cgccacccgu gcgggcgcug ccccugcugc ugcugcuagc ggggccgggg     120
gcugcagccc ccccuuugccu ggacggaagc ccgugugcaa auggaggucg uugcacccag     180
cugcccuccc gggaggcugc cugccugugc ccgccuggcu ggguggguga gcggugucag     240
cuggaggacc ccugucacuc aggccccugu gcuggccgug gugucugcca gaguucagug     300
guggcuggca ccgcccgauu cucaugccgg ugccccgug gcuuccgagg cccugacugc     360
ucccugccag aucccugccu cagcagcccu ugugcccacg gugcccgcug cucaguggg     420 cccgauggac gcuuccucug cuccugccca ccuggcuacc agggccgcag cugccgaagc     480
gacguggaug agugccgggu gggugagccc ugccgccaug guggcaccug ccucaacaca     540
ccuggcuccu uccgcugcca guguccagcu ggcuacacag gccacuaug ugagaaccccc     600 gcggugcccu gucgcccuc accaugccgu aacgggggca ccugcaggca gaguggcgac     660
cucacuuacg acugugccug ucuuccuggg uuugaggguc agaauuguga agugaacgug     720
gacgacuguc caggacaccg augucucaau gggggggacau gcguggaugg cgucaacacc     780
uauaacugcc agugcccucc ugaguggaca ggccaguucu gcacggagga cguggaugag     840
ugucagcugc agcccaacgc cugccacaau ggggguaccu gcuucaacac gcuggguggc     900
cacagcugcg ugugugucaa uggcuggaca ggcgagagcu gcagucagaa uaucgaugac     960
ugugccacag ccgugugcuu ccaugggggcc accugccaug accgcguggc uucuuucuac    1020
ugucccugcc ccaugggcaa gacuggccuc cugugucacc uggaugacgc cugugucagc    1080
aaccccugcc acgaggaugc uaucugugac acaaauccgg ugaacggccg ggccauuugc    1140 accugccccuc ccggccuucac ggguggggca ugugaccagg auguggacga gugcucuauc    1200
```

-continued

```
ggcgccaacc ccugcgagca cuugggcagg ugcgugaaca cgcagggcuc cuuccugugc   1260
cagugcgguc guggcuacac uggaccucgc ugugagaccg augucaacga gugucugucg   1320
gggcccugcc gaaaccaggc cacgugccuc gaccgcauag gccaguucac cuguaucugu   1380
auggcaggcu ucacaggaac cuauugcgag guggacauug acgaguguca gaguagcccc   1440
ugugucaacg gugggguug caaggaccga gucaauggcu ucagcugcac cugccccucg   1500
ggcuucagcg gcuccacgug ucagcuggac guggacgaau gcgccagcac gcccugcagg   1560
aauggcgcca aaugcgugga ccagcccgau ggcuacgagu gccgcugugc cgagggcuuu   1620
gagggcacgc ugugugaucg caacguggac gacugcuccc cugacccaug ccaccauggu   1680
cgcugcgugg auggcaucgc cagcuucuca ugugccugug uccuggcua cacgggcaca   1740 cgcugcgaga gccaggugga cgaaugccgc agccagcccu gccgccaugg cggcaaaugc   1800
cuagaccugg uggacaagua ccucugccgc ugcccuucug ggaccacagg ugugaacugc   1860
gaagugaaca uugacgacug ugccagcaac cccugcaccu uuggagucug ccgugauggc   1920
aucaaccgcu acgacugugu cugccaaccu ggcuucacag ggccccuuug uaacguggag   1980
aucaaugagu gugcuuccag cccaugcggc gagggaggu ccugugugga uggggaaaau   2040
ggcuuccgcu gccucugccc gccuggcucc uugcccccac ucugccuccc cccgagccau   2100
cccugugccc augagcccug cagucacggc aucugcuaug augcaccugg cggguuccgc   2160
ugugugugug agccuggcug gaguggcccc cgcugcagcc agagccuggc ccgagacgcc   2220 ugugagucccc agccgugcag ggccgguggg acaugcagca gcgauggaau ggguuuccac   2280
ugcaccugcc cgccuggugu ccagggacgu cagugugaac uccucucccc cugcaccccg   2340
aaccccugug agcauggggg ccgcugcgag ucugcccccug gccagcugcc ugucugcucc   2400
ugcccccagg gcuggcaaga cccaugccug aacgguggcu cgugccaaga cggcguggc   2460 uccuuuuccu gcuccugccu cccugguuuc gccggcccac gaugcgcccg cgauguggau   2520
gagugccuga gcaaccccug cggccgggc accguaccg accacguggc cuccuucacc   2580
ugcaccugcc cgccgggcua cggaggcuuc cacugcgaac aggaccugcc cgacugcagc   2640
cccagcuccu gcuucaaugg cgggaccugu guggacggc ugaacucguu cagcugccug   2700 ugccguccg gcuacacagg agcccacugc caacaugagg cagaccccug ccucucgcgg   2760
cccugccuac acgggggcgu cugcagcgcc gcccacccug gcuuccgcug caccugccuc   2820
gagagcuuca cgggcccgca gugccagacg cugguggau ggugcagccg ccagccuugu   2880
caaaacgggg gucgcugcgu ccagacuggg gccuauugcc uuugucccc uggaugggagc   2940 ggacgccucu gugacauccg aagcuugccc ugcaggagg ccgcagccca gaucggggug   3000
cggcuggagc agcugugucca ggcgggugg cagugugugg augaagacag cucccacuac   3060
ugcgugugcc cagagggccg uacugguagc cacgugagc aggagugga ccccugcuug   3120 gcccagcccu gccagcaugg ggggaccugc cgguggcuaua uggggggcua caugugugag   3180
ugucuuccug gcuacaaugg ugauaacugu gaggacgacg uggacgagug ugccucccag   3240
cccugccagc acgggguuc augcauugac cucguggccc gcuaucucug cuccugcccc   3300
ccaggaacgc uggggugcu cugcgagauu aaugaggaug acugcggccc aggcccaccg   3360
cuggacucag ggccccgug ccuacacaau ggcaccugcg uggaccuggu ggugguuuc   3420 cgcugcaccu guccccagg auacacuggu uugcgcugcg aggcagacau caaugagugu   3480
cgcucaggug ccugccacgc ggcacacacc cgggacugcc ugcaggaccc aggcggaggu   3540
uuccguugcc uuugucaugc uggcuucuca gguccucgcu gucagacugu ccugucuccc   3600
```

-continued

```
ugcgaguccc agccaugcca gcauggaggc cagugccguc cuagcccggg uccuggggggu    3660 gggcugaccu ucaccuguca cugugcccag ccguucuggg guccgcguug cgagcgggug    3720
gcgcgcuccu gccgggagcu gcagugcccg gugggcguuc caugccagca gacgccccgc    3780
gggccgcgcu gcgccugccc cccaggguug ucgggacccu ccugccgcag cuucccgggg    3840
ucgccgccgg gggccagcaa cgccagcugc                                     3870
```

```
<210> SEQ ID NO 8
<211> LENGTH: 8680
<212> TYPE: RNA
<213> ORGANISM: homo sapien

<400> SEQUENCE: 8
cuucggcgaa guuggcggcg cggaggcugg cccgggacgc gcccggagcc cagggaagga     60
gggaggaggg gagggucgcg gccggccgcc augggggccgg gggcccgugg ccgccgccgc    120
cgccgucgcc cgaugucgcc gccaccgcca ccgccacccg ugcgggcgcu gccccugcug    180
cugcugcuag cggggccggg ggcugcagcc cccccuugcc uggacggaag cccgugugca    240
aauggagguc guugcacccca gcugcccucc cgggaggcug ccugccugug cccgccuggc    300
ugggugggug agcggguguca gcuggaggac cccugucacu caggccccug ugcuggccgu    360
ggugucugcc agaguucagu ggguggcuggc accgccgau ucucaugccg gugcccccgu    420
ggcuuccgag gcccugacug cucccugcca gaucccugcc ucagcagccc uugugcccac    480
ggugcccgcu gcucaguggg gcccgaugga cgcuuccucu gcccugccc accuggcuac    540 cagggccgca gcugccgaag cgacguggau gagugccggg ugggugagcc cugccgccau    600
gguggcaccu gccucaacac accuggcucc uuccgcugcc agugccagc uggcuacaca    660 gggccacuau gugagaaccc cgcggugccc ugugcacccu caccaugccg uaacgggggc    720
accugcaggc agaguggcga ccucacuuac gacugugccu gucuccugg guuugaggggu    780 cagaauugug aagugaacgu ggacgacugu ccaggacacc gaugucucaa ugggggggaca    840 ugcgugggaug gcgucaacac cuauaacugc cagugcccuc cugaguggac aggccaguuc    900
ugcacggagg acguggauga gugucagcug cagcccaacg ccugccacaa uggggguacc    960
ugcuucaaca cgcugggugg ccacagcugc gugugugugca auggcuggac aggcgagagc    1020
ugcagucaga auaucgauga cugugccaca gccgugugcu uccauggggc caccugccau    1080
gaccgcgugg cuucuuucua cugugccugc cccauggggca agacuggccu ccugugucac    1140
cuggaugacg ccugugucag caaccccugc cacgaggaug cuaucugugua cacaaauccg    1200 gugaacggcc gggccauuug caccugccu cccggcuuca cggguggggc augugaccag    1260
gauguggacg agugcucuau cggcgccaac cccugcgagc acuugggcag gugcgugaac    1320
acgcagggcu ccuuccugug ccagugcggu cguggcuaca cuggaccucg cugugagacc    1380
gaugucaacg agugucuguc gggggcccgc cgaaaccagg ccacgugccu cgaccgcaua    1440
ggccaguuca ccuguaucug uauggcaggc uucacaggaa ccuauugcga gguggacauu    1500
gacgaguguc agaguagccc cugugucaac gguggggggcu gcaaggaccg agucaauggc    1560
uucagcugca ccugcccuc gggcuucagc ggcuccacgu ucagcuggga cguggacgaa    1620
ugcgccagca cgcccugcag gaauggcgcc aaaugcgugg accagcccga uggcuacgag    1680
ugccgcugug ccgagggcuu ugaggggcacg cugugugauc gcaacgugga cgacugcucc    1740
ccugacccau gccaccaugg ucgcugcgug gauggcaucg ccagcuucuc augugccgu    1800
```

-continued

```
gcuccuggcu acacgggcac acgcugcgag agccaggugg acgaaugccg cagccagccc    1860
ugccgccaug gcggcaaaug ccuagaccug guggacaagu accucugccg cugcccuucu    1920
gggaccacag gugugaacug cgaagugaac auugacgacu gugccagcaa ccccugcacc    1980
uuuggagucu gccgugaugg caucaaccgc uacgacugug ucugccaacc uggcuucaca    2040 gggcccuuu guaacgugga gaucaaugag ugugcuucca gcccaugcgg cgagggaggu     2100
uccugugugg augggaaaa uggcuuccgc ugccucugcc cgccuggcuc cuugccccca     2160
cucugccucc ccccgagcca ucccugugcc caugagcccu gcagucacgg caucugcuau    2220
gaugcaccug gcggguuccg cugugugugu gagccuggcu ggaguggccc ccgcugcagc     2280
cagagccugg cccgagacgc cugugagucc cagccgugca gggccggugg gacaugcagc     2340
agcgauggaa uggguuucca cugcaccugc ccgccuggug uccagggacg ucagugugaa     2400
cuccucuccc ccugcacccc gaaccccugu gagcaugg99 gccgcugcga gucugccccu     2460
ggccagcugc cugucugcuc cugccuccag ggcuggcaag gcccacgaug ccagcaggau     2520
guggacgagu gugcuggccc cgcacccugu ggcccucaug guaucugcac caaccuggca     2580
gggaguuuca gcugcaccug ccauggaggg uacacuggcc cuuccugcga ucaggacauc     2640
aaugacugug accccaaccc augccugaac gguggcucgu gccaagacgg cgugggcucc     2700
uuuuccugcu ccugccuccc ugguuucgcc ggcccacgau gcgcccgcga uguggaugag     2760
ugccugagca accccugcgg cccgggcacc uguaccgacc acguggccuc cuucaccugc     2820
accugcccgc caggcuacgg aggcuuccac ugcgaacagg accugcccga cugcagcccc     2880
agcuccugcu ucaauggcgg gaccugugug gacggcguga acucguucag cugccugugc     2940 cguccggcu acacaggagc ccacugccaa caugaggcag accccugccu cucgcggccc     3000
ugccuacacg ggggcgucug cagcgccgcc cacccuggcu uccgcugcac cugccucgag     3060
agcuucacgg gcccgcagug ccagacgcug guggauuggu gcagccgcca gccuugucaa     3120 aacgggggguc gcugcgucca gacugggggcc uauugccuuu guccccccugg auggagcgga     3180 cgccucugug acauccgaag cuugcccugc agggaggccg cagcccagau cggggugcgg     3240
cuggagcagc ugugucaggc ggguggggcag ugugguggaug aagacagcuc ccacuacugc     3300
gugugcccag agggccguac ugguagccac ugugagcagg agguggaccc cugcuuggcc     3360
cagcccugcc agcauggggg gaccugccgu ggcuauaugg ggggcuacau gugugagugu     3420
cuuccuggcu acaauggugga uaacugugag gacgacgugg acgagugugc cucccagccc     3480
ugccagcacg ggguucaug cauugaccuc guggcccgcu aucucugcuc cugucccccca     3540 ggaacgcugg ggugcucug cgagauuaau gaggaugacu gcggcccagg cccaccgcug     3600
gacucagggc cccggugccu acacaauggc accugcgugg accugguggg ugguuuccgc     3660
ugcaccuguc ccccaggaua cacugguuug cgcugcgagg cagacaucaa ugagugucgc     3720
ucaggugccu gccacgcggc acacacccgg gacugccugc aggacccagg cggagguuuc     3780
uguugccuuu gucaugcugg cuucucaggu ccucgcuguc agacuguccu gucucccugc     3840
gagucccagc caugccagca uggaggccag ugccgccua gcccggguccc uggggguggg     3900 cugaccuuca ccugucacug ugccagccg uucgggggguc cgcguugcga gcggugggcg     3960
cgcuccugcc gggagcugca gugcccggug ggcgucccau gccagcagac gccccgcggg     4020
ccgcgcugcg ccugccccccc agggguugucg ggacccuccu gccgcagcuu ccggggucg     4080 ccgccggggg ccagcaacgc cagcgcgcg gccgccccu gucuccacgg gggcuccugc     4140
cgccccgcgc cgcucgcgcc cuucuuccgc ugcgcuugcg cgcagggcug gaccgggccg     4200
```

-continued

```
cgcugcgagg cgcccgccgc ggcacccgag gucucggagg agccgcggug cccgcgcgcc   4260
gccugccagg ccaagcgcgg ggaccagcgc ugcgaccgcg agugcaacag cccaggcugc   4320
ggcugggacg cgggcgacug cucgcugagc gugggcgacc ccuggcggca augcgaggcg   4380
cugcagugcu ggcgccucuu caacaacagc cgcucgcgacc ccgccugcag cucgcccgcc   4440
ugccucuacg acaacuucga cugccacgcc gguggccgcg agcgcacuug caacccggug   4500
uacgagaagu acugcgccga ccacuuugcc gacggccgcu gcgaccaggg cugcaacacg   4560
gaggagugcg gcugggaugg gcuggauugu gccagcgagg ugccggcccu gcuggcccgc   4620
ggcgugcugg ugcucacagu gcugcugccg ccagaggagc uacugcguuc cagcgccgac   4680
uuucugcagc ggcucagcgc cauccugcgc accucgcugc gcuuccgccu ggacgcgcac   4740
ggccaggcca uggucuuccc uuaccaccgg ccuaguccug gcuccgaacc ccgggcccgu   4800
cgggagcugg cccccgaggu gaucggcucg guaguaaugc uggagauuga caaccggcuc   4860
ugccugcagu cgccugagaa ugaucacugc uuccccgaug cccagagcgc cgcugacuac   4920
cugggagcgu ugucagcggu ggagcgccug gacuucccgu acccacugcg ggacgugcgg   4980
ggggagccgc uggagccucc agaacccagc guccgcugc ugccacugcu aguggcgggc   5040
gcugucuugc ugcuggucau ucucguccug ggugucaugg uggcccggcg caagcgcgag   5100
cacagcaccc ucugguuccc ugagggcuuc ucacugcaca aggacguggc cucuggucac   5160
aagggccggc gggaacccgu gggccaggac gcgcugggca ugaagaacau ggccaagggu   5220
gagagccuga uggggggagu ggccacagac uggauggaca cagagugccc agaggccaag   5280
cggcuaaagg uagaggagcc aggcaugggg gcugaggagg cuguggauug ccgucagugg   5340
acucaacacc aucugguugc ugcugacauc cgcguggcac cagccauggc acugacacca   5400
ccacagggcg acgcagaugc ugauggcaug gaugucaaug ugcguggccc agauggcuuc   5460
accccgcuaa ugcuggcuuc cuucugugg ggggcucugg agccaaugcc aacugaagag   5520
gaugaggcag augacacauc agcuagcauc aucuccgacc ugaucugcca gggggcucag   5580 cuugggggcac ggacugaccg uacuggcgag acugcuuugc accuggcugc ccguuaugcc   5640
cgugcugaug cagccaagcg gcugcuggau gcuggggcag acaccaaugc ccaggaccac   5700
ucaggccgca cucccugca cacagcuguc acagccgaug cccagggugu cuuccagauu   5760
cucauccgaa accgcucuac agacuuggau gcccgcaugg cagauggcuc aacggcacug   5820
auccuggcgg cccgccuggc aguagagggc augguggaag agcucaucgc cagccaugcu   5880
gaugucaaug cuguggauga gcuugggaaa ucagccuuac acugggcugc ggcugugaac   5940
aacguggaag ccacuuuggc ccugcucaaa aauggagcca auaaggacau gcaggauagc   6000
aaggaggaga ccccccuauu ccuggccgcc cgcgagggca gcuaugaggc ugccaagcug   6060
cuguuggacc acuuugccaa ccgugagauc accgaccacc uggacaggcu gccgcgggac   6120
guagcccagg agagacugca ccaggacauc gugcgcuugc uggaucaacc caguggcccc   6180 cgcagcccccc ccggucccca cggccugggg ccucugcucu guccuccagg ggccuuccuc   6240
ccuggccuca aagcggcaca gucggggucc aagaagagca ggaggcccc cgggaaggcg   6300 gggcuggggc cgcagggcc ccgggggcgg ggcaagaagc ugacgcuggc cugcccgggc   6360
ccccuggcug acagcucggu cacgcugucg cccguggacu cgcuggacuc cccgcggccu   6420
uucggugggc ccccugcuuc cccugguggc uuccccuug aggggcccua ugcagcugcc   6480
acugccacug cagugucucu ggcacagcuu ggguggcccag gccgggcggg ucuagggcgc   6540
```

```
cagcccccug gaggaugugu acucagccug ggccugcuga acccuguggc ugugcccuc      6600 gauugggccc ggcugccccc accugccccu ccaggccccu cguuccgcu gccacuggcg      6660 ccgggacccc agcugcucaa cccagggacc cccgucuccc cgcaggagcg gccccgccu      6720 uaccuggcag ucccaggaca uggcgaggag uacccggcgg cuggggcaca cagcagcccc     6780
ccaaaggccc gcuuccugcg gguucccagu gagcacccuu accugacccc aucccccgaa     6840 ucccugagc acugggccag cccucaccu cccucccucu cagacugguc cgaauccacg       6900
ccuagcccag ccacugccac uggggccaug gccaccacca cuggggcacu gccugcccag     6960
ccacuucccu ugucuguucc cagcucccuu gcucaggccc agaccagcu ggggccccag      7020 ccggaaguua cccccaagag gcaaguguug gccugagacg cucgucaguu cuuagaucuu     7080
gggggccuaa agagaccccc guccugccuc cuuucuuucu cugucucuuc cuuccuuuua     7140
gucuuuuuca uccucuucuc uuuccaccaa cccuccugca uccuugccuu gcagcgugac     7200
cgagauaggu caucagccca gggcuucagu cuuccuuuau uuauaauggg uggggggcuac    7260 cacccacccu cucagucuug ugaagagucu gggaccuccu ucuucccccac uucucucuuc    7320 ccucauuccu uucucucucc uucuggccuc ucauuuccuu acacucugac augaaugaau    7380
uauuauuauu uuuuauuuuc uuuuuuuuuu uacauuuugu auagaaacaa auucauuuaa     7440
acaaacuuau uauuauuauu uuuuacaaaa uauuauauaug gagaugcucc cuccccugu     7500 gaaccccca gugcccccgu ggggcugagu cuguggggccc auucggccaa gcuggauucu     7560
guguaccuag uacacaggca ugacugggau cccguguacc gaguacacga cccagguaug     7620
uaccaaguag gcaccuugg gcgcacccac uggggccagg ggucgggga guguugggag       7680 ccuccuccc acccaccuc ccucacuuca cugcauucca gauggacau guuccauagc        7740 cuugcugggg aagggcccac ugccaacucc cucugcccca gccccacccu uggccaucuc     7800
ccuuugggaa cuaggggggcu gcugguggga aaugggagcc agggcagaug uaugcauucc    7860 uuugugucc uguaaaugug ggacuacaag aagaggagcu gccugagugg uacuuucucu      7920
uccugguaau ccucuggccc agccucaugg cagaauagag guauuuuuag gcuauuuuug     7980
uaauauggcu ucuggucaaa aucccugugu agcugaauuc ccaagcccug cauuguacag     8040 cccccacuc cccucaccac cuaauaaagg aauaguuaac acucaguguu guuggucugu      8100 gucuaggua ggugggggagu ggugcagug ggacuucuau cucccccacc cagggcuaac     8160
uugagcuccc aucuugggggu aaauacauuu gacuugccag ucuacuuaug cuuccucuuu    8220
uggcagauga cuaccgauug gauuagugggu ugucaccuga cuuaagcuga gccaaucaga    8280
uucuuuugcu cgagaacuuu cuuuaaugga gaggcuaaga aaguugucag uuggugggagc    8340 ucuuaagguc acaaucagau uuagaaauau caguggccaa uucgaggugg ugggcaaaga     8400
gacaagcaaa cagggcagaa gaaugaagcu aauauucagg gagaaucaga aaugagagcu     8460
caaauggcuc cuugaggggcu gggggggguua ucucggcucc cagucagguu aucaauucca   8520
guuaauugag uguucauucc auugagauca acagguauuu auuaauugcu uucuaaguau     8580
cugaucaugg uucugcauga auuucacuuu uacuucaugc uccuaugggu uuuggagaua     8640
accuuggacc cauguaauaa auacuucuuu acuugugcca                          8680
```

```
<210> SEQ ID NO 9
<211> LENGTH: 8666
<212> TYPE: RNA
<213> ORGANISM: homo sapien

<400> SEQUENCE: 9
```

-continued

```
gcggcgcgga ggcuggcccg ggacgcgccc ggagcccagg gaaggaggga ggaggggagg      60
gucgcggccg gccgccaugg ggccgggggc ccguggccgc cgccgccgcc gucgcccgau     120
gucgccgcca ccgccaccgc cacccgugcg ggcgcugccc cugcugcugc ugcuagcggg     180
gccgggggcu gcagcccccc cuugccugga cggaagcccg ugugcaaaug gaggucguug     240
cacccagcug cccucccggg aggcugccug ccugugcccg ccuggcuggg ugggugagcg     300
gugucagcug gaggaccccu gucacucagg ccccugugcu ggccguggug ucugccagag     360
uucaguggug gcuggcaccg cccgauucuc augccggugc ccccguggcu uccgaggccc     420
ugacugcucc cugccagauc ccugccucag cagcccuugu gcccacggug cccgcugcuc     480
aguggggccc gauggacgcu uccucugcuc cugcccaccu ggcuaccagg gccgcagcug     540
ccgaagcgac guggaugagu gccggguggg ugagcccugc cgccauggug gcaccugccu     600
caacacaccu ggcuccuucc gcugccagug uccagcuggc uacacagggc cacuauguga     660
gaaccccgcg gugcccugug cacccucacc augccguaac gggggcaccu gcaggcagag     720
uggcgaccuc acuuacgacu gugccugucu uccuggguuu gagggucaga auugugaagu     780
gaacguggac gacuguccag gacaccgaug ucucaauggg gggacaugcg uggauggcgu     840
caacaccuau aacugccagu gcccuccuga guggacaggc caguucugca cggaggacgu     900
ggaugagugu cagcugcagc ccaacgccug ccacaauggg gguaccugcu ucaaacacgcu    960 ggguggccac agcugcgugu gugucaaugg cuggacaggc gagagcugca gucagaauau    1020
cgaugacugu gccacagccg ugugcuucca uggggccacc ugccaugacc gcguggcuuc    1080
uuucuacugu gccugcccca ugggcaagac uggccuccug ugucaccugg augacgccug    1140
ugucagcaac cccugccacg aggaugcuau cugugacaca aauccgguga acggccgggc    1200
cauuugcacc uguccucccg gcuucacggg uggggcaugu gaccaggaug uggacgagug    1260
cucuaucggc gccaaccccu gcgagcacuu gggcaggugc gugaacacgc agggcuccuu    1320
ccugugccag ugcggucgug gcuacacugg accucgcugu gagaccgaug ucaacgagug    1380
ucugucgggg cccugccgaa accaggccac gugccucgac cgcauaggcc aguucaccug    1440
uaucuguaug gcaggcuuca caggaaccua uugcgaggug gacauugacg agugucagag    1500 uagcccccugu gucaacggug gggucugcaa ggaccgaguc aauggcuuca gcugcaccug    1560 cccccucgggc uucagcggcu ccacguguca gcuggacgug gacgaaugcg ccagcacgcc    1620
cugcaggaau ggcgccaaau gcguggacca gcccgauggc uacgagugcc gcugugccga    1680
gggcuuugag ggcacgcgu gugaucgcaa cguggacgac ugcuccccug acccaugcca    1740
ccauggucgc ugcguggaug gcaucgccag cuucucaugu gccugugcuc cuggcuacac    1800
gggcacacgc ugcgagagcc aggggacga augccgcagc cagcccugcc gccauggcgg    1860
caaaugccua gaccuggugg acaaguaccu cugccgcugc ccuucgggga ccacaggugu    1920
gaacugcgaa gugaacauug acgacugugc cagcaacccc ugcaccuuug agcugccg     1980 ugauggcauc aaccgcuacg acugugucug ccaaccuggc uucacagggc cccuuuguaa    2040
cguggagauc aaugaguu cuuccagccc augcggcgag ggaggguccu gugugguaugg    2100 ggaaaauggc uuccgcugcc ucugcccgcc uggcuccuug cccccacucu gccucccccc    2160
gagccauccc ugugcccaug agcccugcag ucacggcauc ugcuaugaug caccuggcgg    2220
guuccgcugu gugugugagc cuggcuggag uggccccgc ugcagccaga gccuggcccg    2280
agacgccugu gagucccagc cgugcagggc cgguggcaca ugcagcagcg auggaauggg    2340
```

-continued

```
uuuccacugc accugcccgc cugguguccg gggacgucag ugugaacucc ucuccccug    2400 caccccgaac cccugugagc augggggccg cugcgagucu gccccuggcc agcugccugu    2460
cugcuccugc ccccagggcu ggcaaggccc acgaugccag caggaugugg acgagugugc    2520
uggccccgca cccuguggcc cucaugguau cugcaccaac cuggcaggga guuucagcug    2580
caccugccau ggaggguaca cuggcccuuc cugcgaucag gacaucaaug acugugaccc    2640
caacccaugc cugaacggug gcucgugcca agacggcgug ggcuccuuuu ccugcuccug    2700
ccucccuggu uucgccggcc cacgaugcgc ccgcgaugug gaugagugcc ugagcaaccc    2760
cugcggcccg ggcaccugua ccgaccacgu ggccuccuuc accugcaccu gcccgccagg    2820
cuacggaggc uuccacugcg aacaggaccu gcccgacugc agccccagcu ccugcuucaa    2880
uggcgggacc uguguggacg gcgugaacuc guucagcugc cugugccguc ccggcuacac    2940
aggagcccac ugccaacaug aggcagaccc cugccucucg cggcccugcc uacacggggg    3000
cgucugcagc gccgcccacc cuggcuuccg cugcaccugc cucgagagcu ucacgggccc    3060
gcagugccag acgcuggugg auuggugcag ccgccagccu ugucaaaacg ggggucgcug    3120
cguccagacu ggggccuauu gccuuugucc cccuggaugg agcggacgcc ucugugacau    3180
ccgaagcuug cccugcaggg aggccgcagc ccagaucggg gugcggcugg agcagcugug    3240
ucaggcgggu gggcagugug uggaugaaga cagcucccac uacugcgugu gcccagaggg    3300
ccguacuggu agccacugug agcaggaggu ggaccccugc uuggcccagc ccugccagca    3360 ugggggggacc ugccguggcu auauggggggg cuacaugugu gagugucuuc cuggcuacaa    3420
uggugauaac ugugaggacg acguggacga gugugccucc cagcccugcc agcacggggg    3480
uucaugcauu gaccucgugg cccgcuaucu cugcuccugu cccccaggaa cgcuggggu    3540 gcucugcgag auuaaugagg augacugcgg cccaggccca ccgcuggacu cagggccccg    3600
gugccuacac aauggcaccu gcguggaccu gguggguggu uuccgcugca ccugucccc    3660 aggauacacu gguuugcgcu gcgaggcaga caucaaugag ugucgcucag gugccugcca    3720
cgcggcacac acccgggacu gccugcagga cccaggcgga gguuucuguu gccuuuguca    3780
ugcuggcuuc ucagguccuc gcugucagac ugucugucu cccugcgagu cccagccaug    3840
ccagcaugga ggccagugcc guccuagccc gggucuuggg ggugggcuga ccuucaccug    3900
ucacugugcc cagccguucu ggggucucgcg uugcgagcgg guggcgcgcu ccugccggga    3960
gcugcagugc ccggugggcg ucccaugcca gcagacgccc cgcgggccgc gcugcgccug    4020
cccccagggg uugucgggac ccuccugccg cagcuucccg gggucgccgc cgggggccag    4080
caacgccagc ugcgcggccg cccccugucu ccacgggggc uccugccgcc ccgcgccgcu    4140
cgcgcccuuc uuccgcugcg cuugcgcgca gggcuggacc gggccgcgcu gcgaggcgcc    4200
cgccgcggca cccgaggucu cggaggagcc gcggugcccg cgcgccgccu gccaggccaa    4260
gcgcggggac cagcgcugcg accgcgagug caacagccca ggcugcggcu gggacggcgg    4320
cgacugcucg cugagcgugg gcgacccug gcggcaaugc gaggcgcugc agugcuggcg    4380
ccucuucaac aacagccgcu gcgaccccgc cugcagcucg cccgccugcc ucuacgacaa    4440
cuucgacugc cacgccggug gccgcgagcg cacuugcaac ccgguguacg agaaguacug    4500
cgccgaccac uuugccgacg gccgcugcga ccagggcugc aacacggagg agugcggcug    4560
ggaugggcug gauugugcca gcgaggugcc ggcccugcug gccgcgcgcg ugcuggugcu    4620
cacagugcug cugccgccag aggagcuacu gcguuccagc gccgacuuuc ugcagcggcu    4680
cagcgccauc cugcgcaccu cgcugcgcuu ccgccuggac gcgcacggcc aggccauggu    4740
```

-continued

```
cuucccuuac caccggccua guccuggcuc cgaaccccgg gcccgucggg agcuggcccc    4800
cgaggugauc ggcucgguag uaaugcugga gauugacaac cggcucugcc ugcagucgcc    4860
ugagaaugau cacugcuucc ccgaugccca gagcgccgcu gacuaccugg gagcguuguc    4920
agcgguggag cgccuggacu ucccguaccc acugcgggac gugcggggg agccgcugga    4980 gccuccagaa cccagcgucc cgcugcugcc acugcuagug gcgggcgcug ucuugcugcu    5040
ggucauucuc guccuggug ucauggggc ccggcgcaag cgcgagcaca gcaccucug    5100 guucccugag ggcuucucac ugcacaagga cguggccucu ggucacaagg gccggcggga    5160
acccgugggc caggacgcgc ugggcaugaa gaacaugcc aagggugaga gccgauggg    5220 ggaggggcc acagacugga uggacacaga gugcccagag gccaagcggc uaaaggugga    5280
ggagccaggc auggggcugu aggaggcugu ggauugccgu caguggacuc aacaccaucu    5340
gguugcugcu gacauccgcg uggcaccagc cauggcacug acaccaccac agggcgacgc    5400
agaugcugau ggcauggaug ucaaugugcg uggcccagau ggcuucaccc cgcuaaugcu    5460
ggcuuccuuc uguggggggg cucuggagcc aaugccaacu gaagaggaug aggcagauga    5520
cacaucagcu agcaucaucu ccgaccugau cugccagggg gcucagcuug gggcacggac    5580
ugaccguacu ggcgagacug cuuugcaccu ggcugcccgu uaugcccgug cugaugcagc    5640
caagcggcug cuggaugcug gggcagacac caaugcccag gaccacucag gccgcacucc    5700
ccugcacaca gcugucacag ccgaugccca gggugucuuc cagauucuca uccgaaaccg    5760
cucuacagac uuggaugccc gcauggcaga uggcucaacg gcacugaucc uggcggcccg    5820
ccuggcagua gagggcaugg uggaagagcu caucgccagc caugcugaug ucaaugcugu    5880
ggaugagcuu gggaaaucag ccuuacacug ggcugcggcu gugaacaacg uggaagccac    5940
uuuggcccug cucaaaaaug gagccaauaa ggacaugcag gauagcaagg aggagacccc    6000
ccuauuccug gccgcccgcg agggcagcua ugaggcugcc aagcugcugu uggaccacuu    6060
ugccaaccgu gagaucaccg accaccugga caggcugccg cgggacguag cccaggagag    6120
acugcaccag gacaucgugc gcuugcugga ucaacccagu gggccccgca gccccccgg    6180 uccccacggc cugggccuc ugcucugucc uccaggggcc uuccuccug gccucaaagc    6240 ggcacagucg ggguccaaga agagcaggag gccccgggg aaggcgggc ugggccgca    6300 ggggcccgg gggcggggca agaagcugac gcuggccugc ccgggccccc uggcugacag    6360
cucggucacg cugucgcccg uggacucgcu ggacuccccg cggccuuucg gugggcccc    6420 ugcuuccccu gguggcuucc cccuugaggg gcccuaugca gcugccacug ccacugcagu    6480
gucucuggca cagcuuggug gcccaggccg ggcgggucua gggcgccagc ccccuggagg    6540
auguguacuc agccuggcc ugcugaaccc uguggcugug ccccucgauu gggcccggcu    6600 gccccaccu gcccccuccag gccccucguu ccugcugcca cuggcgccgg gaccccagcu    6660
gcucaaccca gggaccccg ucuccccgca ggagcggccc ccgccuuacc uggcaguccc    6720
aggacauggc gaggaguacc cggcggcugg ggcacacagc agcccccaa aggcccgcuu    6780 ccugcggguu cccagugagc acccuuaccu gaccccaucc cccgaaucc cugagcacug    6840 ggccagcccc ucaccucccu cccucucaga cugguccgaa uccacgccua gcccagccac    6900
ugccacuggg gccauggcca ccaccacugg ggcacugccu gcccagccac uucccuuguc    6960
uguucccagc ucccuugcuc aggcccagac ccagcugggg cccagccggg aaguuacccc    7020
caagaggcaa guguuggccu gagacgcucg ucaguucuua gaucuugggg gccuaaagag    7080
```

-continued

```
acccccgucc ugccuccuuu cuuucucugu cucuuccuuc cuuuuagucu uuuucauccu    7140
cuucucuuuc caccaacccu ccugcauccu ugccuugcag cgugaccgag auaggucauc    7200
agcccagggc uucagucuuc cuuuauuuau aauggguggg ggcuaccacc cacccucuca    7260
gucuugugaa gagucuggga ccuccuucuu ccccacuucu cucuuccuc auuccuuucu     7320 cucuccuucu ggccucucau uuccuuacac ucugacauga augaauuauu auuauuuuua    7380 uuuuucuuu uuuuuuuaca uuuuguauag aaacaaauuc auuuaaacaa acuuauuauu     7440 auuauuuuu acaaaauaua uauauggaga ugcucccucc cccugugaac cccccagugc    7500
ccccgugggg cugagucugu gggcccauuc ggccaagcug gauucugugu accuaguaca    7560
caggcaugac ugggaucccg uguaccgagu acacgaccca gguauguacc aaguaggcac    7620
ccuugggcgc acccacuggg gccaggggguc gggggagugu ugggagccuc cuccccaccc   7680
caccucccuc acuucacugc auuccagaug ggacauguuc cauagccuug cuggggaagg    7740
gcccacugcc aacucccucu gccccagccc cacccuuggc caucucccuu ugggaacuag    7800
ggggcugcug gugggaaaug ggagccaggg cagauguaug cauuccuuug uguccecgua    7860 aaugugggac uacaagaaga ggagcugccu gagugguacu uucucuuccu gguaauccuc    7920
uggcccagcc ucauggcaga auagagguau uuuuaggcua uuuuuuguaau auggcuucgu    7980 gucaaaaucc cuguguagcu gaauucccaa gcccugcauu guacagcccc ccacucccu     8040 caccaccuaa uaaaggaaua guuaacacuc aguguuguug gucugugucu agguaaaggu    8100
gggaguggug gcaguggggac uucuaucucc cccacccagg gcuaacuuga gcucccaucu    8160 uggggguaaau acauuugacu ugccagucua cuuaugcuuc cucuuuuggc agaugacuac    8220
cgauuggauu agugguuguc accgacuua agcugagcca aucagauucu uuugcucgag     8280
aacuuucuuu aauggagagg cuaagaaagu ugucaguugg uggagcucuu aaggucacaa    8340
ucagauuuag aaauaucagu ggccaauucg agguggugg caaagagaca agcaaacagg     8400
gcagaagaau gaagcuaaua uucagggaga aucagaaaug agagcucaaa uggcuccuug    8460
agggcugggg gggguuaucuc ggcucccagu gcaguuauca auuccaguua auugagugu     8520 cauuccauug agaucaacag guauuuauua auugcuuucu aaguaucuga ucaugguucu    8580
gcaugaauuu cacuuuuacu ucaugcuccu auggguuuug gagauaaccu uggacccaug    8640
uaauaaauac uucuuuacuu gugcca                                         8666
```

<210> SEQ ID NO 10
<211> LENGTH: 3858
<212> TYPE: RNA
<213> ORGANISM: homo sapien

<400> SEQUENCE: 10

```
gggccggggg cccguggccg ccgccgccgc cgucgcccga ugucgccgcc accgccaccg    60
ccacccgugc gggcgcugcc ccugcugcug cugcuagcgg ggccgggggc ugcagccccc     120
ccuugccugg acggaagccc gugugcaaau ggaggucguu gcacccagcu gcccucccgg     180
gaggcugccu gccgugcccc gccuggcugg guggugagc ggugucagcu ggaggacccc      240
ugucacucag gccccugugc uggccguggu gucugccaga guucaguggu ggcuggcacc     300
gcccgauucu caugccggug cccccgugcc uuccgaggcc cugacugcuc ccugccagau     360
cccugccuca gcagcccuug ugcccacggu gcccgcugcu caguggggcc cgauggacgc     420
uuccucugcu ccugccacc uggcuaccag ggccgcagcu gccgaagcga cguggaugag     480 ugccggguggg gugagcccug ccgccauggu ggcaccugcc ucaacacacc uggcuccuuc     540
```

```
cgcugccagu guccagcugg cuacacaggg ccacuaugug agaaccccgc ggugcccugu      600
gcacccucac caugccguaa cgggggcacc ugcaggcaga guggcgaccu cacuuacgac      660
ugugccuguc uuccuggguu ugagggucag aauugugaag ugaacgugga cgacugucca      720
ggacaccgau gucucaaugg ggggacaugc guggauggcg ucaacaccua uaacugccag      780
ugcccuccug aguggacagg ccaguucugc acggaggacg uggaugagug ucagcugcag      840
cccaacgccu gccacaaugg ggguaccugc uucaacacgc ugggguggcca cagcugcgug      900 ugugucaaug gcuggacagg cgagagcugc agucagaaua ucgaugacug ugccacagcc      960
gugugcuucc augggggccac cugccaugac cgcguggcuu cuuucuacug ugccugcccc     1020
augggcaaga cuggccuccu gugucaccug gaugacgccu gugucagcaa ccccugccac     1080
gaggaugcua ucugugacac aaauccggug aacggccggg ccauuugcac cuguccuccc     1140
ggcuucacgg guggggcaug ugaccaggau guggacgagu gcucuaucgg cgccaacccc     1200
ugcgagcacu ugggcaggug cgugaacacg caggcuccu uccugugcca gugcggucgu      1260
ggcuacacug gaccucgcug ugagaccgau gucaacgagu gucugucggg gcccugccga     1320
aaccaggcca cgugccucga ccgcauaggc caguucaccu guaucuguau ggcaggcuuc     1380
acaggaaccu auugcgaggu ggacauugac gagugucaga guagcccug ugucaacggu      1440 ggggucugca aggaccgagu caauggcuuc agcugcaccu gccccucggg cuucagcggc     1500
uccacguguc agcuggacgu ggacgaaugc gccagcacgc ccugcaggaa uggcgccaaa     1560
ugcguggacc agcccgaugg cuacgagugc cgcugugccg agggcuuuga gggcacgcug     1620
ugugaucgca acguggacga cugcuccccu gacccaugcc accaugguucg cugcguggau     1680 ggcaucgcca gcuucucaug ugccugugcu ccuggcuaca cgggcacacg cugcgagagc     1740
cagguggacg aaugccgcag ccagcccugc cgccauggcg gcaaaugccu agaccuggug     1800
gacaaguacc ucugccgcug ccccuucuggg accacaggug ugaacugcga agugaacauu     1860
gacgacugug ccagcaaccc cugcaccuuu ggagucugcc gugauggcau caaccgcuac     1920
gacugugucu gccaaccugg cuucacaggg cccccuuugua acguggagau caaugagugu     1980
gcuuccagcc caugcggcga gggagguucc uguguggaug gggaaaaugg cuuccgcugc     2040
cucugcccgc cuggcuccuu gcccccacuc ugccuccccc cgagccaucc cugugcccau     2100
gagcccugca gucacggcau cugcuaugau gcaccuggcg gguuccgcug uguguguggag     2160 ccuggcugga guggcccccg cugcagccag agccuggccc gagacgccug ugagucccag     2220
ccgugcaggg ccgguggggac augcagcagc gauggaaugg guuuccacug caccugcccg     2280 ccugggugucc agggacguca gugugaacuc cucucccccu gcaccccgaa ccccugugag     2340
caugggggcc gcugcgaguc ugcccccuggc cagcugccug ucugcuccug cccccagggc     2400
uggcaagacc caugccugaa cgguggcucg ugccaagacg gcgugggcuc cuuuuccugc     2460
uccugccucc cugguuucgc cggcccacga ugcgcccgcg auguggauga gugccugagc     2520
aaccccugcg gcccgggcac cuguaccgac cacguggccu ccuucaccug caccugcccg     2580
ccaggcuacg gaggcuucca cugcgaacag gaccugcccg acugcagccc cagcuccugc     2640
uucaauggcg ggaccugugu ggacggcgug aacucguuca gcugccugug ccguccecggc     2700 uacacaggag cccacugcca acaugaggca gaccccugcc ucucgcggcc cugccuacac     2760
gggggcgucu gcagcgccgc ccacccuggc uuccgcugca ccugccucga gagcuucacg     2820
ggcccgcagu gccagacgcu gguggauugg ugcagccgcc agccuuguca aaacgggggu     2880
```

-continued

```
cgcugcgucc agacuggggc cuauugccuu ugucccccug gauggagcgg acgccucugu    2940
gacauccgaa gcuugcccug cagggaggcc gcagcccaga ucgggguggcg gcuggagcag    3000 cugugucagg cggguggggca gugugugggau gaagacagcu cccacuacug cgugugccca    3060
gagggccgua cugguagcca cuguagagcag gaggguggacc ccugcuuggc ccagcccugc    3120
cagcaugggg ggaccugccg uggcuauaug gggggcuaca ugugugagug ucuuccuggc    3180
uacaauggug auaacuguga ggacgacgug gacgagugug ccucccagcc cugccagcac    3240 gggggguucau gcauugaccu cguggcccgc uaucucugcu ccugucccccc aggaacgcug    3300 ggggugcucu gcgagauuaa ugaggaugac ugcggcccag gcccaccgcu ggacucaggg    3360
ccccggugcc uacacaaugg caccugcgug gaccuggugg guggguuuccg cugcaccugu    3420 cccccaggau acacugguuu gcgcugcgag gcagacauca augagugucg cucaggugcc    3480
ugccacgcgg cacacacccg ggacugccug caggacccag gcggagguuu cuguugccuu    3540
ugucaugcug gcuucucagg uccucgcugu cagacugucc ugucucccug cgagucccag    3600
ccaugccagc auggaggcca gugccguccu agcccggguc cuggggguggg gcugaccuuc    3660 accgucacu gugcccagcc guucuggggu ccgcguugcg agcgggguggc gcgcuccugc    3720 cgggagcugc agugcccggu gggcguccca ugccagcaga cgccccgcgg gccgcgcugc    3780
gccugccccc cagggguuguc gggacccucc ugccgcagcu ucccgggguc gccgccgggg    3840
gccagcaacg ccagcugc                                                 3858
```

<210> SEQ ID NO 11
<211> LENGTH: 8091
<212> TYPE: RNA
<213> ORGANISM: homo sapien

<400> SEQUENCE: 11

```
acgcggcgcg gaggcuggcc cgggacgcgc ccggagccca gggaaggagg gaggagggga      60
gggucgcggc cggccgccau gggggccgggg gcccgugggcc gccgccgccg ccgucgcccg     120
augucgccgc caccgccacc gccacccgug cgggcgcugc cccugcugcu gcugcuagcg     180
gggccggggg cugcagcccc cccuugccug gacggaagcc cgugugcaaa uggaggucgu     240
ugcacccagc ugcccucccg ggaggcugcc ugccugugcc cgccuggcug ggugggugag     300
cggugucagc uggaggaccc cugucacuca ggccccugug cuggccgugg ugucugccag     360
aguucagugg uggcuggcac cgcccgauuc ucaugccggu gcccccgugg cuuccgaggc     420
ccugacugcu cccugccaga ucccugccuc agcagcccuu gugcccacgg ugcccgcugc     480 ucagugggggc ccgauggacg cuuccucugc uccugcccac cuggcuacca gggccgcagc     540
ugccgaagcg acguggauga gugccgggug ggugagcccu gccgccaugg uggcaccugc     600
cucaacacac cuggcuccuu ccgcugccag uguccagcug gcuacacagg gccacuaugu     660
gagaaccccg cggugcccug ugcgcccuca ccaugccgua acgggggcac cugcaggcag     720
aguggcgacc ucacuuacga cugugccgu cuuccugggu uugaggggcua gaauugugaa     780 gugaacgugg acgacugucc aggacaccga ugucucaaug gggggacaug cguggauggc     840
gucaacaccu auaacugcca gugccccuccu gaguggacag gccaguucug cacgcgaggac     900 guggaugagu gucagcugca gcccaacgcc ugccacaaug ggggguaccug cuucaacacg     960 cuggguggcc acagcgcgu gugugucaau ggcuggacag gugagagcug cagucagaau    1020
aucgaugacu gugccacagc cgugugcuuc cauggggcca ccugccauga ccgcguggcu    1080
ucuuucuacu gugccugccc caugggcaag acuggccucc ugugucaccu ggaugacgcc    1140
```

-continued

```
ugugucagca accccugcca cgaggaugcu aucugugaca caaauccggu gaacggccgg      1200
gccauuugca ccuguccucc cggcuucacg gguggggcau gugaccagga uguggacgag      1260
ugcucuaucg gcgccaaccc cugcgagcac uugggcaggu gcgugaacac gcagggcucc      1320
uuccugugcc agugcggucg uggcuacacu ggaccucgcu gugagaccga ugucaacgag      1380
ugucugucgg ggcccugccg aaaccaggcc acgugccucg accgcauagg ccaguucacc      1440
uguaucugua uggcaggcuu cacaggaacc uauugcgagg uggacauuga cgagugucag      1500
aguagccccu gugucaacgg uggggucugc aaggaccgag ucaauggcuu cagcugcacc      1560
ugccccucgg gcuucagcgg cuccacugugu cagcuggacg uggacgaaug cgccagcacg      1620
cccugcagga auggcgccaa augcguggac cagcccgaug gcuacgagug ccgcugugcc      1680
gagggcuuug agggcacgcu gugugaucgc aacguggacg acugcucccc ugacccaugc      1740
caccaugguc gcugcgugga uggcaucgcc agcuucucau gugccugugc uccuggcuac      1800
acgggcacac gcugcgagag ccaggguggac gaaugccgca gccagcccug ccgccauggc      1860
ggcaaaugcc uagaccuggu ggacaaguac cucugccgcu gcccuucugg gaccacaggu      1920
gugaacugcg aagugaacau ugacgacugu gccagcaacc ccugcaccuu uggagucugc      1980
cgugauggca ucaaccgcua cgacuguguc ugccaaccug gcuucacagg gcccccuuugu      2040 aacguggaga ucaaugagug ugcuuccagc ccaugcggcg aggggagguuc cugguguggau      2100 ggggaaaaug gcuuccgcug ccucugcccg ccuggcuccu ugccccacu cugccucccc      2160 ccgagccauc ccugugccca ugagcccugc agucacggca ucugcuauga ugcaccuggc      2220
ggguuccgcu gugugugugga gccuggcugg aguggccccc gcugcagcca gagccuggcc      2280
cgagacgccu gugagucccca gccgugcagg gccgguggga caugcagcag cgauggaaug      2340
gguuuccacu gcaccugccc gccugguguc cagggacguc agugugaacu ccucuccccc      2400
ugcaccccga accccuguga gcauggggc cgcugcgagu cugccccugg ccagcugccu      2460
gucugcuccu gccccaggg cuggcaaggc ccacgaugcc agcaggaugu ggacgagugu      2520
gcuggccccg cacccugugg cccucauggu aucugcacca accuggcagg gaguuucagc      2580
ugcaccugcc auggagggua cacuggcccu uccugugauc aggacaucaa ugacugugac      2640
cccaacccau gccugaacgg uggcucgugc caagacggcg ugggcuccuu uuccugcucc      2700
ugccucccug guuucgccgg cccacgaugc gcccgcgaug uggaugagug ccugagcaac      2760
cccugcggcc cgggcaccug uaccgaccac guggccuccu ucaccugcac cugcccgccg      2820
ggcuacggag gcuuccacug cgaacaggac cugcccgacu gcagcuccag cucccugcuuc      2880 aauggcgggga ccugugugga cggcgugaac ucguucagcu gccugugccg ucccggcuac      2940
acaggagccc acugccaaca ugaggcagac cccugccucu cgcggcccug ccuacacggg      3000
ggcgucugca gcgccgccca cccuggcuuc cgcugcaccu gccucgagag cuucacgggc      3060
ccgcagugcc agacgcuggu ggauuggguc agccgccagc uuugucaaaa cgggggucgc      3120
ugcguccaga cuggggccua uugccuuugu ccccuggau ggagcggacg ccucuguguac      3180 auccgaagcu ugcccugcag ggaggccgca gcccagaucg gguucggcu ggagcagcug      3240 ugucaggcgg gugggcagug uguggaugaa gacagcuccc acuacugcgu gugcccagag      3300
ggccguacug guagccacug ugagcaggag guggacccu gcuuggccca gcccugccag      3360
caugggggga ccugccgugg cuauaugggg ggcuacaugu gugagugucu uccuggcuac      3420
aauggugaua acugugagga cgacugggac gagugugccu cccagcccug ccagcacggg      3480
```

-continued

```
gguucaugca uugaccucgu ggcccgcuau cucugcuccu guccccagg aacgcugggg    3540 gugcucugcg agauuaauga ggaugacugc ggcccaggcc caccgcugga cucagggccc    3600
cggugccuac acaauggcac cugcguggac cuggugggug guuuccgcug caccugaccc    3660
ccaggauaca cugguuugcg cugcgaggca gacaucaaug agugucgcuc aggugccugc    3720
cacgcggcac acaccgggga cugccugcag gacccaggcg gagguuucug uugccuuugu    3780
caugcuggcu ucucaggucc ucgcugucag acuguccugu cucccugcga gucccagcca    3840
ugccagcaug gaggccagug ccguccuagc ccggguccug ggggugggcu gaccuucacc    3900
ugucacugug cccagccguu cugggguccg cguugcgagc gggguggcgcg cuccugccgg    3960 gagcugcagu gcccgguggg cgucccaugc cagcagacgc cccgcgggcc gcgcugcgcc    4020 ugcccccccag gguugucggg acccuccugc cgcagcuucc cggggucgcc gccggggcc    4080 agcaacgcca gcugcgcggc cgccccccugu uccacgggg gcuccugccg ccccgcgccg    4140
cucgcgcccu ucuuccgcug cgcuugcgcg cagggcugga ccgggccgcg cugcgaggcg    4200
cccgccgcgg cacccgaggu cucggaggag ccgcggugcc cgcgcgccgc cugccaggcc    4260
aagcgcgggg accagcgcug cgaccgcgag ugcaacagcc caggcugcgg cugggacggc    4320
ggcgacugcu cgcugagcgu gggcgacccc uggcggcaau gcgaggcgcu gcagugcugg    4380
cgccucuuca acaacagccg cugcgacccc gccugcagcu cgcccgccug ccucuacgac    4440
aacuucgacu gccacgccgg uggccgcgag cgcacuugca acccggugua cgagaaguac    4500
ugcgccgacc acuuugccga cggccgcugc gaccagggcu gcaacacgga ggagugcggc    4560
ugggaugggc uggauugugc cagcgaggug ccggcccugc uggcccgcgg cgugcuggug    4620
cucacagugc ugcugccgcc ggaggagcua cugcguucca gcgccgacuu ucugcagcgg    4680
cucagcgcca uccugcgcac cucgcugcgc uuccgccugg acgcgcacgg ccaggccaug    4740
gucuucccuu accaccggcc uaguccuggc uccgaacccc gggcccgucg ggagcuggcc    4800
cccgagguga ucggcucggu aguaaaugcug gagauugaca accggcucug ccugcagucg    4860
ccugagaaug aucacugcuu ccccgaugcc cagagcgccg cugacuaccu gggagcguug    4920
ucagcggugg agcgccugga cuucccguac ccacugcggg acgugcgggg ggagccgcug    4980
gagccuccag aacccagcgu cccgcugcug ccacugcuag uggcgggcgc ugucuugcug    5040
cuggucauuc ucguccuggg ugucauggug gcccggcgca agcgcgagca cagcacccuc    5100 ugguuccccug agggcuucuc acugcacaag gacgcuggccu cuggucacaa gggccggcgg    5160
gaacccgugg gccaggacgc gcugggcaug aagaacaugg ccaaggguga gagccugaug    5220
ggggaggugg ccacagacug gauggacaca gagugcccag aggccaagcg gcuaaaggua    5280
gaggagccag gcauggggggc ugaggaggcu guggauugcc gucaguggac ucaacaccau    5340
cugguugcug cugacauccg cguggcacca gccauggcac ugacaccacc acagggcgac    5400
gcagaugcug auggcaugga ugucaaugug cguggcccag auggcuucac cccgcuaaug    5460
cuggcuuccu ucuguggggg ggcucuggag ccaaugccaa cugaagagga ugaggcagau    5520
gacacaucag cuagcaucau cuccgaccug aucugccagg gggcucagcu uggggcacgg    5580
acugaccgua cuggcgagac ugcuuugcac cuggcugccc guuaugcccg ugcugaugca    5640
gccaagcggc ugcuggaugc uggggcagac accaaugccc aggaccacuc aggccgcacu    5700
ccccugcaca cagcugucac agccgaugcc caggguguu uccagauucu cauccgaaac    5760
cgcucuacag acuuggaugc ccgcauggca gauggcucaa cggcacugau ccuggcggcc    5820
cgccuggcag uagagggcau ggguggaagag cucaucgcca gccaugcuga ugucaaugcu    5880
```

```
guggaugagc uugggaaauc agccuuacac ugggcugcgg cugugaacaa cguggaagcc   5940
acuuuggccc ugcucaaaaa uggagccaau aaggacaugc aggauagcaa ggaggagacc   6000
ccccuauucc uggccgcccg cgagggcagc uaugaggcug ccaagcugcu guuggaccac   6060
uuugccaacc gugagaucac cgaccaccug gacaggcugc cgcgggacgu agcccaggag   6120
agacugcacc aggacaucgu gcgcuugcug gaucaaccca gugggccccg cagcccccc   6180 gguccccacg gccugggggcc ucugcucugu ccuccagggg ccuuccuccc uggccucaaa   6240
gcggcacagu cggggguccaa gaagagcagg aggcccccccg ggaaggcggg gcuggggccg   6300
caggggcccc gggggcgggg caagaagcug acgcuggccu gcccgggccc ccuggcugac   6360
agcucgguca cgcugucgcc cguggacucg cuggacuccc cgcggccuuu cgguggggccc   6420 ccugcuuccc cugguggcuu cccccuugag gggcccuaug cagcugccac ugccacugca   6480
gugucucugg cacagcuugg uggcccaggc cgggcagguc uagggcgcca gcccccugga   6540
ggauguguac ucagccuggg ccugcugaac ccuguggcug ugccccucga uugggcccgg   6600
cugcccccac cugcccccucc aggcccucg uuccugcugc cacuggcgcc gggacccccag   6660 cugcucaacc cagggacccc cgucucccccg caggagcggc ccccgcccuua ccuggcaguc   6720 ccaggacaug gcgaggagua cccgguggcu ggggcacaca gcagcccccc aaaggcccgc   6780
uuccugcggg uucccaguga gcacccuuac cugaccccau ccccccgaauc cccugagcac   6840 ugggccagcc ccucaccucc cuccccucuca gacugguccg aauccacgcc uagcccagcc   6900
acugccacug gggccauggc caccaccacu ggggcacugc cugcccagcc acuucccuug   6960
ucuguuccca gcucccuugc ucaggcccag acccagcugg ggcccccagcc ggaaguuacc   7020 cccaagaggc aaguguuggc cugagacgcu cgucaguucu uagaucuugg gggccuaaag   7080
agacccccgu ccugccuccu uucuuucucu gucucuuccu uccuuuuagu cuuuuucauc   7140
cucuucucuu uccaccaacc cuccugcauc cuugccuugc agcgugaccg agauaggguca   7200 ucagcccagg gcuucagucu uccuuuauuu auaauggggug ggggcuacca cccacccucu   7260
cagucuugug aagagucugg gaccuccuuc uucccccacuu cucucuuccc ucauuccuuu   7320
cucucuccuu cuggccucuc auuuccuuac acucugacau gaaugaauua uuauuauuuu   7380
ucuuuuucuu uuuuuuuuua cauuuuguau agaaacaaau ucauuaaaac aaacuuauua   7440
uuauuauuuu uuacaaaaua uauauaugga gaugcucccu ccccccuguga accccccagu   7500 gcccccgugg ggcugagucu gugggcccau ucggccaagc uggauucugu guaccuagua   7560
cacaggcaug acugggaucc cguguaccga guacacgacc cagguaugua ccaaguaggc   7620
acccuugggc gcacccacug gggccagggg ucgggggagu guugggagcc uccuccccac   7680
cccaccuccu ucacuucacu gcauuccaga uuggacaugu uccauagccu ugcuggggaa   7740
gggcccacug ccaacucccu cugccccagc cccacccuug gccaucuccc uuugggaacu   7800
agggggcugc uggugggaaa ugggagccag ggcagaugua ugcauuccuu uaugucccug   7860
uaaauguggg acuacaagaa gaggagcugc cugagguggua cuuucucuuc cugguaaucc   7920
ucuggcccag ccuuauggca gaauagaggu auuuuuuaggc uauuuuuugua auauggcuuc   7980 uggucaaaau cccuguguag cugaauuccc aagcccugca uuguacagcc ccccacuccc   8040
cucaccaccu aauaaaggaa uaguuaacac ucaaaaaaaa aaaaaaaaa a             8091
```

```
<210> SEQ ID NO 12
<211> LENGTH: 3870
<212> TYPE: RNA
```

-continued

```
<213> ORGANISM: homo sapien

<400> SEQUENCE: 12
ggcgcggagg cuggcccggg ggcccguggc cgccgccgcc gccgucgccc gaugucgccg      60
ccaccgccac cgccacccgu gcgggcgcug ccccugcugc ugcugcuagc ggggccgggg     120
gcugcagccc ccccuugccu ggacggaagc ccgugugcaa auggaggucg uugcacccag     180
cugcccuccc gggaggcugc cugccugugc ccgccuggcu gggugggguga gcggugucag     240 cuggaggacc ccgucacuc aggccccugu gcuggccgug gugucugcca gaguucagug       300
guggcuggca ccgcccgauu cucaugccgg ugccccgug gcuuccgagg cccugacugc       360
ucccugccag aucccugccu cagcagcccu ugugcccacg gugcccgcug cucagugggg      420
cccgauggac gcuuccucug cuccugccca ccuggcuacc agggccgcag cugccgaagc      480
gacguggaug agugccgggu gggugagccc ugccgccaug guggcaccug ccucaacaca      540
ccuggcuccu uccgcugcca guguccagcu ggcuacacag ggccacuaug ugagaacccc      600
gcggugcccu gugcgcccuc accaugccgu aacgggggca ccugcaggca gaguggcgac      660
cucacuuacg acugugccug ucuuccuggg uuugaggguc agaauuguga agugaacgug      720
gacgacuguc caggacaccg augucucaau gggggggacau gcguggaugg cgucaacacc      780
uauaacugcc agugcccucc ugaguggaca ggccaguucu gcacggagga cguggaugag      840
ugucagcugc agcccaacgc cugccacaau gggggguaccu gcuucaacac gcugggugggc      900 cacagcugcg ugugugucaa uggcuggaca ggcgagagcu gcagucagaa uaucgaugac      960
ugugccacag ccgugugcuu ccauggggcc accugccaug accgcguggc uucuuucuac     1020
ugugccugcc ccaugggcaa gacuggccuc cugugucacc uggaugacgc cugugucagc     1080
aaccccugcc acgaggaugc uaucugugac acaaauccgg ugaacggccg ggccauuugc     1140 accguccuc ccggcuucac ggguggggca ugugaccagg auguggacga gugcucuauc      1200
ggcgccaacc ccugcgagca cuugggcagg ugcgugaaca cgcagggcuc cuuccugugc      1260
cagugcgguc guggcuacac uggaccucgc ugugagaccg augucaacga gugucugucg      1320
gggcccugcc gaaaccaggc cacgugccuc gaccgcauag gccaguucac cguaucugu      1380 auggcaggcu ucacaggaac cuauugcgag guggacauug acgaguguca gaguagcccc     1440
ugugucaacg guggggucug caaggaccga gucaauggcu ucagcugcac cugcccucg      1500 ggcuucagcg gcuccacgug ucagcuggac guggacgaau gcgccagcac gcccugcagg     1560
aauggcgcca aaugcgugga ccagcccgau ggcuacgagu gccgcugugc cgagggcuuu     1620
gagggcacgc ugugugaucg caacguggac gacugcuccc cugacccaug ccaccauggu     1680
cgcugcgugg auggcaucgc cagcuucuca ugugccugug uccuggcua cacgggcaca      1740 cgcugcgaga gccaggugga cgaaugccgc agccagcccu gccgccaugg cggcaaaugc     1800
cuagaccugg uggacaagua cccucugccgc ugccuucug ggaccacagg ugugaacugc      1860
gaagugaaca uugacgacug ugccagcaac cccugcaccu uggagucug ccgugauggc       1920 aucaaccgcu acgacugugu cugccaaccu ggcuucacag ggcccuuug uaacguggag       1980 aucaaugagu gugcuuccag cccaugccgc gaggagggu ccugugugga uggggaaaau       2040
ggcuuccgcu gccucugccc gccuggcucc uugcccccac ucugccuccc cccgagccau     2100
cccugugccc augagcccug cagucacggc aucugcuaug augcaccugg cggguuccgc      2160
ugugugugug agccuggcug gagugccccc cgcugcagcc agagccuggc ccgagacgcc      2220 ugugagucc agccgugcag ggccgguggg acaugcagca gcgauggaau ggguuuccac      2280
```

-continued

```
ugcaccugcc cgccuggugu ccagggacgu cagugugaac uccucucccc cugcaccccg      2340
aaccccugug agcauggggg ccgcugcgag ucugccccug gccagcugcc ugucugcucc      2400
ugcccccagg gcuggcaaga cccaugcccug aacgguggcu cgugccaaga cggcgugggc     2460
uccuuuuccu gcuccugccu cccugguuuc gccggccac gaugcgcccg cgauguggau       2520
gagugccuga gcaaccccug cggcccgggc accguaccg accacguggc cuccuucacc       2580
ugcaccugcc cgccgggcua cggaggcuuc cacugcgaac aggaccugcc cgacugcagc      2640
cccagcuccu gcuucaaugg cgggaccugu guggacggcg ugaacucguu cagcugccug      2700
ugccgucccg gcuacacagg agcccacugc caacaugagg cagacccug ccucucgcgg       2760 cccugccuac acggggcgu cugcagcgcc gcccacccug gcuuccgcug caccugccuc       2820
gagagcuuca cgggcccgca gugccagacg cugguggauu ggugcagccg ccagccuugu      2880
caaaacgggg gucgcugcgu ccagacuggg gccuauugcc uuuguccccc uggauggagc      2940
ggacgccucu gugacauccg aagcuugccc ugcaggagg ccgcagccca gaucggggug       3000
cggcuggagc agcugugca ggcgggugg cagugugugg augaagacag cucccacuac        3060
ugcgugugcc cagagggccg uacgguagc cacugugagc aggaggugga ccccugcuug       3120
gcccagcccu gccagcaugg ggggaccugc cguggcuaua uggggggcua caugugugag      3180
ugucuuccug gcuacaaugg ugauaacugu gaggacgacg uggacgagug ugccucccag      3240
cccugccagc acgggggguuc augcauugac cucguggccc gcuaucucug cuccugucccc    3300 ccaggaacgc uggggggugcu cugcgagauu aaugaggaug acugcggccc aggcccaccg      3360
cuggacucag ggccccggug ccuacacaau ggcaccugcg uggaccuggu gggugguuuc      3420
cgcugcaccu gucccccagg auacacuggu uugcgcugcg aggcagacau caaugagugu      3480
cgcucaggug ccugccacgc ggcacacacc cgggacugcc ugcaggaccc aggcggaggu      3540
uucuguugcc uuugucaugc uggcuucuca gguccucgcu gucagacugu ccugucuccc      3600 ugcgagucccc agccaugcca gcauggaggc cagugccguc cuagcccggg uccugggggu     3660
gggcugaccu ucaccuguca cugugcccag ccguucuggg guccgcguug cgagcggguu      3720
gcgcgcuccu gccgggagcu gcagugcccg gugggcgucc caugccagca gacgccccgc      3780
gggccgcgcu gcgccugccc cccagggguug ucgggacccu ccugccgcag cuucccgggg     3840
ucgccgccgg gggccagcaa cgccagcugc                                      3870

<210> SEQ ID NO 13
<211> LENGTH: 8680
<212> TYPE: DNA
<213> ORGANISM: homo sapien

<400> SEQUENCE: 13
cttcggcgaa gttggcggcg cggaggctgg cccgggacgc gcccggagcc cagggaagga        60
gggaggaggg gagggtcgcg gccggccgcc atggggccgg gggcccgtgg ccgccgccgc       120
cgccgtcgcc cgatgtcgcc gccaccgcca ccgccacccg tgcgggcgct gcccctgctg       180
ctgctgctag cggggccggg ggctgcagcc ccccccttgcc tggacggaag cccgtgtgca      240
aatggaggtc gttgcaccca gctgccctcc cgggaggctg cctgcctgtg cccgcctggc       300
tgggtgggtg agcggtgtca gctggaggac ccctgtcact caggcccctg tgctggccgt       360
ggtgtctgcc agagttcagt ggtggctggc accgcccgat tctcatgccg gtgccccgt        420 ggcttccgag gccctgactg ctccctgcca gatccctgcc tcagcagccc ttgtgcccac      480
```

-continued

```
ggtgcccgct gctcagtggg gcccgatgga cgcttcctct gctcctgccc acctggctac    540
cagggccgca gctgccgaag cgacgtggat gagtgccggg tgggtgagcc ctgccgccat    600
ggtggcacct gcctcaacac acctggctcc ttccgctgcc agtgtccagc tggctacaca    660
gggccactat gtgagaaccc cgcggtgccc tgtgcaccct caccatgccg taacgggggc    720
acctgcaggc agagtggcga cctcacttac gactgtgcct gtcttcctgg gtttgagggt    780
cagaattgtg aagtgaacgt ggacgactgt ccaggacacc gatgtctcaa tggggggaca    840
tgcgtggatg gcgtcaacac ctataactgc cagtgccctc ctgagtggac aggccagttc    900
tgcacggagg acgtggatga gtgtcagctg cagcccaacg cctgccacaa tgggggtacc    960
tgcttcaaca cgctgggtgg ccacagctgc gtgtgtgtca atggctggac aggcgagagc   1020
tgcagtcaga atatcgatga ctgtgccaca gccgtgtgct tccatggggc cacctgccat   1080
gaccgcgtgg cttcttttcta ctgtgcctgc cccatgggca agactggcct cctgtgtcac   1140
ctggatgacg cctgtgtcag caaccccctgc cacgaggatg ctatctgtga cacaaatccg   1200
gtgaacggcc gggccatttg cacctgtcct cccggcttca cgggtggggc atgtgaccag   1260
gatgtggacg agtgctctat cggcgccaac ccctgcgagc acttgggcag gtgcgtgaac   1320
acgcagggct ccttcctgtg ccagtgcggt cgtggctaca ctggacctcg ctgtgagacc   1380
gatgtcaacg agtgtctgtc ggggccctgc cgaaaccagg ccacgtgcct cgaccgcata   1440
ggccagttca cctgtatctg tatggcaggc ttcacaggaa cctattgcga ggtggacatt   1500
gacgagtgtc agagtagccc ctgtgtcaac ggtgggggtct gcaaggaccg agtcaatggc   1560
ttcagctgca cctgcccctc gggcttcagc ggctccacgt gtcagctgga cgtggacgaa   1620
tgcgccagca cgcccctgcag gaatggcgcc aaatgcgtgg accagcccga tggctacgag   1680
tgccgctgtg ccgagggctt tgagggcacg ctgtgtgatc gcaacgtgga cgactgctcc   1740
cctgacccat gccaccatgg tcgctgcgtg gatggcatcg ccagcttctc atgtgcctgt   1800
gctcctggct acacgggcac acgctgcgag agccaggtgg acgaatgccg cagccagccc   1860
tgccgccatg gcggcaaatg cctagacctg gtggacaagt acctctgccg ctgcccttct   1920
gggaccacag gtgtgaactg cgaagtgaac attgacgact gtgccagcaa cccctgcacc   1980
tttggagtct gccgtgatgg catcaaccgc tacgactgtg tctgccaacc tggcttcaca   2040 gggcccttt gtaacgtgga gatcaatgag tgtgcttcca gcccatgcgg cgagggaggt   2100
tcctgtgtgg atgggggaaa tggcttccgc tgcctctgcc cgcctggctc cttgcccca   2160 ctctgcctcc ccccgagcca tccctgtgcc catgagccct gcagtcacgg catctgctat   2220
gatgcacctg gcgggttccg ctgtgtgtgt gagcctggct ggagtggccc ccgctgcagc   2280
cagagcctgg cccgagacgc ctgtgagtcc cagccgtgca gggccggtgg acatgcagc   2340 agcgatggaa tgggtttcca ctgcacctgc ccgcctggtg tccagggacg tcagtgtgaa   2400
ctcctctccc cctgcacccc gaacccctgt gagcatgggg gccgctgcga gtctgccct   2460 ggccagctgc ctgtctgctc ctgcccccag ggctggcaag gcccacgatg ccagcaggat   2520
gtggacgagt gtgctggccc cgcaccctgt ggccctcatg gtatctgcac caacctggca   2580
gggagtttca gctgcacctg ccatggaggg tacactggcc cttcctgcga tcaggacatc   2640
aatgactgtg accccaaccc atgcctgaac ggtggctcgt gccaagacgg cgtgggctcc   2700
ttttcctgct cctgcctccc tggtttcgcc ggcccacgat gcgcccgcga gtgtggatgag   2760 tgcctgagca cccctgcgg cccgggcacc tgtaccgacc acgtggcctc cttcacctgc   2820
acctgcccgc caggctacgg aggcttccac tgcgaacagg acctgccga ctgcagcccc   2880
```

```
agctcctgct tcaatggcgg gacctgtgtg gacggcgtga actcgttcag ctgcctgtgc      2940
cgtcccggct acacaggagc ccactgccaa catgaggcag acccctgcct ctcgcggccc      3000
tgcctacacg ggggcgtctg cagcgccgcc caccctggct tccgctgcac ctgcctcgag      3060
agcttcacgg gcccgcagtg ccagacgctg gtggattggt gcagccgcca gccttgtcaa      3120
aacgggggtc gctgcgtcca gactggggcc tattgccttt gtccccctgg atggagcgga      3180
cgcctctgtg acatccgaag cttgccctgc agggaggccg cagcccagat cggggtgcgg      3240
ctggagcagc tgtgtcaggc gggtgggcag tgtgtggatg aagacagctc ccactactgc      3300
gtgtgcccag agggccgtac tggtagccac tgtgagcagg aggtggaccc ctgcttggcc      3360
cagccctgcc agcatggggg gacctgccgt ggctatatgg ggggctacat gtgtgagtgt      3420
cttcctggct acaatggtga taactgtgag gacgacgtgg acgagtgtgc ctcccagccc      3480
tgccagcacg ggggttcatg cattgacctc gtggcccgct atctctgctc ctgtccccca      3540
ggaacgctgg gggtgctctg cgagattaat gaggatgact gcggcccagg cccaccgctg      3600
gactcagggc cccggtgcct acacaatggc acctgcgtgg acctggtggg tggtttccgc      3660
tgcacctgtc ccccaggata cactggtttg cgctgcgagg cagacatcaa tgagtgtcgc      3720
tcaggtgcct gccacgcggc acacacccgg gactgcctgc aggacccagg cggaggtttc      3780
cgttgccttt gtcatgctgg cttctcaggt cctcgctgtc agactgtcct gtctccctgc      3840
gagtcccagc catgccagca tggaggccag tgccgtccta gcccgggtcc tgggggtggg      3900
ctgaccttca cctgtcactg tgcccagccg ttctgggggtc cgcgttgcga gcgggtggcg      3960
cgctcctgcc gggagctgca gtgcccggtg ggcgtcccat gccagcagac gccccgcggg      4020
ccgcgctgcg cctgcccccc agggttgtcg ggaccctcct gccgcagctt cccggggtcg      4080
ccgccggggg ccagcaacgc cagctgcgcg gccgcccccc gtctccacgg gggctcctgc      4140
cgccccgcgc cgctcgcgcc cttcttccgc tgcgcttgcg cgcagggctg gaccgggccg      4200
cgctgcgagg cgcccgccgc ggcacccgag gtctcggagg agccgcggtg cccgcgcgcc      4260
gcctgccagg ccaagcgcgg ggaccagcgc tgcgaccgcg agtgcaacag cccaggctgc      4320
ggctgggacg gcggcgactg ctcgctgagc gtgggcgacc cctggcggca atgcgaggcg      4380
ctgcagtgct ggcgcctctt caacaacagc cgctgcgacc ccgcctgcag ctcgcccgcc      4440
tgcctctacg acaacttcga ctgccacgcc ggtggccgcg agcgcacttg caacccggtg      4500
tacgagaagt actgcgccga ccactttgcc gacggccgct gcgaccaggg ctgcaacacg      4560
gaggagtgcg gctgggatgg gctggattgt gccagcgagg tgccggccct gctggccgc       4620 ggcgtgctgg tgctcacagt gctgctgccg ccagaggagc tactgcgttc cagcgccgac      4680
tttctgcagc ggctcagcgc catcctgcgc acctcgctgc gcttccgcct ggacgcgcac      4740
ggccaggcca tggtcttccc ttaccaccgg cctagtcctg ctccgaacc ccgggcccgt       4800 cgggagctgg cccccgaggt gatcggctcg gtagtaatgc tggagattga caaccggctc      4860
tgcctgcagt cgcctgagaa tgatcactgc ttccccgatg cccagagcgc cgctgactac      4920 ctggagcgt tgtcagcggt ggagcgcctg gacttcccgt acccactgcg ggacgtgcgg       4980
ggggagccgc tggagcctcc agaacccagc gtccgctgc tgccactgct agtggcgggc        5040
gctgtcttgc tgctggtcat tctcgtcctg ggtgtcatgg tggcccggcg caagcgcgag      5100
cacagcaccc tctggttccc tgagggcttc tcactgcaca aggacgtggc ctctggtcac      5160
aagggccggc gggaacccgt gggccaggac gcgctgggca tgaagaacat ggccaagggt      5220
```

-continued

```
gagagcctga tggggggaggt ggccacagac tggatggaca cagagtgccc agaggccaag      5280
cggctaaagg tagaggagcc aggcatgggg gctgaggagg ctgtggattg ccgtcagtgg      5340
actcaacacc atctggttgc tgctgacatc cgcgtggcac cagccatggc actgacacca      5400
ccacagggcg acgcagatgc tgatggcatg gatgtcaatg tgcgtggccc agatggcttc      5460
accccgctaa tgctggcttc cttctgtggg ggggctctgg agccaatgcc aactgaagag      5520
gatgaggcag atgacacatc agctagcatc atctccgacc tgatctgcca gggggctcag      5580 cttgggcac ggactgaccg tactggcgag actgctttgc acctggctgc ccgttatgcc        5640
cgtgctgatg cagccaagcg gctgctggat gctggggcag acaccaatgc ccaggaccac      5700
tcaggccgca ctcccctgca cacagctgtc acagccgatg cccagggtgt cttccagatt      5760
ctcatccgaa accgctctac agacttggat gcccgcatgg cagatggctc aacggcactg      5820
atcctggcgg cccgcctggc agtagagggc atggtggaag agctcatcgc cagccatgct      5880
gatgtcaatg ctgtggatga gcttgggaaa tcagccttac actgggctgc ggctgtgaac      5940
aacgtggaag ccactttggc cctgctcaaa aatggagcca ataaggacat gcaggatagc      6000
aaggaggaga cccccctatt cctggccgcc cgcgagggca gctatgaggc tgccaagctg      6060
ctgttggacc actttgccaa ccgtgagatc accgaccacc tggacaggct gccgcgggac      6120
gtagcccagg agagactgca ccaggacatc gtgcgcttgc tggatcaacc cagtgggccc      6180
cgcagccccc ccggtcccca cggcctgggg cctctgctct gtcctccagg ggccttcctc      6240
cctggcctca aagcggcaca gtcgggggtcc aagaagagca ggaggccccc cgggaaggcg      6300
gggctggggc cgcagggggcc ccggggggcgg ggcaagaagc tgacgctggc ctgcccgggc      6360
cccctggctg acagctcggt cacgctgtcg cccgtggact cgctggactc cccgcggcct      6420
ttcggtgggc cccctgcttc ccctggtggc ttccccttg aggggcccta tgcagctgcc       6480
actgccactg cagtgtctct ggcacagctt ggtggcccag gccggggcggg tctagggcgc      6540 cagcccctg gaggatgtgt actcagcctg ggcctgctga accctgtggc tgtgcccctc       6600
gattgggccc ggctgccccc acctgcccct ccaggcccct cgttcctgct gccactggcg      6660
ccgggacccc agctgctcaa cccagggacc cccgtctccc cgcaggagcg gcccccgcct      6720
tacctggcag tcccaggaca tggcgaggag taccggcgg ctggggcaca cagcagcccc        6780
ccaaaggccc gcttcctgcg ggttcccagt gagcaccctt acctgacccc atccccgaa       6840 tcccctgagc actgggccag cccctcacct ccctccctct cagactggtc cgaatccacg      6900
cctagcccag ccactgccac tggggccatg gccaccacca ctggggcact gcctgcccag      6960
ccacttccct tgtctgttcc cagctccctt gctcaggccc agacccagct ggggccccag      7020
ccggaagtta ccccaagag gcaagtgttg gcctgagacg ctcgtcagtt cttagatctt        7080
gggggcctaa agagacccccc gtcctgcctc ctttctttct ctgtctcttc cttcctttta     7140 gtcttttca tcctcttctc tttccaccaa ccctcctgca tccttgcctt gcagcgtgac       7200
cgagataggt catcagccca gggcttcagt cttcctttat ttataatggg tgggggctac      7260
cacccaccct ctcagtcttg tgaagagtct gggacctcct tcttccccac ttctctcttc      7320
cctcattcct ttctctctcc ttctggcctc tcatttcctt acactctgac atgaatgaat      7380
tattattatt tttattttc tttttttttt tacattttgt atagaaacaa attcatttaa       7440
acaaacttat tattattatt ttttacaaaa tatatatatg gagatgctcc ctccccctgt      7500 gaaccccca gtgcccccgt ggggctgagt ctgtgggccc attcggccaa gctggattct       7560
gtgtacctag tacacaggca tgactgggat cccgtgtacc gagtacacga cccaggtatg      7620
```

-continued

```
taccaagtag gcacccttgg gcgcacccac tggggccagg ggtcggggga gtgttgggag      7680
cctcctcccc accccacctc cctcacttca ctgcattcca gatgggacat gttccatagc      7740
cttgctgggg aagggcccac tgccaactcc ctctgcccca gccccaccct tggccatctc      7800
cctttgggaa ctaggggggct gctggtggga aatgggagcc agggcagatg tatgcattcc     7860
tttgtgtccc tgtaaatgtg ggactacaag aagaggagct gcctgagtgg tactttctct      7920
tcctggtaat cctctggccc agcctcatgg cagaatagag gtattttttag gctatttttg      7980 taatatggct tctggtcaaa atccctgtgt agctgaattc ccaagccctg cattgtacag      8040
ccccccactc ccctcaccac ctaataaagg aatagttaac actcagtgtt gttggtctgt      8100
gtctaggtaa ggtgggggagt ggtggcagtg ggacttctat ctccccccacc cagggctaac    8160 ttgagctccc atcttggggt aaatacattt gacttgccag tctacttatg cttcctcttt      8220
tggcagatga ctaccgattg gattagtggt tgtcacctga cttaagctga gccaatcaga      8280
ttcttttgct cgagaacttt ctttaatgga gaggctaaga aagttgtcag ttggtggagc      8340
tcttaaggtc acaatcagat ttagaaatat cagtggccaa ttcgaggtgg tgggcaaaga      8400
gacaagcaaa cagggcagaa gaatgaagct aatattcagg gagaatcaga aatgagagct      8460
caaatggctc cttgagggct gggggggtta tctcggctcc cagtgcagtt atcaattcca       8520
gttaattgag tgttcattcc attgagatca acaggtattt attaattgct ttctaagtat       8580
ctgatcatgg ttctgcatga atttcacttt tacttcatgc tcctatgggt tttggagata      8640
accttggacc catgtaataa atacttcttt acttgtgcca                            8680
```

```
<210> SEQ ID NO 14
<211> LENGTH: 8666
<212> TYPE: DNA
<213> ORGANISM: homo sapien

<400> SEQUENCE: 14
gcggcgcgga ggctggcccg ggacgcgccc ggagcccagg gaaggaggga ggaggggagg        60
gtcgcggccg gccgccatgg ggccgggggc ccgtggccgc cgccgccgcc gtcgcccgat       120
gtcgccgcca ccgccaccgc cacccgtgcg ggcgctgccc ctgctgctgc tgctagcggg       180 gccggggggct gcagcccccc cttgcctgga cggaagcccg tgtgcaaatg gaggtcgttg       240
cacccagctg ccctcccggg aggctgcctg cctgtgcccg cctggctggg tgggtgagcg       300
gtgtcagctg gaggacccct gtcactcagg ccctgtgct ggccgtggtg tctgccagag        360
ttcagtggtg gctggcaccg cccgattctc atgccggtgc ccccgtggct ccgaggccc        420 tgactgctcc ctgccagatc cctgcctcag cagcccttgt gcccacggtg cccgctgctc       480
agtggggccc gatggacgct tcctctgctc ctgcccacct ggctaccagg gccgcagctg       540
ccgaagcgac gtggatgagt gccgggtggg tgagccctgc cgccatggtg gcacctgcct       600
caacacacct ggctccttcc gctgccagt tccagctggc tacacagggc cactatgtga        660 gaacccccgcg gtgccctgtg caccctcacc atgccgtaac gggggcacct gcaggcagag      720
tggcgacctc acttacgact gtgcctgtct tcctgggtttt gagggtcaga attgtgaagt       780
gaacgtggac gactgtccag acaccgatgt ctctcaatggg gggacatgcg tggatggcgt      840
caacacctat aactgccagt gccctcctga gtggacaggc cagttctgca cggaggacgt       900
ggatgagtgt cagctgcagc ccaacgcctg ccacaatggg ggtacctgct tcaacacgct       960
gggtggccac agctgcgtgt gtgtcaatgg ctggacaggc gagagctgca gtcagaatat      1020
```

-continued

```
cgatgactgt gccacagccg tgtgcttcca tggggccacc tgccatgacc gcgtggcttc   1080
tttctactgt gcctgcccca tgggcaagac tggcctcctg tgtcacctgg atgacgcctg   1140
tgtcagcaac ccctgccacg aggatgctat ctgtgacaca aatccggtga acggccgggc   1200
catttgcacc tgtcctcccg gcttcacggg tggggcatgt gaccaggatg tggacgagtg   1260
ctctatcggc gccaacccct gcgagcactt gggcaggtgc gtgaacacgc agggctcctt   1320
cctgtgccag tgcggtcgtg gctacactgg acctcgctgt gagaccgatg tcaacgagtg   1380
tctgtcgggg ccctgccgaa accaggccac gtgcctcgac cgcataggcc agttcacctg   1440
tatctgtatg gcaggcttca caggaaccta ttgcgaggtg gacattgacg agtgtcagag   1500
tagcccctgt gtcaacggtg gggtctgcaa ggaccgagtc aatggcttca gctgcacctg   1560
cccctcgggc ttcagcggct ccacgtgtca gctggacgtg gacgaatgcg ccagcacgcc   1620
ctgcaggaat ggcgccaaat gcgtggacca gcccgatggc tacgagtgcc gctgtgccga   1680
gggctttgag ggcacgctgt gtgatcgcaa cgtggacgac tgctcccctg acccatgcca   1740
ccatggtcgc tgcgtggatg gcatcgccag cttctcatgt gcctgtgctc ctggctacac   1800
gggcacacgc tgcgagagcc aggtggacga atgccgcagc cagccctgcc gccatggcgg   1860
caaatgccta gacctggtgg acaagtacct ctgccgctgc ccttctggga ccacaggtgt   1920
gaactgcgaa gtgaacattg acgactgtgc cagcaacccc tgcacctttg gagtctgccg   1980
tgatggcatc aaccgctacg actgtgtctg ccaacctggc ttcacagggc ccctttgtaa   2040
cgtggagatc aatgagtgtg cttccagccc atgcggcgag ggaggttcct gtgtggatgg   2100
ggaaaatggc ttccgctgcc tctgcccgcc tggctccttg cccccactct gcctcccccc   2160
gagccatccc tgtgcccatg agccctgcag tcacggcatc tgctatgatg cacctggcgg   2220
gttccgctgt gtgtgtgagc ctggctggag tggcccccgc tgcagccaga gcctggcccg   2280
agacgcctgt gagtcccagc cgtgcagggc cggtgggaca tgcagcagcg atggaatggg   2340
tttccactgc acctgcccgc ctggtgtcca gggacgtcag tgtgaactcc tctcccctg   2400 caccccgaac ccctgtgagc atgggggccg ctgcgagtct gcccctggcc agctgcctgt   2460
ctgctcctgc ccccagggct ggcaaggccc acgatgccag caggatgtgg acagtgtgc   2520 tggccccgca ccctgtggcc ctcatggtat ctgcaccaac ctggcaggga gtttcagctg   2580
cacctgccat ggagggtaca ctggcccctc ctgcgatcag gacatcaatg actgtgaccc   2640
caacccatgc ctgaacggtg gctcgtgcca agacggcgtg ggctcctttt cctgctcctg   2700
cctccctggt ttcgccggcc cacgatgcgc ccgcgatgtg gatgagtgcc tgagcaaccc   2760
ctgcggcccg ggcacctgta ccgaccacgt ggcctccttc acctgcacct gcccgccagg   2820
ctacggaggc ttccactgcg aacaggacct gcccgactgc agcccagct cctgcttcaa   2880 tggcgggacc tgtgtggacg gcgtgaactc gttcagctgc ctgtgccgtc ccggctacac   2940
aggagcccac tgccaacatg aggcagaccc ctgcctctcg cggccctgcc tacacggggg   3000
cgtctgcagc gccgcccacc ctggcttccg ctgcacctgc ctcgagagct tcacgggccc   3060
gcagtgccag acgctggtgg attggtgcag ccgccagcct tgtcaaaacg ggggtcgctg   3120
cgtccagact ggggcctatt gcctttgtcc cctggatgg agcggacgcc tctgtgacat   3180
ccgaagcttg ccctgcaggg aggccgcagc ccagatcggg gtgcggctgg agcagctgtg   3240
tcaggcgggt gggcagtgtg tggatgaaga cagctcccac tactgcgtgt gcccagaggg   3300
ccgtactggt agccactgtg agcaggaggt ggacccctgc ttggcccagc cctgccagca   3360 tgggggggacc tgccgtggct atatgggggg ctacatgtgt gagtgtcttc ctggctacaa   3420
```

```
tggtgataac tgtgaggacg acgtggacga gtgtgcctcc cagccctgcc agcacggggg   3480
ttcatgcatt gacctcgtgg cccgctatct ctgctcctgt cccccaggaa cgctgggggt   3540
gctctgcgag attaatgagg atgactgcgg cccaggccca ccgctggact cagggccccg   3600
gtgcctacac aatggcacct gcgtggacct ggtgggtggt ttccgctgca cctgtccccc   3660
aggatacact ggtttgcgct gcgaggcaga catcaatgag tgtcgctcag gtgcctgcca   3720
cgcggcacac acccgggact gcctgcagga cccaggcgga ggtttccgtt gcctttgtca   3780
tgctggcttc tcaggtcctc gctgtcagac tgtcctgtct ccctgcgagt cccagccatg   3840
ccagcatgga ggccagtgcc gtcctagccc gggtcctggg ggtgggctga ccttcacctg   3900
tcactgtgcc cagccgttct ggggtccgcg ttgcgagcgg gtggcgcgct cctgccggga   3960
gctgcagtgc ccggtggggcg tcccatgcca gcagacgccc cgcgggccgc gctgcgcctg   4020 cccccaggg ttgtcgggac cctcctgccg cagcttcccg gggtcgccgc cggggggccag   4080 caacgccagc tgcgcggccg ccccctgtct ccacgggggc tcctgccgcc ccgcgccgct   4140
cgcgcccttc ttccgctgcg cttgcgcgca gggctggacc gggccgcgct gcgaggcgcc   4200
cgccgcggca cccgaggtct cggaggagcc gcggtgcccg cgcgccgcct gccaggccaa   4260
gcgcggggac cagcgctgcg accgcgagtg caacagccca ggctgcggct gggacggcgg   4320
cgactgctcg ctgagcgtgg gcgacccctg cgggcaatgc gaggcgctgc agtgctggcg   4380
cctcttcaac aacagccgct gcgaccccgc ctgcagctcg cccgcctgcc tctacgacaa   4440
cttcgactgc cacgccggtg gccgcgagcg cacttgcaac ccggtgtacg agaagtactg   4500
cgccgaccac tttgccgacg gccgctgcga ccagggctgc aacacggagg agtgcggctg   4560
ggatgggctg gattgtgcca gcgaggtgcc ggccctgctg gccgcgcgcg tgctggtgct   4620
cacagtgctg ctgccgccag aggagctact gcgttccagc gccgactttc tgcagcggct   4680
cagcgccatc ctgcgcacct cgctgcgctt ccgcctggac gcgcacggcc aggccatggt   4740
cttcccttac caccggccta gtcctggctc cgaaccccgg gcccgtcggg agctggcccc   4800
cgaggtgatc ggctcggtag taatgctgga gattgacaac cggctctgcc tgcagtcgcc   4860
tgagaatgat cactgcttcc ccgatgccca gagcgccgct gactacctgg gagcgttgtc   4920
agcggtggag cgcctggact ccccgtaccc actgcgggac gtgcggggg agccgctgga   4980 gcctccagaa cccagcgtcc cgctgctgcc actgctagtg gcgggcgctg tcttgctgct   5040
ggtcattctc gtcctgggtg tcatggtggc ccggcgcaag cgcgagcaca gcaccctctg   5100
gttccctgag ggcttctcac tgcacaagga cgtggcctct ggtcacaagg ccggcggga   5160 acccgtgggc caggacgcgc tgggcatgaa gaacatggcc aagggtgaga gcctgatggg   5220 ggaggtggc acagactgga tggacacaga gtgcccagag gccaagcggc taaaggtaga   5280
ggagccaggc atggggggctg aggaggctgt ggattgccgt cagtggactc aacaccatct   5340
ggttgctgct gacatccgcg tggcaccagc catggcactg acaccaccac agggcgacgc   5400
agatgctgat ggcatggatg tcaatgtgcg tggcccagat ggcttcaccc cgctaatgct   5460
ggcttccttc tgtgggggg ctctggagcc aatgccaact gaagaggatg aggcagatga   5520
cacatcagct agcatcatct ccgacctgat ctgccagggg gctcagcttg gggcacggac   5580
tgaccgtact ggcgagactg ctttgcacct ggctgcccgt tatgcccgtg ctgatgcagc   5640
caagcggctg ctggatgctg gggcagacac caatgcccag gaccactcag gccgcactcc   5700
cctgcacaca gctgtcacag ccgatgccca gggtgtcttc cagattctca tccgaaaccg   5760
```

-continued

```
ctctacagac ttggatgccc gcatggcaga tggctcaacg gcactgatcc tggcggcccg    5820
cctggcagta gagggcatgg tggaagagct catcgccagc catgctgatg tcaatgctgt    5880
ggatgagctt gggaaatcag ccttacactg ggctgcggct gtgaacaacg tggaagccac    5940
tttggccctg ctcaaaaatg gagccaataa ggacatgcag gatagcaagg aggagacccc    6000
cctattcctg gccgcccgcg agggcagcta tgaggctgcc aagctgctgt tggaccactt    6060
tgccaaccgt gagatcaccg accacctgga caggctgccg cgggacgtag cccaggagag    6120
actgcaccag gacatcgtgc gcttgctgga tcaacccagt gggccccgca gcccccccgg    6180
tccccacggc ctggggcctc tgctctgtcc tccaggggcc ttcctccctg gcctcaaagc    6240
ggcacagtcg gggtccaaga agagcaggag gcccccgggg aaggcggggc tggggccgca    6300 ggggcccecgg gggcgggggca agaagctgac gctggcctgc ccgggccccc tggctgacag    6360
ctcggtcacg ctgtcgcccg tggactcgct ggactccccg cggcctttcg gtgggccccc    6420
tgcttcccct ggtggcttcc cccttgaggg gccctatgca gctgccactg ccactgcagt    6480
gtctctggca cagcttggtg gcccaggccg ggcgggtcta gggcgccagc ccctggagg     6540 atgtgtactc agcctgggcc tgctgaaccc tgtggctgtg cccctcgatt gggcccggct    6600
gcccccacct gcccctccag gcccctcgtt cctgctgcca ctggcgccgg accccagct     6660 gctcaaccca gggaccccg tctcccgcca ggagcggccc ccgccttacc tggcagtccc    6720
aggacatggc gaggagtacc cggcggctgg ggcacacagc agcccccccaa aggcccgctt    6780 cctgcgggtt cccagtgagc acccttacct gaccccatcc cccgaatccc ctgagcactg    6840
ggccagcccc tcacctccct ccctctcaga ctggtccgaa tccacgccta gcccagccac    6900
tgccactggg gccatggcca ccaccactgg ggcactgcct gcccagccac ttcccttgtc    6960
tgttcccagc tcccttgctc aggccagac ccagctgggg cccagccgg aagttacccc     7020 caagaggcaa gtgttggcct gagacgctcg tcagttctta gatcttgggg gcctaaagag    7080 accccgtcc tgcctccttt ctttctctgt ctcttccttc cttttagtct ttttcatcct     7140
cttctctttc caccaaccct cctgcatcct tgccttgcag cgtgaccgag ataggtcatc    7200
agcccagggc ttcagtcttc ctttatttat aatgggtggg ggctaccacc caccctctca    7260
gtcttgtgaa gagtctggga cctccttctt ccccacttct ctcttccctc attcctttct    7320
ctctccttct ggcctctcat ttccttacac tctgacatga atgaattatt attattttta    7380
tttttctttt tttttttaca ttttgtatag aaacaaattc atttaaacaa acttattatt    7440 attattttt acaaaatata tatatggaga tgctccctcc ccctgtgaac cccccagtgc     7500
ccccgtgggg ctgagtctgt gggcccattc ggccaagctg gattctgtgt acctagtaca    7560
caggcatgac tgggatcccg tgtaccgagt acacgaccca ggtatgtacc aagtaggcac    7620
ccttgggcgc acccactggg gccaggggtc gggggagtgt tgggagcctc ctccccaccc    7680
cacctccctc acttcactgc attccagatg ggacatgttc catagccttg ctggggaagg    7740
gcccactgcc aactccctct gccccagccc caccctgc catctcctt tgggaactag       7800 ggggctgctg gtgggaaatg ggagccaggg cagatgtatg cattcctttg tgtccctgta    7860
aatgtgggac tacaagaaga ggagctgcct gagtggtact ttctcttcct ggtaatcctc    7920
tggcccagcc tcatggcaga atagaggtat ttttaggcta tttttgtaat atggcttctg    7980
gtcaaaatcc ctgtgtagct gaattcccaa gccctgcatt gtacagcccc ccactcccct    8040
caccacctaa taaaggaata gttaacactc agtgttgttg gtctgtgtct aggtaaggtg    8100
gggagtggtg gcagtgggac ttctatctcc cccacccagg gctaacttga gctcccatct    8160
```

```
tggggtaaat acatttgact tgccagtcta cttatgcttc ctcttttggc agatgactac      8220
cgattggatt agtggttgtc acctgactta agctgagcca atcagattct tttgctcgag      8280
aactttcttt aatggagagg ctaagaaagt tgtcagttgg tggagctctt aaggtcacaa      8340
tcagatttag aaatatcagt ggccaattcg aggtggtggg caaagagaca agcaaacagg      8400
gcagaagaat gaagctaata ttcagggaga atcagaaatg agagctcaaa tggctccttg      8460
agggctgggg gggttatctc ggctcccagt gcagttatca attccagtta attgagtgtt      8520
cattccattg agatcaacag gtatttatta attgctttct aagtatctga tcatggttct      8580
gcatgaattt cacttttact tcatgctcct atgggttttg gagataacct tggacccatg      8640
taataaatac ttctttactt gtgcca                                          8666

<210> SEQ ID NO 15
<211> LENGTH: 3858
<212> TYPE: DNA
<213> ORGANISM: homo sapien

<400> SEQUENCE: 15
gggccggggg cccgtggccg ccgccgccgc cgtcgcccga tgtcgccgcc accgccaccg        60
ccacccgtgc gggcgctgcc cctgctgctg ctgctagcgg ggccgggggc tgcagccccc       120
ccttgcctgg acggaagccc gtgtgcaaat ggaggtcgtt gcacccagct gccctcccgg       180
gaggctgcct gcctgtgccc gcctggctgg gtgggtgagc ggtgtcagct ggaggacccc       240
tgtcactcag gcccctgtgc tggccgtggt gtctgccaga gttcagtggt ggctggcacc       300
gcccgattct catgccggtg cccccgtggc ttccgaggcc ctgactgctc cctgccagat       360
ccctgcctca gcagcccttg tgcccacggt gcccgctgct cagtggggcc cgatggacgc       420
ttcctctgct cctgcccacc tggctaccag ggccgcagct gccgaagcga cgtggatgag       480
tgccgggtgg gtgagccctg ccgccatggt ggcacctgcc tcaacacacc tggctccttc       540
cgctgccagt gtccagctgg ctacacaggg ccactatgtg agaaccccgc ggtgccctgt       600
gcaccctcac catgccgtaa cggggggcacc tgcaggcaga gtggcgacct cacttacgac       660
tgtgcctgtc ttcctgggtt tgagggtcag aattgtgaag tgaacgtgga cgactgtcca       720
ggacaccgat gtctcaatgg ggggacatgc gtggatggcg tcaacaccta taactgccag       780
tgccctcctg agtggacagg ccagttctgc acggaggacg tggatgagtg tcagctgcag       840
cccaacgcct gccacaatgg gggtacctgc ttcaacacgc tgggtggcca cagctgcgtg       900
tgtgtcaatg gctggacagg cgagagctgc agtcagaata tcgatgactg tgccacagcc       960
gtgtgcttcc atggggccac ctgccatgac cgcgtggctt ctttctactg tgcctgcccc      1020
atgggcaaga ctggcctcct gtgtcacctg gatgacgcct gtgtcagcaa ccccgccac      1080 gaggatgcta tctgtgacac aaatccggtg aacggccggg ccatttgcac ctgtcctccc      1140
ggcttcacgg gtgggcatg tgaccaggat gtggacgagt gctctatcgg cgccaacccc      1200
tgcgagcact gggcaggtg cgtgaacacg cagggctcct tcctgtgcca gtgcggtcgt      1260
ggctacactg gacctcgctg tgagaccgat gtcaacgagt gtctgtcggg gccctgccga      1320
aaccaggcca cgtgcctcga ccgcataggc cagttcacct gtatctgtat ggcaggcttc      1380
acaggaacct attgcgaggt ggacattgac gagtgtcaga gtagcccctg tgtcaacggt      1440
ggggtctgca aggaccgagt caatggcttc agctgcacct gcccctcggg cttcagcggc      1500
tccacgtgtc agctggacgt ggacgaatgc gccagcacgc cctgcaggaa tggcgccaaa      1560
```

```
tgcgtggacc agcccgatgg ctacgagtgc cgctgtgccg agggctttga gggcacgctg      1620
tgtgatcgca acgtggacga ctgctcccct gacccatgcc accatggtcg ctgcgtggat      1680
ggcatcgcca gcttctcatg tgcctgtgct cctggctaca cgggcacacg ctgcgagagc      1740
caggtggacg aatgccgcag ccagccctgc cgccatggcg gcaaatgcct agacctggtg      1800
gacaagtacc tctgccgctg cccttctggg accacaggtg tgaactgcga agtgaacatt      1860
gacgactgtg ccagcaaccc ctgcaccttt ggagtctgcc gtgatggcat caaccgctac      1920
gactgtgtct gccaacctgg cttcacaggg ccccctttgta acgtggagat caatgagtgt      1980
gcttccagcc catgcggcga gggaggttcc tgtgtggatg gggaaaatgg cttccgctgc      2040
ctctgcccgc ctggctcctt gcccccactc tgcctccccc cgagccatcc ctgtgcccat      2100
gagccctgca gtcacggcat ctgctatgat gcacctggcg ggttccgctg tgtgtgtgag      2160
cctggctgga gtggcccccg ctgcagccag agcctggccc gagacgcctg tgagtcccag      2220
ccgtgcaggg ccggtgggac atgcagcagc gatggaatgg gtttccactg cacctgcccg      2280
cctggtgtcc agggacgtca gtgtgaactc ctctcccccct gcaccccgaa ccctgtgag      2340 catgggggcc gctgcgagtc tgcccctggc cagctgcctg tctgctcctg ccccagggc      2400 tggcaagacc catgcctgaa cggtggctcg tgccaagacg gcgtgggctc cttttcctgc      2460
tcctgcctcc ctggtttcgc cggcccacga tgcgcccgcg atgtggatga gtgcctgagc      2520
aacccctgcg gcccgggcac ctgtaccgac cacgtggcct ccttcacctg cacctgcccg      2580
ccaggctacg gaggcttcca ctgcgaacag gacctgcccg actgcagccc cagctcctgc      2640
ttcaatggcg ggacctgtgt ggacggcgtg aactcgttca gctgcctgtg ccgtcccggc      2700
tacacaggag cccactgcca acatgaggca gacccctgcc tctcgcggcc ctgcctacac      2760
gggggcgtct gcagcgccgc ccaccctggc ttccgctgca cctgcctcga gagcttcacg      2820
ggcccgcagt gccagacgct ggtggattgg tgcagccgcc agccttgtca aaacgggggt      2880
cgctgcgtcc agactggggc ctattgcctt tgtcccctg gatggagcgg acgcctctgt      2940
gacatccgaa gcttgccctg cagggaggcc gcagcccaga tcgggtgcg gctggagcag      3000 ctgtgtcagg cgggtgggca gtgtgtggat gaagacagct cccactactg cgtgtgccca      3060
gagggccgta ctggtagcca ctgtgagcag gaggtggacc cctgcttggc ccagccctgc      3120
cagcatgggg ggacctgccg tggctatatg ggggctaca tgtgtgagtg tcttcctggc      3180
tacaatggtg ataactgtga ggacgacgtg gacgagtgtg cctcccagcc ctgccagcac      3240
gggggttcat gcattgacct cgtggcccgc tatctctgct cctgtccccc aggaacgctg      3300
ggggtgctct gcgagattaa tgaggatgac tgcggcccag gcccaccgct ggactcaggg      3360
ccccggtgcc tacacaatgg cacctgcgtg gacctggtgg gtggtttccg ctgcacctgt      3420
cccccaggat acactggttt gcgctgcgag gcagacatca tgagtgtcg ctcaggtgcc      3480 tgccacgcgg cacacacccg ggactgcctg caggacccag gcggaggttt ccgttgcctt      3540
tgtcatgctg gcttctcagg tcctcgctgt cagactgtcc tgtctccctg cgagtcccag      3600
ccatgccagc atggaggcca gtgccgtcct agcccgggtc ctgggggtgg gctgaccttc      3660
acctgtcact gtgcccagcc gttctggggt ccgcgttgcg agcgggtggc gcgctcctgc      3720
cgggagctgc agtgcccggt gggcgtccca tgccagcaga cgcccgcgg ccgcgctgc      3780 gcctgccccc cagggttgtc gggaccctcc tgccgcagct cccgggggtc gccgccgggg      3840
gccagcaacg ccagctgc                                                     3858
```

<210> SEQ ID NO 16
<211> LENGTH: 8091
<212> TYPE: DNA
<213> ORGANISM: homo sapien

<400> SEQUENCE: 16

```
acgcggcgcg gaggctggcc cgggacgcgc ccggagccca gggaaggagg gaggaggggg       60
gggtcgcggc cggccgccat ggggccgggg gcccgtggcc gccgccgccg ccgtcgcccg      120
atgtcgccgc caccgccacc gccacccgtg cgggcgctgc ccctgctgct gctgctagcg      180
gggccggggg ctgcagcccc cccttgcctg gacggaagcc cgtgtgcaaa tggaggtcgt      240
tgcacccagc tgccctcccg ggaggctgcc tgcctgtgcc cgcctggctg ggtgggtgag      300
cggtgtcagc tggaggaccc ctgtcactca ggccctgtg ctggccgtgg tgtctgccag      360
agttcagtgg tggctggcac cgcccgattc tcatgccggt gccccgtgg cttccgaggc      420 cctgactgct ccctgccaga tccctgcctc agcagcccctt gtgcccacgg tgcccgctgc      480
tcagtggggc ccgatggacg cttcctctgc tcctgcccac ctggctacca gggccgcagc      540
tgccgaagcg acgtggatga gtgccgggtg ggtgagccct gccgccatgg tggcacctgc      600
ctcaacacac ctggctcctt ccgctgccag tgtccagctg gctacacagg gccactatgt      660
gagaaccccg cggtgccctg tgcgccctca ccatgccgta acggggcac ctgcaggcag      720 agtggcgacc tcacttacga ctgtgcctgt cttcctgggt ttgagggtca gaattgtgaa      780
gtgaacgtgg acgactgtcc aggacaccga tgtctcaatg gggggacatg cgtggatggc      840
gtcaacacct ataactgcca gtgccctcct gagtggacag gccagttctg cacggaggac      900
gtggatgagt gtcagctgca gcccaacgcc tgccacaatg ggggtacctg cttcaacacg      960
ctgggtggcc acagctgcgt gtgtgtcaat ggctggacag gtgagagctg cagtcagaat     1020
atcgatgact gtgccacagc cgtgtgcttc catggggcca cctgccatga ccgcgtggct     1080
tctttctact gtgcctgccc catgggcaag actggcctcc tgtgtcacct ggatgacgcc     1140
tgtgtcagca acccctgcca cgaggatgct atctgtgaca caaatccggt gaacggccgg     1200
gccatttgca cctgtcctcc cggcttcacg ggtgggcat gtgaccagga tgtggacgag     1260
tgctctatcg gcgccaaccc ctgcgagcac ttgggcaggt gcgtgaacac gcagggctcc     1320
ttcctgtgcc agtgcggtcg tggctacact ggacctcgct gtgagaccga tgtcaacgag     1380
tgtctgtcgg ggcctgccg aaaccaggcc acgtgcctcg accgcatagg ccagttcacc     1440
tgtatctgta tggcaggctt cacaggaacc tattgcgagg tggacattga cgagtgtcag     1500 agtagccct gtgtcaacgg tgggggtctgc aaggaccgag tcaatggctt cagctgcacc     1560
tgcccctcgg gcttcagcgg ctccacgtgt cagctggacg tggacgaatg cgccagcacg     1620
ccctgcagga atggcgccaa atgcgtggac cagcccgatg gctacgagtg ccgctgtgcc     1680
gagggctttg agggcacgct gtgtgatcgc aacgtggacg actgctcccc tgacccatgc     1740
caccatggtc gctgcgtgga tggcatcgcc agcttctcat gtgcctgtgc tcctggctac     1800
acgggcacac gctgcgagag ccaggtggac gaatgccgca gccagccctg ccgccatggc     1860
ggcaaatgcc tagacctggt ggacaagtac ctctgccgct gcccttctgg gaccacaggt     1920
gtgaactgcg aagtgaacat tgacgactgt gccagcaacc cctgcacctt ggagtctgc     1980 cgtgatggca tcaaccgcta cgactgtgtc tgccaacctg gcttcacagg gccccttgt     2040 aacgtggaga tcaatgagtg tgcttccagc ccatgcggcg aggaggttc ctgtgtggat     2100 ggggaaaatg gcttccgctg cctctgcccg cctggctcct gcccccact ctgcctcccc     2160
```

-continued

```
ccgagccatc cctgtgccca tgagccctgc agtcacggca tctgctatga tgcacctggc    2220
gggttccgct gtgtgtgtga gcctggctgg agtggccccc gctgcagcca gagcctggcc    2280
cgagacgcct gtgagtccca gccgtgcagg gccggtggga catgcagcag cgatggaatg    2340
ggtttccact gcacctgccc gcctggtgtc cagggacgtc agtgtgaact cctctccccc    2400
tgcaccccga acccctgtga gcatgggggc cgctgcgagt ctgcccctgg ccagctgcct    2460
gtctgctcct gcccccaggg ctggcaaggc ccacgatgcc agcaggatgt ggacgagtgt    2520
gctggccccg caccctgtgg ccctcatggt atctgcacca acctggcagg gagtttcagc    2580
tgcacctgcc atggagggta cactggccct tcctgtgatc aggacatcaa tgactgtgac    2640
cccaacccat gcctgaacgg tggctcgtgc caagacggcg tgggctcctt ttcctgctcc    2700
tgcctccctg gtttcgccgg cccacgatgc gcccgcgatg tggatgagtg cctgagcaac    2760
ccctgcggcc cgggcacctg taccgaccac gtggcctcct tcacctgcac ctgcccgccg    2820
ggctacggag gcttccactg cgaacaggac ctgcccgact gcagccccag ctcctgcttc    2880
aatggcggga cctgtgtgga cggcgtgaac tcgttcagct gcctgtgccg tcccggctac    2940
acaggagccc actgccaaca tgaggcagac ccctgcctct cgcggccctg cctacacggg    3000
ggcgtctgca gcgccgccca ccctggcttc cgctgcacct gcctcgagag cttcacgggc    3060
ccgcagtgcc agacgctggt ggattggtgc agccgccagc cttgtcaaaa cgggggtcgc    3120
tgcgtccaga ctgggcccta ttgcctttgt cccctggat ggagcggacg cctctgtgac    3180
atccgaagct tgccctgcag ggaggccgca gcccagatcg gggtgcggct ggagcagctg    3240
tgtcaggcgg gtgggcagtg tgtggatgaa gacagctccc actactgcgt gtgcccagag    3300
ggccgtactg gtagccactg tgagcaggag gtggacccct gcttggccca gccctgccag    3360
catgggggga cctgccgtgg ctatatgggg ggctacatgt gtgagtgtct tcctggctac    3420
aatggtgata actgtgagga cgacgtggac gagtgtgcct cccagccctg ccagcacggg    3480
ggttcatgca ttgacctcgt ggcccgctat ctctgctcct gtcccccagg aacgctgggg    3540
gtgctctgcg agattaatga ggatgactgc ggcccaggcc caccgctgga ctcagggccc    3600
cggtgcctac acaatggcac ctgcgtggac ctggtgggtg gtttccgctg cacctgtccc    3660
ccaggataca ctggtttgcg ctgcgaggca gacatcaatg agtgtcgctc aggtgcctgc    3720
cacgcggcac acacccggga ctgcctgcag gacccaggcg gaggtttccg ttgcctttgt    3780
catgctggct tctcaggtcc tcgctgtcag actgtcctgt ctccctgcga gtcccagcca    3840
tgccagcatg gaggccagtg ccgtcctagc ccgggtcctg ggggtgggct gaccttcacc    3900
tgtcactgtg cccagccgtt ctggggtccg cgttgcgagc gggtggcgcg ctcctgccgg    3960
gagctgcagt gccgggtggg cgtcccatgc agcagacgc cccgcgggcc gcgctgcgcc    4020
tgccccccag ggttgtcggg acctcctgc cgcagcttcc cggggtcgcc gccgggggcc    4080
agcaacgcca gctgcgcggc cgccccctgt ctccacgggg gctcctgccg ccccgcgccg    4140
ctcgcgccct tcttccgctg cgcttgcgcg caggctgga ccgggccgcg ctgcgaggcg    4200
cccgccgcgg cacccgaggt ctcggaggag ccgcggtgcc cgcgcgccgc ctgccaggcc    4260
aagcgcgggg accagcgctg cgaccgcgag tgcaacagcc caggctgcgg ctgggacggc    4320
ggcgactgct cgctgagcgt gggcgacccc tggcggcaat gcgaggcgct gcagtgctgg    4380
cgcctcttca caacagccg ctgcgacccc gcctgcagct cgcccgcctg cctctacgac    4440
aacttcgact gccacgccgg tggccgcgag cgcacttgca acccggtgta cgagaagtac    4500
tgcgccgacc actttgccga cggccgctgc gaccagggct gcaacacgga ggagtgcggc    4560
```

-continued

```
tgggatgggc tggattgtgc cagcgaggtg ccggccctgc tggcccgcgg cgtgctggtg    4620
ctcacagtgc tgctgccgcc ggaggagcta ctgcgttcca cgcgccgactt tctgcagcgg   4680 ctcagcgcca tcctgcgcac ctcgctgcgc ttccgcctgg acgcgcacgg ccaggccatg    4740
gtcttccctt accaccggcc tagtcctggc tccgaacccc gggcccgtcg ggagctggcc    4800
cccgaggtga tcggctcggt agtaatgctg gagattgaca accggctctg cctgcagtcg    4860
cctgagaatg atcactgctt cccccgatgcc cagagcgccg ctgactacct gggagcgttg   4920
tcagcggtgg agcgcctgga cttcccgtac ccactgcggg acgtgcgggg ggagccgctg    4980
gagcctccag aacccagcgt cccgctgctg ccactgctag tggcgggcgc tgtcttgctg    5040
ctggtcattc tcgtcctggg tgtcatggtg gcccggcgca agcgcgagca cagcaccctc    5100
tggttccctg agggcttctc actgcacaag gacgtggcct ctggtcacaa gggccggcgg    5160
gaacccgtgg gccaggacgc gctgggcatg aagaacatgg ccaagggtga gagcctgatg    5220
ggggaggtgg ccacagactg gatggacaca gagtgcccag aggccaagcg gctaaaggta    5280
gaggagccag gcatgggggc tgaggaggct gtggattgcc gtcagtggac tcaacaccat    5340
ctggttgctg ctgacatccg cgtggcacca gccatggcac tgacaccacc acagggcgac    5400
gcagatgctg atggcatgga tgtcaatgtg cgtggcccag atggcttcac cccgctaatg    5460
ctggcttcct tctgtggggg ggctctggag ccaatgccaa ctgaagagga tgaggcagat    5520
gacacatcag ctagcatcat ctccgacctg atctgccagg gggctcagct tggggcacgg    5580
actgaccgta ctggcgagac tgctttgcac ctggctgccc gttatgcccg tgctgatgca    5640
gccaagcggc tgctggatgc tggggcagac accaatgccc aggaccactc aggccgcact    5700
cccctgcaca cagctgtcac agccgatgcc caggtgtgtct tccagattct catccgaaac    5760
cgctctacag acttggatgc ccgcatggca gatggctcaa cggcactgat cctggcggcc    5820
cgcctggcag tagagggcat ggtggaagag ctcatcgcca gccatgctga tgtcaatgct    5880
gtggatgagc ttgggaaatc agccttacac tgggctgcgg ctgtgaacaa cgtggaagcc    5940
actttggccc tgctcaaaaa tggagccaat aaggacatgc aggatagcaa ggaggagacc    6000
cccctattcc tggccgcccg cgagggcagc tatgaggctg ccaagctgct gttggaccac    6060
tttgccaacc gtgagatcac cgaccacctg gacaggctgc cgcgggacgt agcccaggag    6120
agactgcacc aggacatcgt gcgcttgctg gatcaaccca gtgggccccg cagcccccc    6180 ggtccccacg gcctgggggcc tctgctctgt cctccagggg ccttcctccc tggcctcaaa    6240
gcggcacagt cggggtccaa gaagagcagg aggcccccccg ggaaggcggg gctgggcccg    6300 cagggggcccc ggggggggggg caagaagctg acgctggcct gcccggggccc cctggctgac   6360 agctcggtca cgctgtcgcc cgtggactcg ctggactccc cgcggccttt cggtgggccc    6420
cctgcttccc ctggtggctt cccccttgag gggccctatg cagctgccac tgccactgca   6480
gtgtctctgg cacagcttgg tggcccaggc cgggcaggtc tagggcgcca gcccctgga    6540 ggatgtgtac tcagcctggg cctgctgaac cctgtggctg tgccctcga ttgggcccgg    6600 ctgccccac ctgcccctcc aggccctcg ttcctgctgc cactggcgcc gggacccag     6660 ctgctcaacc cagggacccc cgtctcccg caggagcggg ccccgcctta cctggcagtc    6720
ccaggacatg gcgaggagta cccggtggct ggggcacaca gcagcccccc aaaggcccgc    6780
ttcctgcggg ttcccagtga gcacccttac ctgaccccat cccccgaatc ccctgagcac    6840
tgggccagcc cctcacctcc ctccctctca gactggtccg aatccacgcc tagcccagcc    6900
```

-continued

```
actgccactg gggccatggc caccaccact ggggcactgc ctgcccagcc acttcccttg      6960
tctgttccca gctcccttgc tcaggcccag acccagctgg ggccccagcc ggaagttacc      7020
cccaagaggc aagtgttggc ctgagacgct cgtcagttct tagatcttgg gggcctaaag      7080 agaccccgt cctgcctcct ttctttctct gtctcttcct tccttttagt cttttttcatc     7140 ctcttctctt tccaccaacc ctcctgcatc cttgccttgc agcgtgaccg agataggtca      7200
tcagcccagg gcttcagtct tcctttattt ataatgggtg ggggctacca cccacctct      7260 cagtcttgtg aagagtctgg gacctccttc ttccccactt ctctcttccc tcattccttt     7320
ctctctcctt ctggcctctc atttccttac actctgacat gaatgaatta ttattatttt     7380 tcttttctt tttttttttta cattttgtat agaaacaaat tcatttaaac aaacttatta     7440
ttattatttt ttacaaaata tatatatgga gatgctccct ccccctgtga accccccagt     7500
gcccccgtgg ggctgagtct gtgggcccat tcggccaagc tggattctgt gtacctagta     7560
cacaggcatg actgggatcc cgtgtaccga gtacacgacc caggtatgta ccaagtaggc     7620
acccttgggc gcacccactg gggccagggg tcgggggagt gttgggagcc tcctccccac     7680
cccacctccc tcacttcact gcattccaga ttggacatgt tccatagcct tgctggggaa     7740
gggcccactg ccaactccct ctgccccagc cccacccttg gccatctccc tttgggaact     7800 aggggggctgc tggtgggaaa tgggagccag ggcagatgta tgcattcctt tatgtccctg    7860
taaatgtggg actacaagaa gaggagctgc ctgagtggta ctttctcttc ctggtaatcc     7920
tctggcccag ccttatggca gaatagaggt attttttaggc tatttttgta atatggcttc    7980
tggtcaaaat ccctgtgtag ctgaattccc aagccctgca ttgtacagcc ccccactccc     8040
ctcaccacct aataaaggaa tagttaacac tcaaaaaaaa aaaaaaaaa a               8091
```

```
<210> SEQ ID NO 17
<211> LENGTH: 3870
<212> TYPE: DNA
<213> ORGANISM: homo sapien

<400> SEQUENCE: 17
ggcgcggagg ctggcccggg ggcccgtggc cgccgccgcc gccgtcgccc gatgtcgccg        60
ccaccgccac cgccacccgt gcgggcgctg cccctgctgc tgctgctagc ggggccggg g      120 gctgcagccc ccccttgcct ggacggaagc ccgtgtgcaa atggaggtcg ttgcacccag       180
ctgccctccc gggaggctgc ctgcctgtgc ccgcctggct gggtgggtga gcggtgtcag       240
ctggaggacc cctgtcactc aggccctgt gctggccgtg gtgtctgcca gagttcagtg        300
gtggctggca ccgcccgatt ctcatgccgg tgccccgtg gcttccgagg ccctgactgc        360
tccctgccag atccctgcct cagcagccct tgtgcccacg gtgcccgctg ctcagtgggg       420
cccgatggac gcttcctctg ctcctgccca cctggctacc agggccgcag ctgccgaagc       480
gacgtggatg agtgccgggt gggtgagccc tgccgccatg gtggcacctg cctcaacaca       540
cctggctcct tccgctgcca gtgtccagct ggctacacag gccactatg tgagaacccc        600 gcggtgccct gtgcgccctc accatgccgt aacggggca cctgcaggca gagtggcgac        660
ctcacttacg actgtgcctg tcttcctggg tttgagggtc agaattgtga agtgaacgtg       720
gacgactgtc aggacaccg atgtctcaat gggggggacat gcgtggatgg cgtcaacacc       780
tataactgcc agtgcctcc tgagtggaca ggccagttct gcacggagga cgtggatgag       840
tgtcagctgc agcccaacgc ctgccacaat ggggggtacc gcttcaacac gctgggtggc       900
cacagctgcg tgtgtgtcaa tggctggaca ggcgagagct gcagtcagaa tatcgatgac       960
```

-continued

```
tgtgccacag ccgtgtgctt ccatgggggcc acctgccatg accgcgtggc ttctttctac      1020
tgtgcctgcc ccatgggcaa gactggcctc ctgtgtcacc tggatgacgc ctgtgtcagc      1080
aacccctgcc acgaggatgc tatctgtgac acaaatccgg tgaacggccg ggccatttgc      1140
acctgtcctc ccggcttcac gggtgggggca tgtgaccagg atgtggacga gtgctctatc      1200
ggcgccaacc cctgcgagca cttgggcagg tgcgtgaaca cgcagggctc cttcctgtgc      1260
cagtgcggtc gtggctacac tggacctcgc tgtgagaccg atgtcaacga gtgtctgtcg      1320
gggccctgcc gaaaccaggc cacgtgcctc gaccgcatag gccagttcac ctgtatctgt      1380
atggcaggct tcacaggaac ctattgcgag gtggacattg acgagtgtca gagtagcccc      1440
tgtgtcaacg gtggggtctg caaggaccga gtcaatggct tcagctgcac ctgcccctcg      1500
ggcttcagcg gctccacgtg tcagctggac gtggacgaat gcgccagcac gccctgcagg      1560
aatggcgcca aatgcgtgga ccagcccgat ggctacgagt gccgctgtgc cgagggcttt      1620
gagggcacgc tgtgtgatcg caacgtggac gactgctccc ctgacccatg ccaccatggt      1680
cgctgcgtgg atggcatcgc cagcttctca tgtgcctgtg ctcctggcta cacgggcaca      1740
cgctgcgaga gccaggtgga cgaatgccgc agccagccct gccgccatgg cggcaaatgc      1800
ctagacctgg tggacaagta cctctgccgc tgcccttctg ggaccacagg tgtgaactgc      1860
gaagtgaaca ttgacgactg tgccagcaac ccctgcacct ttggagtctg ccgtgatggc      1920
atcaaccgct acgactgtgt ctgccaacct ggcttcacag ggccccttttg taacgtggag      1980 atcaatgagt gtgcttccag cccatgcggc gagggaggtt cctgtgtgga tggggaaaat      2040
ggcttccgct gcctctgccc gcctggctcc ttgcccccac tctgcctccc cccgagccat      2100
ccctgtgccc atgagccctg cagtcacggc atctgctatg atgcacctgg cgggttccgc      2160
tgtgtgtgtg agcctggctg gagtggcccc cgctgcagcc agagcctggc ccgagacgcc      2220
tgtgagtccc agccgtgcag ggccggtggg acatgcagca gcgatggaat gggtttccac      2280
tgcacctgcc cgcctggtgt ccaggacgt cagtgtgaac tcctctcccc ctgcacccccg      2340 aacccctgtg agcatggggg ccgctgcgag tctgccccctg gccagctgcc tgtctgctcc      2400
tgcccccagg gctggcaaga cccatgcctg aacggtggct cgtgccaaga cggcgtgggc      2460
tccttttcct gctcctgcct ccctggtttc gccggcccac gatgcgcccg cgatgtggat      2520
gagtgcctga gcaaccccctg cggcccgggc acctgtaccg accacgtggc ctccttcacc      2580
tgcacctgcc cgccggggcta cggaggcttc cactgcgaac aggacctgcc cgactgcagc      2640
cccagctcct gcttcaatgg cgggacctgt gtggacggcg tgaactcgtt cagctgcctg      2700
tgccgtcccg gctacacagg agcccactgc caacatgagg cagacccctg cctctcgcgg      2760
ccctgcctac acggggggcgt ctgcagcgcc gcccaccctg gcttccgctg cacctgcctc      2820
gagagcttca cgggcccgca gtgccagacg ctggtggatt ggtgcagccg ccagccttgt      2880
caaaacgggg gtcgctgcgt ccagactggg gcctattgcc tttgtcccccc tggatggagc      2940 ggacgcctct gtgacatccg aagcttgccc tgcaggggag ccgcagccca gatcgggggtg      3000 cggctggagc agctgtgtca ggcgggtggg cagtgtgtgg atgaagacag ctccccactac      3060 tgcgtgtgcc cagagggccg tactggtagc cactgtgagc aggaggtgga ccctgcttg      3120 gcccagccct gccagcatgg ggggacctgc cgtggctata tgggggggcta catgtgtgag      3180 tgtcttcctg gctacaatgg tgataactgt gaggacgacg tggacgagtg tgcctcccag      3240
ccctgccagc acggggggttc atgcattgac ctcgtggccc gctatctctg ctcctgtccc      3300
```

-continued

```
ccaggaacgc tggggggtgct ctgcgagatt aatgaggatg actgcggccc aggcccaccg     3360
ctggactcag ggccccggtg cctacacaat ggcacctgcg tggacctggt gggtggtttc     3420
cgctgcacct gtcccccagg atacactggt ttgcgctgcg aggcagacat caatgagtgt     3480
cgctcaggtg cctgccacgc ggcacacacc cgggactgcc tgcaggaccc aggcggaggt     3540
ttccgttgcc tttgtcatgc tggcttctca ggtcctcgct gtcagactgt cctgtctccc     3600
tgcgagtccc agccatgcca gcatggaggc cagtgccgtc ctagcccggg tcctgggggt     3660
gggctgacct tcacctgtca ctgtgcccag ccgttctggg gtccgcgttg cgagcgggtg     3720
gcgcgctcct gccgggagct gcagtgcccg gtgggcgtcc catgccagca gacgccccgc     3780
gggccgcgct gcgcctgccc cccagggttg tcgggaccct cctgccgcag cttcccgggg     3840
tcgccgccgg gggccagcaa cgccagctgc                                      3870
```

<210> SEQ ID NO 18
<211> LENGTH: 8680
<212> TYPE: DNA
<213> ORGANISM: homo sapien

<400> SEQUENCE: 18

```
cttcggcgaa gttggcggcg cggaggctgg cccgggacgc gcccggagcc cagggaagga       60
gggaggaggg gagggtcgcg gccggccgcc atggggccgg gggcccgtgg ccgccgccgc      120
cgccgtcgcc cgatgtcgcc gccaccgcca ccgccaccccg tgcgggcgct gccctgctg      180 ctgctgctag cggggccggg ggctgcagcc ccccccttgcc tggacggaag cccgtgtgca      240
aatggaggtc gttgcacccca gctgccctcc cgggaggctg cctgcctgtg cccgcctggc      300
tgggtgggtg agcggtgtca gctggaggac ccctgtcact caggcccctg tgctggccgt      360
ggtgtctgcc agagttcagt ggtggctggc accgcccgat tctcatgccg gtgccccgt      420 ggcttccgag gccctgactg ctccctgcca gatccctgcc tcagcagccc ttgtgcccac      480
ggtgcccgct gctcagtggg gcccgatgga cgcttcctct gctcctgccc acctggctac      540
cagggccgca gctgccgaag cgacgtggat gagtgccggg tgggtgagcc ctgccgccat      600
ggtggcacct gcctcaacac acctggctcc ttccgctgcc agtgtccagc tggctacaca      660
gggccactat gtgagaaccc cgcggtgccc tgtgcaccct caccatgccg taacgggggc      720
acctgcaggc agagtggcga cctcacttac gactgtgcct gtcttcctgg gtttgagggt      780
cagaattgtg aagtgaacgt ggacgactgt ccaggacacc gatgtctcaa tggggggaca      840
tgcgtggatg gcgtcaacac ctataactgc cagtgccctc ctgagtggac aggccagttc      900
tgcacggagg acgtggatga gtgtcagctg cagcccaacg cctgccacaa tggggggtacc      960 tgcttcaaca cgctgggtgg ccacagctgc gtgtgtgtca atggctggac aggcgagagc     1020
tgcagtcaga atatcgatga ctgtgccaca gccgtgtgct tccatgggggc cacctgccat     1080 gaccgcgtgg cttcttttcta ctgtgcctgc cccatgggca agactggcct cctgtgtcac     1140
ctggatgacg cctgtgtcag caacccctgc cacgaggatg ctatctgtga cacaaatccg     1200
gtgaacggcc gggccatttg cacctgtcct cccggcttca cgggtggggc atgtgaccag     1260
gatgtggacg agtgctctat cggcgccaac ccctgcgagc acttgggcag gtgcgtgaac     1320
acgcagggct ccttcctgtg ccagtgcggt cgtggctaca ctggacctcg ctgtgagacc     1380
gatgtcaacg agtgtctgtc gggggccctgc cgaaaccagg ccacgtgcct cgaccgcata     1440
ggccagttca cctgtatctg tatggcaggc ttcacaggaa cctattgcga ggtggacatt     1500
gacgagtgtc agagtagccc ctgtgtcaac ggtggggtct gcaaggaccg agtcaatggc     1560
```

-continued

```
ttcagctgca cctgcccctc gggcttcagc ggctccacgt gtcagctgga cgtggacgaa   1620
tgcgccagca cgccctgcag gaatggcgcc aaatgcgtgg accagcccga tggctacgag   1680
tgccgctgtg ccgagggctt tgagggcacg ctgtgtgatc gcaacgtgga cgactgctcc   1740
cctgacccat gccaccatgg tcgctgcgtg gatggcatcg ccagcttctc atgtgcctgt   1800
gctcctggct acacgggcac acgctgcgag agccaggtgg acgaatgccg cagccagccc   1860
tgccgccatg gcggcaaatg cctagacctg gtggacaagt acctctgccg ctgcccttct   1920
gggaccacag gtgtgaactg cgaagtgaac attgacgact gtgccagcaa cccctgcacc   1980
tttggagtct gccgtgatgg catcaaccgc tacgactgtg tctgccaacc tggcttcaca   2040
gggccccttt gtaacgtgga gatcaatgag tgtgcttcca gcccatgcgg cgagggaggt   2100
tcctgtgtgg atgggaaaa tggcttccgc tgcctctgcc cgcctggctc cttgcccca   2160 ctctgcctcc ccccgagcca tccctgtgcc catgagccct gcagtcacgg catctgctat   2220
gatgcacctg gcgggttccg ctgtgtgtgt gagcctggct ggagtggccc ccgctgcagc   2280
cagagcctgg cccgagacgc ctgtgagtcc cagccgtgca gggccggtgg gacatgcagc   2340
agcgatggaa tgggtttcca ctgcacctgc ccgcctggtg tccagggacg tcagtgtgaa   2400
ctcctctccc cctgcacccc gaaccctgt gagcatgggg gccgctgcga gtctgcccct   2460
ggccagctgc ctgtctgctc ctgcccccag ggctggcaag gcccacgatg ccagcaggat   2520
gtggacgagt gtgctggccc cgcaccctgt ggccctcatg gtatctgcac caacctggca   2580
gggagtttca gctgcacctg ccatggaggg tacactggcc cttcctgcga tcaggacatc   2640
aatgactgtg accccaaccc atgcctgaac ggtggctcgt gccaagacgg cgtgggctcc   2700
ttttcctgct cctgcctccc tggtttcgcc ggcccacgat gcgccgcga tgtggatgag   2760 tgcctgagca acccctgcgg cccgggcacc tgtaccgacc acgtggcctc cttcacctgc   2820
acctgcccgc caggctacgg aggcttccac tgcgaacagg acctgcccga ctgcagcccc   2880
agctcctgct tcaatggcgg gacctgtgtg gacggcgtga actcgttcag ctgcctgtgc   2940
cgtcccggct acacaggagc ccactgccaa catgaggcag accctgcct ctcgcggccc   3000 tgcctacacg ggggcgtctg cagcgccgcc caccctggct tccgctgcac ctgcctcgag   3060
agcttcacgg gccgcagtg ccagacgctg gtggattggt gcagccgcca gccttgtcaa   3120 aacggggtc gctgcgtcca gactggggcc tattgccttt gtccccctgg atggagcgga   3180
cgcctctgtg acatccgaag cttgccctgc agggaggccg cagcccagat cggggtgcgg   3240
ctggagcagc tgtgtcaggc gggtgggcag tgtgtggatg aagacagctc ccactactgc   3300
gtgtgcccag agggccgtac tggtagccac tgtgagcagg aggtggaccc ctgcttggcc   3360
cagccctgcc agcatggggg gacctgccgt ggctatatgg ggggctacat gtgtgagtgt   3420
cttcctggct acaatggtga taactgtgag gacgacgtgg acgagtgtgc ctcccagccc   3480
tgccagcacg ggggttcatg cattgacctc gtggcccgct atctctgctc ctgtccccca   3540
ggaacgctgg gggtgctctg cgagattaat gaggatgact gcggcccagg cccaccgctg   3600
gactcagggc cccggtgcct acacaatggc acctgcgtgg acctggtggg tggtttccgc   3660
tgcacctgtc ccccaggata cactggtttg cgctgcgagg cagacatcaa tgagtgtcgc   3720
tcaggtgcct gccacgcggc acacacccgg gactgcctgc aggacccagg cggaggtttc   3780
tgttgccttt gtcatgctgg cttctcaggt cctcgctgtc agactgtcct gtctccctgc   3840
gagtcccagc catgccagca tggaggccag tgccgtccta gcccgggtcc tggggtgggg   3900
```

-continued

```
ctgaccttca cctgtcactg tgcccagccg ttctgggggtc cgcgttgcga gcgggtggcg      3960
cgctcctgcc gggagctgca gtgcccggtg ggcgtcccat gccagcagac gccccgcggg      4020
ccgcgctgcg cctgcccccc agggttgtcg ggaccctcct gccgcagctt cccggggtcg      4080
ccgccggggg ccagcaacgc cagctgcgcg gccgccccct gtctccacgg gggctcctgc      4140
cgccccgcgc cgctcgcgcc cttcttccgc tgcgcttgcg cgcagggctg gaccgggccg      4200
cgctgcgagg cgcccgccgc ggcacccgag gtctcggagg agccgcggtg cccgcgcgcc      4260
gcctgccagg ccaagcgcgg ggaccagcgc tgcgaccgcg agtgcaacag cccaggctgc      4320
ggctgggacg gcggcgactg ctcgctgagc gtgggcgacc cctggcggca atgcgaggcg      4380
ctgcagtgct ggcgcctctt caacaacagc cgctgcgacc ccgcctgcag ctcgcccgcc      4440
tgcctctacg acaacttcga ctgccacgcc ggtggccgcg agcgcacttg caacccggtg      4500
tacgagaagt actgcgccga ccactttgcc gacggccgct gcgaccaggg ctgcaacacg      4560
gaggagtgcg gctgggatgg gctggattgt gccagcgagg tgccggccct gctggcccgc      4620
ggcgtgctgg tgctcacagt gctgctgccg ccagaggagc tactgcgttc cagcgccgac      4680
tttctgcagc ggctcagcgc catcctgcgc acctcgctgc gcttccgcct ggacgcgcac      4740
ggccaggcca tggtcttccc ttaccaccgg cctagtcctg gctccgaacc ccgggcccgt      4800
cgggagctgg cccccgaggt gatcggctcg gtagtaatgc tggagattga caaccggctc      4860
tgcctgcagt cgcctgagaa tgatcactgc ttccccgatg cccagagcgc cgctgactac      4920
ctgggagcgt tgtcagcggt ggagcgcctg gacttcccgt acccactgcg ggacgtgcgg      4980
ggggagccgc tggagcctcc agaacccagc gtcccgctgc tgccactgct agtggcgggc      5040
gctgtcttgc tgctggtcat tctcgtcctg ggtgtcatgg tggcccggcg caagcgcgag      5100
cacagcaccc tctggttccc tgagggcttc tcactgcaca aggacgtggc ctctggtcac      5160
aagggccggc gggaacccgt gggccaggac gcgctgggca tgaagaacat ggccaagggt      5220
gagagcctga tggggggaggt ggccacagac tggatggaca cagagtgccc agaggccaag      5280
cggctaaagg tagaggagcc aggcatgggg gctgaggagg ctgtggattg ccgtcagtgg      5340
actcaacacc atctggttgc tgctgacatc cgcgtggcac cagccatggc actgacacca      5400
ccacagggcg acgcagatgc tgatggcatg gatgtcaatg tgcgtggccc agatggcttc      5460
accccgctaa tgctggcttc cttctgtggg ggggctctgg agccaatgcc aactgaagag      5520
gatgaggcag atgacacatc agctagcatc atctccgacc tgatctgcca gggggctcag      5580
cttggggcac ggactgaccg tactggcgag actgctttgc acctggctgc ccgttatgcc      5640
cgtgctgatg cagccaagcg gctgctggat gctggggcag acaccaatgc ccaggaccac      5700
tcaggccgca ctcccctgca cacagctgtc acagccgatg cccagggtgt cttccagatt      5760
ctcatccgaa accgctctac agacttggat gcccgcatgg cagatggctc aacggcactg      5820
atcctggcgg cccgcctggc agtagagggc atggtggaag agctcatcgc cagccatgct      5880
gatgtcaatg ctgtggatga gcttgggaaa tcagccttac actgggctgc ggctgtgaac      5940
aacgtggaag ccactttggc cctgctcaaa aatggagcca ataaggacat gcaggatagc      6000
aaggaggaga cccccctatt cctggccgcc cgcgagggca gctatgaggc tgccaagctg      6060
ctgttggacc actttgccaa ccgtgagatc accgaccacc tggacaggct gccgcgggac      6120
gtagcccagg agagactgca ccaggacatc gtgcgcttgc tggatcaacc cagtgggccc      6180
cgcagccccc ccggtcccca cggcctgggg cctctgctct gtcctccagg ggccttcctc      6240
cctggcctca aagcggcaca gtcggggtcc aagaagagca ggaggccccc cgggaaggcg      6300
```

-continued

```
gggctggggc cgcagggggcc ccgggggcgg ggcaagaagc tgacgctggc ctgcccgggc    6360
cccctggctg acagctcggt cacgctgtcg cccgtggact cgctggactc cccgcggcct    6420
ttcggtgggc cccctgcttc ccctggtggc ttcccccttg aggggcccta tgcagctgcc    6480
actgccactg cagtgtctct ggcacagctt ggtggcccag gccgggcggg tctagggcgc    6540 cagcccctg gaggatgtgt actcagcctg ggcctgctga accctgtggc tgtgcccctc    6600
gattgggccc ggctgccccc acctgccct ccaggcccct cgttcctgct gccactggcg    6660
ccgggacccc agctgctcaa cccagggacc cccgtctccc cgcaggagcg gcccccgcct    6720
tacctggcag tcccaggaca tggcgaggag tacccggcgg ctggggcaca cagcagcccc    6780
ccaaaggccc gcttcctgcg ggttcccagt gagcacccctt acctgacccc atcccccgaa    6840
tcccctgagc actgggccag cccctcacct ccctccctct cagactggtc cgaatccacg    6900
cctagcccag ccactgccac tggggccatg gccaccacca ctggggcact gcctgcccag    6960
ccacttccct tgtctgttcc cagctccctt gctcaggccc agaccagct ggggccccag    7020 ccggaagtta cccccaagag gcaagtgttg gcctgagacg ctcgtcagtt cttagatctt    7080
gggggcctaa agagaccccc gtcctgcctc ctttctttct ctgtctcttc cttccttta    7140 gtctttttca tcctcttctc tttccaccaa ccctcctgca tccttgcctt gcagcgtgac    7200
cgagataggt catcagccca gggcttcagt cttcctttat ttataatggg tggggggctac    7260 cacccaccct ctcagtcttg tgaagagtct gggacctcct tcttccccac ttctctcttc    7320
cctcattcct ttctctctcc ttctggcctc tcatttcctt acactctgac atgaatgaat    7380
tattattatt tttatttttc tttttttttt tacattttgt atagaaacaa attcatttaa    7440
acaaacttat tattattatt ttttacaaaa tatatatatg gagatgctcc ctcccccctgt    7500 gaacccccca gtgccccgt ggggctgagt ctgtgggccc attcggccaa gctggattct    7560
gtgtacctag tacacaggca tgactgggat cccgtgtacc gagtacacga cccaggtatg    7620
taccaagtag gcacccttgg gcgcacccac tggggccagg ggtcggggga gtgttgggag    7680
cctcctcccc acccacctc cctcacttca ctgcattcca gatgggacat gttccatagc    7740
cttgctgggg aagggcccac tgccaactcc ctctgcccca gccccaccct tggccatctc    7800
cctttgggaa ctaggggggct gctggtggga aatgggagcc agggcagatg tatgcattcc    7860
tttgtgtccc tgtaaatgtg ggactacaag aagaggagct gcctgagtgg tactttctct    7920
tcctggtaat cctctggccc agcctcatgg cagaatagag gtattttag gctattttg    7980 taatatggct tctggtcaaa atccctgtgt agctgaattc ccaagccctg cattgtacag    8040
ccccccactc ccctcaccac ctaataaagg aatagttaac actcagtgtt gttggtctgt    8100
gtctaggtaa ggtggggagt ggtggcagtg ggacttctat ctcccccacc cagggctaac    8160
ttgagctccc atcttggggt aaatacattt gacttgccag tctacttatg cttcctcttt    8220
tggcagatga ctaccgattg gattagtggt tgtcacctga cttaagctga gccaatcaga    8280 ttctttttgct cgagaacttt ctttaatgga gaggctaaga aagttgtcag ttggtggagc    8340
tcttaaggtc acaatcagat ttagaaatat cagtggccaa ttcgaggtgg tgggcaaaga    8400
gacaagcaaa cagggcagaa gaatgaagct aatattcagg gagaatcaga aatgagagct    8460
caaatggctc cttgagggct ggggggggtta tctcggctcc cagtgcagtt atcaattcca    8520
gttaattgag tgttcattcc attgagatca acaggtattt attaattgct ttctaagtat    8580
ctgatcatgg ttctgcatga atttcacttt tacttcatgc tcctatgggt tttggagata    8640
```

-continued

```
accttggacc catgtaataa atacttcttt acttgtgcca                          8680

<210> SEQ ID NO 19
<211> LENGTH: 8666
<212> TYPE: DNA
<213> ORGANISM: homo sapien

<400> SEQUENCE: 19
gcggcgcgga ggctggcccg ggacgcgccc ggagcccagg gaaggaggga ggaggggagg     60
gtcgcggccg gccgccatgg ggccgggggc ccgtggccgc cgccgccgcc gtcgcccgat    120
gtcgccgcca ccgccaccgc caccgtgcg ggcgctgccc ctgctgctgc tgctagcggg     180
gccgggggct gcagcccccc cttgcctgga cggaagcccg tgtgcaaatg gaggtcgttg    240
cacccagctg ccctcccggg aggctgcctg cctgtgcccg cctggctggg tgggtgagcg    300
gtgtcagctg gaggaccctt gtcactcagg cccctgtgct ggccgtggtg tctgccagag    360
ttcagtggtg gctggcaccg cccgattctc atgccggtgc ccccgtggct tccgaggccc    420
tgactgctcc ctgccagatc cctgcctcag cagcccttgt gcccacggtg cccgctgctc     480
agtggggccc gatggacgct tcctctgctc ctgcccacct ggctaccagg gccgcagctg    540
ccgaagcgac gtggatgagt gccgggtggg tgagccctgc cgccatggtg gcacctgcct    600
caacacacct ggctccttcc gctgccagtg tccagctggc tacacagggc cactatgtga    660
gaaccccgcg gtgccctgtg caccctcacc atgccgtaac gggggcacct gcaggcagag    720
tggcgacctc acttacgact gtgcctgtct tcctgggttt gagggtcaga attgtgaagt    780
gaacgtggac gactgtccag dacaccgatg tctcaatggg gggacatgcg tggatggcgt    840
caacacctat aactgccagt gccctcctga gtggacaggc cagttctgca cggaggacgt    900
ggatgagtgt cagctgcagc ccaacgcctg ccacaatggg ggtacctgct tcaacacgct    960
gggtggccac agctgcgtgt gtgtcaatgg ctggacaggc gagagctgca gtcagaatat   1020
cgatgactgt gccacagccg tgtgcttcca tggggccacc tgccatgacc gcgtggcttc   1080
tttctactgt gcctgcccca tgggcaagac tggcctcctg tgtcacctgg atgacgcctg   1140
tgtcagcaac ccctgccacg aggatgctat ctgtgacaca aatccggtga acggccgggc   1200
catttgcacc tgtcctcccg gcttcacggg tgggggcatgt gaccaggatg tggacgagtg   1260
ctctatcggc gccaacccct gcgagcactt gggcaggtgc gtgaacacgc agggctcctt   1320
cctgtgccag tgcggtcgtg gctacactgg acctcgctgt gagaccgatg tcaacgagtg   1380
tctgtcgggg ccctgccgaa accaggccac gtgcctcgac cgcataggcc agttcacctg   1440
tatctgtatg gcaggcttca caggaaccta ttgcgaggtg gacattgacg agtgtcagag   1500 tagccctgt gtcaacggtg gggtctgcaa ggaccgagtc aatggcttca gctgcacctg   1560
cccctcgggc ttcagcggct ccacgtgtca gctggacgtg gacgaatgcg ccagcacgcc   1620
ctgcaggaat ggcgccaaat gcgtggacca gcccgatggc tacgagtgcc gctgtgccga   1680
gggctttgag ggcacgctgt gtgatcgcaa cgtggacgac tgctcccctg acccatgcca   1740
ccatggtcgc tgcgtggatg gcatcgccag cttctcatgt gcctgtgctc ctggctacac   1800
gggcacacgc tgcgagagcc aggtggacga atgccgcagc cagcccgcc gccatggcgg   1860 caaatgccta gacctggtgg acaagtacct ctgccgctgc cttctgggaa ccacaggtgt   1920
gaactgcgaa gtgaacattg acgactgtgc cagcaacccc tgcacctttg gagtctgccg   1980
tgatggcatc aaccgctacg actgtgtctg ccaacctggc ttcacagggc ccctttgtaa   2040
cgtggagatc aatgagtgtg cttccagccc atgcggcgag ggaggttcct gtgtggatgg   2100
```

```
ggaaaatggc ttccgctgcc tctgcccgcc tggctccttg cccccactct gcctccccc    2160 gagccatccc tgtgcccatg agccctgcag tcacggcatc tgctatgatg cacctggcgg    2220
gttccgctgt gtgtgtgagc ctggctggag tggcccccgc tgcagccaga gcctggcccg    2280
agacgcctgt gagtcccagc cgtgcagggc cggtgggaca tgcagcagcg atggaatggg    2340
tttccactgc acctgcccgc ctggtgtcca gggacgtcag tgtgaactcc tctcccctg    2400 cacccccgaac ccctgtgagc atgggggccg ctgcgagtct gcccctggcc agctgcctgt    2460
ctgctcctgc ccccagggct ggcaaggccc acgatgccag caggatgtgg acgagtgtgc    2520
tggccccgca ccctgtggcc ctcatggtat ctgcaccaac ctggcaggga gtttcagctg    2580
cacctgccat ggagggtaca ctggcccttc ctgcgatcag dacatcaatg actgtgaccc    2640
caacccatgc ctgaacggtg gctcgtgcca agacggcgtg ggctccttttt cctgctcctg    2700 cctccctggt ttcgccggcc cacgatgcgc ccgcgatgtg gatgagtgcc tgagcaaccc    2760
ctgcggcccg ggcacctgta ccgaccacgt ggcctccttc acctgcacct gcccgccagg    2820
ctacggaggc ttccactgcg aacaggacct gcccgactgc agccccagct cctgcttcaa    2880
tggcgggacc tgtgtggacg gcgtgaactc gttcagctgc ctgtgccgtc ccggctacac    2940
aggagcccac tgccaacatg aggcagaccc ctgcctctcg cggccctgcc tacacggggg    3000
cgtctgcagc gccgcccacc ctggcttccg ctgcacctgc ctcgagagct tcacgggccc    3060
gcagtgccag acgctggtgg attggtgcag ccgccagcct tgtcaaaacg ggggtcgctg    3120
cgtccagact ggggcctatt gcctttgtcc ccctggatgg agcggacgcc tctgtgacat    3180
ccgaagcttg ccctgcaggg aggccgcagc ccagatcggg gtgcggctgg agcagctgtg    3240
tcaggcgggt gggcagtgtg tggatgaaga cagctcccac tactgcgtgt gcccagaggg    3300
ccgtactggt agccactgtg agcaggaggt ggacccctgc ttggcccagc cctgccagca    3360 tgggggggacc tgccgtggct atatgggggg ctacatgtgt gagtgtcttc ctggctacaa    3420
tggtgataac tgtgaggacg acgtggacga gtgtgcctcc cagccctgcc agcacggggg    3480
ttcatgcatt gacctcgtgg cccgctatct ctgctcctgt cccccaggaa cgctgggggt    3540
gctctgcgag attaatgagg atgactgcgg cccaggccca ccgctggact cagggccccg    3600
gtgcctacac aatggcacct gcgtggacct ggtgggtggt ttccgctgca cctgtcccc    3660 aggatacact ggttttgcgct gcgaggcaga catcaatgag tgtcgctcag gtgcctgcca    3720
cgcggcacac acccgggact gcctgcagga cccaggcgga ggtttctgtt gcctttgtca    3780
tgctggcttc tcaggtcctc gctgtcagac tgtcctgtct ccctgcgagt cccagccatg    3840
ccagcatgga ggccagtgcc gtcctagccc gggtcctggg ggtgggctga ccttcacctg    3900
tcactgtgcc cagccgttct ggggtccgcg ttgcgagcgg gtggcgcgct cctgccggga    3960
gctgcagtgc ccggtgggcg tcccatgcca gcagacgccc cgcgggccgc gctgcgcctg    4020 cccccccaggg ttgtcgggac cctcctgccg cagcttcccg gggtcgccgc cgggggccag    4080
caacgccagc tgcgcggccg ccccctgtct ccacgggggc tcctgccgcc ccgcgccgct    4140
cgcgcccttc ttccgctgcg cttgcgcgca gggctggacc gggccgcgct gcgaggcgcc    4200
cgccgcggca cccgaggtct cggaggagcc gcggtgcccg cgccgcgcct gccaggccaa    4260 gcgcgggggac cagcgctgcg accgcgagtg caacagccca ggctgcggct gggacggcgg    4320
cgactgctcg ctgagcgtgg gcgaccccctg gcggcaatgc gaggcgctgc agtgctggcg    4380
cctcttcaac aacagccgct gcgacccccgc ctgcagctcg cccgcctgcc tctacgacaa    4440
```

-continued

```
cttcgactgc cacgccggtg gccgcgagcg cacttgcaac ccggtgtacg agaagtactg    4500
cgccgaccac tttgccgacg gccgctgcga ccagggctgc aacacggagg agtgcggctg    4560
ggatgggctg gattgtgcca gcgaggtgcc ggccctgctg gcccgcggcg tgctggtgct    4620
cacagtgctg ctgccgccag aggagctact gcgttccagc gccgactttc tgcagcggct    4680
cagcgccatc ctgcgcacct cgctgcgctt ccgcctggac gcgcacggcc aggccatggt    4740
cttcccttac caccggccta gtcctggctc cgaaccccgg gcccgtcggg agctggcccc    4800
cgaggtgatc ggctcggtag taatgctgga gattgacaac cggctctgcc tgcagtcgcc    4860
tgagaatgat cactgcttcc ccgatgccca gagcgccgct gactacctgg gagcgttgtc    4920
agcggtggag cgcctggact tcccgtaccc actgcgggac gtgcgggggg agccgctgga    4980
gcctccagaa cccagcgtcc cgctgctgcc actgctagtg gcgggcgctg tcttgctgct    5040
ggtcattctc gtcctgggtg tcatggtggc ccggcgcaag cgcgagcaca gcaccctctg    5100
gttccctgag ggcttctcac tgcacaagga cgtggcctct ggtcacaagg ccggcgggga    5160
acccgtgggc caggacgcgc tgggcatgaa gaacatggcc aagggtgaga gcctgatggg    5220
ggaggtggcc acagactgga tggacacaga gtgcccagag gccaagcggc taaaggtaga    5280
ggagccaggc atggggctg aggaggctgt ggattgccgt cagtggactc aacaccatct    5340
ggttgctgct gacatccgcg tggcaccagc catggcactg acaccaccac agggcgacgc    5400
agatgctgat ggcatggatg tcaatgtgcg tggcccagat ggcttcaccc cgctaatgct    5460
ggcttccttc tgtgggggg ctctggagcc aatgccaact gaagaggatg aggcagatga    5520
cacatcagct agcatcatct ccgacctgat ctgccagggg gctcagcttg gggcacggac    5580
tgaccgtact ggcgagactg ctttgcacct ggctgcccgt tatgcccgtg ctgatgcagc    5640
caagcggctg ctggatgctg gggcagacac caatgcccag gaccactcag gccgcactcc    5700
cctgcacaca gctgtcacag ccgatgccca gggtgtcttc cagattctca tccgaaaccg    5760
ctctacagac ttggatgccc gcatggcaga tggctcaacg gcactgatcc tggcggcccg    5820
cctggcagta gagggcatgg tggaagagct catcgccagc catgctgatg tcaatgctgt    5880
ggatgagctt gggaaatcag ccttacactg ggctgcggct gtgaacaacg tggaagccac    5940
tttggccctg ctcaaaaatg gagccaataa ggacatgcag gatagcaagg aggagacccc    6000
cctattcctg gccgcccgcg agggcagcta tgaggctgcc aagctgctgt tggaccactt    6060
tgccaaccgt gagatcaccg accacctgga caggctgccg cgggacgtag cccaggagag    6120
actgcaccag gacatcgtgc gcttgctgga tcaacccagt gggccccgca gcccccccgg    6180 tcccccacggc ctggggcctc tgctctgtcc tccaggggcc ttcctccctg gcctcaaagc    6240
ggcacagtcg gggtccaaga agagcaggag gcccccgggg aaggcggggc tggggccgca    6300 ggggcccgg gggcggggca agaagctgac gctggcctgc ccgggccccc tggctgacag    6360
ctcggtcacg ctgtcgcccg tggactcgct ggactccccg cggccttcg gtgggccccc    6420 tgcttcccct ggtggcttcc cccttgaggg gccctatgca gctgccactg ccactgcagt    6480
gtctctggca cagcttggtg gcccaggccg ggcgggtcta gggcgccagc cccctggagg    6540
atgtgtactc agcctgggcc tgctgaaccc tgtggctgtg cccctcgatt gggcccggct    6600 gccccacct gcccctccag gcccctcgtt cctgctgcca ctggcgccgg acccccagct    6660
gctcaaccca gggaccccg tctcccgca ggagcggccc ccgccttacc tggcagtccc    6720
aggacatggc gaggagtacc cggcggctgg ggcacacagc agcccccaa aggcccgctt    6780 cctgcgggtt cccagtgagc accttacct gaccccatcc cccgaatccc ctgagcactg    6840
```

-continued

```
ggccagcccc tcacctccct ccctctcaga ctggtccgaa tccacgccta gcccagccac      6900
tgccactggg gccatggcca ccaccactgg ggcactgcct gcccagccac ttcccttgtc      6960
tgttcccagc tcccttgctc aggcccagac ccagctgggg ccccagccgg aagttacccc      7020
caagaggcaa gtgttggcct gagacgctcg tcagttctta gatcttgggg gcctaaagag      7080
acccccgtcc tgcctccttt ctttctctgt ctcttccttc cttttagtct ttttcatcct      7140
cttctctttc caccaaccct cctgcatcct tgccttgcag cgtgaccgag ataggtcatc      7200
agcccagggc ttcagtcttc ctttatttat aatgggtggg ggctaccacc caccctctca      7260
gtcttgtgaa gagtctggga cctccttctt ccccacttct ctcttccctc attcctttct      7320
ctctccttct ggcctctcat ttccttacac tctgacatga atgaattatt attattttta      7380
tttttctttt tttttttaca ttttgtatag aaacaaattc atttaaacaa acttattatt      7440
attatttttt acaaaatata tatatggaga tgctccctcc ccctgtgaac cccccagtgc      7500
ccccgtgggg ctgagtctgt gggcccattc ggccaagctg gattctgtgt acctagtaca      7560
caggcatgac tgggatcccg tgtaccgagt acacgaccca ggtatgtacc aagtaggcac      7620
ccttgggcgc acccactggg gccaggggtc ggggagtgt tgggagcctc ctccccaccc      7680
cacctccctc acttcactgc attccagatg ggacatgttc catagccttg ctggggaagg      7740
gcccactgcc aactccctct gccccagccc caccettggc catctccctt tgggaactag      7800
ggggctgctg gtgggaaatg ggagccaggg cagatgtatg cattcctttg tgtccctgta      7860
aatgtgggac tacaagaaga ggagctgcct gagtggtact ttctcttcct ggtaatcctc      7920
tggcccagcc tcatggcaga atagaggtat ttttaggcta tttttgtaat atggcttctg      7980
gtcaaaatcc ctgtgtagct gaattcccaa gccctgcatt gtacagcccc ccactcccct      8040
caccacctaa taaaggaata gttaacactc agtgttgttg gtctgtgtct aggtaaggtg      8100
gggagtggtg gcagtgggac ttctatctcc cccacccagg gctaacttga gctcccatct      8160
tggggtaaat acatttgact tgccagtcta cttatgcttc ctcttttggc agatgactac      8220
cgattggatt agtggttgtc acctgactta agctgagcca atcagattct tttgctcgag      8280
aactttcttt aatggagagg ctaagaaagt tgtcagttgg tggagctctt aaggtcacaa      8340
tcagatttag aaatatcagt ggccaattcg aggtggtggg caaagagaca agcaaacagg      8400
gcagaagaat gaagctaata ttcagggaga atcagaaatg agagctcaaa tggctccttg      8460
agggctgggg gggttatctc ggctcccagt gcagttatca attccagtta attgagtgtt      8520
cattccattg agatcaacag gtatttatta attgctttct aagtatctga tcatggttct      8580
gcatgaattt cactttact tcatgctcct atgggttttg gagataacct tggacccatg       8640 taataaaatac ttctttactt gtgcca                                          8666
```

<210> SEQ ID NO 20
<211> LENGTH: 3858
<212> TYPE: DNA
<213> ORGANISM: homo sapien

<400> SEQUENCE: 20

```
gggccggggg cccgtggccg ccgccgccgc cgtcgcccga tgtcgccgcc accgccaccg        60
ccacccgtgc gggcgctgcc cctgctgctg ctgctagcgg ggccgggggc tgcagcccc        120 ccttgcctgg acgaagcccc gtgtgcaaat ggaggtcgtt gcacccagct gcctccogg        180 gaggctgcct gcctgtgccc gcctggctgg gtgggtgagc ggtgtcagct ggaggacccc        240
```

-continued

```
tgtcactcag gcccctgtgc tggccgtggt gtctgccaga gttcagtggt ggctggcacc      300
gcccgattct catgccggtg cccccgtggc ttccgaggcc ctgactgctc cctgccagat      360
ccctgcctca gcagcccttg tgcccacggt gcccgctgct cagtggggcc cgatggacgc      420
ttcctctgct cctgcccacc tggctaccag ggccgcagcc gccgaagcga cgtggatgag      480
tgccgggtgg gtgagccctg ccgccatggt ggcacctgcc tcaacacacc tggctccttc      540
cgctgccagt gtccagctgg ctacacaggg ccactatgtg agaacccgc ggtgccctgt       600 gcaccctcac catgccgtaa cggggggcacc tgcaggcaga gtggcgacct cacttacgac      660
tgtgcctgtc ttcctgggtt tgagggtcag aattgtgaag tgaacgtgga cgactgtcca      720
ggacaccgat gtctcaatgg ggggacatgc gtggatggcg tcaacaccta taactgccag      780
tgccctcctg agtggacagg ccagttctgc acggaggacg tggatgagtg tcagctgcag      840
cccaacgcct gccacaatgg gggtacctgc ttcaacacgc tgggtggcca cagctgcgtg      900
tgtgtcaatg gctggacagg cgagagctgc agtcagaata tcgatgactg tgccacagcc      960
gtgtgcttcc atggggccac ctgccatgac cgcgtggctt ctttctactg tgcctgcccc     1020
atgggcaaga ctggcctcct gtgtcacctg gatgacgcct gtgtcagcaa ccctgccac      1080 gaggatgcta tctgtgacac aaatccggtg aacggccggg ccatttgcac ctgtcctccc     1140
ggcttcacgg gtgggcatg tgaccaggat gtggacgagt gctctatcgg cgccaacccc     1200
tgcgagcact gggcaggtg cgtgaacacg cagggctcct tcctgtgcca gtgcggtcgt      1260
ggctacactg gacctcgctg tgagaccgat gtcaacgagt gtctgtcggg gccctgccga     1320
aaccaggcca cgtgcctcga ccgcataggc cagttcacct gtatctgtat ggcaggcttc     1380
acaggaacct attgcgaggt ggacattgac gagtgtcaga gtagccctg tgtcaacggt      1440 ggggtctgca aggaccgagt caatggcttc agctgcacct gcccctcggg cttcagcggc     1500
tccacgtgtc agctggacgt ggacgaatgc gccagcacgc cctgcaggaa tggcgccaaa     1560
tgcgtggacc agcccgatgg ctacgagtgc cgctgtgccg agggctttga gggcacgctg     1620
tgtgatcgca acgtggacga ctgctcccct gacccatgcc accatggtcg ctgcgtggat     1680
ggcatcgcca gcttctcatg tgcctgtgct cctggctaca cgggcacacg ctgcgagagc     1740
caggtggacg aatgccgcag ccagccctgc cgccatggcg gcaaatgcct agacctggtg     1800
gacaagtacc tctgccgctg cccttctggg accacaggtg tgaactgcga agtgaacatt     1860
gacgactgtg ccagcaaccc ctgcaccttt ggagtctgcc gtgatggcat caaccgctac     1920
gactgtgtct gccaacctgg cttcacaggg cccctttgta cgtggagat caatgagtgt      1980 gcttccagcc catgcggcga gggaggttcc tgtgtggatg gggaaaatgg cttccgctgc     2040
ctctgcccgc ctggctcctt gcccccactc tgcctccccc cgagccatcc ctgtgcccat     2100
gagccctgca gtcacggcat ctgctatgat gcacctggcg ggttccgctg tgtgtgtgag     2160
cctggctgga gtggcccccg ctgcagccag agcctggccc gagacgcctg tgagtcccag     2220
ccgtgcaggg ccggtgggac atgcagcagc gatggaatgg gtttccactg cacctgcccg     2280
cctggtgtcc agggacgtca gtgtgaactc ctctcccct gcacccgaa cccctgtgag      2340 catgggggcc gctgcgagtc tgcccctggc cagctgcctg tctgctcctg cccccagggc     2400
tggcaagacc catgcctgaa cggtggctcg tgccaagacg gcgtgggctc cttttcctgc     2460
tcctgcctcc ctggtttcgc cggcccacga tgcgcccgcg atgtggatga gtgcctgagc     2520
aacccctgcg gcccgggcac ctgtaccgac cacgtggcct ccttcacctg cacctgcccg     2580
ccaggctacg gaggcttcca ctgcgaacag gacctgcccg actgcagccc cagctcctgc     2640
```

-continued

```
ttcaatggcg ggacctgtgt ggacggcgtg aactcgttca gctgcctgtg ccgtcccggc     2700
tacacaggag cccactgcca acatgaggca gacccctgcc tctcgcggcc ctgcctacac     2760 ggggggcgtct gcagcgccgc ccaccctggc ttccgctgca cctgcctcga gagcttcacg    2820
ggcccgcagt gccagacgct ggtggattgg tgcagccgcc agccttgtca aaacgggggt     2880
cgctgcgtcc agactggggc ctattgcctt tgtcccctg gatggagcgg acgcctctgt      2940
gacatccgaa gcttgccctg cagggaggcc gcagcccaga tcggggtgcg gctggagcag     3000
ctgtgtcagg cgggtgggca gtgtgtggat gaagacagct cccactactg cgtgtgccca     3060
gagggccgta ctggtagcca ctgtgagcag gaggtggacc cctgcttggc ccagccctgc     3120
cagcatgggg ggacctgccg tggctatatg gggggctaca tgtgtgagtg tcttcctggc    3180
tacaatggtg ataactgtga ggacgacgtg gacgagtgtg cctcccagcc ctgccagcac     3240 ggggggttcat gcattgacct cgtggcccgc tatctctgct cctgtccccc aggaacgctg    3300
ggggtgctct gcgagattaa tgaggatgac tgcggcccag gcccaccgct ggactcaggg     3360 cccccggtgcc tacacaatgg cacctgcgtg gacctggtgg gtggtttccg ctgcacctgt    3420
cccccaggat acactggttt gcgctgcgag gcagacatca atgagtgtcg ctcaggtgcc     3480
tgccacgcgg cacacacccg ggactgcctg caggacccag gcggaggttt ctgttgcctt     3540
tgtcatgctg gcttctcagg tcctcgctgt cagactgtcc tgtctccctg cgagtcccag     3600
ccatgccagc atggaggcca gtgccgtcct agcccgggtc ctggggtgtgg gctgaccttc     3660 acctgtcact gtgcccagcc gttctggggt ccgcgttgcg agcgggtggc gcgctcctgc     3720
cgggagctgc agtgcccggt gggcgtccca tgccagcaga cgccccgcgg gccgcgctgc     3780
gcctgccccc cagggttgtc gggaccctcc tgccgcagct tcccggggtc gccgccgggg     3840
gccagcaacg ccagctgc                                                   3858
```

```
<210> SEQ ID NO 21
<211> LENGTH: 8091
<212> TYPE: DNA
<213> ORGANISM: homo sapien

<400> SEQUENCE: 21
acgcggcgcg gaggctggcc cgggacgcgc ccggagccca gggaaggagg gaggaggggga     60 gggtcgcggc cggccgccat ggggccgggg gcccgtggcc gccgccgcg ccgtcgcccg      120 atgtcgccgc caccgccacc gccacccgtg cgggcgctgc ccctgctgct gctgctagcg     180
gggccggggg ctgcagcccc cccttgcctg gacggaagcc cgtgtgcaaa tggaggtcgt     240
tgcacccagc tgccctcccg ggaggctgcc tgcctgtgcc cgcctggctg ggtgggtgag     300
cggtgtcagc tggaggaccc ctgtcactca ggccctgtg ctggccgtgg tgtctgccag       360
agttcagtgg tggctggcac cgcccgattc tcatgccggt gccccgtgg cttccgaggc      420 cctgactgct ccctgccaga tccctgcctc agcagccctt gtgcccacgg tgcccgctgc     480
tcagtggggc ccgatggacg cttcctctgc tcctgccac ctggctacca gggccgcagc       540
tgccgaagcg acgtggatga gtgcgggtg ggtgagccct gccgccatgg tggcacctgc      600
ctcaacacac ctggctcctt ccgctgccag tgtccagctg ctacacagg gccactatgt        660 gagaaccccg cggtgccctg tgcgccctca ccatgccgta acggggcac ctgcaggcag       720 agtggcgacc tcacttacga ctgtgcctgt cttcctgggt ttgagggtca gaattgtgaa     780
gtgaacgtgg acgactgtcc aggacaccga tgtctcaatg gggggacatg cgtggatggc     840
```

-continued

```
gtcaacacct ataactgcca gtgccctcct gagtggacag gccagttctg cacggaggac    900
gtggatgagt gtcagctgca gcccaacgcc tgccacaatg ggggtacctg cttcaacacg    960
ctgggtggcc acagctgcgt gtgtgtcaat ggctggacag gtgagagctg cagtcagaat   1020
atcgatgact gtgccacagc cgtgtgcttc catggggcca cctgccatga ccgcgtggct   1080
tctttctact gtgcctgccc catgggcaag actggcctcc tgtgtcacct ggatgacgcc   1140
tgtgtcagca acccctgcca cgaggatgct atctgtgaca caaatccggt gaacggccgg   1200
gccatttgca cctgtcctcc cggcttcacg ggtgggggcat gtgaccagga tgtggacgag   1260
tgctctatcg gcgccaaccc ctgcgagcac ttgggcaggt gcgtgaacac gcagggctcc   1320
ttcctgtgcc agtgcggtcg tggctacact ggacctcgct gtgagaccga tgtcaacgag   1380
tgtctgtcgg ggccctgccg aaaccaggcc acgtgcctcg accgcatagg ccagttcacc   1440
tgtatctgta tggcaggctt cacaggaacc tattgcgagg tggacattga cgagtgtcag   1500
agtagcccct gtgtcaacgg tggggtctgc aaggaccgag tcaatggctt cagctgcacc   1560
tgcccctcgg gcttcagcgg ctccacgtgt cagctggacg tggacgaatg cgccagcacg   1620
ccctgcagga atggcgccaa atgcgtggac cagcccgatg gctacgagtg ccgctgtgcc   1680
gagggctttg agggcacgct gtgtgatcgc aacgtggacg actgctcccc tgacccatgc   1740
caccatggtc gctgcgtgga tggcatcgcc agcttctcat gtgcctgtgc tcctggctac   1800
acgggcacac gctgcgagag ccaggtggac gaatgccgca gccagccctg ccgccatggc   1860
ggcaaatgcc tagacctggt ggacaagtac ctctgccgct gcccttctgg gaccacaggt   1920
gtgaactgcg aagtgaacat tgacgactgt gccagcaacc cctgcacctt tggagtctgc   1980
cgtgatggca tcaaccgcta cgactgtgtc tgccaacctg gcttcacagg gccccctttgt   2040 aacgtggaga tcaatgagtg tgcttccagc ccatgcggcg agggaggttc ctgtgtggat   2100
ggggaaaatg gcttccgctg cctctgcccg cctggctcct gcccccact ctgcctcccc   2160 ccgagccatc cctgtgccca tgagccctgc agtcacggca tctgctatga tgcacctggc   2220
gggttccgct gtgtgtgtga gcctggctgg agtggccccc gctgcagcca gagcctggcc   2280
cgagacgcct gtgagtccca gccgtgcagg gccggtggga catgcagcag cgatggaatg   2340
ggtttccact gcacctgccc gcctggtgtc cagggacgtc agtgtgaact cctctccccc   2400 tgcacccga accctgtga gcatgggggc cgctgcgagt ctgcccctgg ccagctgcct   2460
gtctgctcct gcccccaggg ctggcaaggc ccacgatgcc agcaggatgt ggacgagtgt   2520
gctggccccg caccctgtgg ccctcatggt atctgcacca acctggcagg gagtttcagc   2580
tgcacctgcc atggagggta cactggccct tcctgtgatc aggacatcaa tgactgtgac   2640
cccaacccat gcctgaacgg tggctcgtgc aagacggcg tgggctcctt ttcctgctcc   2700
tgcctccctg gtttcgccgg cccacgatgc gcccgcgatg tggatgagtg cctgagcaac   2760
ccctgcggcc cgggcacctg taccgaccac gtggcctcct tcacctgcac ctgcccgccg   2820
ggctacggag gcttccactg cgaacaggac ctgcccgact gcagcccag ctcctgcttc   2880 aatggcggga cctgtgtgga cggcgtgaac tcgttcagct gcctgtgccg tcccggctac   2940
acaggagccc actgccaaca tgaggcagac ccctgcctct cgcggccctg cctacacggg   3000
ggcgtctgca gcgccgccca ccctggcttc cgctgcacct gcctcgagag cttcacgggc   3060
ccgcagtgcc agacgctggt ggattggtgc agccgccagc cttgtcaaaa cgggggtcgc   3120
tgcgtccaga ctggggccta ttgcctttgt ccccctggat ggagcggacg cctctgtgac   3180
atccgaagct tgccctgcag ggaggccgca gcccagatcg gggtgcggct ggagcagctg   3240
```

-continued

```
tgtcaggcgg gtgggcagtg tgtggatgaa gacagctccc actactgcgt gtgcccagag    3300
ggccgtactg gtagccactg tgagcaggag gtggaccccct gcttggccca gccctgccag   3360 catggggga cctgccgtgg ctatatgggg ggctacatgt gtgagtgtct tcctggctac     3420
aatggtgata actgtgagga cgacgtggac gagtgtgcct cccagccctg ccagcacggg    3480
ggttcatgca ttgacctcgt ggcccgctat ctctgctcct gtcccccagg aacgctgggg    3540
gtgctctgcg agattaatga ggatgactgc ggcccaggcc caccgctgga ctcagggccc    3600
cggtgcctac acaatggcac ctgcgtggac ctggtgggtg gtttccgctg cacctgtccc    3660
ccaggataca ctggtttgcg ctgcgaggca gacatcaatg agtgtcgctc aggtgcctgc    3720
cacgcggcac acacccggga ctgcctgcag gacccaggcg gaggtttctg ttgcctttgt    3780
catgctggct tctcaggtcc tcgctgtcag actgtcctgt ctccctgcga gtcccagcca    3840
tgccagcatg gaggccagtg ccgtcctagc ccgggtcctg ggggtgggct gaccttcacc    3900
tgtcactgtg cccagccgtt ctgggtccg cgttgcgagc gggtggcgcg ctcctgccgg     3960
gagctgcagt gcccggtggg cgtcccatgc cagcagacgc cccgcgggcc gcgctgcgcc    4020
tgccccccag ggttgtcggg accctcctgc cgcagcttcc cggggtcgcc gccgggggcc     4080
agcaacgcca gctgcgcggc cgccccctgt ctccacgggg gctcctgccg ccccgcgccg    4140
ctcgcgccct tcttccgctg cgcttgcgcg cagggctgga ccgggccgcg ctgcgaggcg     4200
cccgccgcgg cacccgaggt ctcggaggag ccgcggtgcc cgcgcgccgc ctgccaggcc    4260
aagcgcgggg accagcgctg cgaccgcgag tgcaacagcc caggctgcgg ctgggacggc    4320
ggcgactgct cgctgagcgt gggcgacccc tggcggcaat gcgaggcgct gcagtgctgg    4380
cgcctcttca caacagccg ctgcgacccc gcctgcagct cgcccgcctg cctctacgac     4440
aacttcgact gccacgccgg tggccgcgag cgcacttgca acccggtgta cgagaagtac    4500
tgcgccgacc actttgccga cggccgctgc gaccagggct gcaacacgga ggagtgcggc    4560
tgggatgggc tggattgtgc cagcgaggtg ccggccctgc tggcccgcgg cgtgctggtg    4620
ctcacagtgc tgctgccgcc ggaggagcta ctgcgttcca gcgccgactt tctgcagcgg    4680
ctcagcgcca tcctgcgcac ctcgctgcgc ttccgcctgg acgcgcacgg ccaggccatg    4740
gtcttccctt accaccggcc tagtcctggc tccgaacccc gggcccgtcg ggagctggcc    4800
cccgaggtga tcggctcggt agtaatgctg gagattgaca accggctctg cctgcagtcg    4860
cctgagaatg atcactgctt ccccgatgcc cagagcgccg ctgactacct gggagcgttg    4920
tcagcggtgg agcgcctgga cttcccgtac ccactgcggg acgtgcgggg ggagccgctg    4980
gagcctccag aacccagcgt cccgctgctg ccactgctag tggcgggcgc tgtcttgctg    5040
ctggtcattc tcgtcctggg tgtcatggtg gcccggcgca agcgcgagca cagcaccctc    5100
tggttccctg agggcttctc actgcacaag gacgtggcct ctggtcacaa gggccggcgg    5160
gaacccgtgg gccaggacgc gctgggcatg aagaacatgg ccaagggtga gagcctgatg    5220
ggggaggtgg ccacagactg gatggacaca gagtgcccag aggccaagcg gctaaaggta    5280
gaggagccag gcatggggc tgaggaggct gtggattgcc gtcagtggac tcaacaccat    5340
ctggttgctg ctgacatccg cgtggcacca gccatggcac tgacaccacc acagggcgac    5400
gcagatgctg atggcatgga tgtcaatgtg cgtggcccag atggcttcac cccgctaatg    5460
ctggcttcct tctgtggggg ggctctggag ccaatgccaa ctgaagagga tgaggcagat    5520
gacacatcag ctagcatcat ctccgacctg atctgccagg gggctcagct tggggcacgg    5580
```

-continued

```
actgaccgta ctggcgagac tgctttgcac ctggctgccc gttatgcccg tgctgatgca   5640
gccaagcggc tgctggatgc tggggcagac accaatgccc aggaccactc aggccgcact   5700
cccctgcaca cagctgtcac agccgatgcc cagggtgtct tccagattct catccgaaac   5760
cgctctacag acttggatgc ccgcatggca gatggctcaa cggcactgat cctggcggcc   5820
cgcctggcag tagagggcat ggtggaagag ctcatcgcca gccatgctga tgtcaatgct   5880
gtggatgagc ttgggaaatc agccttacac tgggctgcgg ctgtgaacaa cgtggaagcc   5940
actttggccc tgctcaaaaa tggagccaat aaggacatgc aggatagcaa ggaggagacc   6000
cccctattcc tggccgcccg cgagggcagc tatgaggctg ccaagctgct gttggaccac   6060
tttgccaacc gtgagatcac cgaccacctg gacaggctgc cgcgggacgt agcccaggag   6120
agactgcacc aggacatcgt gcgcttgctg gatcaaccca gtgggccccg cagcccccc   6180 ggtccccacg gcctggggcc tctgctctgt cctccagggg ccttcctccc tggcctcaaa   6240
gcggcacagt cggggtccaa gaagagcagg aggcccccg ggaaggcggg gctggggccg   6300
caggggcccc ggggcggg caagaagctg acgctggcct gcccgggccc cctggctgac   6360
agctcggtca cgctgtcgcc cgtggactcg ctggactccc cgcggccttt cggtgggccc   6420
cctgcttccc ctggtggctt cccccttgag gggccctatg cagctgccac tgccactgca   6480
gtgtctctgg cacagcttgg tggcccaggc cgggcaggtc tagggcgcca gcccctgga   6540 ggatgtgtac tcagcctggg cctgctgaac cctgtggctg tgccctcga ttgggcccgg   6600 ctgccccac ctgcccctcc aggccctcg ttcctgctgc cactggcgcc gggaccccag   6660
ctgctcaacc cagggacccc cgtctccccg caggagcggc ccccgcctta cctggcagtc   6720
ccaggacatg gcgaggagta cccggtggct ggggcacaca gcagccccc aaaggcccgc   6780 ttcctgcggg ttcccagtga gcacccttac ctgaccccat cccccgaatc ccctgagcac   6840
tgggccagcc cctcacctcc ctccctctca gactggtccg aatccacgcc tagcccagcc   6900
actgccactg gggccatggc caccaccact ggggcactgc ctgcccagcc acttcccttg   6960
tctgttccca gctcccttgc tcaggcccag acccagctgg ggccccagcc ggaagttacc   7020
cccaagaggc aagtgttggc ctgagacgct cgtcagttct tagatcttgg gggcctaaag   7080
agacccccgt cctgcctcct ttctttctct gtctcttcct tccttttagt cttttttcatc   7140 ctcttctctt tccaccaacc ctcctgcatc cttgccttgc agcgtgaccg agataggtca   7200
tcagcccagg gcttcagtct tcctttattt ataatgggtg ggggctacca cccaccctct   7260
cagtcttgtg aagagtctgg gacctccttc ttccccactt ctctcttccc tcattccttt   7320
ctctctcctt ctggcctctc atttccttac actctgacat gaatgaatta ttattatttt   7380 tcttttttctt ttttttttta cattttgtat agaaacaaat tcatttaaac aaacttatta   7440
ttattatttt ttacaaaata tatatatgga gatgctccct ccccctgtga accccccagt   7500
gcccccgtgg ggctgagtct gtgggcccat tcggccaagc tggattctgt gtacctagta   7560
cacaggcatg actgggatcc cgtgtaccga gtacacgacc caggtatgta ccaagtaggc   7620 accccttgggc gcacccactg gggccagggg tcgggggagt gttgggagcc tcctcccac   7680 cccacctccc tcacttcact gcattccaga ttggacatgt tccatagcct tgctggggaa   7740
gggcccactg ccaactccct ctgccccagc cccacccttg gccatctccc tttgggaact   7800 aggggggctgc tggtgggaaa tgggagccag ggcagatgta tgcattcctt tatgtccctg   7860
taaatgtggg actacaagaa gaggagctgc ctgagtggta cttttctcttc ctggtaatcc   7920 tctggcccag ccttatggca gaatagaggt attttttaggc tatttttgta atatggcttc   7980
```

-continued

```
tggtcaaaat ccctgtgtag ctgaattccc aagccctgca ttgtacagcc ccccactccc    8040
ctcaccacct aataaaggaa tagttaacac tcaaaaaaaa aaaaaaaaa a              8091

<210> SEQ ID NO 22
<211> LENGTH: 3870
<212> TYPE: DNA
<213> ORGANISM: homo sapien

<400> SEQUENCE: 22
ggcgcggagg ctggcccggg ggcccgtggc cgccgccgcc gccgtcgccc gatgtcgccg     60
ccaccgccac cgccacccgt gcgggcgctg cccctgctgc tgctgctagc ggggccgggg    120
gctgcagccc cccttgcct ggacggaagc ccgtgtgcaa atggaggtcg ttgcacccag     180
ctgccctccc gggaggctgc ctgcctgtgc ccgcctggct gggtgggtga gcggtgtcag    240
ctggaggacc cctgtcactc aggccctgt gctggccgtg gtgtctgcca gagttcagtg     300
gtggctggca ccgcccgatt ctcatgccgg tgccccgtg gcttccgagg ccctgactgc     360
tccctgccag atccctgcct cagcagccct tgtgcccacg gtgcccgctg ctcagtgggg    420
cccgatggac gcttcctctg ctcctgccca cctggctacc agggccgcag ctgccgaagc    480
gacgtggatg agtgccgggt gggtgagccc tgccgccatg gtggcacctg cctcaacaca    540
cctggctcct tccgctgcca gtgtccagct ggctacacag ggccactatg tgagaacccc    600
gcggtgccct gtgcgccctc accatgccgt aacgggggca cctgcaggca gagtggcgac    660
ctcacttacg actgtgcctg tcttcctggg tttgagggtc agaattgtga agtgaacgtg    720
gacgactgtc caggacaccg atgtctcaat gggggggacat gcgtggatgg cgtcaacacc    780
tataactgcc agtgccctcc tgagtggaca ggccagttct gcacggagga cgtggatgag    840
tgtcagctgc agcccaacgc ctgccacaat gggggtacct gcttcaacac gctgggtggc    900
cacagctgcg tgtgtgtcaa tggctggaca ggcgagagct gcagtcagaa tatcgatgac    960
tgtgccacag ccgtgtgctt ccatggggcc acctgccatg accgcgtggc ttctttctac   1020
tgtgcctgcc ccatgggcaa gactggcctc ctgtgtcacc tggatgacgc ctgtgtcagc   1080
aacccctgcc acgaggatgc tatctgtgac acaaatccgg tgaacggccg ggccatttgc   1140
acctgtcctc ccggcttcac gggtgggggca tgtgaccagg atgtggacga gtgctctatc   1200
ggcgccaacc cctgcgagca cttgggcagg tgcgtgaaca cgcagggctc cttcctgtgc   1260
cagtgcggtc gtggctacac tggacctcgc tgtgagaccg atgtcaacga gtgtctgtcg   1320
gggccctgcc gaaaccaggc cacgtgcctc gaccgcatag gccagttcac ctgtatctgt   1380
atggcaggct tcacaggaac ctattgcgag gtggacattg acgagtgtca gagtagcccc   1440
tgtgtcaacg gtggggtctg caaggaccga gtcaatggct tcagctgcac ctgcccctcg   1500
ggcttcagcg gctccacgtg tcagctggac gtggacgaat gcgccagcac gccctgcagg   1560
aatggcgcca aatgcgtgga ccagcccgat ggctacgagt gccgctgtgc cgagggcttt   1620
gagggcacgc tgtgtgatcg caacgtggac gactgctccc ctgacccatg ccaccatggt   1680
cgctgcgtgg atggcatcgc cagcttctca tgtgcctgtg ctcctggcta cacgggcaca   1740
cgctgcgaga gccaggtgga cgaatgccgc agccagccct gccgccatgg cggcaaatgc   1800
ctagacctgg tggacaagta cctctgccgc tgcccttctg gaccacagg tgtgaactgc   1860 gaagtgaaca ttgacgactg tgccagcaac ccctgcacct tggagtctg ccgtgatggc   1920 atcaaccgct acgactgtgt ctgccaacct ggcttcacag ggccccttg taacgtggag   1980
```

-continued

```
atcaatgagt gtgcttccag cccatgcggc gagggaggtt cctgtgtgga tggggaaaat    2040
ggcttccgct gcctctgccc gcctggctcc ttgcccccac tctgcctccc cccgagccat    2100
ccctgtgccc atgagccctg cagtcacggc atctgctatg atgcacctgg cgggttccgc    2160
tgtgtgtgtg agcctggctg gagtggcccc cgctgcagcc agagcctggc ccgagacgcc    2220
tgtgagtccc agccgtgcag ggccggtggg acatgcagca gcgatggaat gggtttccac    2280
tgcacctgcc cgcctggtgt ccagggacgt cagtgtgaac tcctctcccc ctgcaccccg    2340
aacccctgtg agcatggggg ccgctgcgag tctgccctg gccagctgcc tgtctgctcc    2400
tgcccccagg gctggcaaga cccatgcctg aacggtggct cgtgccaaga cggcgtgggc    2460
tccttttcct gctcctgcct ccctggtttc gccggcccac gatgcgcccg cgatgtggat    2520
gagtgcctga gcaaccctg cggcccgggc acctgtaccg accacgtggc ctccttcacc    2580
tgcacctgcc cgccgggcta cggaggcttc cactgcgaac aggacctgcc cgactgcagc    2640
cccagctcct gcttcaatgg cgggacctgt gtggacggcg tgaactcgtt cagctgcctg    2700
tgccgtcccg gctacacagg agcccactgc caacatgagg cagacccctg cctctcgcgg    2760
ccctgcctac acggggcgt ctgcagcgcc gcccaccctg gcttccgctg cacctgcctc    2820
gagagcttca cgggcccgca gtgccagacg ctggtggatt ggtgcagccg ccagccttgt    2880
caaaacgggg gtcgctgcgt ccagactggg gcctattgcc tttgtccccc tggatggagc    2940
ggacgcctct gtgacatccg aagcttgccc tgcaggagg ccgcagccca gatcggggtg    3000
cggctggagc agctgtgtca ggcgggtggg cagtgtgtgg atgaagacag ctcccactac    3060
tgcgtgtgcc cagagggccg tactggtagc cactgtgagc aggaggtgga cccctgcttg    3120
gcccagccct gccagcatgg ggggacctgc cgtggctata tgggggggcta catgtgtgag    3180 tgtcttcctg gctacaatgg tgataactgt gaggacgacg tggacgagtg tgcctcccag    3240
ccctgccagc acggggggttc atgcattgac ctcgtggccc gctatctctg ctcctgtccc    3300
ccaggaacgc tgggggtgct ctgcgagatt aatgaggatg actgcggccc aggcccaccg    3360
ctggactcag ggcccggtg cctacacaat ggcacctgcg tggacctggt gggtggtttc    3420
cgctgcacct gtccccagg atacactggt ttgcgctgcg aggcagacat caatgagtgt    3480
cgctcaggtg cctgccacgc ggcacacacc cgggactgcc tgcaggaccc aggcggaggt    3540
ttctgttgcc tttgtcatgc tggcttctca ggtcctcgct gtcagactgt cctgtctccc    3600
tgcgagtccc agccatgcca gcatggaggc cagtgccgtc ctagcccggg tcctggggggt    3660 gggctgacct tcacctgtca ctgtgcccag ccgttctggg tccgcgttg cgagcgggtg    3720 gcgcgctcct gccgggagct gcagtgcccg gtgggcgtcc catgccagca gacgcccgc    3780 gggccgcgct gcgcctgccc cccagggttg tcgggaccct cctgccgcag cttcccgggg    3840
tcgccgccgg gggccagcaa cgccagctgc                                      3870
```

<210> SEQ ID NO 23
<211> LENGTH: 1286
<212> TYPE: PRT
<213> ORGANISM: homo sapien

<400> SEQUENCE: 23

```
Gly Pro Gly Ala Arg Gly Arg Arg Arg Arg Arg Pro Met Ser Pro
1               5                   10                  15

Pro Pro Pro Pro Pro Val Arg Ala Leu Pro Leu Leu Leu Leu Leu
            20                  25                  30

Ala Gly Pro Gly Ala Ala Ala Pro Pro Cys Leu Asp Gly Ser Pro Cys
```

```
           35                    40                    45

Ala Asn Gly Gly Arg Cys Thr Gln Leu Pro Ser Arg Glu Ala Ala Cys
           50                    55                    60

Leu Cys Pro Pro Gly Trp Val Gly Glu Arg Cys Gln Leu Glu Asp Pro
65                    70                    75                    80

Cys His Ser Gly Pro Cys Ala Gly Arg Gly Val Cys Gln Ser Ser Val
                     85                    90                    95

Val Ala Gly Thr Ala Arg Phe Ser Cys Arg Cys Pro Arg Gly Phe Arg
                     100                   105                   110

Gly Pro Asp Cys Ser Leu Pro Asp Pro Cys Leu Ser Ser Pro Cys Ala
                     115                   120                   125

His Gly Ala Arg Cys Ser Val Gly Pro Asp Gly Arg Phe Leu Cys Ser
           130                   135                   140

Cys Pro Pro Gly Tyr Gln Gly Arg Ser Cys Arg Ser Asp Val Asp Glu
145                   150                   155                   160

Cys Arg Val Gly Glu Pro Cys Arg His Gly Gly Thr Cys Leu Asn Thr
                     165                   170                   175

Pro Gly Ser Phe Arg Cys Gln Cys Pro Ala Gly Tyr Thr Gly Pro Leu
                     180                   185                   190

Cys Glu Asn Pro Ala Val Pro Cys Ala Pro Ser Pro Cys Arg Asn Gly
           195                   200                   205

Gly Thr Cys Arg Gln Ser Gly Asp Leu Thr Tyr Asp Cys Ala Cys Leu
           210                   215                   220

Pro Gly Phe Glu Gly Gln Asn Cys Glu Val Asn Val Asp Asp Cys Pro
225                   230                   235                   240

Gly His Arg Cys Leu Asn Gly Gly Thr Cys Val Asp Gly Val Asn Thr
                     245                   250                   255

Tyr Asn Cys Gln Cys Pro Pro Glu Trp Thr Gly Gln Phe Cys Thr Glu
           260                   265                   270

Asp Val Asp Glu Cys Gln Leu Gln Pro Asn Ala Cys His Asn Gly Gly
           275                   280                   285

Thr Cys Phe Asn Thr Leu Gly Gly His Ser Cys Val Cys Val Asn Gly
           290                   295                   300

Trp Thr Gly Glu Ser Cys Ser Gln Asn Ile Asp Asp Cys Ala Thr Ala
305                   310                   315                   320

Val Cys Phe His Gly Ala Thr Cys His Asp Arg Val Ala Ser Phe Tyr
                     325                   330                   335

Cys Ala Cys Pro Met Gly Lys Thr Gly Leu Leu Cys His Leu Asp Asp
                     340                   345                   350

Ala Cys Val Ser Asn Pro Cys His Glu Asp Ala Ile Cys Asp Thr Asn
           355                   360                   365

Pro Val Asn Gly Arg Ala Ile Cys Thr Cys Pro Pro Gly Phe Thr Gly
           370                   375                   380

Gly Ala Cys Asp Gln Asp Val Asp Glu Cys Ser Ile Gly Ala Asn Pro
385                   390                   395                   400

Cys Glu His Leu Gly Arg Cys Val Asn Thr Gln Gly Ser Phe Leu Cys
                     405                   410                   415

Gln Cys Gly Arg Gly Tyr Thr Gly Pro Arg Cys Glu Thr Asp Val Asn
                     420                   425                   430

Glu Cys Leu Ser Gly Pro Cys Arg Asn Gln Ala Thr Cys Leu Asp Arg
           435                   440                   445

Ile Gly Gln Phe Thr Cys Ile Cys Met Ala Gly Phe Thr Gly Thr Tyr
           450                   455                   460
```

-continued

```
Cys Glu Val Asp Ile Asp Glu Cys Gln Ser Ser Pro Cys Val Asn Gly
465             470             475             480

Gly Val Cys Lys Asp Arg Val Asn Gly Phe Ser Cys Thr Cys Pro Ser
                485             490             495

Gly Phe Ser Gly Ser Thr Cys Gln Leu Asp Val Asp Glu Cys Ala Ser
            500             505             510

Thr Pro Cys Arg Asn Gly Ala Lys Cys Val Asp Gln Pro Asp Gly Tyr
            515             520             525

Glu Cys Arg Cys Ala Glu Gly Phe Glu Gly Thr Leu Cys Asp Arg Asn
        530             535             540

Val Asp Asp Cys Ser Pro Asp Pro Cys His His Gly Arg Cys Val Asp
545             550             555             560

Gly Ile Ala Ser Phe Ser Cys Ala Cys Ala Pro Gly Tyr Thr Gly Thr
                565             570             575

Arg Cys Glu Ser Gln Val Asp Glu Cys Arg Ser Gln Pro Cys Arg His
            580             585             590

Gly Gly Lys Cys Leu Asp Leu Val Asp Lys Tyr Leu Cys Arg Cys Pro
            595             600             605

Ser Gly Thr Thr Gly Val Asn Cys Glu Val Asn Ile Asp Asp Cys Ala
        610             615             620

Ser Asn Pro Cys Thr Phe Gly Val Cys Arg Asp Gly Ile Asn Arg Tyr
625             630             635             640

Asp Cys Val Cys Gln Pro Gly Phe Thr Gly Pro Leu Cys Asn Val Glu
                645             650             655

Ile Asn Glu Cys Ala Ser Ser Pro Cys Gly Glu Gly Gly Ser Cys Val
            660             665             670

Asp Gly Glu Asn Gly Phe Arg Cys Leu Cys Pro Pro Gly Ser Leu Pro
            675             680             685

Pro Leu Cys Leu Pro Pro Ser His Pro Cys Ala His Glu Pro Cys Ser
        690             695             700

His Gly Ile Cys Tyr Asp Ala Pro Gly Gly Phe Arg Cys Val Cys Glu
705             710             715             720

Pro Gly Trp Ser Gly Pro Arg Cys Ser Gln Ser Leu Ala Arg Asp Ala
                725             730             735

Cys Glu Ser Gln Pro Cys Arg Ala Gly Gly Thr Cys Ser Ser Asp Gly
            740             745             750

Met Gly Phe His Cys Thr Cys Pro Pro Gly Val Gln Gly Arg Gln Cys
            755             760             765

Glu Leu Leu Ser Pro Cys Thr Pro Asn Pro Cys Glu His Gly Gly Arg
        770             775             780

Cys Glu Ser Ala Pro Gly Gln Leu Pro Val Cys Ser Cys Pro Gln Gly
785             790             795             800

Trp Gln Asp Pro Cys Leu Asn Gly Gly Ser Cys Gln Asp Gly Val Gly
            805             810             815

Ser Phe Ser Cys Ser Cys Leu Pro Gly Phe Ala Gly Pro Arg Cys Ala
            820             825             830

Arg Asp Val Asp Glu Cys Leu Ser Asn Pro Cys Gly Pro Gly Thr Cys
            835             840             845

Thr Asp His Val Ala Ser Phe Thr Cys Thr Cys Pro Pro Gly Tyr Gly
        850             855             860

Gly Phe His Cys Glu Gln Asp Leu Pro Asp Cys Ser Pro Ser Ser Cys
865             870             875             880
```

```
Phe Asn Gly Gly Thr Cys Val Asp Gly Val Asn Ser Phe Ser Cys Leu
              885               890               895

Cys Arg Pro Gly Tyr Thr Gly Ala His Cys Gln His Glu Ala Asp Pro
          900               905               910

Cys Leu Ser Arg Pro Cys Leu His Gly Gly Val Cys Ser Ala Ala His
      915               920               925

Pro Gly Phe Arg Cys Thr Cys Leu Glu Ser Phe Thr Gly Pro Gln Cys
      930               935               940

Gln Thr Leu Val Asp Trp Cys Ser Arg Gln Pro Cys Gln Asn Gly Gly
945               950               955               960

Arg Cys Val Gln Thr Gly Ala Tyr Cys Leu Cys Pro Pro Gly Trp Ser
              965               970               975

Gly Arg Leu Cys Asp Ile Arg Ser Leu Pro Cys Arg Glu Ala Ala Ala
          980               985               990

Gln Ile Gly Val Arg Leu Glu Gln  Leu Cys Gln Ala Gly  Gly Gln Cys
          995               1000               1005

Val Asp  Glu Asp Ser Ser His  Tyr Cys Val Cys Pro  Glu Gly Arg
    1010               1015               1020

Thr Gly  Ser His Cys Glu Gln  Glu Val Asp Pro Cys  Leu Ala Gln
    1025               1030               1035

Pro Cys  Gln His Gly Gly Thr  Cys Arg Gly Tyr Met  Gly Gly Tyr
    1040               1045               1050

Met Cys  Glu Cys Leu Pro Gly  Tyr Asn Gly Asp Asn  Cys Glu Asp
    1055               1060               1065

Asp Val  Asp Glu Cys Ala Ser  Gln Pro Cys Gln His  Gly Gly Ser
    1070               1075               1080

Cys Ile  Asp Leu Val Ala Arg  Tyr Leu Cys Ser Cys  Pro Pro Gly
    1085               1090               1095

Thr Leu  Gly Val Leu Cys Glu  Ile Asn Glu Asp Asp  Cys Gly Pro
    1100               1105               1110

Gly Pro  Pro Leu Asp Ser Gly  Pro Arg Cys Leu His  Asn Gly Thr
    1115               1120               1125

Cys Val  Asp Leu Val Gly Gly  Phe Arg Cys Thr Cys  Pro Pro Gly
    1130               1135               1140

Tyr Thr  Gly Leu Arg Cys Glu  Ala Asp Ile Asn Glu  Cys Arg Ser
    1145               1150               1155

Gly Ala  Cys His Ala Ala His  Thr Arg Asp Cys Leu  Gln Asp Pro
    1160               1165               1170

Gly Gly  Gly Phe Arg Cys Leu  Cys His Ala Gly Phe  Ser Gly Pro
    1175               1180               1185

Arg Cys  Gln Thr Val Leu Ser  Pro Cys Glu Ser Gln  Pro Cys Gln
    1190               1195               1200

His Gly  Gly Gln Cys Arg Pro  Ser Pro Gly Pro Gly  Gly Gly Leu
    1205               1210               1215

Thr Phe  Thr Cys His Cys Ala  Gln Pro Phe Trp Gly  Pro Arg Cys
    1220               1225               1230

Glu Arg  Val Ala Arg Ser Cys  Arg Glu Leu Gln Cys  Pro Val Gly
    1235               1240               1245

Val Pro  Cys Gln Gln Thr Pro  Arg Gly Pro Arg Cys  Ala Cys Pro
    1250               1255               1260

Pro Gly  Leu Ser Gly Pro Ser  Cys Arg Ser Phe Pro  Gly Ser Pro
    1265               1270               1275

Pro Gly  Ala Ser Asn Ala Ser  Cys
```

```
        1280                1285

<210> SEQ ID NO 24
<211> LENGTH: 2321
<212> TYPE: PRT
<213> ORGANISM: homo sapien

<400> SEQUENCE: 24

Met Gly Pro Gly Ala Arg Gly Arg Arg Arg Arg Arg Pro Met Ser
1               5                   10                  15

Pro Pro Pro Pro Pro Pro Val Arg Ala Leu Pro Leu Leu Leu Leu
                20                  25                  30

Leu Ala Gly Pro Gly Ala Ala Ala Pro Pro Cys Leu Asp Gly Ser Pro
            35                  40                  45

Cys Ala Asn Gly Gly Arg Cys Thr Gln Leu Pro Ser Arg Glu Ala Ala
    50                  55                  60

Cys Leu Cys Pro Pro Gly Trp Val Gly Glu Arg Cys Gln Leu Glu Asp
65                  70                  75                  80

Pro Cys His Ser Gly Pro Cys Ala Gly Arg Gly Val Cys Gln Ser Ser
                85                  90                  95

Val Val Ala Gly Thr Ala Arg Phe Ser Cys Arg Cys Pro Arg Gly Phe
            100                 105                 110

Arg Gly Pro Asp Cys Ser Leu Pro Asp Pro Cys Leu Ser Ser Pro Cys
            115                 120                 125

Ala His Gly Ala Arg Cys Ser Val Gly Pro Asp Gly Arg Phe Leu Cys
    130                 135                 140

Ser Cys Pro Pro Gly Tyr Gln Gly Arg Ser Cys Arg Ser Asp Val Asp
145                 150                 155                 160

Glu Cys Arg Val Gly Glu Pro Cys Arg His Gly Gly Thr Cys Leu Asn
                165                 170                 175

Thr Pro Gly Ser Phe Arg Cys Gln Cys Pro Ala Gly Tyr Thr Gly Pro
                180                 185                 190

Leu Cys Glu Asn Pro Ala Val Pro Cys Ala Pro Ser Pro Cys Arg Asn
            195                 200                 205

Gly Gly Thr Cys Arg Gln Ser Gly Asp Leu Thr Tyr Asp Cys Ala Cys
    210                 215                 220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
                245                 250                 255

Thr Tyr Asn Cys Gln Cys Pro Pro Glu Trp Thr Gly Gln Phe Cys Thr
                260                 265                 270

Glu Asp Val Asp Glu Cys Gln Leu Gln Pro Asn Ala Cys His Asn Gly
            275                 280                 285

Gly Thr Cys Phe Asn Thr Leu Gly Gly His Ser Cys Val Cys Val Asn
    290                 295                 300

Gly Trp Thr Gly Glu Ser Cys Ser Gln Asn Ile Asp Asp Cys Ala Thr
305                 310                 315                 320

Ala Val Cys Phe His Gly Ala Thr Cys His Asp Arg Val Ala Ser Phe
                325                 330                 335

Tyr Cys Ala Cys Pro Met Gly Lys Thr Gly Leu Leu Cys His Leu Asp
            340                 345                 350

Asp Ala Cys Val Ser Asn Pro Cys His Glu Asp Ala Ile Cys Asp Thr
            355                 360                 365
```

```
Asn Pro Val Asn Gly Arg Ala Ile Cys Thr Cys Pro Pro Gly Phe Thr
    370             375             380

Gly Gly Ala Cys Asp Gln Asp Val Asp Glu Cys Ser Ile Gly Ala Asn
385             390             395             400

Pro Cys Glu His Leu Gly Arg Cys Val Asn Thr Gln Gly Ser Phe Leu
            405             410             415

Cys Gln Cys Gly Arg Gly Tyr Thr Gly Pro Arg Cys Glu Thr Asp Val
            420             425             430

Asn Glu Cys Leu Ser Gly Pro Cys Arg Asn Gln Ala Thr Cys Leu Asp
            435             440             445

Arg Ile Gly Gln Phe Thr Cys Ile Cys Met Ala Gly Phe Thr Gly Thr
    450             455             460

Tyr Cys Glu Val Asp Ile Asp Glu Cys Gln Ser Ser Pro Cys Val Asn
465             470             475             480

Gly Gly Val Cys Lys Asp Arg Val Asn Gly Phe Ser Cys Thr Cys Pro
            485             490             495

Ser Gly Phe Ser Gly Ser Thr Cys Gln Leu Asp Val Asp Glu Cys Ala
            500             505             510

Ser Thr Pro Cys Arg Asn Gly Ala Lys Cys Val Asp Gln Pro Asp Gly
            515             520             525

Tyr Glu Cys Arg Cys Ala Glu Gly Phe Glu Gly Thr Leu Cys Asp Arg
    530             535             540

Asn Val Asp Asp Cys Ser Pro Asp Pro Cys His His Gly Arg Cys Val
545             550             555             560

Asp Gly Ile Ala Ser Phe Ser Cys Ala Cys Ala Pro Gly Tyr Thr Gly
            565             570             575

Thr Arg Cys Glu Ser Gln Val Asp Glu Cys Arg Ser Gln Pro Cys Arg
            580             585             590

His Gly Gly Lys Cys Leu Asp Leu Val Asp Lys Tyr Leu Cys Arg Cys
            595             600             605

Pro Ser Gly Thr Thr Gly Val Asn Cys Glu Val Asn Ile Asp Asp Cys
    610             615             620

Ala Ser Asn Pro Cys Thr Phe Gly Val Cys Arg Asp Gly Ile Asn Arg
625             630             635             640

Tyr Asp Cys Val Cys Gln Pro Gly Phe Thr Gly Pro Leu Cys Asn Val
            645             650             655

Glu Ile Asn Glu Cys Ala Ser Ser Pro Cys Gly Glu Gly Gly Ser Cys
            660             665             670

Val Asp Gly Glu Asn Gly Phe Arg Cys Leu Cys Pro Pro Gly Ser Leu
            675             680             685

Pro Pro Leu Cys Leu Pro Pro Ser His Pro Cys Ala His Glu Pro Cys
    690             695             700

Ser His Gly Ile Cys Tyr Asp Ala Pro Gly Gly Phe Arg Cys Val Cys
705             710             715             720

Glu Pro Gly Trp Ser Gly Pro Arg Cys Ser Gln Ser Leu Ala Arg Asp
            725             730             735

Ala Cys Glu Ser Gln Pro Cys Arg Ala Gly Gly Thr Cys Ser Ser Asp
            740             745             750

Gly Met Gly Phe His Cys Thr Cys Pro Pro Gly Val Gln Gly Arg Gln
            755             760             765

Cys Glu Leu Leu Ser Pro Cys Thr Pro Asn Pro Cys Glu His Gly Gly
    770             775             780

Arg Cys Glu Ser Ala Pro Gly Gln Leu Pro Val Cys Ser Cys Pro Gln
```

257                                                                                  258

```
785              790              795              800

Gly Trp Gln Gly Pro Arg Cys Gln Gln Asp Val Asp Glu Cys Ala Gly
            805              810              815

Pro Ala Pro Cys Gly Pro His Gly Ile Cys Thr Asn Leu Ala Gly Ser
            820              825              830

Phe Ser Cys Thr Cys His Gly Gly Tyr Thr Gly Pro Ser Cys Asp Gln
            835              840              845

Asp Ile Asn Asp Cys Asp Pro Asn Pro Cys Leu Asn Gly Gly Ser Cys
850              855              860

Gln Asp Gly Val Gly Ser Phe Ser Cys Ser Cys Leu Pro Gly Phe Ala
865              870              875              880

Gly Pro Arg Cys Ala Arg Asp Val Asp Glu Cys Leu Ser Asn Pro Cys
            885              890              895

Gly Pro Gly Thr Cys Thr Asp His Val Ala Ser Phe Thr Cys Thr Cys
            900              905              910

Pro Pro Gly Tyr Gly Gly Phe His Cys Glu Gln Asp Leu Pro Asp Cys
            915              920              925

Ser Pro Ser Ser Cys Phe Asn Gly Gly Thr Cys Val Asp Gly Val Asn
930              935              940

Ser Phe Ser Cys Leu Cys Arg Pro Gly Tyr Thr Gly Ala His Cys Gln
945              950              955              960

His Glu Ala Asp Pro Cys Leu Ser Arg Pro Cys Leu His Gly Gly Val
            965              970              975

Cys Ser Ala Ala His Pro Gly Phe Arg Cys Thr Cys Leu Glu Ser Phe
            980              985              990

Thr Gly Pro Gln Cys Gln Thr Leu  Val Asp Trp Cys Ser  Arg Gln Pro
            995              1000              1005

Cys Gln  Asn Gly Gly Arg Cys  Val Gln Thr Gly Ala  Tyr Cys Leu
    1010              1015              1020

Cys Pro  Pro Gly Trp Ser Gly  Arg Leu Cys Asp Ile  Arg Ser Leu
    1025              1030              1035

Pro Cys  Arg Glu Ala Ala Ala  Gln Ile Gly Val Arg  Leu Glu Gln
    1040              1045              1050

Leu Cys  Gln Ala Gly Gly Gln  Cys Val Asp Glu Asp  Ser Ser His
    1055              1060              1065

Tyr Cys  Val Cys Pro Glu Gly  Arg Thr Gly Ser His  Cys Glu Gln
    1070              1075              1080

Glu Val  Asp Pro Cys Leu Ala  Gln Pro Cys Gln His  Gly Gly Thr
    1085              1090              1095

Cys Arg  Gly Tyr Met Gly Gly  Tyr Met Cys Glu Cys  Leu Pro Gly
    1100              1105              1110

Tyr Asn  Gly Asp Asn Cys Glu  Asp Asp Val Asp Glu  Cys Ala Ser
    1115              1120              1125

Gln Pro  Cys Gln His Gly Gly  Ser Cys Ile Asp Leu  Val Ala Arg
    1130              1135              1140

Tyr Leu  Cys Ser Cys Pro Pro  Gly Thr Leu Gly Val  Leu Cys Glu
    1145              1150              1155

Ile Asn  Glu Asp Asp Cys Gly  Pro Gly Pro Pro Leu  Asp Ser Gly
    1160              1165              1170

Pro Arg  Cys Leu His Asn Gly  Thr Cys Val Asp Leu  Val Gly Gly
    1175              1180              1185

Phe Arg  Cys Thr Cys Pro Pro  Gly Tyr Thr Gly Leu  Arg Cys Glu
    1190              1195              1200
```

```
Ala Asp Ile Asn Glu Cys Arg  Ser Gly Ala Cys His  Ala Ala His
    1205              1210              1215

Thr Arg Asp Cys Leu Gln Asp  Pro Gly Gly Gly Phe  Arg Cys Leu
    1220              1225              1230

Cys His Ala Gly Phe Ser Gly  Pro Arg Cys Gln Thr  Val Leu Ser
    1235              1240              1245

Pro Cys Glu Ser Gln Pro Cys  Gln His Gly Gly Gln  Cys Arg Pro
    1250              1255              1260

Ser Pro Gly Pro Gly Gly Gly  Leu Thr Phe Thr Cys  His Cys Ala
    1265              1270              1275

Gln Pro Phe Trp Gly Pro Arg  Cys Glu Arg Val Ala  Arg Ser Cys
    1280              1285              1290

Arg Glu Leu Gln Cys Pro Val  Gly Val Pro Cys Gln  Gln Thr Pro
    1295              1300              1305

Arg Gly Pro Arg Cys Ala Cys  Pro Pro Gly Leu Ser  Gly Pro Ser
    1310              1315              1320

Cys Arg Ser Phe Pro Gly Ser  Pro Pro Gly Ala Ser  Asn Ala Ser
    1325              1330              1335

Cys Ala Ala Ala Pro Cys Leu  His Gly Gly Ser Cys  Arg Pro Ala
    1340              1345              1350

Pro Leu Ala Pro Phe Phe Arg  Cys Ala Cys Ala Gln  Gly Trp Thr
    1355              1360              1365

Gly Pro Arg Cys Glu Ala Pro  Ala Ala Ala Pro Glu  Val Ser Glu
    1370              1375              1380

Glu Pro Arg Cys Pro Arg Ala  Ala Cys Gln Ala Lys  Arg Gly Asp
    1385              1390              1395

Gln Arg Cys Asp Arg Glu Cys  Asn Ser Pro Gly Cys  Gly Trp Asp
    1400              1405              1410

Gly Gly Asp Cys Ser Leu Ser  Val Gly Asp Pro Trp  Arg Gln Cys
    1415              1420              1425

Glu Ala Leu Gln Cys Trp Arg  Leu Phe Asn Asn Ser  Arg Cys Asp
    1430              1435              1440

Pro Ala Cys Ser Ser Pro Ala  Cys Leu Tyr Asp Asn  Phe Asp Cys
    1445              1450              1455

His Ala Gly Gly Arg Glu Arg  Thr Cys Asn Pro Val  Tyr Glu Lys
    1460              1465              1470

Tyr Cys Ala Asp His Phe Ala  Asp Gly Arg Cys Asp  Gln Gly Cys
    1475              1480              1485

Asn Thr Glu Glu Cys Gly Trp  Asp Gly Leu Asp Cys  Ala Ser Glu
    1490              1495              1500

Val Pro Ala Leu Leu Ala Arg  Gly Val Leu Val Leu  Thr Val Leu
    1505              1510              1515

Leu Pro Pro Glu Glu Leu Leu  Arg Ser Ser Ala Asp  Phe Leu Gln
    1520              1525              1530

Arg Leu Ser Ala Ile Leu Arg  Thr Ser Leu Arg Phe  Arg Leu Asp
    1535              1540              1545

Ala His Gly Gln Ala Met Val  Phe Pro Tyr His Arg  Pro Ser Pro
    1550              1555              1560

Gly Ser Glu Pro Arg Ala Arg  Arg Glu Leu Ala Pro  Glu Val Ile
    1565              1570              1575

Gly Ser Val Val Met Leu Glu  Ile Asp Asn Arg Leu  Cys Leu Gln
    1580              1585              1590
```

-continued

```
Ser Pro  Glu Asn Asp His Cys  Phe Pro Asp Ala Gln  Ser Ala Ala
    1595             1600             1605

Asp Tyr  Leu Gly Ala Leu Ser  Ala Val Glu Arg Leu  Asp Phe Pro
    1610             1615             1620

Tyr Pro  Leu Arg Asp Val Arg  Gly Glu Pro Leu Glu  Pro Pro Glu
    1625             1630             1635

Pro Ser  Val Pro Leu Leu Pro  Leu Leu Val Ala Gly  Ala Val Leu
    1640             1645             1650

Leu Leu  Val Ile Leu Val Leu  Gly Val Met Val Ala  Arg Arg Lys
    1655             1660             1665

Arg Glu  His Ser Thr Leu Trp  Phe Pro Glu Gly Phe  Ser Leu His
    1670             1675             1680

Lys Asp  Val Ala Ser Gly His  Lys Gly Arg Arg Glu  Pro Val Gly
    1685             1690             1695

Gln Asp  Ala Leu Gly Met Lys  Asn Met Ala Lys Gly  Glu Ser Leu
    1700             1705             1710

Met Gly  Glu Val Ala Thr Asp  Trp Met Asp Thr Glu  Cys Pro Glu
    1715             1720             1725

Ala Lys  Arg Leu Lys Val Glu  Glu Pro Gly Met Gly  Ala Glu Glu
    1730             1735             1740

Ala Val  Asp Cys Arg Gln Trp  Thr Gln His His Leu  Val Ala Ala
    1745             1750             1755

Asp Ile  Arg Val Ala Pro Ala  Met Ala Leu Thr Pro  Pro Gln Gly
    1760             1765             1770

Asp Ala  Asp Ala Asp Gly Met  Asp Val Asn Val Arg  Gly Pro Asp
    1775             1780             1785

Gly Phe  Thr Pro Leu Met Leu  Ala Ser Phe Cys Gly  Gly Ala Leu
    1790             1795             1800

Glu Pro  Met Pro Thr Glu Glu  Asp Glu Ala Asp Asp  Thr Ser Ala
    1805             1810             1815

Ser Ile  Ile Ser Asp Leu Ile  Cys Gln Gly Ala Gln  Leu Gly Ala
    1820             1825             1830

Arg Thr  Asp Arg Thr Gly Glu  Thr Ala Leu His Leu  Ala Ala Arg
    1835             1840             1845

Tyr Ala  Arg Ala Asp Ala Ala  Lys Arg Leu Leu Asp  Ala Gly Ala
    1850             1855             1860

Asp Thr  Asn Ala Gln Asp His  Ser Gly Arg Thr Pro  Leu His Thr
    1865             1870             1875

Ala Val  Thr Ala Asp Ala Gln  Gly Val Phe Gln Ile  Leu Ile Arg
    1880             1885             1890

Asn Arg  Ser Thr Asp Leu Asp  Ala Arg Met Ala Asp  Gly Ser Thr
    1895             1900             1905

Ala Leu  Ile Leu Ala Ala Arg  Leu Ala Val Glu Gly  Met Val Glu
    1910             1915             1920

Glu Leu  Ile Ala Ser His Ala  Asp Val Asn Ala Val  Asp Glu Leu
    1925             1930             1935

Gly Lys  Ser Ala Leu His Trp  Ala Ala Ala Val Asn  Asn Val Glu
    1940             1945             1950

Ala Thr  Leu Ala Leu Leu Lys  Asn Gly Ala Asn Lys  Asp Met Gln
    1955             1960             1965

Asp Ser  Lys Glu Glu Thr Pro  Leu Phe Leu Ala Ala  Arg Glu Gly
    1970             1975             1980

Ser Tyr  Glu Ala Ala Lys Leu  Leu Leu Asp His Phe  Ala Asn Arg
```

```
       1985              1990              1995

Glu Ile  Thr Asp His Leu Asp  Arg Leu Pro Arg Asp  Val Ala Gln
   2000              2005              2010

Glu Arg  Leu His Gln Asp Ile  Val Arg Leu Leu Asp  Gln Pro Ser
   2015              2020              2025

Gly Pro  Arg Ser Pro Pro Gly  Pro His Gly Leu Gly  Pro Leu Leu
   2030              2035              2040

Cys Pro  Pro Gly Ala Phe Leu  Pro Gly Leu Lys Ala  Ala Gln Ser
   2045              2050              2055

Gly Ser  Lys Lys Ser Arg Arg  Pro Pro Gly Lys Ala  Gly Leu Gly
   2060              2065              2070

Pro Gln  Gly Pro Arg Gly Arg  Gly Lys Lys Leu Thr  Leu Ala Cys
   2075              2080              2085

Pro Gly  Pro Leu Ala Asp Ser  Ser Val Thr Leu Ser  Pro Val Asp
   2090              2095              2100

Ser Leu  Asp Ser Pro Arg Pro  Phe Gly Gly Pro Pro  Ala Ser Pro
   2105              2110              2115

Gly Gly  Phe Pro Leu Glu Gly  Pro Tyr Ala Ala Ala  Thr Ala Thr
   2120              2125              2130

Ala Val  Ser Leu Ala Gln Leu  Gly Gly Pro Gly Arg  Ala Gly Leu
   2135              2140              2145

Gly Arg  Gln Pro Pro Gly Gly  Cys Val Leu Ser Leu  Gly Leu Leu
   2150              2155              2160

Asn Pro  Val Ala Val Pro Leu  Asp Trp Ala Arg Leu  Pro Pro Pro
   2165              2170              2175

Ala Pro  Pro Gly Pro Ser Phe  Leu Leu Pro Leu Ala  Pro Gly Pro
   2180              2185              2190

Gln Leu  Leu Asn Pro Gly Thr  Pro Val Ser Pro Gln  Glu Arg Pro
   2195              2200              2205

Pro Pro  Tyr Leu Ala Val Pro  Gly His Gly Glu Glu  Tyr Pro Ala
   2210              2215              2220

Ala Gly  Ala His Ser Ser Pro  Pro Lys Ala Arg Phe  Leu Arg Val
   2225              2230              2235

Pro Ser  Glu His Pro Tyr Leu  Thr Pro Ser Pro Glu  Ser Pro Glu
   2240              2245              2250

His Trp  Ala Ser Pro Ser Pro  Pro Ser Leu Ser Asp  Trp Ser Glu
   2255              2260              2265

Ser Thr  Pro Ser Pro Ala Thr  Ala Thr Gly Ala Met  Ala Thr Thr
   2270              2275              2280

Thr Gly  Ala Leu Pro Ala Gln  Pro Leu Pro Leu Ser  Val Pro Ser
   2285              2290              2295

Ser Leu  Ala Gln Ala Gln Thr  Gln Leu Gly Pro Gln  Pro Glu Val
   2300              2305              2310

Thr Pro  Lys Arg Gln Val Leu  Ala
   2315              2320

<210> SEQ ID NO 25
<211> LENGTH: 1289
<212> TYPE: PRT
<213> ORGANISM: homo sapien

<400> SEQUENCE: 25

Gly Ala Glu Ala Gly Pro Gly Ala Arg Gly Arg Arg Arg Arg Arg
1                 5                 10                15
```

-continued

```
Pro Met Ser Pro Pro Pro Pro Pro Pro Val Arg Ala Leu Pro Leu
            20              25                  30

Leu Leu Leu Leu Ala Gly Pro Gly Ala Ala Ala Pro Pro Cys Leu Asp
            35              40                  45

Gly Ser Pro Cys Ala Asn Gly Gly Arg Cys Thr Gln Leu Pro Ser Arg
        50              55              60

Glu Ala Ala Cys Leu Cys Pro Pro Gly Trp Val Gly Glu Arg Cys Gln
65              70              75                  80

Leu Glu Asp Pro Cys His Ser Gly Pro Cys Ala Gly Arg Gly Val Cys
            85              90                  95

Gln Ser Ser Val Val Ala Gly Thr Ala Arg Phe Ser Cys Arg Cys Pro
            100             105             110

Arg Gly Phe Arg Gly Pro Asp Cys Ser Leu Pro Asp Pro Cys Leu Ser
            115             120             125

Ser Pro Cys Ala His Gly Ala Arg Cys Ser Val Gly Pro Asp Gly Arg
        130             135             140

Phe Leu Cys Ser Cys Pro Pro Gly Tyr Gln Gly Arg Ser Cys Arg Ser
145             150             155             160

Asp Val Asp Glu Cys Arg Val Gly Glu Pro Cys Arg His Gly Gly Thr
            165             170             175

Cys Leu Asn Thr Pro Gly Ser Phe Arg Cys Gln Cys Pro Ala Gly Tyr
            180             185             190

Thr Gly Pro Leu Cys Glu Asn Pro Ala Val Pro Cys Ala Pro Ser Pro
            195             200             205

Cys Arg Asn Gly Gly Thr Cys Arg Gln Ser Gly Asp Leu Thr Tyr Asp
        210             215             220

Cys Ala Cys Leu Pro Gly Phe Glu Gly Gln Asn Cys Glu Val Asn Val
225             230             235             240

Asp Asp Cys Pro Gly His Arg Cys Leu Asn Gly Gly Thr Cys Val Asp
            245             250             255

Gly Val Asn Thr Tyr Asn Cys Gln Cys Pro Pro Glu Trp Thr Gly Gln
        260             265             270

Phe Cys Thr Glu Asp Val Asp Glu Cys Gln Leu Gln Pro Asn Ala Cys
            275             280             285

His Asn Gly Gly Thr Cys Phe Asn Thr Leu Gly Gly His Ser Cys Val
    290             295             300

Cys Val Asn Gly Trp Thr Gly Glu Ser Cys Ser Gln Asn Ile Asp Asp
305             310             315             320

Cys Ala Thr Ala Val Cys Phe His Gly Ala Thr Cys His Asp Arg Val
            325             330             335

Ala Ser Phe Tyr Cys Ala Cys Pro Met Gly Lys Thr Gly Leu Leu Cys
            340             345             350

His Leu Asp Asp Ala Cys Val Ser Asn Pro Cys His Glu Asp Ala Ile
        355             360             365

Cys Asp Thr Asn Pro Val Asn Gly Arg Ala Ile Cys Thr Cys Pro Pro
        370             375             380

Gly Phe Thr Gly Gly Ala Cys Asp Gln Asp Val Asp Glu Cys Ser Ile
385             390             395             400

Gly Ala Asn Pro Cys Glu His Leu Gly Arg Cys Val Asn Thr Gln Gly
            405             410             415

Ser Phe Leu Cys Gln Cys Gly Arg Gly Tyr Thr Gly Pro Arg Cys Glu
            420             425             430

Thr Asp Val Asn Glu Cys Leu Ser Gly Pro Cys Arg Asn Gln Ala Thr
```

```
              435                 440                 445

Cys Leu Asp Arg Ile Gly Gln Phe Thr Cys Ile Cys Met Ala Gly Phe
    450                 455                 460

Thr Gly Thr Tyr Cys Glu Val Asp Ile Asp Glu Cys Gln Ser Ser Pro
465                 470                 475                 480

Cys Val Asn Gly Gly Val Cys Lys Asp Arg Val Asn Gly Phe Ser Cys
                    485                 490                 495

Thr Cys Pro Ser Gly Phe Ser Gly Ser Thr Cys Gln Leu Asp Val Asp
                500                 505                 510

Glu Cys Ala Ser Thr Pro Cys Arg Asn Gly Ala Lys Cys Val Asp Gln
        515                 520                 525

Pro Asp Gly Tyr Glu Cys Arg Cys Ala Glu Gly Phe Glu Gly Thr Leu
    530                 535                 540

Cys Asp Arg Asn Val Asp Asp Cys Ser Pro Asp Pro Cys His His Gly
545                 550                 555                 560

Arg Cys Val Asp Gly Ile Ala Ser Phe Ser Cys Ala Cys Ala Pro Gly
                565                 570                 575

Tyr Thr Gly Thr Arg Cys Glu Ser Gln Val Asp Glu Cys Arg Ser Gln
            580                 585                 590

Pro Cys Arg His Gly Gly Lys Cys Leu Asp Leu Val Asp Lys Tyr Leu
        595                 600                 605

Cys Arg Cys Pro Ser Gly Thr Thr Gly Val Asn Cys Glu Val Asn Ile
    610                 615                 620

Asp Asp Cys Ala Ser Asn Pro Cys Thr Phe Gly Val Cys Arg Asp Gly
625                 630                 635                 640

Ile Asn Arg Tyr Asp Cys Val Cys Gln Pro Gly Phe Thr Gly Pro Leu
                645                 650                 655

Cys Asn Val Glu Ile Asn Glu Cys Ala Ser Ser Pro Cys Gly Glu Gly
            660                 665                 670

Gly Ser Cys Val Asp Gly Glu Asn Gly Phe Arg Cys Leu Cys Pro Pro
        675                 680                 685

Gly Ser Leu Pro Pro Leu Cys Leu Pro Pro Ser His Pro Cys Ala His
    690                 695                 700

Glu Pro Cys Ser His Gly Ile Cys Tyr Asp Ala Pro Gly Gly Phe Arg
705                 710                 715                 720

Cys Val Cys Glu Pro Gly Trp Ser Gly Pro Arg Cys Ser Gln Ser Leu
                725                 730                 735

Ala Arg Asp Ala Cys Glu Ser Gln Pro Cys Arg Ala Gly Gly Thr Cys
                740                 745                 750

Ser Ser Asp Gly Met Gly Phe His Cys Thr Cys Pro Pro Gly Val Gln
            755                 760                 765

Gly Arg Gln Cys Glu Leu Leu Ser Pro Cys Thr Pro Asn Pro Cys Glu
        770                 775                 780

His Gly Gly Arg Cys Glu Ser Ala Pro Gly Gln Leu Pro Val Cys Ser
785                 790                 795                 800

Cys Pro Gln Gly Trp Gln Asp Pro Cys Leu Asn Gly Gly Ser Cys Gln
                805                 810                 815

Asp Gly Val Gly Ser Phe Ser Cys Ser Cys Leu Pro Gly Phe Ala Gly
            820                 825                 830

Pro Arg Cys Ala Arg Asp Val Asp Glu Cys Leu Ser Asn Pro Cys Gly
        835                 840                 845

Pro Gly Thr Cys Thr Asp His Val Ala Ser Phe Thr Cys Thr Cys Pro
    850                 855                 860
```

-continued

```
Pro Gly Tyr Gly Gly Phe His Cys Glu Gln Asp Leu Pro Asp Cys Ser
865                 870                 875                 880

Pro Ser Ser Cys Phe Asn Gly Gly Thr Cys Val Asp Gly Val Asn Ser
                885                 890                 895

Phe Ser Cys Leu Cys Arg Pro Gly Tyr Thr Gly Ala His Cys Gln His
            900                 905                 910

Glu Ala Asp Pro Cys Leu Ser Arg Pro Cys Leu His Gly Gly Val Cys
            915                 920                 925

Ser Ala Ala His Pro Gly Phe Arg Cys Thr Cys Leu Glu Ser Phe Thr
    930                 935                 940

Gly Pro Gln Cys Gln Thr Leu Val Asp Trp Cys Ser Arg Gln Pro Cys
945                 950                 955                 960

Gln Asn Gly Gly Arg Cys Val Gln Thr Gly Ala Tyr Cys Leu Cys Pro
                965                 970                 975

Pro Gly Trp Ser Gly Arg Leu Cys Asp Ile Arg Ser Leu Pro Cys Arg
                980                 985                 990

Glu Ala Ala Ala Gln Ile Gly Val  Arg Leu Glu Gln Leu  Cys Gln Ala
        995                 1000                1005

Gly Gly  Gln Cys Val Asp Glu  Asp Ser Ser His Tyr  Cys Val Cys
    1010                1015                1020

Pro Glu  Gly Arg Thr Gly Ser  His Cys Glu Gln Glu  Val Asp Pro
    1025                1030                1035

Cys Leu  Ala Gln Pro Cys Gln  His Gly Gly Thr Cys  Arg Gly Tyr
    1040                1045                1050

Met Gly  Gly Tyr Met Cys Glu  Cys Leu Pro Gly Tyr  Asn Gly Asp
    1055                1060                1065

Asn Cys  Glu Asp Asp Val Asp  Glu Cys Ala Ser Gln  Pro Cys Gln
    1070                1075                1080

His Gly  Gly Ser Cys Ile Asp  Leu Val Ala Arg Tyr  Leu Cys Ser
    1085                1090                1095

Cys Pro  Pro Gly Thr Leu Gly  Val Leu Cys Glu Ile  Asn Glu Asp
    1100                1105                1110

Asp Cys  Gly Pro Gly Pro Pro  Leu Asp Ser Gly Pro  Arg Cys Leu
    1115                1120                1125

His Asn  Gly Thr Cys Val Asp  Leu Val Gly Gly Phe  Arg Cys Thr
    1130                1135                1140

Cys Pro  Pro Gly Tyr Thr Gly  Leu Arg Cys Glu Ala  Asp Ile Asn
    1145                1150                1155

Glu Cys  Arg Ser Gly Ala Cys  His Ala Ala His Thr  Arg Asp Cys
    1160                1165                1170

Leu Gln  Asp Pro Gly Gly Gly  Phe Arg Cys Leu Cys  His Ala Gly
    1175                1180                1185

Phe Ser  Gly Pro Arg Cys Gln  Thr Val Leu Ser Pro  Cys Glu Ser
    1190                1195                1200

Gln Pro  Cys Gln His Gly Gly  Gln Cys Arg Pro Ser  Pro Gly Pro
    1205                1210                1215

Gly Gly  Gly Leu Thr Phe Thr  Cys His Cys Ala Gln  Pro Phe Trp
    1220                1225                1230

Gly Pro  Arg Cys Glu Arg Val  Ala Arg Ser Cys Arg  Glu Leu Gln
    1235                1240                1245

Cys Pro  Val Gly Val Pro Cys  Gln Gln Thr Pro Arg  Gly Pro Arg
    1250                1255                1260
```

-continued

```
Cys Ala  Cys Pro Pro Gly Leu  Ser Gly Pro Ser Cys  Arg Ser Phe
    1265             1270              1275

Pro Gly  Ser Pro Pro Gly Ala  Ser Asn Ala Ser
    1280             1285

<210> SEQ ID NO 26
<211> LENGTH: 1286
<212> TYPE: PRT
<213> ORGANISM: homo sapien

<400> SEQUENCE: 26

Gly Pro Gly Ala Arg Gly Arg Arg Arg Arg Arg Pro Met Ser Pro
1               5                10              15

Pro Pro Pro Pro Pro Pro Val Arg Ala Leu Pro Leu Leu Leu Leu Leu
            20              25              30

Ala Gly Pro Gly Ala Ala Ala Pro Pro Cys Leu Asp Gly Ser Pro Cys
        35              40              45

Ala Asn Gly Gly Arg Cys Thr Gln Leu Pro Ser Arg Glu Ala Ala Cys
    50              55              60

Leu Cys Pro Pro Gly Trp Val Gly Glu Arg Cys Gln Leu Glu Asp Pro
65              70              75              80

Cys His Ser Gly Pro Cys Ala Gly Arg Gly Val Cys Gln Ser Ser Val
            85              90              95

Val Ala Gly Thr Ala Arg Phe Ser Cys Arg Cys Pro Arg Gly Phe Arg
            100             105             110

Gly Pro Asp Cys Ser Leu Pro Asp Pro Cys Leu Ser Ser Pro Cys Ala
            115             120             125

His Gly Ala Arg Cys Ser Val Gly Pro Asp Gly Arg Phe Leu Cys Ser
    130             135             140

Cys Pro Pro Gly Tyr Gln Gly Arg Ser Cys Arg Ser Asp Val Asp Glu
145             150             155             160

Cys Arg Val Gly Glu Pro Cys Arg His Gly Gly Thr Cys Leu Asn Thr
            165             170             175

Pro Gly Ser Phe Arg Cys Gln Cys Pro Ala Gly Tyr Thr Gly Pro Leu
            180             185             190

Cys Glu Asn Pro Ala Val Pro Cys Ala Pro Ser Pro Cys Arg Asn Gly
    195             200             205

Gly Thr Cys Arg Gln Ser Gly Asp Leu Thr Tyr Asp Cys Ala Cys Leu
    210             215             220

Pro Gly Phe Glu Gly Gln Asn Cys Glu Val Asn Val Asp Asp Cys Pro
225             230             235             240

Gly His Arg Cys Leu Asn Gly Gly Thr Cys Val Asp Gly Val Asn Thr
            245             250             255

Tyr Asn Cys Gln Cys Pro Pro Glu Trp Thr Gly Gln Phe Cys Thr Glu
            260             265             270

Asp Val Asp Glu Cys Gln Leu Gln Pro Asn Ala Cys His Asn Gly Gly
            275             280             285

Thr Cys Phe Asn Thr Leu Gly Gly His Ser Cys Val Cys Val Asn Gly
            290             295             300

Trp Thr Gly Glu Ser Cys Ser Gln Asn Ile Asp Asp Cys Ala Thr Ala
305             310             315             320

Val Cys Phe His Gly Ala Thr Cys His Asp Arg Val Ala Ser Phe Tyr
            325             330             335

Cys Ala Cys Pro Met Gly Lys Thr Gly Leu Leu Cys His Leu Asp Asp
            340             345             350
```

```
Ala Cys Val Ser Asn Pro Cys His Glu Asp Ala Ile Cys Asp Thr Asn
        355                 360                 365

Pro Val Asn Gly Arg Ala Ile Cys Thr Cys Pro Pro Gly Phe Thr Gly
        370                 375                 380

Gly Ala Cys Asp Gln Asp Val Asp Glu Cys Ser Ile Gly Ala Asn Pro
385                 390                 395                 400

Cys Glu His Leu Gly Arg Cys Val Asn Thr Gln Gly Ser Phe Leu Cys
                405                 410                 415

Gln Cys Gly Arg Gly Tyr Thr Gly Pro Arg Cys Glu Thr Asp Val Asn
                420                 425                 430

Glu Cys Leu Ser Gly Pro Cys Arg Asn Gln Ala Thr Cys Leu Asp Arg
                435                 440                 445

Ile Gly Gln Phe Thr Cys Ile Cys Met Ala Gly Phe Thr Gly Thr Tyr
        450                 455                 460

Cys Glu Val Asp Ile Asp Glu Cys Gln Ser Ser Pro Cys Val Asn Gly
465                 470                 475                 480

Gly Val Cys Lys Asp Arg Val Asn Gly Phe Ser Cys Thr Cys Pro Ser
                485                 490                 495

Gly Phe Ser Gly Ser Thr Cys Gln Leu Asp Val Asp Glu Cys Ala Ser
                500                 505                 510

Thr Pro Cys Arg Asn Gly Ala Lys Cys Val Asp Gln Pro Asp Gly Tyr
                515                 520                 525

Glu Cys Arg Cys Ala Glu Gly Phe Glu Gly Thr Leu Cys Asp Arg Asn
        530                 535                 540

Val Asp Asp Cys Ser Pro Asp Pro Cys His His Gly Arg Cys Val Asp
545                 550                 555                 560

Gly Ile Ala Ser Phe Ser Cys Ala Cys Ala Pro Gly Tyr Thr Gly Thr
                565                 570                 575

Arg Cys Glu Ser Gln Val Asp Glu Cys Arg Ser Gln Pro Cys Arg His
                580                 585                 590

Gly Gly Lys Cys Leu Asp Leu Val Asp Lys Tyr Leu Cys Arg Cys Pro
                595                 600                 605

Ser Gly Thr Thr Gly Val Asn Cys Glu Val Asn Ile Asp Asp Cys Ala
        610                 615                 620

Ser Asn Pro Cys Thr Phe Gly Val Cys Arg Asp Gly Ile Asn Arg Tyr
625                 630                 635                 640

Asp Cys Val Cys Gln Pro Gly Phe Thr Gly Pro Leu Cys Asn Val Glu
                645                 650                 655

Ile Asn Glu Cys Ala Ser Ser Pro Cys Gly Glu Gly Gly Ser Cys Val
                660                 665                 670

Asp Gly Glu Asn Gly Phe Arg Cys Leu Cys Pro Pro Gly Ser Leu Pro
                675                 680                 685

Pro Leu Cys Leu Pro Pro Ser His Pro Cys Ala His Glu Pro Cys Ser
        690                 695                 700

His Gly Ile Cys Tyr Asp Ala Pro Gly Gly Phe Arg Cys Val Cys Glu
705                 710                 715                 720

Pro Gly Trp Ser Gly Pro Arg Cys Ser Gln Ser Leu Ala Arg Asp Ala
                725                 730                 735

Cys Glu Ser Gln Pro Cys Arg Ala Gly Gly Thr Cys Ser Ser Asp Gly
                740                 745                 750

Met Gly Phe His Cys Thr Cys Pro Pro Gly Val Gln Gly Arg Gln Cys
        755                 760                 765
```

-continued

```
Glu Leu Leu Ser Pro Cys Thr Pro Asn Pro Cys Glu His Gly Gly Arg
    770             775             780

Cys Glu Ser Ala Pro Gly Gln Leu Pro Val Cys Ser Cys Pro Gln Gly
785             790             795             800

Trp Gln Asp Pro Cys Leu Asn Gly Gly Ser Cys Gln Asp Gly Val Gly
            805             810             815

Ser Phe Ser Cys Ser Cys Leu Pro Gly Phe Ala Gly Pro Arg Cys Ala
            820             825             830

Arg Asp Val Asp Glu Cys Leu Ser Asn Pro Cys Gly Pro Gly Thr Cys
            835             840             845

Thr Asp His Val Ala Ser Phe Thr Cys Thr Cys Pro Pro Gly Tyr Gly
    850             855             860

Gly Phe His Cys Glu Gln Asp Leu Pro Asp Cys Ser Pro Ser Ser Cys
865             870             875             880

Phe Asn Gly Gly Thr Cys Val Asp Gly Val Asn Ser Phe Ser Cys Leu
            885             890             895

Cys Arg Pro Gly Tyr Thr Gly Ala His Cys Gln His Glu Ala Asp Pro
            900             905             910

Cys Leu Ser Arg Pro Cys Leu His Gly Gly Val Cys Ser Ala Ala His
    915             920             925

Pro Gly Phe Arg Cys Thr Cys Leu Glu Ser Phe Thr Gly Pro Gln Cys
    930             935             940

Gln Thr Leu Val Asp Trp Cys Ser Arg Gln Pro Cys Gln Asn Gly Gly
945             950             955             960

Arg Cys Val Gln Thr Gly Ala Tyr Cys Leu Cys Pro Pro Gly Trp Ser
            965             970             975

Gly Arg Leu Cys Asp Ile Arg Ser Leu Pro Cys Arg Glu Ala Ala Ala
            980             985             990

Gln Ile Gly Val Arg Leu Glu Gln  Leu Cys Gln Ala Gly  Gly Gln Cys
        995             1000             1005

Val Asp Glu Asp Ser Ser His  Tyr Cys Val Cys Pro  Glu Gly Arg
    1010             1015             1020

Thr Gly Ser His Cys Glu Gln  Glu Val Asp Pro Cys  Leu Ala Gln
    1025             1030             1035

Pro Cys Gln His Gly Gly Thr  Cys Arg Gly Tyr Met  Gly Gly Tyr
    1040             1045             1050

Met Cys Glu Cys Leu Pro Gly  Tyr Asn Gly Asp Asn  Cys Glu Asp
    1055             1060             1065

Asp Val Asp Glu Cys Ala Ser  Gln Pro Cys Gln His  Gly Gly Ser
    1070             1075             1080

Cys Ile Asp Leu Val Ala Arg  Tyr Leu Cys Ser Cys  Pro Pro Gly
    1085             1090             1095

Thr Leu Gly Val Leu Cys Glu  Ile Asn Glu Asp Asp  Cys Gly Pro
    1100             1105             1110

Gly Pro Pro Leu Asp Ser Gly  Pro Arg Cys Leu His  Asn Gly Thr
    1115             1120             1125

Cys Val Asp Leu Val Gly Gly  Phe Arg Cys Thr Cys  Pro Pro Gly
    1130             1135             1140

Tyr Thr Gly Leu Arg Cys Glu  Ala Asp Ile Asn Glu  Cys Arg Ser
    1145             1150             1155

Gly Ala Cys His Ala Ala His  Thr Arg Asp Cys Leu  Gln Asp Pro
    1160             1165             1170

Gly Gly Gly Phe Cys Cys Leu  Cys His Ala Gly Phe  Ser Gly Pro
```

-continued

```
            1175              1180              1185

Arg Cys Gln Thr Val Leu Ser  Pro Cys Glu Ser Gln  Pro Cys Gln
    1190              1195              1200

His Gly  Gly Gln Cys Arg Pro  Ser Pro Gly Pro Gly  Gly Gly Leu
    1205              1210              1215

Thr Phe  Thr Cys His Cys Ala  Gln Pro Phe Trp Gly  Pro Arg Cys
    1220              1225              1230

Glu Arg  Val Ala Arg Ser Cys  Arg Glu Leu Gln Cys  Pro Val Gly
    1235              1240              1245

Val Pro  Cys Gln Gln Thr Pro  Arg Gly Pro Arg Cys  Ala Cys Pro
    1250              1255              1260

Pro Gly  Leu Ser Gly Pro Ser  Cys Arg Ser Phe Pro  Gly Ser Pro
    1265              1270              1275

Pro Gly  Ala Ser Asn Ala Ser  Cys
    1280              1285

<210> SEQ ID NO 27
<211> LENGTH: 2321
<212> TYPE: PRT
<213> ORGANISM: homo sapien

<400> SEQUENCE: 27

Met Gly Pro Gly Ala Arg Gly Arg Arg Arg Arg Arg Pro Met Ser
1               5                10                15

Pro Pro Pro Pro Pro Pro Val Arg Ala Leu Pro Leu Leu Leu Leu
                20                25                30

Leu Ala Gly Pro Gly Ala Ala Ala Pro Pro Cys Leu Asp Gly Ser Pro
        35                40                45

Cys Ala Asn Gly Gly Arg Cys Thr Gln Leu Pro Ser Arg Glu Ala Ala
    50                55                60

Cys Leu Cys Pro Pro Gly Trp Val Gly Glu Arg Cys Gln Leu Glu Asp
65                70                75                80

Pro Cys His Ser Gly Pro Cys Ala Gly Arg Gly Val Cys Gln Ser Ser
            85                90                95

Val Val Ala Gly Thr Ala Arg Phe Ser Cys Arg Cys Pro Arg Gly Phe
            100               105               110

Arg Gly Pro Asp Cys Ser Leu Pro Asp Pro Cys Leu Ser Ser Pro Cys
        115               120               125

Ala His Gly Ala Arg Cys Ser Val Gly Pro Asp Gly Arg Phe Leu Cys
    130               135               140

Ser Cys Pro Pro Gly Tyr Gln Gly Arg Ser Cys Arg Ser Asp Val Asp
145               150               155               160

Glu Cys Arg Val Gly Glu Pro Cys Arg His Gly Gly Thr Cys Leu Asn
            165               170               175

Thr Pro Gly Ser Phe Arg Cys Gln Cys Pro Ala Gly Tyr Thr Gly Pro
            180               185               190

Leu Cys Glu Asn Pro Ala Val Pro Cys Ala Pro Ser Pro Cys Arg Asn
        195               200               205

Gly Gly Thr Cys Arg Gln Ser Gly Asp Leu Thr Tyr Asp Cys Ala Cys
    210               215               220

Leu Pro Gly Phe Glu Gly Gln Asn Cys Glu Val Asn Val Asp Asp Cys
225               230               235               240

Pro Gly His Arg Cys Leu Asn Gly Gly Thr Cys Val Asp Gly Val Asn
            245               250               255
```

```
Thr Tyr Asn Cys Gln Cys Pro Pro Glu Trp Thr Gly Gln Phe Cys Thr
            260             265             270

Glu Asp Val Asp Glu Cys Gln Leu Gln Pro Asn Ala Cys His Asn Gly
        275             280             285

Gly Thr Cys Phe Asn Thr Leu Gly Gly His Ser Cys Val Cys Val Asn
    290             295             300

Gly Trp Thr Gly Glu Ser Cys Ser Gln Asn Ile Asp Asp Cys Ala Thr
305             310             315             320

Ala Val Cys Phe His Gly Ala Thr Cys His Asp Arg Val Ala Ser Phe
            325             330             335

Tyr Cys Ala Cys Pro Met Gly Lys Thr Gly Leu Leu Cys His Leu Asp
            340             345             350

Asp Ala Cys Val Ser Asn Pro Cys His Glu Asp Ala Ile Cys Asp Thr
            355             360             365

Asn Pro Val Asn Gly Arg Ala Ile Cys Thr Cys Pro Pro Gly Phe Thr
    370             375             380

Gly Gly Ala Cys Asp Gln Asp Val Asp Glu Cys Ser Ile Gly Ala Asn
385             390             395             400

Pro Cys Glu His Leu Gly Arg Cys Val Asn Thr Gln Gly Ser Phe Leu
            405             410             415

Cys Gln Cys Gly Arg Gly Tyr Thr Gly Pro Arg Cys Glu Thr Asp Val
            420             425             430

Asn Glu Cys Leu Ser Gly Pro Cys Arg Asn Gln Ala Thr Cys Leu Asp
        435             440             445

Arg Ile Gly Gln Phe Thr Cys Ile Cys Met Ala Gly Phe Thr Gly Thr
    450             455             460

Tyr Cys Glu Val Asp Ile Asp Glu Cys Gln Ser Ser Pro Cys Val Asn
465             470             475             480

Gly Gly Val Cys Lys Asp Arg Val Asn Gly Phe Ser Cys Thr Cys Pro
            485             490             495

Ser Gly Phe Ser Gly Ser Thr Cys Gln Leu Asp Val Asp Glu Cys Ala
            500             505             510

Ser Thr Pro Cys Arg Asn Gly Ala Lys Cys Val Asp Gln Pro Asp Gly
            515             520             525

Tyr Glu Cys Arg Cys Ala Glu Gly Phe Glu Gly Thr Leu Cys Asp Arg
    530             535             540

Asn Val Asp Asp Cys Ser Pro Asp Pro Cys His His Gly Arg Cys Val
545             550             555             560

Asp Gly Ile Ala Ser Phe Ser Cys Ala Cys Ala Pro Gly Tyr Thr Gly
            565             570             575

Thr Arg Cys Glu Ser Gln Val Asp Glu Cys Arg Ser Gln Pro Cys Arg
            580             585             590

His Gly Gly Lys Cys Leu Asp Leu Val Asp Lys Tyr Leu Cys Arg Cys
            595             600             605

Pro Ser Gly Thr Thr Gly Val Asn Cys Glu Val Asn Ile Asp Asp Cys
    610             615             620

Ala Ser Asn Pro Cys Thr Phe Gly Val Cys Arg Asp Gly Ile Asn Arg
625             630             635             640

Tyr Asp Cys Val Cys Gln Pro Gly Phe Thr Gly Pro Leu Cys Asn Val
            645             650             655

Glu Ile Asn Glu Cys Ala Ser Ser Pro Cys Gly Glu Gly Gly Ser Cys
            660             665             670

Val Asp Gly Glu Asn Gly Phe Arg Cys Leu Cys Pro Pro Gly Ser Leu
```

-continued

```
                   675                 680                 685

Pro Pro Leu Cys Leu Pro Pro Ser His Pro Cys Ala His Glu Pro Cys
    690                 695                 700

Ser His Gly Ile Cys Tyr Asp Ala Pro Gly Gly Phe Arg Cys Val Cys
705                 710                 715                 720

Glu Pro Gly Trp Ser Gly Pro Arg Cys Ser Gln Ser Leu Ala Arg Asp
                725                 730                 735

Ala Cys Glu Ser Gln Pro Cys Arg Ala Gly Gly Thr Cys Ser Ser Asp
                740                 745                 750

Gly Met Gly Phe His Cys Thr Cys Pro Pro Gly Val Gln Gly Arg Gln
                755                 760                 765

Cys Glu Leu Leu Ser Pro Cys Thr Pro Asn Pro Cys Glu His Gly Gly
    770                 775                 780

Arg Cys Glu Ser Ala Pro Gly Gln Leu Pro Val Cys Ser Cys Pro Gln
785                 790                 795                 800

Gly Trp Gln Gly Pro Arg Cys Gln Gln Asp Val Asp Glu Cys Ala Gly
                805                 810                 815

Pro Ala Pro Cys Gly Pro His Gly Ile Cys Thr Asn Leu Ala Gly Ser
                820                 825                 830

Phe Ser Cys Thr Cys His Gly Gly Tyr Thr Gly Pro Ser Cys Asp Gln
                835                 840                 845

Asp Ile Asn Asp Cys Asp Pro Asn Pro Cys Leu Asn Gly Gly Ser Cys
    850                 855                 860

Gln Asp Gly Val Gly Ser Phe Ser Cys Ser Cys Leu Pro Gly Phe Ala
865                 870                 875                 880

Gly Pro Arg Cys Ala Arg Asp Val Asp Glu Cys Leu Ser Asn Pro Cys
                885                 890                 895

Gly Pro Gly Thr Cys Thr Asp His Val Ala Ser Phe Thr Cys Thr Cys
                900                 905                 910

Pro Pro Gly Tyr Gly Gly Phe His Cys Glu Gln Asp Leu Pro Asp Cys
                915                 920                 925

Ser Pro Ser Ser Cys Phe Asn Gly Gly Thr Cys Val Asp Gly Val Asn
    930                 935                 940

Ser Phe Ser Cys Leu Cys Arg Pro Gly Tyr Thr Gly Ala His Cys Gln
945                 950                 955                 960

His Glu Ala Asp Pro Cys Leu Ser Arg Pro Cys Leu His Gly Gly Val
                965                 970                 975

Cys Ser Ala Ala His Pro Gly Phe Arg Cys Thr Cys Leu Glu Ser Phe
                980                 985                 990

Thr Gly Pro Gln Cys Gln Thr Leu  Val Asp Trp Cys Ser  Arg Gln Pro
                995                 1000                1005

Cys Gln  Asn Gly Gly Arg Cys  Val Gln Thr Gly Ala  Tyr Cys Leu
    1010                1015                1020

Cys Pro  Pro Gly Trp Ser Gly  Arg Leu Cys Asp Ile  Arg Ser Leu
    1025                1030                1035

Pro Cys  Arg Glu Ala Ala Ala  Gln Ile Gly Val Arg  Leu Glu Gln
    1040                1045                1050

Leu Cys  Gln Ala Gly Gly Gln  Cys Val Asp Glu Asp  Ser Ser His
    1055                1060                1065

Tyr Cys  Val Cys Pro Glu Gly  Arg Thr Gly Ser His  Cys Glu Gln
    1070                1075                1080

Glu Val  Asp Pro Cys Leu Ala  Gln Pro Cys Gln His  Gly Gly Thr
    1085                1090                1095
```

-continued

```
Cys Arg  Gly Tyr Met Gly Gly  Tyr Met Cys Glu Cys  Leu Pro Gly
    1100             1105              1110

Tyr Asn  Gly Asp Asn Cys Glu  Asp Asp Val Asp Glu  Cys Ala Ser
    1115             1120              1125

Gln Pro  Cys Gln His Gly Gly  Ser Cys Ile Asp Leu  Val Ala Arg
    1130             1135              1140

Tyr Leu  Cys Ser Cys Pro Pro  Gly Thr Leu Gly Val  Leu Cys Glu
    1145             1150              1155

Ile Asn  Glu Asp Asp Cys Gly  Pro Gly Pro Pro Leu  Asp Ser Gly
    1160             1165              1170

Pro Arg  Cys Leu His Asn Gly  Thr Cys Val Asp Leu  Val Gly Gly
    1175             1180              1185

Phe Arg  Cys Thr Cys Pro Pro  Gly Tyr Thr Gly Leu  Arg Cys Glu
    1190             1195              1200

Ala Asp  Ile Asn Glu Cys Arg  Ser Gly Ala Cys His  Ala Ala His
    1205             1210              1215

Thr Arg  Asp Cys Leu Gln Asp  Pro Gly Gly Gly Phe  Cys Cys Leu
    1220             1225              1230

Cys His  Ala Gly Phe Ser Gly  Pro Arg Cys Gln Thr  Val Leu Ser
    1235             1240              1245

Pro Cys  Glu Ser Gln Pro Cys  Gln His Gly Gly Gln  Cys Arg Pro
    1250             1255              1260

Ser Pro  Gly Pro Gly Gly Gly  Leu Thr Phe Thr Cys  His Cys Ala
    1265             1270              1275

Gln Pro  Phe Trp Gly Pro Arg  Cys Glu Arg Val Ala  Arg Ser Cys
    1280             1285              1290

Arg Glu  Leu Gln Cys Pro Val  Gly Val Pro Cys Gln  Gln Thr Pro
    1295             1300              1305

Arg Gly  Pro Arg Cys Ala Cys  Pro Pro Gly Leu Ser  Gly Pro Ser
    1310             1315              1320

Cys Arg  Ser Phe Pro Gly Ser  Pro Pro Gly Ala Ser  Asn Ala Ser
    1325             1330              1335

Cys Ala  Ala Ala Pro Cys Leu  His Gly Gly Ser Cys  Arg Pro Ala
    1340             1345              1350

Pro Leu  Ala Pro Phe Phe Arg  Cys Ala Cys Ala Gln  Gly Trp Thr
    1355             1360              1365

Gly Pro  Arg Cys Glu Ala Pro  Ala Ala Ala Pro Glu  Val Ser Glu
    1370             1375              1380

Glu Pro  Arg Cys Pro Arg Ala  Ala Cys Gln Ala Lys  Arg Gly Asp
    1385             1390              1395

Gln Arg  Cys Asp Arg Glu Cys  Asn Ser Pro Gly Cys  Gly Trp Asp
    1400             1405              1410

Gly Gly  Asp Cys Ser Leu Ser  Val Gly Asp Pro Trp  Arg Gln Cys
    1415             1420              1425

Glu Ala  Leu Gln Cys Trp Arg  Leu Phe Asn Asn Ser  Arg Cys Asp
    1430             1435              1440

Pro Ala  Cys Ser Ser Pro Ala  Cys Leu Tyr Asp Asn  Phe Asp Cys
    1445             1450              1455

His Ala  Gly Gly Arg Glu Arg  Thr Cys Asn Pro Val  Tyr Glu Lys
    1460             1465              1470

Tyr Cys  Ala Asp His Phe Ala  Asp Gly Arg Cys Asp  Gln Gly Cys
    1475             1480              1485
```

-continued

```
Asn Thr Glu Glu Cys Gly Trp Asp Gly Leu Asp Cys Ala Ser Glu
    1490              1495              1500

Val Pro Ala Leu Leu Ala Arg Gly Val Leu Val Leu Thr Val Leu
    1505              1510              1515

Leu Pro Pro Glu Glu Leu Leu Arg Ser Ser Ala Asp Phe Leu Gln
    1520              1525              1530

Arg Leu Ser Ala Ile Leu Arg Thr Ser Leu Arg Phe Arg Leu Asp
    1535              1540              1545

Ala His Gly Gln Ala Met Val Phe Pro Tyr His Arg Pro Ser Pro
    1550              1555              1560

Gly Ser Glu Pro Arg Ala Arg Arg Glu Leu Ala Pro Glu Val Ile
    1565              1570              1575

Gly Ser Val Val Met Leu Glu Ile Asp Asn Arg Leu Cys Leu Gln
    1580              1585              1590

Ser Pro Glu Asn Asp His Cys Phe Pro Asp Ala Gln Ser Ala Ala
    1595              1600              1605

Asp Tyr Leu Gly Ala Leu Ser Ala Val Glu Arg Leu Asp Phe Pro
    1610              1615              1620

Tyr Pro Leu Arg Asp Val Arg Gly Glu Pro Leu Glu Pro Pro Glu
    1625              1630              1635

Pro Ser Val Pro Leu Leu Pro Leu Leu Val Ala Gly Ala Val Leu
    1640              1645              1650

Leu Leu Val Ile Leu Val Leu Gly Val Met Val Ala Arg Arg Lys
    1655              1660              1665

Arg Glu His Ser Thr Leu Trp Phe Pro Glu Gly Phe Ser Leu His
    1670              1675              1680

Lys Asp Val Ala Ser Gly His Lys Gly Arg Arg Glu Pro Val Gly
    1685              1690              1695

Gln Asp Ala Leu Gly Met Lys Asn Met Ala Lys Gly Glu Ser Leu
    1700              1705              1710

Met Gly Glu Val Ala Thr Asp Trp Met Asp Thr Glu Cys Pro Glu
    1715              1720              1725

Ala Lys Arg Leu Lys Val Glu Glu Pro Gly Met Gly Ala Glu Glu
    1730              1735              1740

Ala Val Asp Cys Arg Gln Trp Thr Gln His His Leu Val Ala Ala
    1745              1750              1755

Asp Ile Arg Val Ala Pro Ala Met Ala Leu Thr Pro Pro Gln Gly
    1760              1765              1770

Asp Ala Asp Ala Asp Gly Met Asp Val Asn Val Arg Gly Pro Asp
    1775              1780              1785

Gly Phe Thr Pro Leu Met Leu Ala Ser Phe Cys Gly Gly Ala Leu
    1790              1795              1800

Glu Pro Met Pro Thr Glu Glu Asp Glu Ala Asp Asp Thr Ser Ala
    1805              1810              1815

Ser Ile Ile Ser Asp Leu Ile Cys Gln Gly Ala Gln Leu Gly Ala
    1820              1825              1830

Arg Thr Asp Arg Thr Gly Glu Thr Ala Leu His Leu Ala Ala Arg
    1835              1840              1845

Tyr Ala Arg Ala Asp Ala Ala Lys Arg Leu Leu Asp Ala Gly Ala
    1850              1855              1860

Asp Thr Asn Ala Gln Asp His Ser Gly Arg Thr Pro Leu His Thr
    1865              1870              1875

Ala Val Thr Ala Asp Ala Gln Gly Val Phe Gln Ile Leu Ile Arg
```

-continued

```
          1880            1885            1890

Asn Arg Ser Thr Asp Leu Asp  Ala Arg Met Ala Asp  Gly Ser Thr
    1895            1900            1905

Ala Leu Ile Leu Ala Ala Arg  Leu Ala Val Glu Gly  Met Val Glu
    1910            1915            1920

Glu Leu Ile Ala Ser His Ala  Asp Val Asn Ala Val  Asp Glu Leu
    1925            1930            1935

Gly Lys Ser Ala Leu His Trp  Ala Ala Ala Val Asn  Asn Val Glu
    1940            1945            1950

Ala Thr Leu Ala Leu Leu Lys  Asn Gly Ala Asn Lys  Asp Met Gln
    1955            1960            1965

Asp Ser Lys Glu Glu Thr Pro  Leu Phe Leu Ala Ala  Arg Glu Gly
    1970            1975            1980

Ser Tyr Glu Ala Ala Lys Leu  Leu Leu Asp His Phe  Ala Asn Arg
    1985            1990            1995

Glu Ile Thr Asp His Leu Asp  Arg Leu Pro Arg Asp  Val Ala Gln
    2000            2005            2010

Glu Arg Leu His Gln Asp Ile  Val Arg Leu Leu Asp  Gln Pro Ser
    2015            2020            2025

Gly Pro Arg Ser Pro Pro Gly  Pro His Gly Leu Gly  Pro Leu Leu
    2030            2035            2040

Cys Pro Pro Gly Ala Phe Leu  Pro Gly Leu Lys Ala  Ala Gln Ser
    2045            2050            2055

Gly Ser Lys Lys Ser Arg Arg  Pro Pro Gly Lys Ala  Gly Leu Gly
    2060            2065            2070

Pro Gln Gly Pro Arg Gly Arg  Gly Lys Lys Leu Thr  Leu Ala Cys
    2075            2080            2085

Pro Gly Pro Leu Ala Asp Ser  Ser Val Thr Leu Ser  Pro Val Asp
    2090            2095            2100

Ser Leu Asp Ser Pro Arg Pro  Phe Gly Gly Pro Pro  Ala Ser Pro
    2105            2110            2115

Gly Gly Phe Pro Leu Glu Gly  Pro Tyr Ala Ala Ala  Thr Ala Thr
    2120            2125            2130

Ala Val Ser Leu Ala Gln Leu  Gly Gly Pro Gly Arg  Ala Gly Leu
    2135            2140            2145

Gly Arg Gln Pro Pro Gly Gly  Cys Val Leu Ser Leu  Gly Leu Leu
    2150            2155            2160

Asn Pro Val Ala Val Pro Leu  Asp Trp Ala Arg Leu  Pro Pro Pro
    2165            2170            2175

Ala Pro Pro Gly Pro Ser Phe  Leu Leu Pro Leu Ala  Pro Gly Pro
    2180            2185            2190

Gln Leu Leu Asn Pro Gly Thr  Pro Val Ser Pro Gln  Glu Arg Pro
    2195            2200            2205

Pro Pro Tyr Leu Ala Val Pro  Gly His Gly Glu Glu  Tyr Pro Ala
    2210            2215            2220

Ala Gly Ala His Ser Ser Pro  Pro Lys Ala Arg Phe  Leu Arg Val
    2225            2230            2235

Pro Ser Glu His Pro Tyr Leu  Thr Pro Ser Pro Glu  Ser Pro Glu
    2240            2245            2250

His Trp Ala Ser Pro Ser Pro  Pro Ser Leu Ser Asp  Trp Ser Glu
    2255            2260            2265

Ser Thr Pro Ser Pro Ala Thr  Ala Thr Gly Ala Met  Ala Thr Thr
    2270            2275            2280
```

```
Thr Gly  Ala Leu Pro Ala Gln  Pro Leu Pro Leu Ser  Val Pro Ser
    2285             2290             2295

Ser Leu  Ala Gln Ala Gln Thr  Gln Leu Gly Pro Gln  Pro Glu Val
    2300             2305             2310

Thr Pro  Lys Arg Gln Val Leu  Ala
    2315             2320

<210> SEQ ID NO 28
<211> LENGTH: 1289
<212> TYPE: PRT
<213> ORGANISM: homo sapien

<400> SEQUENCE: 28

Gly Ala Glu Ala Gly Pro Gly Ala Arg Gly Arg Arg Arg Arg Arg
1               5               10              15

Pro Met Ser Pro Pro Pro Pro Pro Pro Val Arg Ala Leu Pro Leu
            20              25              30

Leu Leu Leu Leu Ala Gly Pro Gly Ala Ala Ala Pro Pro Cys Leu Asp
        35              40              45

Gly Ser Pro Cys Ala Asn Gly Gly Arg Cys Thr Gln Leu Pro Ser Arg
    50              55              60

Glu Ala Ala Cys Leu Cys Pro Pro Gly Trp Val Gly Glu Arg Cys Gln
65              70              75              80

Leu Glu Asp Pro Cys His Ser Gly Pro Cys Ala Gly Arg Gly Val Cys
            85              90              95

Gln Ser Ser Val Val Ala Gly Thr Ala Arg Phe Ser Cys Arg Cys Pro
        100             105             110

Arg Gly Phe Arg Gly Pro Asp Cys Ser Leu Pro Asp Pro Cys Leu Ser
        115             120             125

Ser Pro Cys Ala His Gly Ala Arg Cys Ser Val Gly Pro Asp Gly Arg
    130             135             140

Phe Leu Cys Ser Cys Pro Pro Gly Tyr Gln Gly Arg Ser Cys Arg Ser
145             150             155             160

Asp Val Asp Glu Cys Arg Val Gly Glu Pro Cys Arg His Gly Gly Thr
            165             170             175

Cys Leu Asn Thr Pro Gly Ser Phe Arg Cys Gln Cys Pro Ala Gly Tyr
            180             185             190

Thr Gly Pro Leu Cys Glu Asn Pro Ala Val Pro Cys Ala Pro Ser Pro
        195             200             205

Cys Arg Asn Gly Gly Thr Cys Arg Gln Ser Gly Asp Leu Thr Tyr Asp
    210             215             220

Cys Ala Cys Leu Pro Gly Phe Glu Gly Gln Asn Cys Glu Val Asn Val
225             230             235             240

Asp Asp Cys Pro Gly His Arg Cys Leu Asn Gly Gly Thr Cys Val Asp
            245             250             255

Gly Val Asn Thr Tyr Asn Cys Gln Cys Pro Pro Glu Trp Thr Gly Gln
            260             265             270

Phe Cys Thr Glu Asp Val Asp Glu Cys Gln Leu Gln Pro Asn Ala Cys
        275             280             285

His Asn Gly Gly Thr Cys Phe Asn Thr Leu Gly Gly His Ser Cys Val
    290             295             300

Cys Val Asn Gly Trp Thr Gly Glu Ser Cys Ser Gln Asn Ile Asp Asp
305             310             315             320

Cys Ala Thr Ala Val Cys Phe His Gly Ala Thr Cys His Asp Arg Val
```

```
              325              330              335

Ala Ser Phe Tyr Cys Ala Cys Pro Met Gly Lys Thr Gly Leu Leu Cys
          340              345              350

His Leu Asp Asp Ala Cys Val Ser Asn Pro Cys His Glu Asp Ala Ile
          355              360              365

Cys Asp Thr Asn Pro Val Asn Gly Arg Ala Ile Cys Thr Cys Pro Pro
          370              375              380

Gly Phe Thr Gly Gly Ala Cys Asp Gln Asp Val Asp Glu Cys Ser Ile
385              390              395              400

Gly Ala Asn Pro Cys Glu His Leu Gly Arg Cys Val Asn Thr Gln Gly
          405              410              415

Ser Phe Leu Cys Gln Cys Gly Arg Gly Tyr Thr Gly Pro Arg Cys Glu
          420              425              430

Thr Asp Val Asn Glu Cys Leu Ser Gly Pro Cys Arg Asn Gln Ala Thr
          435              440              445

Cys Leu Asp Arg Ile Gly Gln Phe Thr Cys Ile Cys Met Ala Gly Phe
          450              455              460

Thr Gly Thr Tyr Cys Glu Val Asp Ile Asp Glu Cys Gln Ser Ser Pro
465              470              475              480

Cys Val Asn Gly Gly Val Cys Lys Asp Arg Val Asn Gly Phe Ser Cys
          485              490              495

Thr Cys Pro Ser Gly Phe Ser Gly Ser Thr Cys Gln Leu Asp Val Asp
          500              505              510

Glu Cys Ala Ser Thr Pro Cys Arg Asn Gly Ala Lys Cys Val Asp Gln
          515              520              525

Pro Asp Gly Tyr Glu Cys Arg Cys Ala Glu Gly Phe Glu Gly Thr Leu
          530              535              540

Cys Asp Arg Asn Val Asp Asp Cys Ser Pro Asp Pro Cys His His Gly
545              550              555              560

Arg Cys Val Asp Gly Ile Ala Ser Phe Ser Cys Ala Cys Ala Pro Gly
          565              570              575

Tyr Thr Gly Thr Arg Cys Glu Ser Gln Val Asp Glu Cys Arg Ser Gln
          580              585              590

Pro Cys Arg His Gly Gly Lys Cys Leu Asp Leu Val Asp Lys Tyr Leu
          595              600              605

Cys Arg Cys Pro Ser Gly Thr Thr Gly Val Asn Cys Glu Val Asn Ile
          610              615              620

Asp Asp Cys Ala Ser Asn Pro Cys Thr Phe Gly Val Cys Arg Asp Gly
625              630              635              640

Ile Asn Arg Tyr Asp Cys Val Cys Gln Pro Gly Phe Thr Gly Pro Leu
          645              650              655

Cys Asn Val Glu Ile Asn Glu Cys Ala Ser Ser Pro Cys Gly Glu Gly
          660              665              670

Gly Ser Cys Val Asp Gly Glu Asn Gly Phe Arg Cys Leu Cys Pro Pro
          675              680              685

Gly Ser Leu Pro Pro Leu Cys Leu Pro Pro Ser His Pro Cys Ala His
          690              695              700

Glu Pro Cys Ser His Gly Ile Cys Tyr Asp Ala Pro Gly Gly Phe Arg
705              710              715              720

Cys Val Cys Glu Pro Gly Trp Ser Gly Pro Arg Cys Ser Gln Ser Leu
          725              730              735

Ala Arg Asp Ala Cys Glu Ser Gln Pro Cys Arg Ala Gly Gly Thr Cys
          740              745              750
```

-continued

```
Ser Ser Asp Gly Met Gly Phe His Cys Thr Cys Pro Pro Gly Val Gln
        755               760               765

Gly Arg Gln Cys Glu Leu Leu Ser Pro Cys Thr Pro Asn Pro Cys Glu
        770               775               780

His Gly Gly Arg Cys Glu Ser Ala Pro Gly Gln Leu Pro Val Cys Ser
785               790               795               800

Cys Pro Gln Gly Trp Gln Asp Pro Cys Leu Asn Gly Gly Ser Cys Gln
                805               810               815

Asp Gly Val Gly Ser Phe Ser Cys Ser Cys Leu Pro Gly Phe Ala Gly
                820               825               830

Pro Arg Cys Ala Arg Asp Val Asp Glu Cys Leu Ser Asn Pro Cys Gly
        835               840               845

Pro Gly Thr Cys Thr Asp His Val Ala Ser Phe Thr Cys Thr Cys Pro
        850               855               860

Pro Gly Tyr Gly Gly Phe His Cys Glu Gln Asp Leu Pro Asp Cys Ser
865               870               875               880

Pro Ser Ser Cys Phe Asn Gly Gly Thr Cys Val Asp Gly Val Asn Ser
                885               890               895

Phe Ser Cys Leu Cys Arg Pro Gly Tyr Thr Gly Ala His Cys Gln His
                900               905               910

Glu Ala Asp Pro Cys Leu Ser Arg Pro Cys Leu His Gly Gly Val Cys
        915               920               925

Ser Ala Ala His Pro Gly Phe Arg Cys Thr Cys Leu Glu Ser Phe Thr
        930               935               940

Gly Pro Gln Cys Gln Thr Leu Val Asp Trp Cys Ser Arg Gln Pro Cys
945               950               955               960

Gln Asn Gly Gly Arg Cys Val Gln Thr Gly Ala Tyr Cys Leu Cys Pro
                965               970               975

Pro Gly Trp Ser Gly Arg Leu Cys Asp Ile Arg Ser Leu Pro Cys Arg
                980               985               990

Glu Ala Ala Ala Gln Ile Gly Val  Arg Leu Glu Gln Leu  Cys Gln Ala
        995               1000                 1005

Gly Gly  Gln Cys Val Asp Glu  Asp Ser Ser His Tyr  Cys Val Cys
    1010               1015               1020

Pro Glu  Gly Arg Thr Gly Ser  His Cys Glu Gln Glu  Val Asp Pro
    1025               1030               1035

Cys Leu  Ala Gln Pro Cys Gln  His Gly Gly Thr Cys  Arg Gly Tyr
    1040               1045               1050

Met Gly  Gly Tyr Met Cys Glu  Cys Leu Pro Gly Tyr  Asn Gly Asp
    1055               1060               1065

Asn Cys  Glu Asp Asp Val Asp  Glu Cys Ala Ser Gln  Pro Cys Gln
    1070               1075               1080

His Gly  Gly Ser Cys Ile Asp  Leu Val Ala Arg Tyr  Leu Cys Ser
    1085               1090               1095

Cys Pro  Pro Gly Thr Leu Gly  Val Leu Cys Glu Ile  Asn Glu Asp
    1100               1105               1110

Asp Cys  Gly Pro Gly Pro Pro  Leu Asp Ser Gly Pro  Arg Cys Leu
    1115               1120               1125

His Asn  Gly Thr Cys Val Asp  Leu Val Gly Gly Phe  Arg Cys Thr
    1130               1135               1140

Cys Pro  Pro Gly Tyr Thr Gly  Leu Arg Cys Glu Ala  Asp Ile Asn
    1145               1150               1155
```

-continued

Glu Cys Arg Ser Gly Ala Cys His Ala Ala His Thr Arg Asp Cys
    1160                1165                1170

Leu Gln Asp Pro Gly Gly Gly Phe Cys Cys Leu Cys His Ala Gly
    1175                1180                1185

Phe Ser Gly Pro Arg Cys Gln Thr Val Leu Ser Pro Cys Glu Ser
    1190                1195                1200

Gln Pro Cys Gln His Gly Gly Gln Cys Arg Pro Ser Pro Gly Pro
    1205                1210                1215

Gly Gly Gly Leu Thr Phe Thr Cys His Cys Ala Gln Pro Phe Trp
    1220                1225                1230

Gly Pro Arg Cys Glu Arg Val Ala Arg Ser Cys Arg Glu Leu Gln
    1235                1240                1245

Cys Pro Val Gly Val Pro Cys Gln Gln Thr Pro Arg Gly Pro Arg
    1250                1255                1260

Cys Ala Cys Pro Pro Gly Leu Ser Gly Pro Ser Cys Arg Ser Phe
    1265                1270                1275

Pro Gly Ser Pro Pro Gly Ala Ser Asn Ala Ser
    1280                1285

<210> SEQ ID NO 29
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 29
atacactggt ttgcgctgcg agg                                                    23

<210> SEQ ID NO 30
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 30
tctcaggtaa gcgttggcga agg                                                    23

<210> SEQ ID NO 31
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 31
ctacatgctc ccgctcgctc agg                                                    23

<210> SEQ ID NO 32
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 32
ctcaggtaag cgttggcgaa ggg                                                    23

<210> SEQ ID NO 33
<211> LENGTH: 23
<212> TYPE: DNA

-continued

<213> ORGANISM: artificial sequence
<220> FEATURE:
<223> OTHER INFORMATION: gRNA Recognition Sequence

<400> SEQUENCE: 33
tcaggtaagc gttggcgaag ggg                                              23

<210> SEQ ID NO 34
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 34
gacatcaatg agtgtcgctc agg                                              23

<210> SEQ ID NO 35
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 35
agtcccgggt gtgtgccgcg tgg                                              23

<210> SEQ ID NO 36
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 36
ctggcttctc aggtaagcgt tgg                                              23

<210> SEQ ID NO 37
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 37
gcatgtagat cagccacaat ggg                                              23

<210> SEQ ID NO 38
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 38
gacaggacag tctgacagcg agg                                              23

<210> SEQ ID NO 39
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 39
atgtagatca gccacaatgg ggg                                              23

-continued

```
<210> SEQ ID NO 40
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 40
agcatgtaga tcagccacaa tgg                                                   23

<210> SEQ ID NO 41
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 41
acagcgagga cctgagcgag cgg                                                   23

<210> SEQ ID NO 42
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 42
gtaagcgttg gcgaaggggc tgg                                                   23

<210> SEQ ID NO 43
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 43
catgtagatc agccacaatg ggg                                                   23
```